US009428475B2

(12) United States Patent
Scott et al.

(10) Patent No.: US 9,428,475 B2
(45) Date of Patent: *Aug. 30, 2016

(54) IMINOTHIADIAZINE DIOXIDE COMPOUNDS AS BACE INHIBITORS, COMPOSITIONS, AND THEIR USE

(71) Applicant: Merck Sharp & Dohme Corp., Rahway, NJ (US)

(72) Inventors: Jack D. Scott, Scotch Plains, NJ (US); Andrew W. Stamford, Chatham, NJ (US); Eric J. Gilbert, Scotch Plains, NJ (US); Jared N. Cumming, Garwood, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/221,650

(22) Filed: Mar. 21, 2014

(65) Prior Publication Data
US 2014/0206675 A1    Jul. 24, 2014

Related U.S. Application Data

(62) Division of application No. 13/392,297, filed as application No. PCT/US2010/051553 on Oct. 6, 2010, now Pat. No. 8,729,071.

(60) Provisional application No. 61/249,685, filed on Oct. 8, 2009.

(51) Int. Cl.
| | |
|---|---|
| *A61K 31/549* | (2006.01) |
| *C07D 285/18* | (2006.01) |
| *A61K 31/00* | (2006.01) |
| *A61K 31/54* | (2006.01) |
| *A61K 45/06* | (2006.01) |
| *C07D 403/12* | (2006.01) |
| *C07D 401/14* | (2006.01) |
| *C07D 401/12* | (2006.01) |
| *C07D 403/04* | (2006.01) |
| *C07D 417/04* | (2006.01) |

(Continued)

(52) U.S. Cl.
CPC ............ *C07D 285/18* (2013.01); *A61K 31/00* (2013.01); *A61K 31/54* (2013.01); *A61K 45/06* (2013.01); *C07C 309/30* (2013.01); *C07D 213/89* (2013.01); *C07D 401/12* (2013.01); *C07D 401/14* (2013.01); *C07D 403/04* (2013.01); *C07D 403/12* (2013.01); *C07D 417/04* (2013.01); *C07D 417/10* (2013.01); *C07D 417/12* (2013.01); *C07D 417/14* (2013.01); *C07D 471/04* (2013.01); *C07D 487/04* (2013.01); *C07D 495/04* (2013.01); *A61K 31/495* (2013.01); *A61K 31/549* (2013.01); *C07D 213/26* (2013.01); *C07D 239/14* (2013.01)

(58) Field of Classification Search
CPC . C07D 147/12; C07D 417/12; A61K 31/549
See application file for complete search history.

(56) References Cited

U.S. PATENT DOCUMENTS

| | | | |
|---|---|---|---|
| 5,534,520 | A | 7/1996 | Fisher et al. |
| 6,683,091 | B2 | 1/2004 | Asberom et al. |

(Continued)

FOREIGN PATENT DOCUMENTS

| | | |
|---|---|---|
| EP | 1942105 | 7/2008 |
| JP | 2012250933 | 12/2012 |

(Continued)

OTHER PUBLICATIONS

M.S. Malamas et al., 53 Journal of Medicinal Chemistry, 1146-1158 (2010).*

(Continued)

*Primary Examiner* — Alexander R Pagano
(74) *Attorney, Agent, or Firm* — Keith D. MacMillan; John C. Todaro

(57) ABSTRACT

In its many embodiments, the present invention provides certain iminothiadiazine dioxide compounds, including compounds Formula (I): (I) and include stereoisomers thereof, and pharmaceutically acceptable salts of said compounds stereoisomers, wherein each of $R^1$, $R^2$, $R^3$, $R^4$, $R^5$, $R^9$, ring A, ring B, m, n, p, -$L_1$-, $L_2$-, and $L_3$- is selected independently and as defined herein. The novel iminothiadiazine dioxide compounds of the invention have surprisingly been found to exhibit properties which are expected to render them advantageous as BACE inhibitors and/or for the treatment and prevention of various pathologies related to β-amyloid (Aβ) production. Pharmaceutical compositions comprising one or more such compounds (alone and in combination nation with one or more other active agents), and methods for their preparation and use in treating pathologies associated with amyloid beta (Aβ) protein, including Alzheimers disease, are also disclosed.

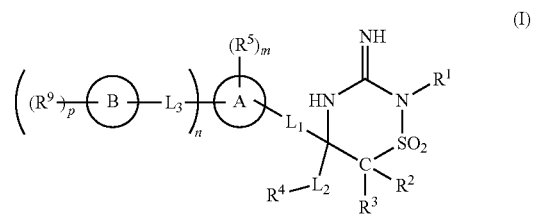

28 Claims, No Drawings

(51) Int. Cl.
    *C07D 417/12*     (2006.01)
    *C07D 417/14*     (2006.01)
    *C07D 471/04*     (2006.01)
    *C07D 495/04*     (2006.01)
    *C07D 213/89*     (2006.01)
    *C07D 417/10*     (2006.01)
    *C07C 309/30*     (2006.01)
    *C07D 487/04*     (2006.01)
    C07D 213/26     (2006.01)
    A61K 31/495     (2006.01)
    C07D 239/14     (2006.01)

(56) References Cited

U.S. PATENT DOCUMENTS

| | | | |
|---|---|---|---|
| 7,648,983 B2 | 1/2010 | Audia et al. | |
| 7,994,167 B2 | 8/2011 | Frank et al. | |
| 8,338,413 B1 | 12/2012 | Rueeger | |
| 8,563,543 B2 * | 10/2013 | Scott et al. | 514/222.5 |
| 8,569,310 B2 * | 10/2013 | Iserloh et al. | 514/256 |
| 8,729,071 B2 * | 5/2014 | Scott et al. | 514/222.5 |
| 8,940,748 B2 * | 1/2015 | Scott et al. | 514/256 |
| 2006/0034848 A1 | 2/2006 | Kinoshita et al. | |
| 2006/0281730 A1 | 12/2006 | Zhu et al. | |
| 2007/0072925 A1 | 3/2007 | Malamas et al. | |
| 2007/0287692 A1 | 12/2007 | Wu et al. | |
| 2007/0299087 A1 | 12/2007 | Berg et al. | |
| 2008/0200445 A1 | 8/2008 | Zhu et al. | |
| 2009/0023762 A1 | 1/2009 | Berg et al. | |
| 2009/0062282 A1 | 3/2009 | Albert et al. | |
| 2009/0209755 A1 | 8/2009 | Suzuki et al. | |
| 2010/0075957 A1 | 3/2010 | Tamura et al. | |
| 2010/0317850 A1 | 12/2010 | Suzuki et al. | |
| 2011/0009395 A1 | 1/2011 | Audia et al. | |
| 2011/0046122 A1 | 2/2011 | Andreini et al. | |
| 2011/0152253 A1 | 6/2011 | Motoki et al. | |
| 2012/0035195 A1 | 2/2012 | Banner et al. | |
| 2012/0184540 A1 | 7/2012 | Andreini et al. | |
| 2012/0189642 A1 | 7/2012 | Scott et al. | |
| 2012/0195881 A1 | 8/2012 | Iserloh et al. | |
| 2012/0196863 A1 | 8/2012 | Andreini et al. | |
| 2012/0202803 A1 | 8/2012 | Hilpert et al. | |
| 2012/0258961 A1 | 10/2012 | Suzuki et al. | |
| 2012/0258962 A1 | 10/2012 | Hilpert et al. | |
| 2012/0302549 A1 | 11/2012 | Narquizian et al. | |
| 2014/0296221 A1 * | 10/2014 | Scott et al. | 514/222.5 |

FOREIGN PATENT DOCUMENTS

| | | |
|---|---|---|
| WO | WO9004917 | 5/1990 |
| WO | WO9304047 | 3/1993 |
| WO | WO9614844 | 5/1996 |
| WO | WO0051992 | 9/2000 |
| WO | WO03035613 | 5/2003 |
| WO | WO03097641 | 11/2003 |
| WO | WO2004062625 | 7/2004 |
| WO | WO2005004802 | 1/2005 |
| WO | WO2005004803 | 1/2005 |
| WO | WO2005014540 | 2/2005 |
| WO | WO2005016876 | 2/2005 |
| WO | WO2005032471 | 4/2005 |
| WO | WO2005051914 | 6/2005 |
| WO | WO2005058311 | 6/2005 |
| WO | WO2005065195 | 7/2005 |
| WO | WO2005103020 | 11/2005 |
| WO | WO2005103043 | 11/2005 |
| WO | WO2005108358 | 11/2005 |
| WO | WO2006002004 | 1/2006 |
| WO | WO2006009653 | 1/2006 |
| WO | WO2006009655 | 1/2006 |
| WO | WO2006014762 | 2/2006 |
| WO | WO2006014944 | 2/2006 |
| WO | WO2006041404 | 4/2006 |
| WO | WO2006041405 | 4/2006 |
| WO | WO2006044497 | 4/2006 |
| WO | WO2006057983 | 6/2006 |
| WO | WO2006060109 | 6/2006 |
| WO | WO2006065277 | 6/2006 |
| WO | WO 2006065277 A2 * | 6/2006 |
| WO | WO2006076284 | 7/2006 |
| WO | WO2006078576 | 7/2006 |
| WO | WO2006078577 | 7/2006 |
| WO | WO2006122773 | 11/2006 |
| WO | WO2006138192 | 12/2006 |
| WO | WO2006138195 | 12/2006 |
| WO | WO2006138217 | 12/2006 |
| WO | WO2006138230 | 12/2006 |
| WO | WO2006138264 | 12/2006 |
| WO | WO2006138265 | 12/2006 |
| WO | WO2006138266 | 12/2006 |
| WO | WO2007005366 | 1/2007 |
| WO | WO2007005404 | 1/2007 |
| WO | WO2007011810 | 1/2007 |
| WO | WO2007016012 | 2/2007 |
| WO | WO2007019078 | 2/2007 |
| WO | WO2007019111 | 2/2007 |
| WO | WO2007038271 | 4/2007 |
| WO | WO2007078813 | 4/2007 |
| WO | WO2007049532 | 5/2007 |
| WO | WO2007050721 | 5/2007 |
| WO | WO2007053506 | 5/2007 |
| WO | WO2007058580 | 5/2007 |
| WO | WO2007058581 | 5/2007 |
| WO | WO2007058583 | 5/2007 |
| WO | WO2007058601 | 5/2007 |
| WO | WO2007058602 | 5/2007 |
| WO | WO2007058862 | 5/2007 |
| WO | WO2007073284 | 6/2007 |
| WO | WO2007093621 | 8/2007 |
| WO | WO2007100536 | 9/2007 |
| WO | WO2007114771 | 10/2007 |
| WO | WO2007145568 | 12/2007 |
| WO | WO2007145569 | 12/2007 |
| WO | WO2007145570 | 12/2007 |
| WO | WO2007145571 | 12/2007 |
| WO | WO2007146225 | 12/2007 |
| WO | WO2007149033 | 12/2007 |
| WO | WO2008022024 | 2/2008 |
| WO | WO2008030412 | 3/2008 |
| WO | WO2008036316 | 3/2008 |
| WO | WO2008045250 | 4/2008 |
| WO | WO2008054698 | 5/2008 |
| WO | WO2008063114 | 5/2008 |
| WO | WO2008073365 | 6/2008 |
| WO | WO2008073370 | 6/2008 |
| WO | WO2008076043 | 6/2008 |
| WO | WO2008076044 | 6/2008 |
| WO | WO2008076045 | 6/2008 |
| WO | WO2008076046 | 6/2008 |
| WO | WO2008133273 | 6/2008 |
| WO | WO2008133274 | 6/2008 |
| WO | WO2008103351 | 8/2008 |
| WO | WO 2008103351 A2 * | 8/2008 |
| WO | WO2008115552 | 9/2008 |
| WO | WO2008118379 | 10/2008 |
| WO | WO2009005470 | 1/2009 |
| WO | WO2009005471 | 1/2009 |
| WO | WO2011009897 | 1/2009 |
| WO | WO2009015917 | 2/2009 |
| WO | WO2009020580 | 2/2009 |
| WO | WO2009022961 | 2/2009 |
| WO | WO2009091016 | 7/2009 |
| WO | WO2009103626 | 8/2009 |
| WO | WO2009108550 | 9/2009 |
| WO | WO2009131974 | 10/2009 |
| WO | WO2009131975 | 10/2009 |
| WO | WO2009134617 | 11/2009 |
| WO | WO2009136350 | 11/2009 |
| WO | WO2009151098 | 12/2009 |
| WO | WO2010013302 | 2/2010 |
| WO | WO2010013794 | 2/2010 |
| WO | WO2010021680 | 2/2010 |
| WO | WO2010030954 | 3/2010 |

(56) References Cited

FOREIGN PATENT DOCUMENTS

| | | |
|---|---|---|
| WO | WO2010038686 | 4/2010 |
| WO | WO2010047372 | 4/2010 |
| WO | WO2010048149 | 4/2010 |
| WO | WO2010056194 | 5/2010 |
| WO | WO2010056195 | 5/2010 |
| WO | WO2010056196 | 5/2010 |
| WO | WO2010063718 | 6/2010 |
| WO | WO2010094242 | 8/2010 |
| WO | WO2010105179 | 9/2010 |
| WO | WO2010113848 | 10/2010 |
| WO | WO2010128058 | 11/2010 |
| WO | WO2011002407 | 1/2011 |
| WO | WO2011002408 | 1/2011 |
| WO | WO2011002409 | 1/2011 |
| WO | WO2011005738 | 1/2011 |
| WO | WO2011009898 | 1/2011 |
| WO | WO2011009943 | 1/2011 |
| WO | WO2011020806 | 2/2011 |
| WO | WO2011029803 | 3/2011 |
| WO | WO2011044181 | 4/2011 |
| WO | WO2011044184 | 4/2011 |
| WO | WO2011044185 | 4/2011 |
| WO | WO2011044187 | 4/2011 |
| WO | WO2011058763 | 5/2011 |
| WO | WO2011069934 | 6/2011 |
| WO | WO2011070029 | 6/2011 |
| WO | WO2011070781 | 6/2011 |
| WO | WO2011071057 | 6/2011 |
| WO | WO2011071109 | 6/2011 |
| WO | WO2011071135 | 6/2011 |
| WO | WO2011072064 | 6/2011 |
| WO | WO2011077726 | 6/2011 |
| WO | WO2011080176 | 7/2011 |
| WO | WO2011090911 | 7/2011 |
| WO | WO2011106414 | 9/2011 |
| WO | WO2011115928 | 9/2011 |
| WO | WO2011115938 | 9/2011 |
| WO | WO2011123674 | 10/2011 |
| WO | WO2011130347 | 10/2011 |
| WO | WO2011130741 | 10/2011 |
| WO | WO2011138293 | 11/2011 |
| WO | WO2011142716 | 11/2011 |
| WO | WO2011154374 | 12/2011 |
| WO | WO2011154431 | 12/2011 |
| WO | WO2012006953 | 1/2012 |
| WO | WO2012040641 | 3/2012 |
| WO | WO2012057247 | 5/2012 |
| WO | WO2012057248 | 5/2012 |
| WO | WO2012071279 | 5/2012 |
| WO | WO2012071458 | 5/2012 |

OTHER PUBLICATIONS

F. Yang et al., 280 the Journal of Biological Chemistry, 5892-5901 (2004).*
I. Hussain et al., 100 Journal of Neurochemistry, 902-809 (2007).*
D.A. Wolk et al., 65 Annals of Neurology, 557-568 (2009).*
I. Blasko et al., 29 Neurobiology of Aging, 1-11 (2008).*
A. Forsberg et al., 29 Neurobiology of Aging, 1456-1465 (2008).*
D. Van Dam et al., 164 British Journal of Pharmacology, 185-1300 (2011).*
Abramov, et al., Amyloid—as a positive endogenous regulator of release probability at hippocampal synapses, Nature Neuroscience 12, 1567-1576 (2009) Published online: Nov. 22, 2009 | doi:10.1038/nn.2433.
Barton, et al., On the Structure of Some Substituted 4,6-Pyrimidinones, Department of Organic Chemistry, College of Medicine, Jagiellonian University, Ingardena 3, 30-060-Krakow, Poland, Polish J. Chem., 69, 235-245 (1995), revised manuscript Oct. 25, 1994.
Bayden, et al., Web application for studying the free energy of binding and protonation states of protein-ligand complexes based on HINT, J Comput Aided Mol Des (2009) 23:621-632.
Chiriano, et al., Sequential Virtual Screening Approach to the Identification of Small Organic Molecules as Potential BACE-1 Inhibitors, Chem Biol Drug Des 2011; 77: 268-271.
Cho, et al, S-Nitrosylation of Drp1 Mediates β-Amyloid-Related Mitochondrial Fission and Neuronal Injury, Science Apr. 3, 2009: vol. 324 No. 5923 pp. 102-105.
European Search Report and Supplementary European Search Report and Opinion for EP2485591, Feb. 4, 2013.
PCT Search Report for International Application WO2011044187, Apr. 14, 2011.
PCT Written Opinion for International Application WO2011044187, Apr. 8, 2012.
European Search Report and Supplementary European Search Report and Opinion for EP10822567.3, Feb. 21, 2013.
PCT Search Report for International Application WO2011/044181, Apr. 14, 2011.
PCT Written Opinion for International Application WO2011/044181, Apr. 8, 2012.
European Search Report and Supplementary European Search Report and Opinion for EP2485920, mailed Mar. 25, 2013.
PCT Search Report for International Application WO2011044185, Apr. 30, 2012.
PCT Written Opinion for International Application WO2011044185, Apr. 30, 2012.
European Search Report and Supplementary European Search Report and Opinion for EP2485590, Apr. 12, 2013.
PCT Search Report for International Application WO2011044184, Apr. 14, 2011.
PCT Written Opinion for International Application WO2011044184, Apr. 8, 2012.
Cole, et al., Review: The Alzheimer's disease B-secretase enzyme, BACEI, , Molecular Neurodegeneration 2007, 2:22, Published Nov. 15, 2007.
Copending U.S. Appl. No. 13/390,856, Afluorosulfur Imino Heterocyclic Compounds as BACE-1 Inhibitors, Compositions, and Their Use, filed U.S. Appl. No. 13/390,856.
Copending U.S. Appl. No. 13/391,441, Pentafluorosulfur Imino Heterocyclic Compounds as BACE-1 Inhibitors, Compositions, and Their Use, filed Oct. 6, 2010.
Copending U.S. Appl. No. 13/392,955, Imino Thiadiazine Dioxide Compounds as BACE-1 Inhibitors, Compositions, and Their Use, filed Oct. 6, 2010.
Cumming JN, et al. Piperazine sulfonamide BACE1 inhibitors: Design, synthesis, and in vivo characterization. Bioorg Med Chem Lett. 2010;20:2837-42.
Cumming JN, et al. Rational design of novel, potent piperazinone and imidazolidinone BACE1 inhibitors. Bioorg Med Chem Lett. 2008;18:3236-41.
Cumming JN, et al. Structure based design of iminohydantoin BACE1 inhibitors: identification of an orally available, centrally active BACE1 inhibitor. Bioorg Med Chem Lett. Apr. 1, 2012;22(7):2444-9. doi: 10.1016/j.bmcl.2012.02.013.
Cumming, et al., Design and development of cyclic amine BACE1 inhibitors, Current Opinion in Drug Discovery and Development, 2004, 7(4), 536-556.
Edwards, et al., Application of Fragment-Based Lead Generation to the Discovery of Novel, Cyclic Amidine p-Secretase Inhibitors with Nanomolar Potency, Cellular Activity, and High Ligand Efficiency, 1. Med. Chenl. 2007,50, 5912-5925.
Evin, et al., BACE Inhibitors as Potential Drugs for the Treatment of Alzheimer's Disease: Focus on Bioactivity, Recent Patents on CNS Drug Discovery, 2011, 6, 91-106.
Farah, et al., Reduced BACE1 Activity Enhances Clearance of Myelin Debris and Regeneration of Axons in the Injured Peripheral Nervous System, The Journal of Neuroscience, Apr. 13, 2011 • 31(15):5744-5754.
Getchell, et al., 3-Nitrotyrosine immunoreactivity in olfactory receptor neurons of patients with Alzheimer's disease: implications for impaired odor sensitivity, Neurobiology of Aging 24 (2003) 663-673., accepted Oct. 8, 2002, pp. 663-673.
Ginman, et al., "Core refinement toward permeable B-Secretase (BACE-1) Inhibitors with low hERG Activity", Journal of Medicinal Chemistry, Rec'd Aug. 12, 2012.

(56) References Cited

OTHER PUBLICATIONS

Gravenfors, et al., "New Aminimidazoles as B-Secretase (BACE-1) inhibitors Showing amylod-B (AB) lowering in the brain", Journal of Medicinal Chemistry, 2012, 55, 9297-9311.
Guo, et al., Targeting Amyloid-B in Glaucoma Treatment, pp. 13444-13449, PNAS, Aug. 14, 2007, vol. 104, No. 33.
Hilpert, et al., "B-Secretase (BACE1) Inhibitors with high in vivo efficacy suitable for clinical evaluation of Alzheimer's disease", Journal of Medicinal Chemistry, 2013, 56, 3980-3995.
Huang, et al., "Structure- and Property-Based Design of Aminooxazoline Xanthines as selective, orally efficacious, and CNS Penetrable BACE inhibitors for the treatment of Alzheimer's disease", Journal of Medicinal Chemistry, Special Issue: Alzheimer's Disease, 2012, 55, 9156-9169.
Huang, et al., Pharmacophore Model Construction of ,8-Secretase Inhibitors, Acta Chimica Sinica, vol. 66, No. 16, 2008, pp. 1889-1897. (English Abstract).
Hunt, et al., "Spirocyclic B-Site Amyloid Precursor Protein Cleaving Enzyme 1 (BACE1) Inhibitors: From hit to Lowering of Cerebralspinal fluid (CSF) Amyloid-B in a higher species", Journal of Medicinal Chemistry 2013, 56, 3379-3403.
Iserloh U, et al. Discovery of an orally efficacious 4-phenoxypyrrolidine-based BACE-1 inhibitor. Bioorg Med Chem Lett. 2008;18:418-22.
Iserloh U, et al. Potent pyrrolidine- and piperidine-based BACE-1 inhibitors. Bioorg Med Chem Lett. 2008;18:414-7.
Jin, et al., Evidence for dimeric BACE-mediated APP processing, Biochemical and Biophysical Research Communications 393 (2010) 21-27.
Loane, et al., Amyloid Precursor Protein Secretases as Therapeutic Targets for Traumatic Brain Injury, Nature Medicine, Advance Online Publication, Received Aug. 27, 2008; accepted Feb. 18, 2009; published online Mar. 15, 2009; doi:10.1038/nm.1940, pp. 1-3.
Luo, et al., mice deficient in BACE1, the Alzheimer's B-secretase, have normal phenotype and abolished B-amyloid, Nature Neuroscience, vol. 4, No. 3, Mar. 2001.
Malamas, et al., Aminoimidazoles as potent and selective human B-secretase (BACE1) inhibitors, J. Med. Chem., 2009, 52, 6314-6323.
Malamas, et al., Design and Synthesis of 5,50-Disubstituted Aminohydantoins as Potent and Selective Human β-Secretase (BACE1) Inhibitors, J. Med. Chem. 2010, 53, 1146-1158 (Published on Web Dec. 7, 2009).
Malamas, et al., Design and synthesis of aminohydantoins as potent and selective human b-secretase (BACE1) inhibitors with enhanced brain permeability, Bioorganic & Medicinal Chemistry Letters 20 (2010) 6597-6605.
Malamas, et al., Di-substituted pyridinyl aminohydantoins as potent and highly selective human b-secretase (BACE1) inhibitors, Bioorganic & Medicinal Chemistry 18 (2010) 630-639.
Malamas, et al., New pyrazolyl and thienyl aminohydantoins as potent BACE1 inhibitors: Exploring the S20 region, Bioorganic & Medicinal Chemistry Letters 21 (2011) 5164-5170.
Malamas, et al., Novel pyrrolyl 2-aminopyridines as potent and selective human b-secretase (BACE1) inhibitors, Bioorganic & Medicinal Chemistry Letters 20 (2010) 2068-2073 (Available online Feb. 23, 2010).
Mandal M, et al., Design and validation of bicyclic iminopyrimidinones as beta amyloid cleaving enzyme-1 (BACE1) inhibitors: conformational constraint to favor a bioactive conformation. J Med Chem. Nov. 8, 2012;55(21):9331-45. doi: 10.1021/jm301039c.
May, et al., Robust Central Reduction of B Amyloid in Humans with an Orally Available, Non-Peptidic B-Secretase Inhibitor, The Journal of Neuroscience, Nov. 16, 2011 • 31(46):16507-16516 • 16507.
McConlogue, et al., Partial reduction of BACE1 as dramatic effects on Alzheimer's plaque and synaptic pathology in APP transgenic mice, J. Biological Chem., vol. 282, No. 36, pp. 26326-26334, Sep. 7, 2007.
Nowak, et al., Discovery and initial optimization of 5,50-disubstituted aminohydantoins as potent b-secretase (BACE1) inhibitors, Bioorganic & Medicinal Chemistry Letters 20 (2010) 632-635. (Available online Nov. 20, 2009).
Ohno, et al., BACE1 deficiency rescues memory deficits and Cholinergic function in a mouse model of Alzheimer's disease, Neuron, vol. 41, 27-33, Jan. 8, 2004.
Ohno, et al.BACE1 gene deletion prevents neuron loss and memory deficits in 5XFAD APP/PS1 transgenic mice, Neurobiology of disease 26 (2006), pp. 134-145.
Osherovich, L. AB's Dry (AMD) Humor, SciBX 4(26); doi:10. 1038/scibx.2011.727, Published online Jun. 30, 2011.
Probst, et al., Small-molecule BACE1 inhibitors: a patent literature review, Expert Opinion on Therapeutic Patents, (2006-2011), 2012, 22(5):511-540.
Roberds, et al., BACE knockout mice are healthy despite lacking the primary B-secretase activity in the brain: implications for Alzheimer's disease therapeutics, Human Mol. Genetics, vol. 10, No. 12, pp. 1317-1324. Apr. 3, 2004.
Scott, et al., "Novel Imino Pyrimidinone B-Secretase (BACE1) Inhibitors. P1 Thiophenes", Poster presentation, American Chemical Society, Sprint 2011.
Solloway, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 12, 2012.
Southan, BACE2 as a New Diabetes Target: a patent review 2010-2012, Expert Opinion on Therapeutic Patents, 2013, Informa UK, Ltd., ISSN 1354-3776, e-1744-7674.
Sperling, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 11, 2012.
Stachel, et al., Structure-Based Design of Potent and Selective Cell-Permeable Inhibitors of Human Beta-Secretase (BACE-1), J. Med. Chem., 2004, vol. 47, pp. 6447-6450.
Stamford, et al., "Fragment-based discovery of BACE1 inhibitors, Potential disease-modifying agents for the treatment of Alzheimer's disease", Slide Presentation R. Bryan Miller Symposium, UC Davis, Mar. 7-8, 2013.
Stamford, et al., Discovery of an Orally Available, Brain Penetrant BACE1 Inhibitor That Affords Robust CNS Aβ Reduction, ACS Med. Chem. Lett. Jul. 12, 2012, 3, 897-902.
Stamford, et al., Inhibitors of BACE for treating Alzheimer's disease: a fragment-based drug discovery story, Current Opinion in Chemical Biology;.v:17 i:3 p. 320-328; Jun. 2013 Elsevier.
Statchel, et al., Conformationally biased P3 amide replacements of b-secretase inhibitors, S. J. Stachel et al. / Bioorg. Med. Chem. Lett. 16 (2006) 641-644.
Statchel, et al., Discovery of aminoheterocycles as a novel b-secretase inhibitor class: pH dependence on binding activity part 1, Bioorganic & Medicinal Chemistry Letters 19 (2009) 2977-2980.
Swahn, et al., "Aminimidazoles as BACE-1 inhibitors: The challenge to achieve in vivo brain efficacy", Bioorganic and Medicinal Chemistry Letters, 22 (2012) 1854-1859.
Swahn, et al., "Design and synthesis of beta-site amyloid precursor protein cleaving enzyme (BACE1) inhibitors with in vivo brain reduction of B-amyloid peptides", Journal of Medicinal Chemistry, 2012, 55, 9346-9361.
Tresadern, et al., Rational design and synthesis of aminopiperazinones as b-secretase (BACE) inhibitors, Bioorganic & Medicinal Chemistry Letters 21 (2011) 7255-7260.
Wang YS, et al., Application of fragment-based NMR screening, X-ray crystallography, structure-based design, and focused chemical library design to identify novel microM leads for the development of nM BACE-1 (beta-site APP cleaving enzyme 1) inhibitors. J Med Chem. 2010;53:942-50.

(56) References Cited

OTHER PUBLICATIONS

Weiner, Further insights into Alzheimer disease pathogenesis, Weiner, M.W. Nat. Rev. Neurol. 9, 65-66 (2013); published online Jan. 22, 2013.

Welch, J.T., et al., The synthesis and biological activity of pentafluorosulfanyl analogs of fluoxetine, fenfluramine, and norfenfluramine, Bioorganic & Medicinal Chemistry; v:15 i:21 p. 6659-6666; Nov. 1, 2007.

Wyss DF, et al., Combining NMR and X-ray crystallography in fragment-based drug discovery: discovery of highly potent and selective BACE-1 inhibitors. Top Curr Chem. 2012;317:83-114. doi: 10.1007/128_2011_183.

Zhi, et al., Self-organizing molecular field analysis on human b-secretase nonpeptide inhibitors: 5, 5-disubstituted aminohydantoins, European Journal of Medicinal Chemistry 46 (2011) 58-64.

Zhou, et al., An efficient synthesis of 2-amino-4-(4-fluoro-3-(2-fluoropyridin-3-yl)phenyl)-4-(4-methoxy-3-methylphenyl)-1-methyl-1H-imidazol-5(4H)-one, a potent BACE1 inhibitor, ARKIVOC 2010 (vi) 84-88.

Zhou, et al., Pyridinyl aminohydantoins as small molecule BACE1 inhibitors, Bioorganic & Medicinal Chemistry Letters 20 (2010) 2326-2329 (Available online Feb. 12, 2010).

Zhu, et al., Discovery of Cyclic Acylguanidines as Highly Potent and Selective β-Site Amyloid Cleaving Enzyme (BACE) Inhibitors: Part I;Inhibitor Design and Validation),1, J. Med. Chem. 2010, 53, 951-965.

\* cited by examiner

IMINOTHIADIAZINE DIOXIDE COMPOUNDS AS BACE INHIBITORS, COMPOSITIONS, AND THEIR USE

CROSS REFERENCE TO RELATED APPLICATIONS

This application is a Divisional Application of U.S. patent application Ser. No. 13/392,297, filed on Mar. 16, 2012, which is a national stage application filed under 35 U.S.C. 371 of International Patent Application No. PCT/US2010/051553, filed on Oct. 6, 2010, which claims priority to U.S. Provisional Application No. 61/249,685, filed on Oct. 8, 2009, each of which is incorporated herein by reference.

FIELD OF THE INVENTION

This invention provides certain iminothiadiazine dioxide compounds and compositions comprising these compounds. The novel iminothiadiazine dioxide compounds of the invention have surprisingly been found to exhibit properties which are expected to render them advantageous as RACE inhibitors and/or for the treatment and prevention of various pathologies related to β-amyloid ("Aβ") production.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity near the position near the N-terminus of Aβ, and by gamma-secretase activity at a position near the C-terminus of Aβ. (APP is also cleaved by α-secretase activity, resulting in the secreted, non-arnyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forrest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to formed amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and LAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets for traumatic brain injury. (Loane et al., "Amyloid precursor protein secretases as therapeutic targets for traumatic brain injury", Nature Medicine, Advance Online Publication, published online Mar. 15, 2009.) Still other diverse pathologies characterized by the inappropriate formation and deposition of Aβ or fragments thereof, and/or by the presence of amyloid fibrils, and/or for which inhibitor(s) of BACE-1 is expected to be of therapeutic value are discussed further hereinbelow.

The therapeutic potential of inhibiting the deposition of Aβ has motivated many groups to characterize BACE-1 and to identify inhibitors of BACE-1 and of other secretase enzyme inhibitors. Examples from the patent literature are growing and include WO2006009653, WO2007005404, WO2007005366, WO2007038271, WO2007016012, US2005/0282826, US2007072925, WO2007149033, WO2007145568, WO2007145569, WO2007145570, WO2007145571, WO2007114771, US20070299087, WO2005/016876, WO2005/014540, WO2005/058311, WO2006/065277, WO2006/014762, WO2006/014944, WO2006/138195, WO2006/138264, WO2006/138192, WO2006/138217, WO2007/050721, WO2007/053506, WO2007/146225, WO2006/138230, WO2006/138265, WO2006/138266, WO2007/053506, WO2007/146225, WO2008/073365, WO2008/073370, WO2008/103351, US2009/041201, US2009/041202, and WO2010/047372.

SUMMARY OF THE INVENTION

The present invention provides certain iminothiadiazine dioxide compounds which are collectively or individually referred to herein as "compound(s) of the invention", as described herein. The novel iminothiadiazine dioxide compounds of the invention have surprisingly been found to exhibit properties which are expected to render them advantageous as BACE inhibitors and/or for the treatment and prevention of the various pathologies described herein.

In each of the various embodiments of the compounds of the invention described herein, each variable including those of Formulas (I), (IA), (IA-1), (IA-2), (II), (IIA), (IIA-1), and (IIA-2), and the various embodiments thereof, each variable is selected independently of the others unless otherwise indicated.

In each of the various embodiments of the compounds of the invention described herein, including those of Formulas (I), (IA), (IA-1), (IA-2), (II), (IIA), (IIA-1), and (IIA-2), and the various embodiments thereof and the compounds of the examples, such formulas and examples are intended to encompass all forms of the compounds such as, for example, any solvates, hydrates, stereoisomers, and tautomers of said compounds and of any pharmaceutically acceptable salts thereof.

In one embodiment, the compounds of the invention have the structural Formula (I):

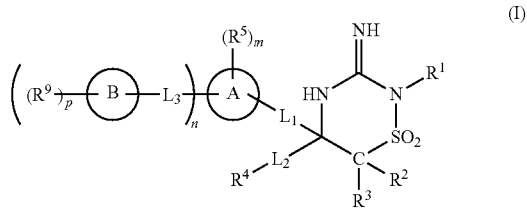

and include tautomers, solvates, prodrugs, and esters thereof, and pharmaceutically acceptable salts of said compounds, tautomers, solvates, prodrugs, and esters, wherein:

-$L_1$- represents a bond or a divalent moiety selected from the group consisting of -alkyl-, -haloalkyl-, -heteroalkyl-, -alkenyl-, and -alkynyl-;

-$L_2$- represents a bond or a divalent moiety selected from the group consisting of -alkyl-, -haloalkyl-, -heteroalkyl-, -alkenyl-, and -alkynyl-;

each -$L_3$- independently represents a bond or a divalent moiety independently selected from the group consisting of -alkyl-, -haloalkyl-, -heteroalkyl-, -alkenyl-, —N($R^7$)—, —NHC(O)—, —C(O)NH—, —NHS(O)$_2$—, —S(O)$_2$NH—, —O-alkyl-, -alkyl-O—, -haloalkyl-NH—, and —NH-haloalkyl-;

m, n, and p are each independently selected integers, wherein:

m is 0 or more;

n is 0 or more; and p is 0 or more, wherein the maximum value of the sum of m and n is the maximum number of available substitutable hydrogen atoms on ring A, and wherein the maximum value of p is the maximum number of available substitutable hydrogen atoms on ring B;

$R^1$ is selected from the group consisting of: H, alkyl, haloalkyl, heteroalkyl, heterohaloalkyl, cycloalkyl, heterocycloalkyl, heterocycloalkylalkyl-, aryl, arylalkyl-, heteroaryl, and heteroarylalkyl-, wherein each of said alkyl, haloalkyl, heteroalkyl, heterohaloalkyl, cycloalkyl, cycloalkylalkyl-, heterocycloalkyl, heterocycloalkylalkyl-, aryl, arylalkyl-, heteroaryl, and heteroarylalkyl- of $R^1$ is unsubstituted or substituted with one or more independently selected $R^{10}$ groups;

$R^2$ is selected from the group consisting of H, halo, alkyl, haloalkyl, and heteroalkyl, wherein each of said alkyl and said haloalkyl of $R^2$ is unsubstituted or substituted with one or more independently selected $R^{10}$ groups;

$R^3$ is selected from the group consisting of H, halo, alkyl, haloalkyl, and heteroalkyl, wherein each of said alkyl and said haloalkyl of $R^2$ is unsubstituted or substituted with one or more independently selected $R^{10}$ groups;

$R^4$ is selected from the group consisting of alkyl, aryl, heteroaryl, cycloalkyl, cycloalkenyl, heterocycloalkyl, and heterocycloalkenyl, wherein each of said alkyl, aryl, heteroaryl, cycloalkyl, cycloalkenyl, heterocycloalkyl, and heterocycloalkenyl of $R^4$ is unsubstituted or substituted with one or more independently selected $R^{10}$ groups;

ring A is selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each ring B (when present) is independently selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each $R^5$ (when present) is independently selected from the group consisting of halo, —CN, —SF$_5$, —OSF$_5$, —NO$_2$, —Si($R^6$)$_3$, —P(O)(O$R^7$)$_2$, —P(O)(O$R^7$)($R^7$), —N($R^8$)$_2$, —N$R^8$C(O)$R^7$, —N$R^8$S(O)$_2R^7$, —N$R^8$C(O)N($R^8$)$_2$, —N$R^8$C(O)O$R^7$, —C(O)$R^7$, —C(O)$_2R^7$, —C(O)N($R^8$)$_2$, —S(O)$R^7$, —S(O)$_2R^7$, —S(O)$_2$N($R^8$)$_2$, —S$R^7$, alkyl, haloalkyl, haloalkoxy, heteroalkyl, alkenyl, alkynyl, cycloalkyl, heterocycloalkyl, aryl, and heteroaryl, wherein each said alkyl, haloalkyl, haloalkoxy, heteroalkyl, alkenyl, alkynyl, cycloalkyl, heterocycloalkyl, aryl, and heteroaryl of $R^5$ (when present) is optionally independently unsubstituted or further substituted with one or more independently selected groups selected from the group consisting of lower alkyl, lower alkenyl, lower alkynyl, lower heteroalkyl, halo, —CN, —SF$_5$, —OSF$_5$, —NO$_2$, —N($R^8$)$_2$, —C(O)N($R^8$)$_2$, and cycloalkyl;

each $R^6$ (when present) is independently selected from the group consisting of alkyl, aryl, arylalkyl-, haloalkyl, cycloalkyl, cycloalkylalkyl-, heteroaryl, and heteroarylalkyl-;

each $R^7$ (when present) is independently selected from the group consisting of H, alkyl, alkenyl, heteroalkyl, haloalkyl, aryl, arylalkyl-, heteroaryl, heteroarylalkyl-, cycloalkyl, cycloalkylalkyl-, heterocycloalkyl, and heterocycloalkylalkyl-;

each $R^8$ (when present) is independently selected from the group consisting of H, alkyl, alkenyl, heteroalkyl, haloalkyl, haloalkenyl, aryl, arylalkyl-, heteroaryl, heteroarylalkyl-, cycloalkyl, cycloalkylalkyl-, heterocycloalkyl, and heterocycloalkylalkyl-;

each $R^9$ (when present) is independently selected from the group consisting of: halogen, —CN, —SF$_5$, —OSF$_5$, —NO$_2$, —Si($R^6$)$_3$, —P(O)(O$R^7$)$_2$, —P(O)$_2$(O$R^7$)($R^7$), —N($R^8$)$_2$, —N$R^8$C(O)$R^7$, —N$R^8$S(O)$_2R^7$, —N$R^8$C(O)N($R^8$)$_2$, —N$R^8$C(O)O$R^7$, —C(O)$R^7$, —C(O)$_2R^7$, —C(O)N($R^8$)$_2$, —S(O)$R^7$, —S(O)$_2R^7$, —S(O)$_2$N($R^8$)$_2$, —S$R^7$, alkyl, haloalkyl, heteroalkyl, alkenyl, alkynyl, aryl, arylalkyl-, cycloalkyl, heteroaryl, heteroarylalkyl-, and heterocycloalkyl;

each $R^{10}$ (when present) is independently selected from the group consisting of halo, —CN, —NO$_2$, —Si($R^6$)$_3$, —P(O)(O$R^7$)$_2$, —P(O)(O$R^7$)($R^7$), —N($R^8$)$_2$, —N$R^8$C(O)$R^7$, —N$R^8$S(O)$_2R^7$, —N$R^8$C(O)N($R^8$)$_2$, —N$R^8$C(O)O$R^7$, —C(O)$R^7$, —C(O)$_2R^7$, —C(O)N($R^8$)$_2$, —S(O)$R^7$, —S(O)$_2R^7$, —S(O)$_2$N($R^8$)$_2$, —S$R^7$, alkyl, haloalkyl, haloalkoxy, heteroalkyl, alkenyl, alkynyl, and cycloalkyl, wherein each said alkyl, haloalkyl, haloalkoxy, heteroalkyl, alkenyl, alkynyl, and cycloalkyl of $R^{10}$ (when present) is optionally independently unsubstituted or further substituted with one or more independently selected groups selected from the group consisting of lower alkyl, lower alkenyl, lower alkynyl, lower heteroalkyl, halo, —CN, —NO$_2$, —N($R^8$)$_2$, —O$R^7$, and —C(O)N($R^8$)$_2$.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an amyloid β pathology (Aβ pathology) and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents suitable for treating the patient being treated.

These and other embodiments of the invention, which are described in detail below or will become readily apparent to those of ordinary skill in the art, are included within the scope of the invention.

DETAILED DESCRIPTION

In one embodiment, the compounds of the invention have the structural Formula (I) as described above.

In one embodiment, the compounds of the invention have the structural Formula (IA):

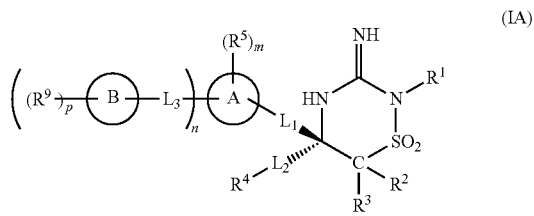

(IA)

and include tautomers, and prodrugs thereof, and pharmaceutically acceptable salts, and solvates of said compounds, tautomers, and prodrugs, wherein $R^1$, $L_1$, $L_2$, $L_3$, $R^2$, $R^3$, $R^4$, $R^5$, $R^9$, ring A, ring B, m, n, and p are each as defined in Formula (I).

In one embodiment, the compounds of the invention have the structural Formula (IA-1):

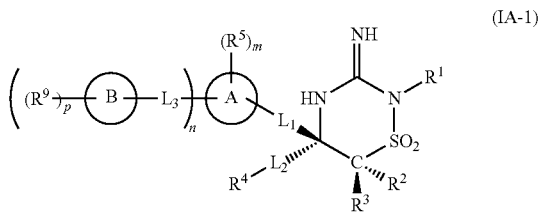

(IA-1)

and include tautomers, and prodrugs thereof, and pharmaceutically acceptable salts, and solvates of said compounds, tautomers, and prodrugs, wherein $R^1$, $L_1$, $L_2$, $L_3$, $R^2$, $R^3$, $R^4$, $R^5$, $R^9$, ring A, ring B, m, n, and p are each as defined in Formula (I).

In one embodiment, the compounds of the invention have the structural Foiuiula (IA-2):

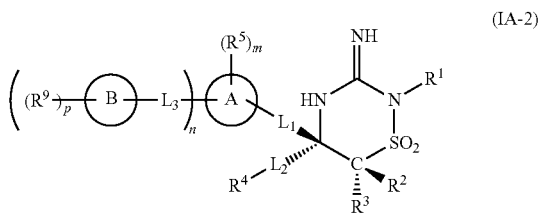

(IA-2)

and include tautomers, and prodrugs thereof, and pharmaceutically acceptable salts, and solvates of said compounds, tautomers, and prodrugs, wherein $R^1$, $L_1$, $L_2$, $L_3$, $R^2$, $R^3$, $R^4$, $R^5$, $R^9$, ring A, ring B, m, n, and p are each as defined in Formula (I).

In one embodiment, in each of Formulas (I), (IA), (IA-1) and (IA-2), $R^1$ is selected from the group consisting of H, lower alkyl, and cyclopropyl.

In one embodiment, in each of Formulas (I), (IA), (IA-1), and (IA-2), $R^1$ is selected from the group consisting of H and methyl.

In one embodiment, in each of Formulas (I), (IA), (IA-1), and (IA-2), $R^1$ is H.

In one embodiment, in each of Formulas (I), (IA), (IA-1), and (IA-2), $R^1$ is methyl.

In one embodiment, in each of Formulas (I), (IA), (IA-1), and (IA-2), $R^2$ is H.

In one embodiment, in each of Formulas (I), (IA), (IA-1), and (IA-2):
$R^1$ is selected from the group consisting of H, lower alkyl, and cyclopropyl; and
$R^2$ is H.

In one embodiment, in each of Formulas (I), (IA), (IA-1), and (IA-2), $R^3$ is H and $R^2$ is H.

In one embodiment, in each of Formulas (I), (IA), (IA-1), and (IA-2), $R^3$ is selected from the group consisting H, alkyl, haloalkyl, and heteroalkyl.

In one embodiment, in each of Formulas (I), (IA), (IA-1), and (IA-2), $R^3$ is selected from the group consisting H, lower alkyl, halo lower alkyl, and lower alkyl ether.

In one embodiment, in each of Formulas (I), (IA), (IA-1), and (IA-2), $R^3$ is selected from the group consisting H, alkyl, haloalkyl, and heteroalkyl; and $R^2$ is H.

In one embodiment, in each of Formulas (I), (IA), (IA-1), and (IA-2), $R^3$ is selected from the group consisting H, lower alkyl, halo lower alkyl, and lower alkyl ether; and $R^2$ is H.

In one embodiment, in each of Formulas (I), (IA), (IA-1), and (IA-2), -$L_2$- is a bond and $R^4$ is lower alkyl.

In one embodiment, in each of Formulas (I), (IA), (IA-1), and (IA-2), -$L_2$- is a bond and $R^4$ is methyl.

In one embodiment, in each of Formulas (I), (IA), (IA-1), and (IA-2), $R^1$ is lower alkyl, $R^2$ is H, -$L_2$- is a bond, and $R^4$ is alkyl.

In one embodiment, the compounds of the invention have the structural Formula (II):

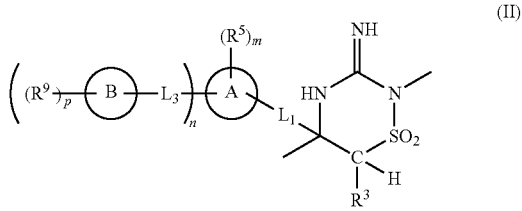

(II)

and include tautomers, and prodrugs thereof, and pharmaceutically acceptable salts, and solvates of said compounds, tautomers, and prodrugs, wherein $R^3$, $L_1$, $L_2$, ring A, ring B, $R^5$, $R^9$, m, n, and p are each as defined in Formula (I).

In one embodiment, the compounds of the invention have the structural Formula (IIA):

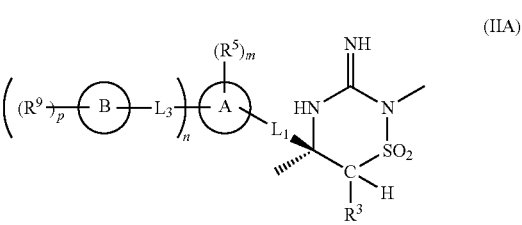

(IIA)

and include tautomers, and prodrugs thereof, and pharmaceutically acceptable salts, and solvates of said compounds, tautomers, and prodrugs, wherein $R^3$, $L_1$, $L_3$, ring A, ring B, $R^5$, $R^9$, m, n, and p are each as defined in Formula (I).

In one embodiment, the compounds of the invention have the structural Formula (IIA-1):

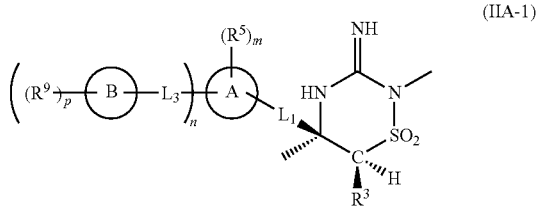

(IIA-1)

and include tautomers, and prodrugs thereof, and pharmaceutically acceptable salts, and solvates of said compounds, tautomers, and prodrugs, wherein $R^3$, $L_1$, $L_3$, ring A, ring 13, $R^5$, $R^9$, m, n, and p are each as defined in Formula (I).

In one embodiment, the compounds of the invention have the structural Formula (IIA-2):

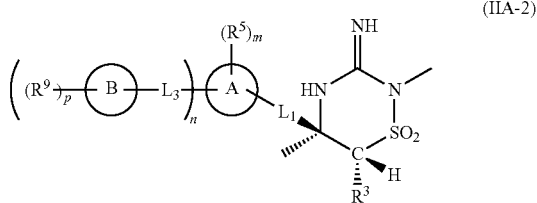

(IIA-2)

and include tautomers, and prodrugs thereof, and pharmaceutically acceptable salts, and solvates of said compounds, tautomers, and prodrugs, wherein $R^3$, $L_1$, $L_3$, ring A, ring B, $R^5$, $R^9$, m, n, and p are each as defined in Formula (I).

In one embodiment, in each of Formulas (II), (IIA), (IIA-1), and (II-A2), $R^3$ is selected from the group consisting H, alkyl, haloalkyl, and heteroalkyl.

In one embodiment, in each of Formulas (II), (IIA), (IIA-1), and (IIA-2), $R^3$ is selected from the group consisting H, lower alkyl, halo lower alkyl, and lower alkyl ether.

In one embodiment, in each of Formulas (II), (IIA), (IIA-1), and (II-A2), $R^3$ is H.

In one embodiment, in each of Formulas (II), (IIA), (IIA-1), and (II-A2):
-$L_1$- represents a bond or a divalent moiety selected from the group consisting of -alkyl-, -haloalkyl-, -heteroalkyl-, and -alkenyl-.

In one embodiment, in each of Formulas (II), (IIA), (IIA-1), and (II-A2):
-$L_1$- represents a divalent moiety selected from the group consisting of -alkyl-, -haloalkyl-, -heteroalkyl-, and -alkenyl-.

-$L_1$- represents a divalent moiety selected from the group consisting of -alkyl-, and -haloalkyl-.

In one embodiment, in each of Formulas (II), (IIA), (IIA-1), and (II-A2):
-$L_1$- represents a bond or a divalent lower alkyl moiety.

In one embodiment, in each of Formulas (II), (IIA), (IIA-1), and (II-A2):
-$L_1$- represents a bond, —CH$_2$—, or —CH$_2$CH$_2$—.

In one embodiment, in each of Formulas (II), (IIA), (IIA-1), and (H-A2):
-$L_1$- represents a bond.

In one embodiment, in each of Formulas (II), (IIA), (IIA-1), and (II-A2):
-$L_1$- represents a divalent lower alkyl moiety.

In one embodiment, in each of Formulas (II), (IIA), (IIA-1), and (II-A2):
-$L_1$- represents —CH$_2$—.

In one embodiment, in each of Formulas (II), (IIA), (IIA-1), and (II-A2):
-$L_1$- represents —CH$_2$CH$_2$—.

In one embodiment, in each of Formulas (I), (IA), (IA-1), (IA-2), (II), (IIA), (IIA-1), and (IIA-2), n is 0 and m is 1 or more.

In one embodiment, in each of Formulas (I), (IA), (IA-1), (IA-2), (II), (IIA), (IIA-1), and (IIA-2), n is 1 or more, p is 0 or more, and m is 0.

In one embodiment, in each of Formulas (I), (IA), (IA-1), (IA-2), (ID, (IIA), (IIA-1), and (IIA-2), n is 1, p is 0 or more, and m is 0 or more.

In one embodiment, in each of Formulas (I), (IA), (IA-1), (IA-2), (II), (IIA), (IIA-1), and (IIA-2), n is 1, p is 0 or more, and m is 0, 1, 2, or 3.

In one embodiment, in each of Formulas (I), (IA), (IA-1), (IA-2), (II), (IIA), (IIA-1), and (IIA-2), n is 1, p is 0 or more, and m is 0, 1, or 2.

In one embodiment, in each of Formulas (I), (IA), (IA-1), (IA-2), (II), (IIA), (IIA-1), and (IIA-2), n is 1, p is 0 or more, and m is 0 ar 1.

In one embodiment, in each of Formulas (I), (IA), (IA-1), (IA-2), (II), (IIA), (IIA-1), and (IIA-2), n is 1, p is 0 or more, and m is 1.

In one embodiment, in each of Formulas (I), (IA), (IA-1), (IA-2), (II), (IIA), (IIA-1), and (IIA-2), n is 1, p is 0 or more, and m is 2.

In one embodiment, in each of Formulas (I), (IA), (IA-1), (IA-2), (II), (IIA), (IIA-1), and (IIA-2), n is 1, p is 0 or more, and m is 3.

In one embodiment, in each of Formulas (I), (IA), (IA-1), (IA-2), (II), (IIA), (IIA-1), and (IIA-2): -$L_1$- represents a bond or —CH$_2$—.

In one embodiment, in each of Formulas (I), (IA), (IA-1), (IA-2), (II), (IIA), (IIA-1), and (IIA-2):

ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, and thienopyrazolyl.

In one embodiment, in each of Formulas (I), (IA), (IA-1), (IA-2), (II), (IIA), (IIA-1), and (IIA-2):

ring A is selected from the group consisting of phenyl, pyridyl, thienyl, thiazolyl, naphthyl, isoquinolinyl, benzothienyl, benzimidazolyl, indazolyl, indolyl, and thienopyrazolyl.

In one embodiment, in each of Formulas (I), (IA), (IA-1), (IA-2), (II), (IIA), (IIA-1), and (IIA-2):

each -$L_3$- independently represents a bond or a divalent moiety selected from the group consisting of —NHC(O), —C(O)NH—, —NHS(O)$_2$—, —S(O)$_2$NH—, —O—CH$_2$—, —CH$_2$—O—, —NHCH$_2$—, —CH$_2$NH—, and —CH(CF$_3$)NH—.

In one embodiment, in each of Formulas (I), (IA), (IA-1), (IA-2), (II), (IIA), (IIA-1), and (IIA-2):

each -L$_3$- independently represents a bond or a divalent moiety selected from the group consisting of —NHC(O)— and —C(O)NH—.

In one embodiment, in each of Formulas (I), (IA), (IA-1), (IA-2), (II), (IIA), (IIA-1), and (IIA-2):

n is 1 and -L$_3$- is represents a bond or a divalent moiety selected from the group consisting of —NHC(O)— and —C(O)NH—.

In one embodiment, in each of Formulas (I), (IA), (IA-1), (IA-2), (II), (IIA), (IIA-1), and (IIA-2):

n is 1 and -L$_3$- represents a bond.

In one embodiment, in each of Formulas (I), (IA), (IA-1), (IA-2), (II), (IIA), (IIA-1), and (IIA-2):

n is 1 and -L$_3$- is a divalent moiety selected from the group consisting of —NHC(O)— and —C(O)NH—.

In one embodiment, in each of Formulas (I), (IA), (IA-1), (IA-2), (II), (IIA), (IIA-1), and (IIA-2):

n is 1 and -L$_3$- is —C(O)NH—.

In one embodiment, in each of Formulas (I), (IA), (IA-1), (IA-2), (II), (IIA), (IIA-1), and (IIA-2):

n is 1 and -L$_3$- is —NHC(O)—.

In one embodiment, in each of Formulas (I), (IA), (IA-1), (IA-2), (II), (IIA), (IIA-1), and (IIA-2):

n is 1 or more;
p is 0 or more; and
each ring B is independently selected from the group consisting of phenyl, pyridyl, pyrimidinyl, oxazolyl, isoxazolyl, pyrazinyl, thienyl, pyrazolyl, furanyt thiazolyl, pyridazinyl, isothiazolyl, isoxazolyl, isothiazolyl, indolyl, pyrrolopyridinyl, and pyrrolopyrimidinyl.

In one embodiment, in each of Formulas (I), (IA), (IA-1), (IA-2), (II), (IIA), (IIA-1), and (IIA-2):

n is 1 or more;
p is 0 or more; and
each ring B is independently selected from the group consisting of phenyl, pyridyl, pyrimidinyl, oxazolyl, thiazolyl, isoxazolyl, isothiazolyl, indolyl, pyrrolopyridyl, and pyrrolopyrimidinyl.

In one embodiment, in each of Formulas (I), (IA), (IA-1), (IA-2), (II), (IIA), (IIA-1), and (IIA-2):

m is 1 or more and each R$^5$ group is independently selected from the group consisting of halogen, —CN, —SF$_5$, —OSF$_5$, —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$NR$^8$)$_2$, —OR$^7$, —SR$^7$, lower alkyl, lower haloalkyl, lower heteroalkyl, lower alkynyl, cycloalkyl, heteroaryl, and heterocycloalkyl.

In one embodiment, in each of Formulas (I), (IA), (IA-1), (IA-2), (II), (IIA), (IIA-1), and (IIA-2):

m is 1 or more and each R$^5$ group is independently selected from the group consisting of halogen, —CN, —SF$_5$, —N(R$^8$)$_2$, —OR$^7$, —SR$^7$, lower alkyl, lower haloalkyl, lower heteroalkyl, lower alkynyl, and cycloalkyl.

In one embodiment, in each of Formulas (I), (IA), (IA-1), (IA-2), (II), (IIA), (IIA-1), and (IIA-2):

m is 1 or more and each R$^5$ group is independently selected from the group consisting of halogen, —CN, —SF$_5$, —N(R$^8$)$_2$, —OR$^7$, —SR$^7$, lower alkyl, lower haloalkyl, lower heteroalkyl, lower alkynyl, and cyclopropyl.

In one embodiment, in each of Formulas (I), (IA), (IA-1), (IA-2), (II), (IIA), (IIA-1), and (IIA-2):

m is 0 or more, n is 1 or more, p is 1 or more, and each R$^9$ group is independently selected from the group consisting of halogen, —CN, —SF$_5$, —OSF$_5$, —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —SR$^7$, lower alkyl, lower haloalkyl, lower heteroalkyl, lower alkynyl, aryl, arylalkyl-, cycloalkyl, heteroaryl, heteroarylalkyl-, and heterocycloalkyl.

In one embodiment, in each of Formulas (I), (IA), (IA-1), (IA-2), (II), (IIA), (IIA-1), and (IIA-2):

m is 0 or more, n is 1 or more, p is 1 or more, and each R$^9$ group is independently selected from the group consisting of halogen, —CN, —SF$_5$, —N(R$^8$)$_2$, —SR$^7$, lower alkyl, lower haloalkyl, lower heteroalkyl, lower alkynyl, phenyl, benzyl, and cycloalkyl.

In one embodiment, in each of Formulas (I), (IA), (IA-1), (IA-2), (II), (IIA), (IIA-1), and (IIA-2):

m is 0 or more, n is 1 or more, p is 1 or more, and each R$^9$ group is independently selected from the group consisting of halogen, —CN, —SF$_5$, —N(R$^8$)$_2$, —OR$^7$, —SR$^7$, lower alkyl, lower haloalkyl, lower heteroalkyl, lower alkynyl, phenyl, benzyl, and cyclopropyl.

In one embodiment, in each of Formulas (I), (IA), (IA-1), (IA-2), (II), (IIA), (IIA-1), and (IIA-2), n is 0 and the moiety:

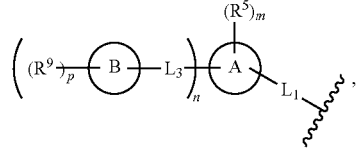

has the form

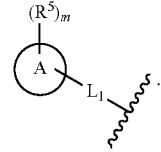

In one embodiment, in each of Formulas (I), (IA), (IA-1), (IA-2), (II), (IIA), (IIA-1), and (IIA-2):

n is 0;
m is 1 or more;
the moiety:

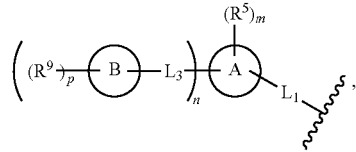

has the form

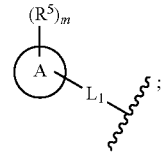

-L$_1$- represents a bond, —CH$_2$—, or —CH$_2$CH$_2$—;
ring A is selected from the group consisting of phenyl, pyridyl, pyrazinyl, furanyl, thienyl, pyrimidinyl, pyridazinyl, thiazolyl, oxazolyl, benzothienyl, benzimidazolyl, indazolyl, indolyl, and thienopyrazolyl; and each $R^5$ group is independently selected from the group consisting of halogen, —CN, —SF$_5$, —N(R$^8$)$_2$, —OR$^7$, —SR$^7$, lower alkyl, lower haloalkyl, lower heteroalkyl, lower alkynyl, and cycloalkyl.

In one embodiment, in each of Formulas (I), (IA), (IA-1), (IA-2), (II), (IIA), (IIA-1), and (IIA-2):

n is 0;

the moiety:

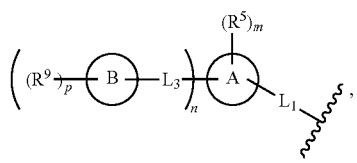

has the form

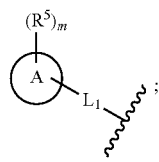

-L$_1$- represents a bond, —CH$_2$—, or —CH$_2$CH$_2$—;

ring A is selected from the group consisting of phenyl, pyridyl, pyrazinyl, furanyl, thienyl, pyrimidinyl, pyridazinyl, thiazolyl, oxazolyl, benzothienyl, benzimidazolyl, indazolyl, indolyl, and thienopyrazolyl;

m is 0 or more; and each $R^5$ group (when present) is independently selected from the group consisting of halogen, —CN, —SF$_5$, —N(R$^8$)$_2$, —SR$^7$, lower alkyl, lower haloalkyl, lower heteroalkyl, lower alkynyl, and cycloalkyl.

In one embodiment, in each of Formulas (I), (IA), (IA-1), (IA-2), (II), (IIA), (IIA-1), and (IIA-2):

ring A is selected from the group consisting of phenyl, pyridyl, pyrazinyl, furanyl, thienyl, pyrimidinyl, pyridazinyl, thiazolyl, oxazolyl, benzothienyl, benzimidazolyl, indazolyl, indolyl, and thienopyrazolyl;

m is 0 or more;

each $R^5$ group (when present) is independently selected from the group consisting of halogen, —CN, —SF$_5$, —N(R$^5$)$_2$, —SR$^7$, lower alkyl, lower haloalkyl, lower heteroalkyl, lower alkynyl, and cycloalkyl;

n is 1;

-L$_3$- represents a bond or a divalent moiety selected from the group consisting of —NHC(O)— and —C(O)NH—;

ring B is selected from the group consisting of phenyl, pyridyl, pyrazinyl, furanyl, thienyl, pyrimidinyl, pyridazinyl, thiazolyl, oxazolyl, isoxazolyl, isothiazolyl, indolyl, pyrrolopyridyl, and pyrrolopyrimidinyl;

p is 0 or more; and each $R^9$ group (when present) is independently selected from the group consisting of halogen, —CN, —SF$_5$, —N(R$^8$)$_2$, —SR$^7$, lower alkyl, lower haloalkyl, lower heteroalkyl, lower alkynyl, phenyl, benzyl, and cycloalkyl.

In one embodiment, in each of Formulas (I), (IA), (IA-1), (IA-2), (II), (IIA), (IIA-1), and (IIA-2):

-L$_1$- represents a bond;

ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, and thienopyrazolyl.

m is 0 or more;

each $R^5$ group (when present) is independently selected from the group consisting of halogen, —CN, —SF$_5$, —N(R$^8$)$_2$, —OR$^7$, —SR$^7$, lower alkyl, lower haloalkyl, lower heteroalkyl, lower alkynyl, and cyclopropyl;

n is 1;

-L$_3$- represents a bond or a divalent moiety selected from the group consisting of —NHC(O)—, —C(O)NH—, —NHS(O)$_2$—, —S(O)$_2$NH—, —O—CH$_2$—, —CH$_2$—O—, —NHCH$_2$—, —CH$_2$NH—, and —CH(CF$_3$)NH—;

ring B is selected from the group consisting of phenyl, pyridyl, pyrimidinyl, oxazolyl, isoxazolyl, pyrazinyl, thienyl, pyrazolyl, furanyl, thiazolyl, pyridazinyl, isothiazolyl, isoxazolyl, isothiazolyl, indolyl, pyrrolopyridinyl, and pyrrolopyrimidinyl;

p is 0 or more; and each $R^9$ group (when present) is independently selected from the group consisting of halogen, —CN, —SF$_5$, —OSF$_5$, —N(R$^8$)$_2$, —NR$^8$C(O)R$^7$, —NR$^8$S(O)$_2$R$^7$, —NR$^8$C(O)N(R$^8$)$_2$, —NR$^8$C(O)OR$^7$, —C(O)R$^7$, —C(O)$_2$R$^7$, —C(O)N(R$^8$)$_2$, —S(O)R$^7$, —S(O)$_2$R$^7$, —S(O)$_2$N(R$^8$)$_2$, —OR$^7$, —SR$^7$, lower alkyl, lower haloalkyl, lower heteroalkyl, lower alkynyl, aryl, arylalkyl-, cycloalkyl, heteroaryl, heteroarylalkyl-, and heterocycloalkyl. In one such embodiment, m and p are each independently 0, 1, 2, or 3 up to the maximum number of substitutable hydrogen atoms.

In one such embodiment, each $R^5$ (when present) is independently selected from the group consisting of halo.

In one such embodiment, each $R^9$ (when present) is independently selected from the group consisting of alkyl, alkenyl, alkynyl, haloalkyl, heteroalkyl, halo-substituted heteroalkyl, halo, —O-alkyl, —O-alkyl-OH, —O-deuteroalkyl, —O-heteroalkyl, —O-heteroalkyl-aryl, —O-haloalkyl, heteroaryl, alkyl-substituted heteroaryl, cycloalkyl, —O-alkyl-cycloalkyl, —O-cycloalkyl, OH, heterocycloalkyl, halo-substituted heteroaryl, CN, —S(F)$_5$, —S-alkyl, and —S(O)$_2$alkyl.

In another embodiment, the present invention encompasses deuterates of the compounds of the invention, or tautomers thereof, or a pharmaceutically acceptable salt of said deuterated compound or tautomer of the invention. Specific, non-limiting examples of deuterated compounds of the invention are as described and exemplified herein and include, deuterated compounds of Formulas (I$^d$), (II$^d$), and (III$^d$). Those of ordinary skill in the art will readily appreciate that, in addition to the non-limiting examples shown, other available hydrogen atoms may be deuterated in a similar manner as described hereinbelow. Such deuterated compounds are also to be considered as being among the compounds of the invention. The resulting compound is referred to herein as a "deuterated" compound of the invention or, alternatively, as "deuterate(s)" of compounds of the invention. The compounds of the invention may be deuterated in a manner known to those of ordinary skill in the art, e.g., as described herein.

Thus, in one non-limiting embodiment, deuterated compounds of the invention have the structural Formula (I^d):

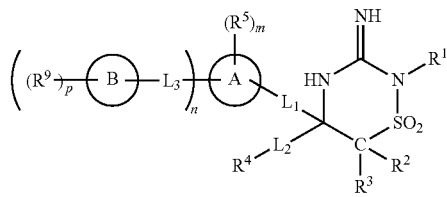

wherein:

one or more hydrogen atoms present in R^1, R^2, R^3, R^4, R^5 (when present) and/or R^9 (when present), or one or more of any available hydrogen atom(s) present on ring A or ring B (when present) is replaced by deuterium; and each of the remaining variables is as defined in Formula (I), or as described in any of the embodiments described herein, e.g., those of Formulas (IA), (IA-1), (IA-2), (II), (IIA), (IIA-1), and (IIA-2) and the various embodiments thereof, are also within the scope of the compounds of Formula (I^d).

For example, in one non-limiting embodiment, in Formula (I^d), R^1 is —CD_3 and each of R^2, R^3, R^4, R^5, R^9, -L_1-, -L_2-, -L_3-, ring A, ring B, m, n, and p are as defined in Formula (I) or as in any one of (IA), (IA-1), (IA-2), (II), (II-A), (II-A1), or (II-A2), or the various embodiments described herein.

As another example, in another non-limiting embodiment, in Formula (I^d), R^2 is D and each of R^1, R^3, R^4, R^5, R^9, -L_1-, -L_2-, -L_3-, ring A, ring B, m, n, and p are as defined in Formula (I) or as in any one of (IA), (IA-1), (IA-2), (II), (II-A), (II-A1), or (II-A2), or the various embodiments described herein.

As another example, in another non-limiting embodiment, in Formula (I^d), R^3 is D and each of R^1, R^2, R^4, R^5, R^9, -L_1-, -L_2-, -L_3-, ring A, ring B, m, n, and p are as defined in Formula (I) or as in any one of (IA), (IA-1), (IA-2), (II), (II-A), (II-A1), or (II-A2), or the various embodiments described herein.

As another example, in another non-limiting embodiment, in Formula (I^d), R^4 is partially or fully deuterated lower alkyl and each of R^1, R^2, R^3, R^5, R^9, -L_1-, -L_2-, -L_3-, ring A, ring B, n, and p are as defined in Formula (I) or as in any one of (IA), (IA-1), (IA-2), (II), (II-A), (II-A1), or (II-A2), or the various embodiments described herein.

As another example, in another non-limiting embodiment, in Formula (I^d), R^5 is D and each of R^1, R^2, R^3, R^4, R^9, -L_1-, -L_2-, -L_3-, ring A, ring B, m, n, and p are as defined in Formula (I) or as in any one of (IA), (IA-1), (IA-2), (II), (II-A), (II-A1), or (II-A2), or the various embodiments described herein.

As another example, in another non-limiting embodiment, in Formula (I^d), R^9 is D and each of R^1, R^2, R^3, R^4, R^5, -L_2-, -L_3-, ring A, ring B, m, n, and p are as defined in Formula (I) or as in any one of (IA), (IA-1), (IA-2), (II), (II-A), (II-A1), or (II-A2), or the various embodiments described herein.

By way of further illustration, in another non-limiting embodiment, deuterated compounds of the invention have the structural Formula (II^d):

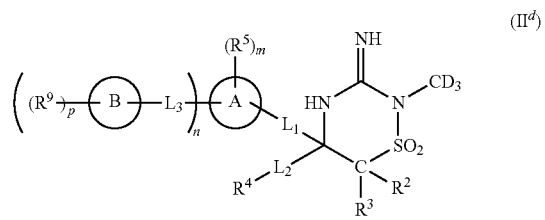

wherein:

the moiety —CD_3 represents a deuterated form of the moiety —CH_3; and each of the remaining variables is as defined in Formula (I), or as described in any of the embodiments described herein, e.g., those of formulas (IA), (IA-1), (IA-2), (II), (II-A), (II-A1), and (II-A2), and the various embodiments thereof, are also within the scope of the compounds of Formula (II^d).

By way of further illustration, in another non-limiting embodiment, deuterated compounds of the invention have the structural Formula (III^d):

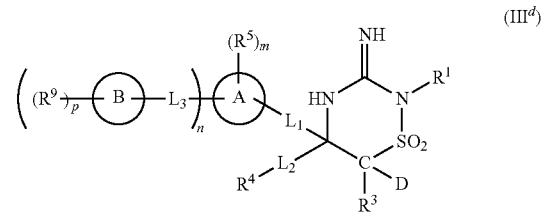

wherein:

the moiety -D represents a deuterated form of hydrogen; and each of the remaining variables is as defined in Formula (I), or as described in any of the embodiments described herein, e.g., those of formulas (IA), (IA-1), (IA-2), (II), (II-A), (II-A1), and (II-A2), and the various embodiments thereof, are also within the scope of the compounds of Formula (III^d). In one embodiment, in Formula (III^d), R^3 is D.

By way of further illustration, in another non-limiting embodiment, deuterated compounds of the invention have the structural Formula (IV^d):

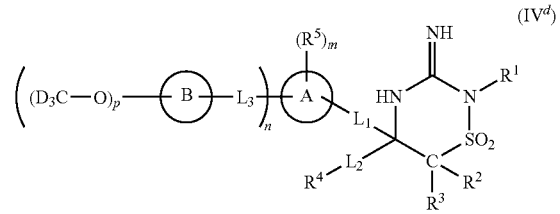

wherein:

the moiety -D represents a deuterated form of hydrogen; and each of the remaining variables is as defined in Formula (I), or as described in any of the embodiments described herein, e.g., those of formulas (IA), (IA-1), (IA-2), (II), (II-A), (II-A1), and (II-A2), and the various embodiments thereof, are also within the scope of the compounds of Formula (IV^d).

In another embodiment, the present invention encompasses a stereoisomer or racemic mixture of a compound of the invention, or a tautomer thereof, or a pharmaceutically acceptable salt of said compound or said tautomer. It shall be appreciated that, while the present invention encompasses all stereoisomers and racemic mixtures of the compounds of the invention, the stereoconfiguration shown in the structural formulas and in the examples are also contemplated as being within the scope of the invention.

In another embodiment, 1 to 3 carbon atoms of the compounds of the invention may be replaced with 1 to 3 silicon atoms so long as all valency requirements are satisfied.

In another embodiment, the compounds of the invention are each of the compounds of the tables below and have a structure shown for the corresponding example in the preparative examples below.

The present invention includes tautomers and stereoisomers of each of the example compounds of the invention, and pharmaceutically acceptable salts and solvates of said compounds, said stereoisomers, and/or said tautomers. Such tautomers and stereosiomers of each of the example compounds, and pharmaceutically and solvates of said compounds, said stereoisomers, and/or said tautomers, each represent additional embodiments of the invention.

In another embodiment, the invention provides a composition comprising at least one compound of the invention, or a tautomer or stereoisomer thereof, or salt or solvate of said compound, said stereoisomer, or said tautomer, and a suitable carrier or diluent.

In another embodiment, the invention provides a pharmaceutical composition comprising at least one compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a pharmaceutical composition comprising at least one solvate of a compound of the invention, or a tautomer or isomer thereof, or pharmaceutically acceptable salt or solvate of said compound or said tautomer, and a pharmaceutically acceptable carrier or diluent.

In another embodiment, the invention provides a pharmaceutical composition comprising at least one pharmaceutically acceptable salt of a compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a pharmaceutical composition comprising at least one tautomer of a compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a pharmaceutical composition comprising at least one compound of the invention, or a tautomer or stereoisomer thereof, or pharmaceutically acceptable salt or solvate of said compound, said stereoisomer, or said tautomer, together with at least one additional therapeutic agent, and a pharmaceutically acceptable carrier or diluent.

Non-limiting examples of additional therapeutic agents for use in combination with the compounds of the invention include drugs selected from the group consisting of: (a) drugs useful for the treatment of Alzheimer's disease and/or drugs useful for treating one or more symptoms of Alzheimer's disease, (b) drugs useful for inhibiting the synthesis Aβ, and (c) drugs useful for treating neurodegenerative diseases.

Additional non-limiting examples of additional therapeutic agents for use in combination with the compounds of the invention include drugs useful for the treatment, prevention, delay of onset, amelioration of any pathology associated with Aβ and/or a symptom thereof. Non-limiting examples of pathologies associated with Aβ include: Alzheimer's disease, Down's syndrome, Parkinson's disease, memory loss, memory loss associated with Alzheimer's disease, memory loss associated with Parkinson's disease, attention deficit symptoms, attention deficit symptoms associated with Alzheimer's disease, Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, traumatic brain injury ("TBI"), and Creutzfeld-Jakob disease, comprising administering to said patient at least one compound of the invention, or a tautomer or isomer thereof, or pharmaceutically acceptable salt or solvate of said compound or said tautomer, in an amount effective to inhibit said pathology or pathologies.

In embodiments of the invention comprising at least one additional therapeutic agent, additional non-limiting examples of additional therapeutic agents for use in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; in GluR2/3 antagonists; Prostaglandin EP2 receptor antagonists; PAM inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

In another embodiment, the invention provides a pharmaceutical composition comprising an effective amount of one or more (e.g., one compounds of the invention, and effective amount of one or more cholinesterase inhibitors (e.g., acetyl- and/or butyrylchlolinesterase inhibitors), and a pharmaceutically acceptable carrier.

In another embodiment, the invention provides a pharmaceutical composition comprising an effective amount of one or more (e.g., one) compounds of the invention, and effective amount of one or more muscarinic agonists or antagonists (e.g., $m_1$ agonists or $m_2$ antagonists), and a pharmaceutically acceptable carrier.

In one embodiment, the invention provides combinations comprising an effective (i.e., therapeutically effective) amount of one or more compounds of the invention, in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), N-methyl-D-aspartate receptor inhibitors (such as, for example, Namenda® (memantine HCl)); anti-amyloid antibodies (such as bapineuzumab, Wyeth/Elan), gamma secretase inhibitors, gamma secretase modulators, and beta secretase inhibitors other than the compounds of the invention.

In one embodiment, the invention provides combinations comprising an effective (i.e., therapeutically effective) amount of one or more compounds of the invention, in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), N-methyl-D-aspartate receptor inhibitors (such as, for example, Namenda® (memantine HCl)).

In one embodiment, the invention provides combinations comprising an effective (i.e., therapeutically effective) amount of one or more compounds of the invention, in combination with an effective (i.e., therapeutically effective) amount of one or more gamma secretase inhibitors.

In one embodiment, the invention provides combinations comprising an effective (i.e., therapeutically effective) amount of one or more compounds of the invention, in combination with an effective (i.e., therapeutically effective) amount of one or more gamma secretase modulators.

In one embodiment, the invention provides combinations comprising an effective (i.e., therapeutically effective) amount of one or more compounds of the invention, or a tautomer or stereoisomer thereof, or pharmaceutically acceptable salt or solvate of said compound, said stereoisomer, or said tautomer, in combination with an effective (i.e., therapeutically effective) amount of one or more gamma secretase inhibitors and in further combination with one or more gamma secretase modulators.

In another embodiment, the invention provides a compound of the invention, or a tautomer or stereoisomer thereof, or pharmaceutically acceptable salt or solvate of said compound, said stereoisomer, or said tautomer, in pure form, in isolated form, and/or in isolated and pure form.

Prodrugs of the compounds of the invention, or tautomers or stereoisomers thereof, or pharmaceutically acceptable salts or solvates of said compounds, said stereoisomers, and/or said tautomers, are also contemplated as being included within the scope of the invention, and are described more fully below.

Deuterates of the compounds of the invention, or tautomers or stereoisomers of said deuterates, or pharmaceutically acceptable salts or solvates of said deuterates, said stereoisomers, and/or said tautomers, are also contemplated as being included within the scope of the invention, and are described more fully above.

In another embodiment, the invention provides a method of preparing a pharmaceutical composition comprising the step of admixing at least one compound of the invention, or a tautomer or stereoisomer thereof, or pharmaceutically acceptable salt or solvate of said compound, said stereoisomer, or said tautomer, and a pharmaceutically acceptable carrier or diluent.

In another embodiment, the invention provides a method of inhibiting β-secretase comprising exposing a population of cells expressing β-secretase to at least one compound of the invention, or a tautomer or stereoisomer thereof, or pharmaceutically acceptable salt or solvate of said compound, said stereoisomer, or said tautomer, in an amount effective to inhibit β-secretase.

In another embodiment, the invention provides a method of inhibiting β-secretase in a patient in need thereof comprising administering at least one compound of the invention, or a tautomer or stereoisomer thereof, or pharmaceutically acceptable salt or solvate of said compound, said stereoisomer, or said tautomer, in a therapeutically effective amount to inhibit β-secretase in said patient.

In another embodiment, the invention provides a method of inhibiting BACE-1 comprising exposing a population of cells expressing BACE-1 to at least one compound of the invention, or a tautomer or stereoisomer thereof, or pharmaceutically acceptable salt or solvate of said compound or said tautomer, in an amount effective to inhibit BACE-1 in said cells. In one such embodiment, said population of cells is in vivo. In another such embodiment, said population of cells is ex vivo. In another such embodiment, said population of cells is in vitro.

In another embodiment, the invention provides a method of inhibiting BACE-2 comprising exposing a population of cells expressing BACE-2 to at least one compound of the invention, or a tautomer or stereoisomer thereof, or pharmaceutically acceptable salt or solvate of said compound or said tautomer, in an amount effective to inhibit BACE-2 in said cells. In one such embodiment, said population of cells is in vivo. In another such embodiment, said population of cells is ex vivo. In another such embodiment, said population of cells is in vitro.

In another embodiment, the invention provides a method of inhibiting BACE-1 in a patient in need thereof comprising administering to said patient at least one compound of the invention, or a tautomer or stereoisomer thereof, or pharmaceutically acceptable salt or solvate of said compound, said stereoisomer, or said tautomer, in a therapeutically effective amount to inhibit BACE-1 in said patient.

In another embodiment, the invention provides a method of inhibiting BACE-2 in a patient in need thereof comprising administering to said patient at least one compound of the invention, or a tautomer or stereoisomer thereof, or pharmaceutically acceptable salt or solvate of said compound, said stereoisomer, or said tautomer, in a therapeutically effective amount to inhibit BACE-2 in said patient.

In another embodiment, the invention provides a method of inhibiting the formation of Aβ from APP in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ formation.

In another embodiment, the invention provides a method of inhibiting the formation of Aβ plaque in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ plaque formation.

In another embodiment, the invention provides a method of inhibiting the formation of Aβ fibrils in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of inhibiting the formation of Aβ oligomers in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of inhibiting the formation of Aβ fibrils and Aβ oligomers in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of inhibiting the formation of senile plaques and/or neurofibrillary tangles in a patient in need thereof, comprising administering to said patient at least one compound of the invention, or a tautomer or stereoisomer thereof, or pharmaceutically acceptable salt or solvate of said compound, said stereoisomer, or said tautomer, in an amount effective to inhibit said Aβ fibril formation.

In another embodiment, the invention provides a method of treating, preventing, and/or delaying the onset of an amyloid β pathology ("Aβ pathology") and/or one or more symptoms of said pathology comprising administering at least one compound of the invention, or a tautomer or stereoisomer thereof, or pharmaceutically acceptable salt or solvate of said compound, said stereoisomer, or said tautomer, to a patient in need thereof in an amount effective to treat said pathology.

In another embodiment, the invention provides a method of treating, preventing, and/or delaying the onset of one or more pathologies associated with Aβ and/or one or more symptoms of one or more pathologies associated with Aβ. Non-limiting examples of pathologies associated with. Aβ include: Alzheimer's disease, Down's syndrome, Parkinson's disease, memory loss, memory loss associated with Alzheimer's disease, memory loss associated with Parkinson's disease, attention deficit symptoms, attention deficit symptoms associated with Alzheimer's disease, Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, diabetes-associated amyloidogenesis, hemodialysis complications (from $β_2$ microglobulins and complications arising therefrom in hemodialysis patients), scrapie, bovine spongiform encephalitis, traumatic brain injury ("TBI") and Creutzfeld-Jakob disease, comprising administering to said patient at least one compound of the invention, or a tautomer or stereoisomer thereof, or pharmaceutically acceptable salt or solvate of said compound, said stereoisomer, or said tautomer, in an amount effective to inhibit said pathology or pathologies.

In one embodiment, the invention provides a method of treating one or more neurodegenerative diseases, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), alone or optionally in combination with one or more additional therapeutic agents useful in treating one or more neurodegenerative diseases, to a patient in need of such treatment.

In one embodiment, the invention provides a method of inhibiting the deposition of amyloid protein (e.g., amyloid beta protein) in, on or around neurological tissue (e.g., the brain), comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), alone or optionally in combination with one or more additional therapeutic agents useful in treating one or more neurodegenerative diseases, to a patient in need of such treatment.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), alone or optionally in combination with one or more additional therapeutic agents useful in treating Alzheimer's disease, to a patient in need of such treatment.

In one embodiment, the invention provides a method of treating Down's syndrome, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), alone or optionally in combination with an effective (e.g., therapeutucially effective) amount of one or more additional active agents useful in treating Down's syndrome, to a patient in need of such treatment.

In one embodiment, the invention provides a method of treating mild cognitive impairment, comprising administering an effective amount of one or more (e.g., one) compounds of the invention (or a tautomer or stereoisomer thereof, or pharmaceutically acceptable salt or solvate of said compound, said stereoisomer, or said tautomer), alone or optionally in combination with one or more additional active agents useful in treating mild cognitive impairment, to a patient in need of such treatment.

In one embodiment, the invention provides a method of treating glaucoma, comprising administering an effective amount of one or more (e.g., one) compounds of the invention (or a tautomer or stereoisomer thereof, or pharmaceutically acceptable salt or solvate of said compound, said stereoisomer, or said tautomer), alone or optionally in combination with one or more additional active agents useful in treating glaucoma, to a patient in need of such treatment.

In one embodiment, the invention provides a method of treating cerebral amyloid angiopathy, comprising administering an effective amount of one or more (e.g., one) compounds of the invention (or a tautomer or stereoisomer thereof, or pharmaceutically acceptable salt or solvate of said compound, said stereoisomer, or said tautomer), alone or optionally in combination with one or more additional active agents useful in treatingcerebral amyloid angiopathy, to a patient in need of such treatment. to a patient in need of treatment.

In one embodiment, the invention provides a method of treating stroke, comprising administering an effective amount of one or more (e.g., one) compounds of the invention (or a tautomer or stereoisomer thereof, or pharmaceutically acceptable salt or solvate of said compound, said stereoisomer, or said tautomer), alone or optionally in combination with one or more additional active agents useful in treating stroke, to a patient in need of such treatment.

In one embodiment, the invention provides a method of treating dementia, comprising administering an effective amount of one or more (e.g., one) compounds of the invention (or a tautomer or stereoisomer thereof, or pharmaceutically acceptable salt or solvate of said compound, said stereoisomer, or said tautomer), alone or optionally in combination with one or more additional active agents useful in treating dementia, to a patient in need of such treatment. to a patient in need of treatment.

In one embodiment, the invention provides a method of treating microgliosis, comprising administering an effective amount of one or more (e.g., one) compounds of the invention (or a tautomer or stereoisomer thereof, or pharmaceutically acceptable salt or solvate of said compound, said stereoisomer, or said tautomer), alone or optionally in combination with one or more additional active agents useful in treating microgliosis, to a patient in need of such treatment.

In one embodiment, the invention provides a method of treating brain inflammation, comprising administering an effective amount of one or more (e.g., one) compounds of the invention (or a tautomer or stereoisomer thereof, or pharmaceutically acceptable salt or solvate of said compound, said stereoisomer, or said tautomer), alone or optionally in combination with one or more additional active agents useful in treating brain inflammation, to a patient in need of such treatment.

In one embodiment, the invention provides a method of treating traumatic brain injury, comprising administering an effective amount of one or more (e.g., one) compounds of the invention (or a tautomer oar stereoisomer thereof, or pharmaceutically acceptable salt or solvate of said compound, said stereoisomer, or said tautomer), alone or optionally in combination with one or more additional active agents useful in treating traumatic brain injury, to a patient in need of such treatment.

In one embodiment, the invention provides a method of treating olfactory function loss, comprising administering an effective amount of one or more (e.g., one) compounds of the invention (or a tautomer or stereoisomer thereof, or pharmaceutically acceptable salt or solvate of said compound, said stereoisomer, or said tautomer), alone or optionally in combination with one or more additional active agents useful in treating olfactory function loss, to a patient in need of such treatment.

In one embodiment, in each of the above recited methods of treatment, said one or more additional therapeutic agent is selected from one or more cholinesterase inhibitors (such as, for example, (±)-2,3-dihydro-5,6-dimethoxy-2-[[1-(phenylmethyl)-4-piperidinyl]methyl]-1H inden-1-one hydrochloride, i.e., donepezil hydrochloride, available as the Aricept® brand of donepezil hydrochloride).

In one embodiment, in each of the above recited methods of treatment, said one or more additional therapeutic agent is selected from the group consisting of Aβ antibody inhibitors, gamma secretase inhibitors, gamma secretase modulators, and beta secretase inhibitors other than a compound of the invention.

In one embodiment, in each of the above recited methods of treatment, said one or more additional therapeutic agent is Exelon (rivastigmine).

In one embodiment, in each of the above recited methods of treatment, said one or more additional therapeutic agent is selected from Cognex (tacrine).

In one embodiment, in each of the above recited methods of treatment, said one or more additional therapeutic agent is selected from Tau kinase inhibitor (e.g., GSK3beta inhibitor, cdk5 inhibitor, ERK inhibitor).

In one embodiment, in each of the above recited methods of treatment, said one or more additional therapeutic agent is selected from an anti-Aβ vaccine.

In one embodiment, in each of the above recited methods of treatment, said one or more additional therapeutic agent is selected from an APP ligand.

In one embodiment, in each of the above recited methods of treatment, said one or more additional therapeutic agent is selected from one or more agents that upregulate insulin degrading enzyme and/or neprilysin.

In one embodiment, in each of the above recited methods of treatment, said one or more additional therapeutic agent is selected from one or more cholesterol lowering agents. Non-limiting examples of said cholesterol lowerin agents include: statins such as Atorvastatin, Fluvastatin, Lovastatin, Mevastatin, Pitavastatin, Pravastatin, Rosuvastatin, Simvastatin, and cholesterol absorption inhibitors such as Ezetimibe and phytonutrients.

In one embodiment, in each of the above recited methods of treatment, said one or more additional therapeutic agent is selected from one or more fibrates. Non-limiting examples of said fibtrates include clofibrate, Clofibride, Etofibrate, and Aluminium Clofibrate.

In one embodiment, in each of the above recited methods of treatment, said one or more additional therapeutic agent is selected from one or more LXR agonists.

In one embodiment, in each of the above recited methods of treatment, said one or more additional therapeutic agent is selected from one or more LRP mimics.

In one embodiment, in each of the above recited methods of treatment, said one or more additional therapeutic agent is selected from one or more 5-HT6 receptor antagonists.

In one embodiment, in each of the above recited methods of treatment, said one or more additional therapeutic agent is selected from one or more nicotinic receptor agonists.

In one embodiment, in each of the above recited methods of treatment, said one or more additional therapeutic agent is selected from one or more H3 receptor antagonists.

In one embodiment, in each of the above recited methods of treatment, said one or more additional therapeutic agent is selected from one or more histone deacetylase inhibitors.

In one embodiment, in each of the above recited methods of treatment, said one or more additional therapeutic agent is selected from one or more hsp90 inhibitors.

In one embodiment, in each of the above recited methods of treatment, said one or more additional therapeutic agent is selected from one or more m1 muscarinic receptor agonists.

In one embodiment, in each of the above recited methods of treatment, said one or more additional therapeutic agent is selected from one or more 5-HT6 receptor antagonists, mGluR1, and mGluR5 positive allosteric modulators or agonists.

In one embodiment, in each of the above recited methods of treatment, said one or more additional therapeutic agent is selected from one or more mGluR2/3 antagonists.

In one embodiment, in each of the above recited methods of treatment, said one or more additional therapeutic agent is selected from one or more anti-inflammatory agents that can reduce neuroinflammation.

In one embodiment, in each of the above recited methods of treatment, said one or more additional therapeutic agent is selected from one or more prostaglandin EP2 receptor antagonists.

In one embodiment, in each of the above recited methods of treatment, said one or more additional therapeutic agent is selected from one or more PAI-1 inhibitors.

In one embodiment, in each of the above recited methods of treatment, said one or more additional therapeutic agent is selected from one or more agents that can induce Aβ efflux. One non-limiting example of an agent that can induce Aβ influx is gelsolin.

In one embodiment, the invention provides a kit comprising, in separate containers, in a single package, pharmaceutical compositions for use in combination, wherein one container comprises an effective amount of a compound of the invention (or a tautomer or stereoisomer thereof, or pharmaceutically acceptable salt or solvate of said compound, said stereoisomer, or said tautomer) in a pharmaceutically acceptable carrier, and, optionally, another container (i.e., a second container) comprises an effective amount of another pharmaceutically active ingredient (as described below), the combined quantities of the compound of the invention and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) inhibit BACE.

In its various embodiments, the invention provides any one of the methods disclosed above and below wherein the compound(s) of the invention is a compound or compounds selected from the group consisting of the exemplary compounds of the invention described below.

In its various embodiments, the invention provides any one of the pharmaceutical compositions disclosed above and below wherein the compound(s) of the invention is a compound or compounds selected from the group consisting of the exemplary compounds of the invention described below.

Other embodiments of this invention are directed to any one of the embodiments above or below that are directed to compounds of the invention, or the use of compounds of the invention (e.g. the embodiments directed to methods of treatment, pharmaceutical compositions and kits).

In another embodiment, the invention provides for the use of a compound of the invention, or a tautomer or stereoisomer thereof, or pharmaceutically acceptable salt or solvate of said compound, said stereoisomer, or said tautomer, in the manufacture of a medicament for use in the treatment, the delay of onset, and/or the prevention of one or more Aβ pathologies and/or in the treatment, the delay of onset, and/or the prevention of one or more symptoms of one or more Aβ pathologies,

DEFINITIONS

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not specifically defined in the context of the embodiment is as defined in Formula (I). Any carbon as well as heteroatom with unsatisfied valences in the text, schemes, examples and Tables herein is assumed to have the sufficient number of hydrogen atom(s) to satisfy the valences.

As described herein, the "example compounds of the invention" (or "example compounds" or "examples") include, collectively and individually, each of the compounds set forth with example numbers in the preparative examples.

As described herein, variables such as $R^1$, $R^2$, $R^3$, and $R^4$ may be unsubstituted or substituted with one or more $R^5$ groups. It shall be understood that the upper limit of the number of substituents (referred to in the phrase "one or more substituents") is the number of available hydrogen atoms on the relevant moiety ($R^1$, $R^2$, $R^3$, or $R^4$) that are available for replacement by a substituent which will result in a chemically stable moiety.

As described herein, one or more of the variables -$L_1$-, -$L_2$-, and -$L_3$- of the general formulae optionally independently represent a bond. It shall be understood that where such a variable represents a bond, the moieties which are shown connected by that variable are directly attached by covalent bond. Thus, by way of non-limiting illustration, a compound of Formula (I) wherein -$L_1$-, -$L_2$- and -$L_3$- each represent a bond can be shown as:

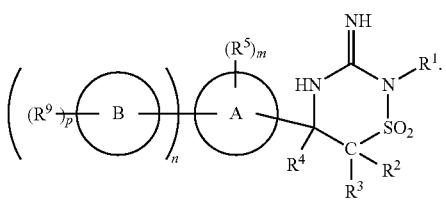

The moiety

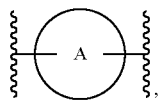

which may be optionally substituted as described herein, represents a ring referred to herein as "ring A."

The moiety

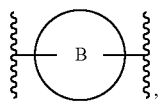

which may be optionally substituted as described herein, represents a ring referred to herein as "ring B."

"At least one" means one or more than one, for example, 1, 2, or 3, or in another example, 1 or 2, or in another example 1.

In the various Formulas of the compounds of the invention, e.g., in Formula (I), n, and p are each independently selected integers, wherein:

m is 0 or more;
n is 0 or more; and
p is 0 or more, wherein the maximum value of the sum of m and n is the maximum number of available substitutable hydrogen atoms on ring A, and wherein the maximum value of p is the maximum number of available substitutable hydrogen atoms on ring B. Except for salt forms, the "maximum number of available substitutable hydrogen atoms" refers to the maximum number that will result in a neutral molecule.

By way of non-limiting illustration, when ring A is a

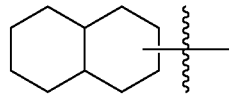

group, the maximum value of the sum of m and n 17. When ring A is a

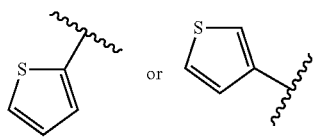 [SMILES: *c1cccs1 ; *c1ccsc1]

group, the maximum value of the sum of m and n is 3.

In the compounds of the invention, e.g., in Formula (I), each of ring A and ring B (when present) is selected from the group consisting of a monocyclic aryl, a monocyclic heteroaryl, a monocyclic cycloalkyl, a monocyclic cycloalkenyl, a monocyclic heterocycloalkyl, a monocyclic heterocycloalkenyl, and a multicyclic group, each of which groups may be unsubstituted or optionally further substituted as shown in Formula (I).

As used herein, the term "monocyclic aryl" refers to phenyl.

As used herein, the term "monocyclic heteroaryl" refers to a 4- to 7-membered monocyclic heteroaryl group comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridone, thiazolyl, isothiazolyl, oxazolyl, isoxazolyl, pyrazolyl, furazanyl, pyrrolyl, pyrazolyl, triazolyl, thiadiazolyl (e.g., 1,2,4-thiadiazolyl), pyrazinyl, pyridazinyl, imidazolyl, and triazinyl (e.g., 1,2,4-triazinyl), and oxides thereof.

As used herein, the term "monocyclic cycloalkyl" refers to a 3- to 7-membered monocyclic cycloalkyl group. Non-limiting examples of monocyclic cycloalkyl groups include cyclopropyl, cyclobutyl, cyclopentyl, cyclohexyl, and cycloheptyl.

As used herein, the term "monocyclic cycloalkenyl" refers to a non-aromatic 3- to 7-membered cycloalkyl group which contains one or more carbon-carbon double bonds. Non-limiting examples include cyclopropenyl, cyclobutenyl, cyclopentenyl, cyclohexenyl, and cycloheptenyl.

As used herein, the term "monocyclic heterocycloalkyl" refers to a 4- to 7-membered monocyclic heterocycloalkyl group comprising from 1 to 4 ring heteroatoms, said ring heteroatoms being independently selected from the group consisting of N,N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolidinyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof.

Non-limiting examples of lower alkyl-substituted oxetanyl include the moiety:

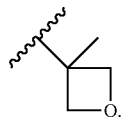

As used herein, the term "monocyclic heterocycloalkenyl" refers to a 4- to 7-membered monocyclic heterocycloalkenyl group comprising from 1 to 4 ring heteroatoms, said ring heteroatoms being independently selected from the group consisting of N,N-oxide, O, S, S-oxide, S(O), and S(O)$_2$. The point of attachment to the parent moiety is to any available ring carbon or ring heteroatom. Non-limiting examples of monocyclic heterocycloalkenyl groups include 1,2,3,4- tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof.

As used herein, the term "multicyclic group" refers to a fused ring system comprising two (bicyclic), three (tricyclic), or more fused rings, wherein each ring of the fused ring system is independently selected from the group consisting of phenyl, monocyclic heteroaryl, monocyclic cycloalkyl, monocyclic cycloalkenyl, monocyclic heterocycloalkyl, and monocyclic heterocycloalkenyl. The point of attachment to the parent moiety is to any available ring carbon or (if present) ring heteroatom on any of the fused rings.

It shall be understood that each of the following multicyclic groups pictured may be unsubstituted or substituted, as described herein. Only the point of attachment to the parent moiety is shown by the wavy line.

The term multicyclic groups includes bicyclic aromatic groups. Non-limiting examples of multicyclic groups which are bicyclic aromatic groups include:

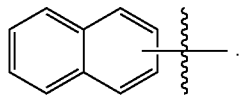

The term multicyclic groups includes bicyclic heteroaromatic groups comprising from 1 to 3 or more ring heteroatoms, each said ring heteroatom being independently selected from the group consisting of N, O, and S, S(O), S(O)$_2$, and oxides of N, O, and S, and oxides thereof. Non-limiting examples of multicyclic groups which are bicyclic heteroaromatic groups comprising from 1 to 3 ring heteroatoms, each said ring heteroatom being independently selected from N, O, and S include the following, and oxides thereof:

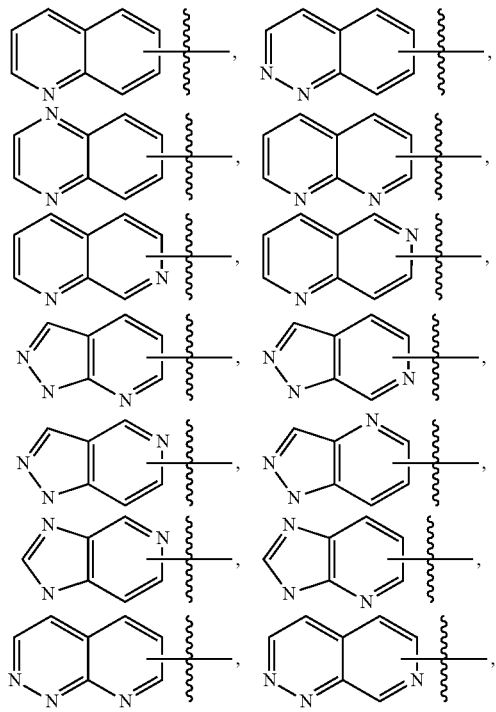

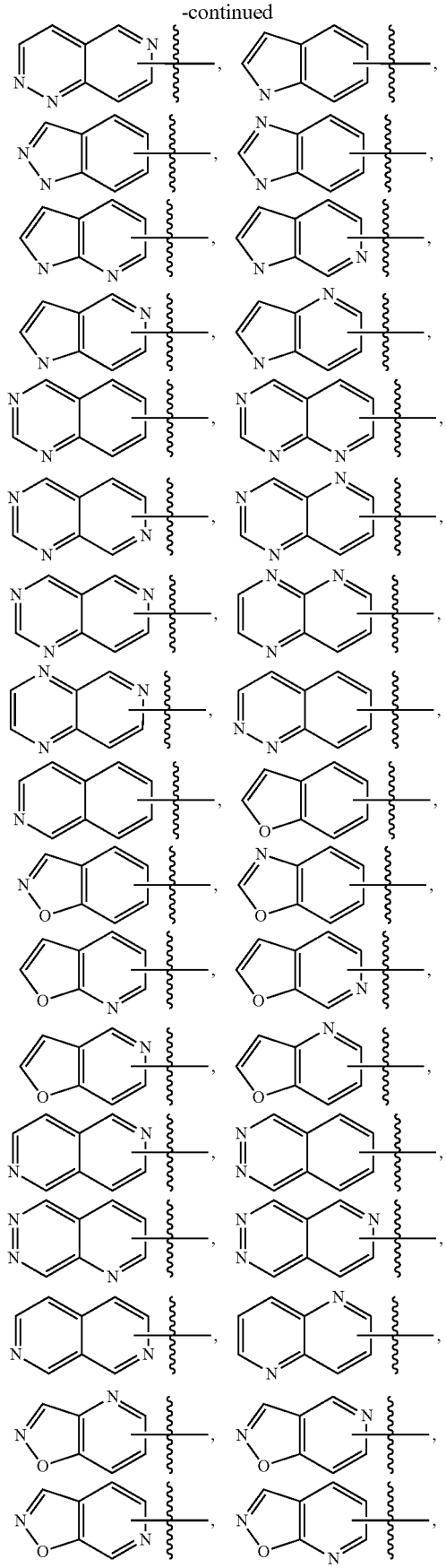

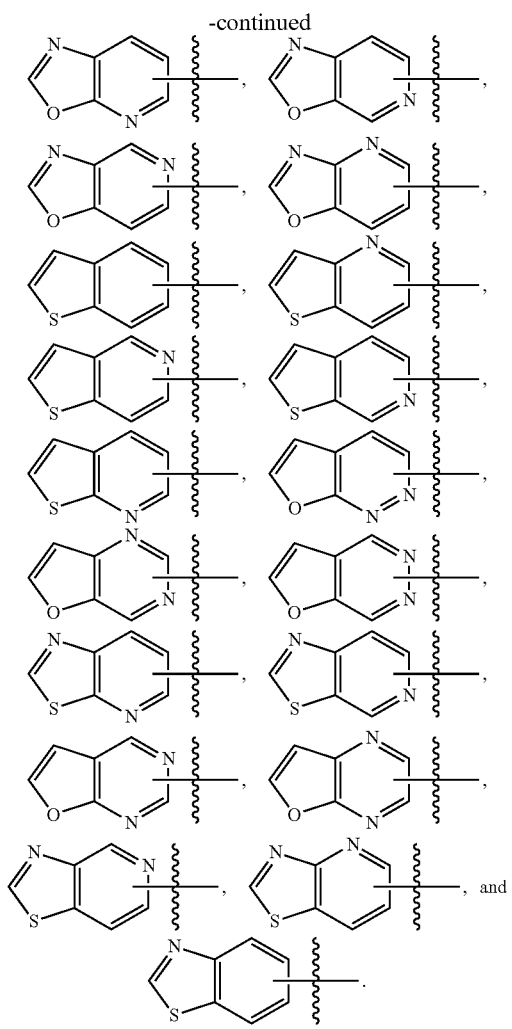

The term multicyclic groups includes saturated bicyclic cycloalkyl groups. Non-limiting examples of multicyclic groups which are saturated bicyclic cycloalkyl groups include the following:

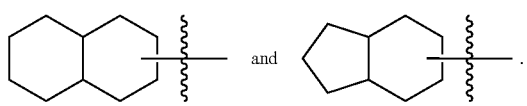

The term multicyclic group includes partially unsaturated bicyclic cycloalkyl groups. Non-limiting examples of multicyclic groups which comprise partially unsaturated bicyclic cycloalkyl groups include the following:

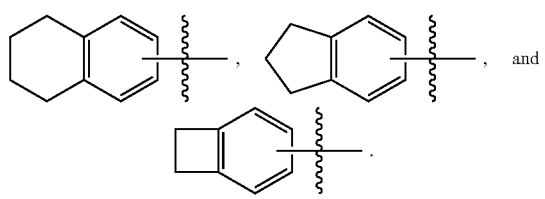

The term multicyclic groups includes partially or fully saturated bicyclic groups comprising from 1 to 3 ring heteroatoms, each said ring heteroatom is independently selected from the group consisting of N, O, and S, S(O), S(O)$_2$, and oxides of N and S. Such rings may also optionally contain one or more oxo groups, as defined herein. Non-limiting examples of multicyclic groups which are partially or fully saturated bicyclic groups comprising from 1 to 3 ring heteroatoms, each said ring heteroatom being independently selected from N, O, and S include the following, and oxides thereof:

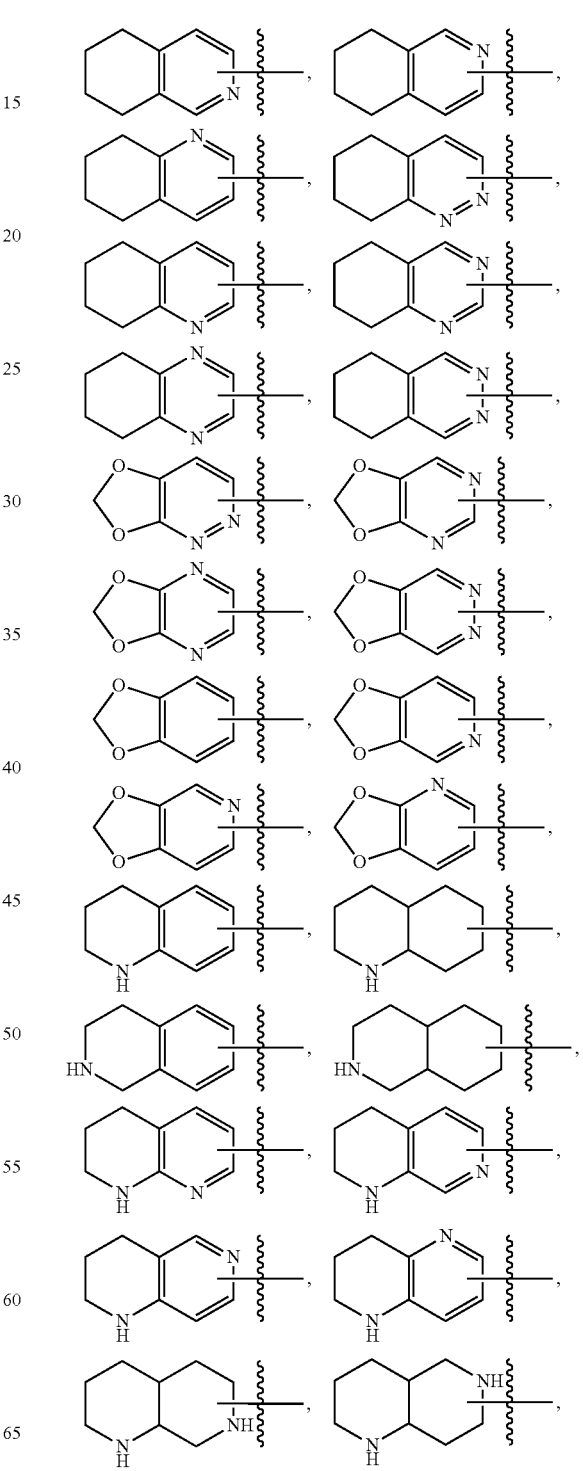

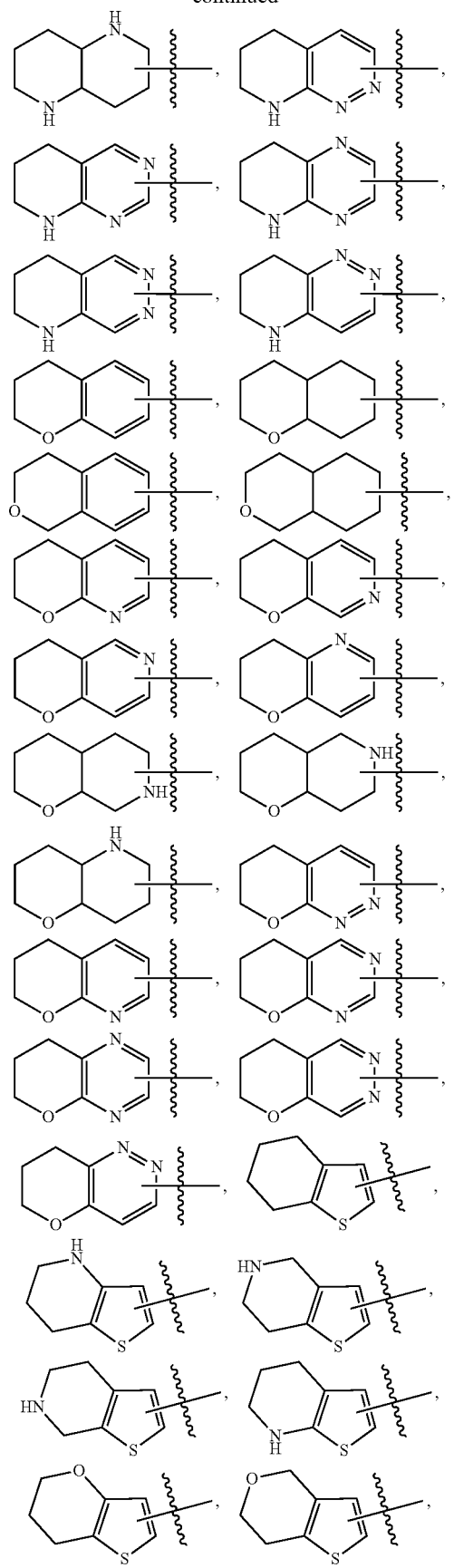
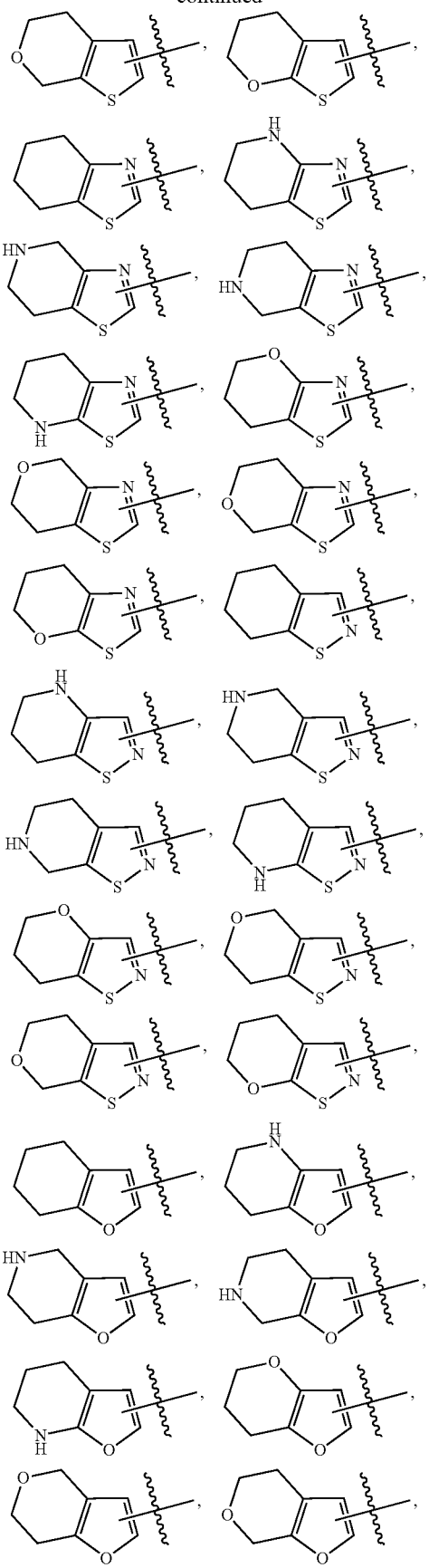

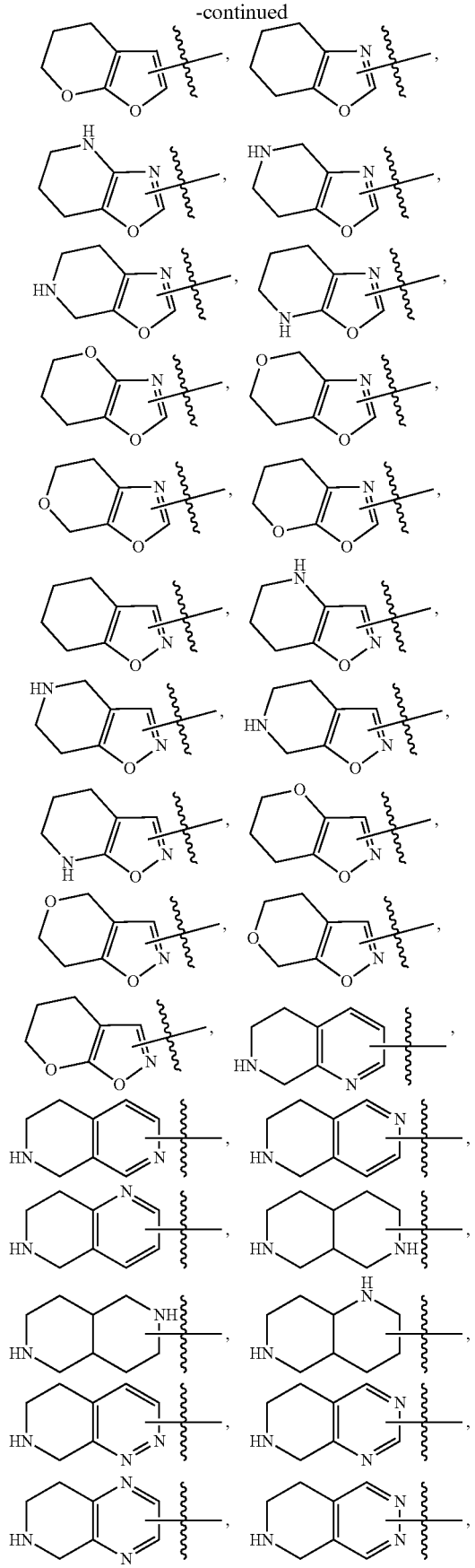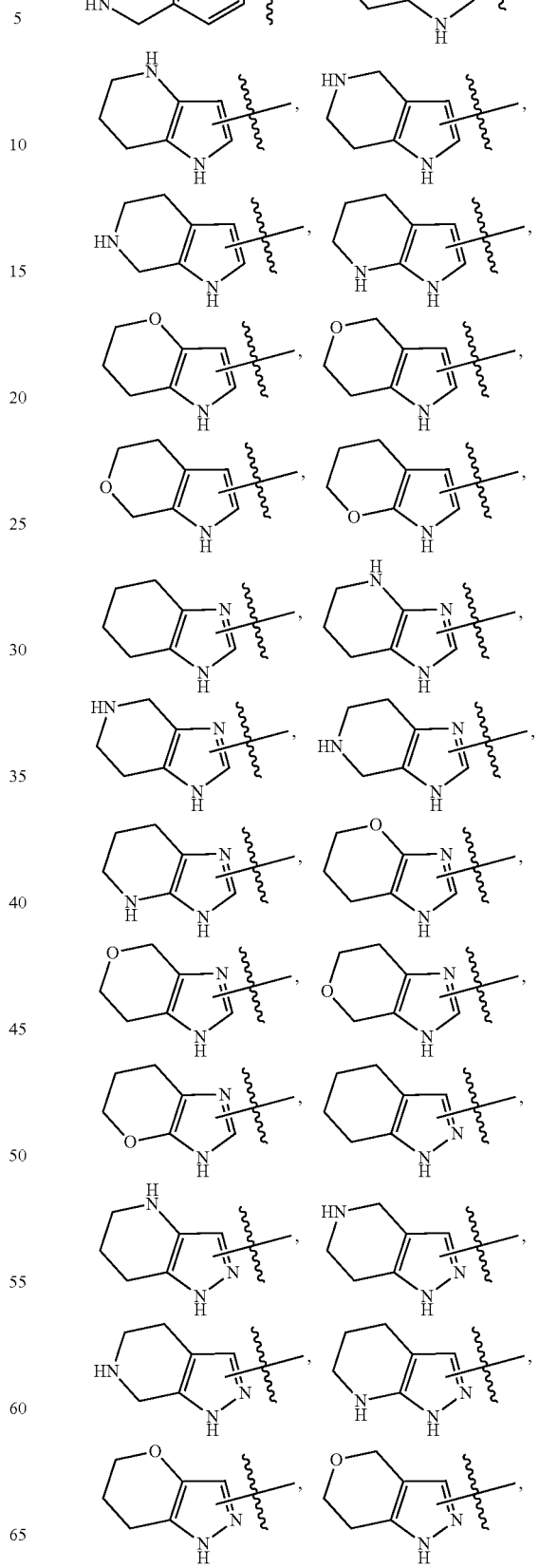

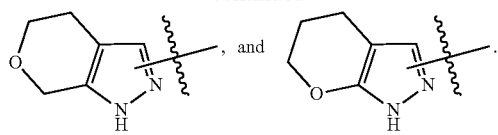, and

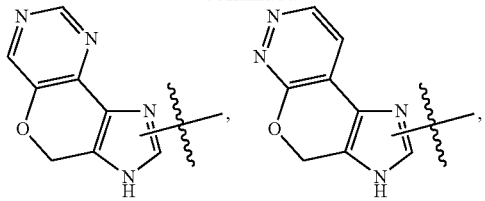

The term multicyclic groups includes aromatic tricyclic groups, cycloalkyl tricyclic groups, as well as heteroaromatic and partially and fully saturated tricyclic groups. For tricyclic groups comprising ring heteroatoms, said tricyclic groups comprise one or more (e.g., from 1 to 5) ring heteroatoms, wherein each said ring heteroatom is independently selected from N, O, and S, S(O), S(O)$_2$, and oxides of N, O, and S: Non-limiting examples of tricyclic multicyclic groups include the following, and, where possible, oxides thereof:

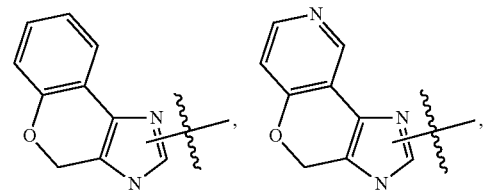
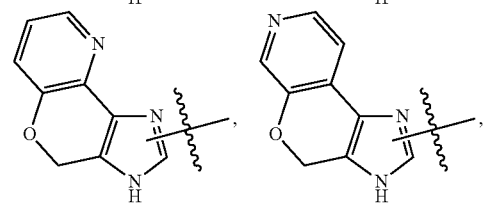
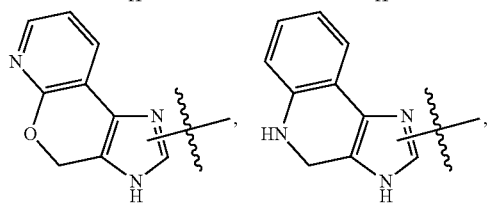
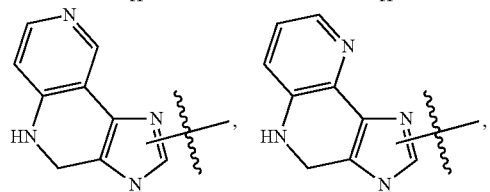
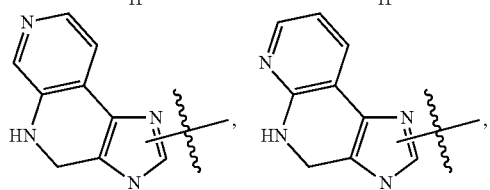
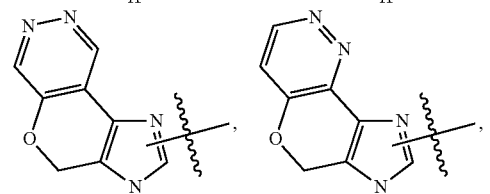
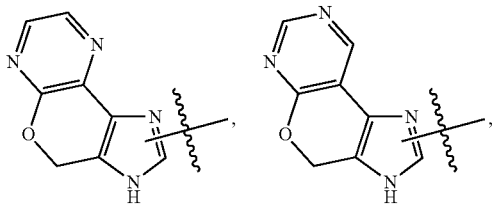
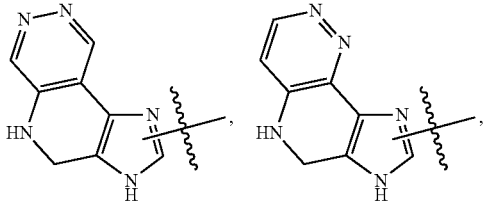
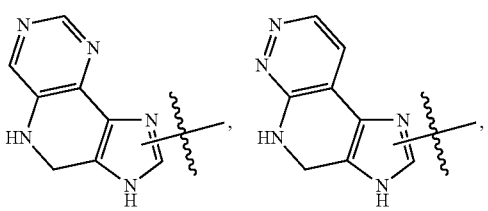
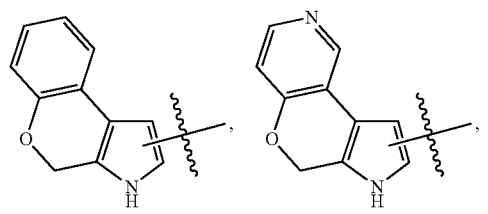
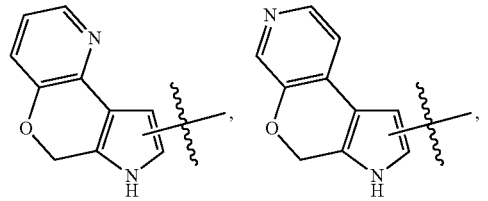
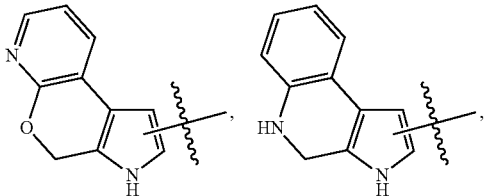

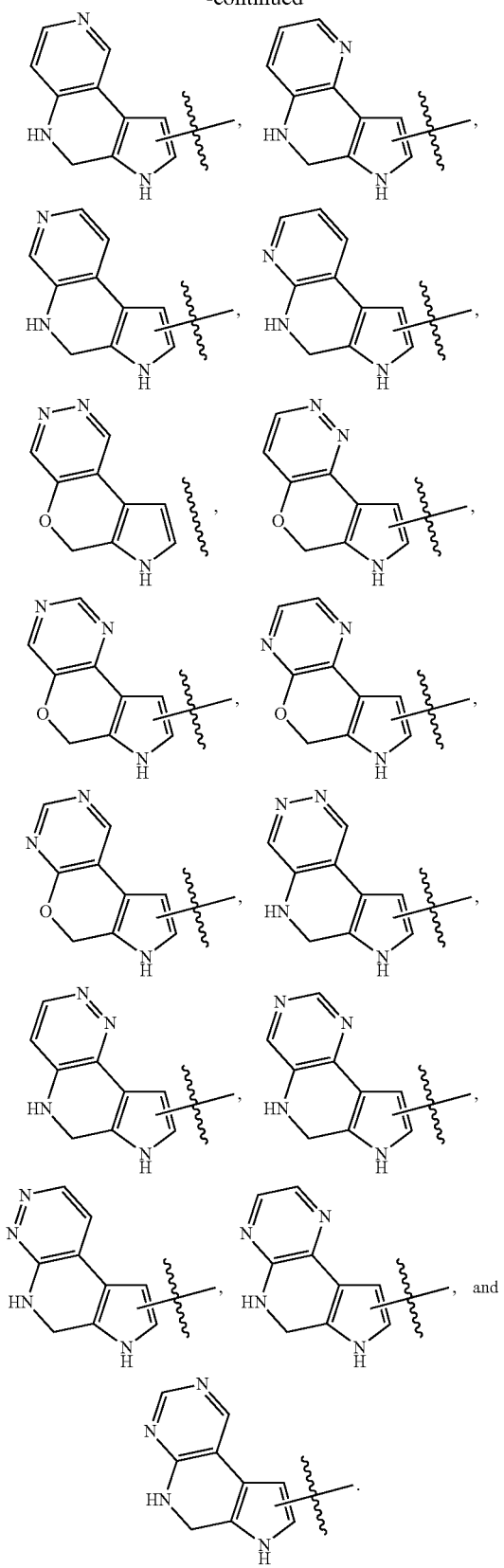

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH (alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

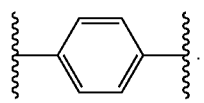

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH═CH—, —C(CH$_3$)═CH—, and —CH═CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (alternatively referred to as thiophenyl), pyrimidinyl, pyridone (including N-substituted pyridones), isoxazolyl, isothiazolyl, oxazolyl, thiazolyl, pyrazolyl, fitrazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

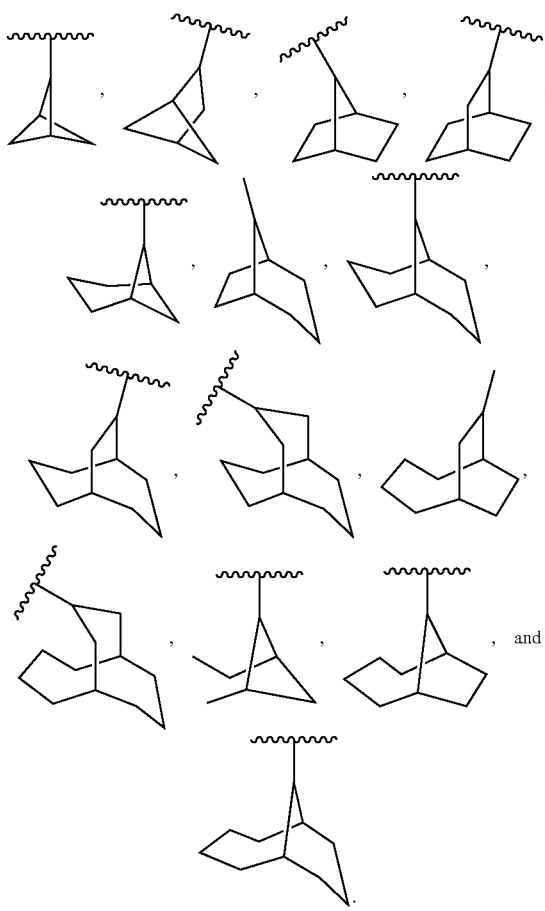

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom (i.e., heterocyclyl includes rings having a carbonyl group in the ring). Such =O groups may be referred to herein as "oxo," as described below.

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclenyl includes rings having a carbonyl group in the ring). Example of such moiety is pyrrolidenone (or pyrrolone):

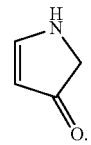

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

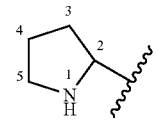

there is no —OH attached directly to carbons marked 2 and 5.

"Arylcycloalkyl" (or "arylfused cycloalkyl") means a group derived from a fused aryl and cycloalkyl as defined herein. Preferred arylcycloalkyls are those wherein aryl is phenyl (which may be referred to as "benzofused") and cycloalkyl consists of about 5 to about 6 ring atoms. The arylcycloalkyl can be optionally substituted as described herein. Non-limiting examples of suitable arylcycloalkyls include indanyl benzofused cycloalkyl) and 1,2,3,4-tetrahydronaphthyl and the like. The bond to the parent moiety is through a non-aromatic carbon atom.

"Arylheterocycloalkyl" (or "arylfused heterocycloalkyl") means a group derived from a fused aryl and heterocycloalkyl as defined herein. Preferred arylheterocycloalkyls are those wherein aryl is phenyl (which may be referred to as "benzofused") and heterocycloalkyl consists of about 5 to about 6 ring atoms. The arylheterocycloalkyl can be optionally substituted, and/or contain the oxide or oxo, as described herein. Non-limiting examples of suitable arylfused heterocycloalkyls include:

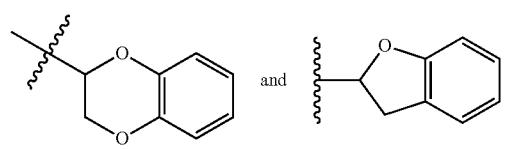 [SMILES: *C1COc2ccccc2O1 ; *C1Cc2ccccc2O1]

The bond to the parent moiety is through a non-aromatic carbon atom.

It is also understood that the terms "arylfused aryl", "arylfused cycloalkyl", "arylfused cycloalkenyl", "arylfused heterocycloalkyl", arylfused heterocycloalkenyl", "arylfused heteroaryl", "cycloalkylfused aryl", "cycloalkylfused cycloalkyl", "cycloalkylfused cycloalkenyl", "cycloalkylfused heterocycloalkyl", "cycloalkylfused heterocycloalkenyl", "cycloalkylfused heteroaryl", "cycloalkenylfused aryl", "cycloalkenylfused cycloalkyl", "cycloalkenylfused cycloalkenyl", "cycloalkenylfused heterocycloalkyl", "cycloalkenylfused heterocycloalkenyl", "cycloalkenylfused heteroaryl", "heterocycloalkylfused aryl", "heterocycloalkylfused cycloalkyl", "heterocycloalkylfused cycloalkenyl", "heterocycloalkylfused heterocycloalkyl", "heterocycloalkylfused heterocycloalkenyl", "heterocycloalkylfused heteroaryl", "heterocycloalkenylfused aryl", "heterocycloalkenylfused cycloalkyl", "heterocycloalkenylfused cycloalkenyl", "heterocycloalkenylfused heterocycloalkyl", "heterocycloalkenylfused heterocycloalkenyl", "heterocycloalkenylfused heteroaryl", "heteroarylfused aryl", "heteroarylfused cycloalkyl", "heteroarylfused cycloalkenyl", "heteroarylfused heterocycloalkyl", "heteroarylfused heterocycloalkenyl", and "heteroarylfused heteroaryl" are similarly represented by the combination of the groups aryl, cycloalkyl, cycloalkenyl, heterocycloalkyl, heterocycloalkenyl, and heteroaryl, as previously described. Any such groups may be unsubstituted or substituted with one or more ring system substituents at any available position as described herein.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety.

Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

Similarly, "arylfused arylalkyl-", arylfused cycloalkylalkyl-, etc., means an arylfused aryl group, arylfused cycloalkyl group, etc. linked to a parent moiety through an alkyl group. Preferred groups contain a lower alkyl group. Such alkyl groups may be straight or branched, unsubstituted and/or substituted as described herein.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-pyridinylmethyl, quinolinylmethyl, and quinolin-3-ylmethyl, and the like. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl-group in which alkyl is as previously defined. Preferred cyanoalkyls contain lower alkyl. Non-limiting examples of suitable cyanoalkyl groups include cyanomethyl and 2-cyanoethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Heteroaroyl" means an heteroaryl-C(O)— group in which the heteroaryl group is as previously described. The bond to the parent moiety is through the carbonyl. Non-limiting examples of suitable groups include pyridoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" (or "arylalkyloxy") means an aralkyl-O— group (an arylaklyl-O— group) in which the aralkyl group is as previously described. Non-limiting examples of suitable aralkyloxy groups include benzyloxy and 1- or 2-naphthalenemethoxy. The bond to the parent moiety is through the ether oxygen.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more substituents. The bond to the parent moiety is through a non-aromatic carbon atom.

"Arylalkynyl" means a group derived from a aryl and alkenyl as defined herein. Preferred arylalkynyls are those wherein aryl is phenyl and the alkynyl consists of about 3 to about 6 atoms. The arylalkynyl can be optionally substituted by one or more substituents. The bond to the parent moiety is through a non-aromatic carbon atom.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Alyloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Alkylsulfonyl" means an aryl-S($O_2$)— group. The bond to the parent moiety is through the sulfonyl.

"Spirocycloalkyl" means a cycloalkyl group attached to a parent moiety by replacement of two available hydrogen atoms at a single carbon atom. Non-limiting examples of spirocycloalkyl wherein the parent moiety is a cycloalkyl include Spiro[2.5]octane, Spiro[2.4]heptane, etc. The moiety may optionally be substituted as described herein. Non-limiting spirocycloalkyl groups include spirocyclopropyl, spriorcyclobutyl, spirocycloheptyl, and spirocyclohexyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^8$ in —N($R^8$)$_2$, or a variable appears more than once in a structure presented herein, the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods compris-ing the use of "at least one compound of the invention, e.g., of Formula (II)," one to three compounds of the invention, e.g., of Formula (II) can be administered at the same time, preferably one.

Compounds of the invention may contain one or more rings having one or more ring system substituents. "Ring system substituent" means a substituent attached to an aromatic or non-aromatic ring system which, for example, replaces an available hydrogen on the ring system. Ring system substituents may be the same or different, each being as described herein or independently selected from the group consisting of alkyl, alkenyl, alkynyl, haloalkyl, heteroalkyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—$NH_2$, —C(=NH)—$NH_2$, —C(=NH)—NH(alkyl), $Y_1Y_2N$—, $Y_1Y_2$N-alkyl-, $Y_1Y_2$NC(O)—, $Y_1Y_2NSO_2$— and —$SO_2N_1Y_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are rings such as heteroaryl, cycloalkyl, cycloalkenyl, heterocycloalkyl, and heterocycloalkenyl rings. Additional non-limiting examples include methylene dioxy, ethylenedioxy, —C($CH_3$)$_2$— and the like which form moieties such as, for example:

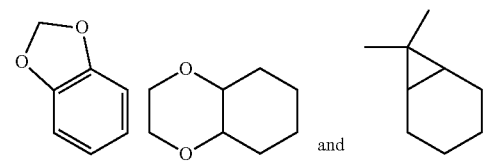

The line — as a bond generally indicates a mixture of, or either of, the possible isomers, e.g., containing (R)- and (S)-stereochemistry. For example:

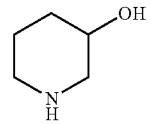

indicates a mixture of, or either of,

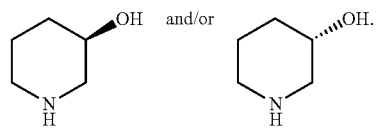

The wavy line ⁓, as used herein, indicates a point of attachment to the rest of the compound.

Lines drawn into the ring systems, such as, for example:

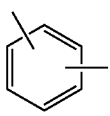

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

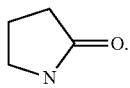

In this specification, where there are multiple oxygen and/or sulfur atoms in a ring system, there cannot be any adjacent oxygen and/or sulfur present in said ring system.

It is noted that the carbon atoms for compounds of the invention may be replaced with 1 to 3 silicon atoms so long as all valency requirements are satisfied.

As well known in the art, a bond drawn from a particular atom wherein no moiety is depicted at the terminal end of the bond indicates a methyl group bound through that bond to the atom, unless stated otherwise. For example:

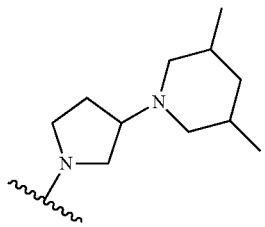 [SMILES: *N1CCC(N2CC(C)CC(C)C2)C1]

represents

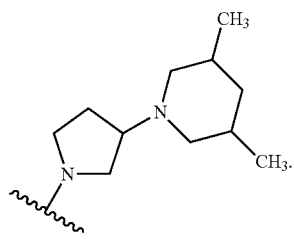 [SMILES: *N1CCC(N2CC(C)CC(C)C2)C1]

In the compounds of Formula (I)

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-(C1-C2)alkyl and piperidino-, pyrrolidino- or morpholino($C_2$-$C_3$)alkyl, and the like.

Similarly, if a compound of the invention contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, —C(OH)C(O)OY$^1$ wherein Y' is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$) acyl glycerol.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

It is also possible that the compounds of the invention may exist in different tautomeric forms, and all such forms are embraced within the scope of the invention. Also, for example, all keto-enol and imine-enamine forms of the compounds are included in the invention. Thus, for example, the compounds of the invention conforming to the formula:

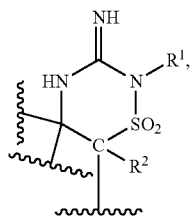

and their tautomers:

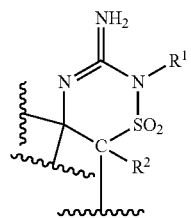

are both contemplated as being within the scope of the compounds of the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of the invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H or D) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent. Non-limiting examples of deuterated compounds of the invention are described hereinbelow.

Polymorphic forms of the compounds of the invention, and of the salts, solvates, esters and prodrugs of the compounds of the invention, are intended to be included in the present invention.

Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

As discussed above, the amount and frequency of administration of the compounds of the invention and/or the pharmaceutically acceptable salts thereof will be regulated according to the judgment of the attending clinician considering such factors as age, condition and size of the patient as well as severity of the symptoms being treated.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of the invention, or a pharmaceutically acceptable salt, solvate, ester or prodrug thereof, and an effective amount of one or more additional agents described above.

The pharmacological properties of the compounds of this invention may be confirmed by a number of pharmacological assays. Certain assays are exemplified elsewhere in this document.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

In one embodiment, the compound is administered orally.

In some embodiments, it may be advantageous for the pharmaceutical preparation comparing one or more compounds of the invention be prepared in a unit dosage form. In such forms, the preparation is subdivided into suitably sized unit doses containing appropriate quantities of the active component, e.g., an effective amount to achieve the desired purpose.

PREPARATIVE EXAMPLES

Compounds of the invention can be made using procedures known in the art. The following reaction schemes show typical procedures, but those skilled in the art will recognize that other procedures can also be suitable.

Techniques, solvents and reagents may be referred to by their following abbreviations:

| | |
|---|---|
| Thin layer chromatography: TLC | liquid chromatography mass spectrometry: LCMS |
| High performance liquid chromatography: HPLC | milliliters: mL |
| ethyl acetate: AcOEt or EtOAc | millimoles: mmol |
| methanol: MeOH | micromoles: μmol |
| ether or diethyl ether: Et$_2$O | microliters: μl |
| tetrahydrofuran: THF | grams: g |
| Acetonitrile: MeCN or ACN | milligrams: mg |
| 1,2-dimethoxyethane: DME | N-iodosuccinimide: NIS |
| Trifluoroacetic acid: TFA | room temperature (ambient, about 25° C.): rt (or RT) |
| Dimethylacetamide: DMA | |
| Dimethylformamide: DMF | Retention time: t$_R$ |
| Dimethylsulfoxide: DMSO | N-bramosuccinimide: NBS |
| triethylamine: Et$_3$N or TEA | Methyl magnesium bromide: MeMgBr |
| tert-Butoxycarbonyl: t-Boc or Boc | iron(III) acetylacetonate: Fe(acac)$_3$ |
| 2-(Trimethylsilyl)ethoxycarbonyl: Teoc | Diphenylphosphoryl azide: DPPA |
| 1-(3-Dimethylaminopropyl)-3-ethylcarbodiimide hydrochloride: EDCI | John-Phos 2-dicyclohexylphosphino-2',4',6'-triisopropyl biphenyl: X-Phos |
| Diisopropylethylamine: DIEA or iPr$_2$NEt | |
| Diisopropylamine: iPr$_2$NH | 2-(1H-7-Azabenzotriazol-1-yl)-1,1,3,3-tetramethyl uronium hexafluorophosphate: HATU |
| 2-(Trimethylsilyl)ethanol: TMSethanol | |
| 3-Chloroperoxybenzoic acid: mCPBA | |
| n-Butyllithium: nBuLi | Concentrated: conc. |
| lithium diisopropylamide: LDA | Tetrabutyl ammonium fluoride: TBAF |
| [1,1'Bis(diphenylphosphino)ferrocene]dichloropalladium(II): PdCl$_2$dppf | 2-Dicyclohexylphosphino-2',6'-diisopropoxy-1,1'-biphenyl: RuPhos |
| Palladium(II) acetate: Pd(OAc)$_2$ | Tetrakis(triphenylphosphine)palladium: Pd(PPh$_3$)$_4$ |
| Methanesulfonyl chloride: MeSO$_2$Cl | |
| Benzyl: Bn | |
| 4-methoxy benzyl: PMB | |
| Phenyl: Ph | |
| Ethanol: EtOH | |
| Liter: L | |
| Minutes: min | |
| Reverse phase: RP | |
| Hexanes: Hex | |
| Methylene Chloride: DCM | |
| Acetic acid: HOAc or AcOH | |
| Saturated: Sat (or sat) | |

Bis(2-oxo-3-oxazolidinyl) phosphinic
chloride: BOPCl
4-(dimethylamino)pyridine: DMAP
Molar: M
2-((trimethylsilyl)ethoxy)methyl: SEM
Diisopropyl azodicarboxylate: DIAD
Triethylborane: Et$_3$B
Tris(dibenzylideneacetone)dipalladium(0):
Pd$_2$dba$_3$
Pyridine: Pyr
(2-Biphenyl)di-tert-butylphosphine:

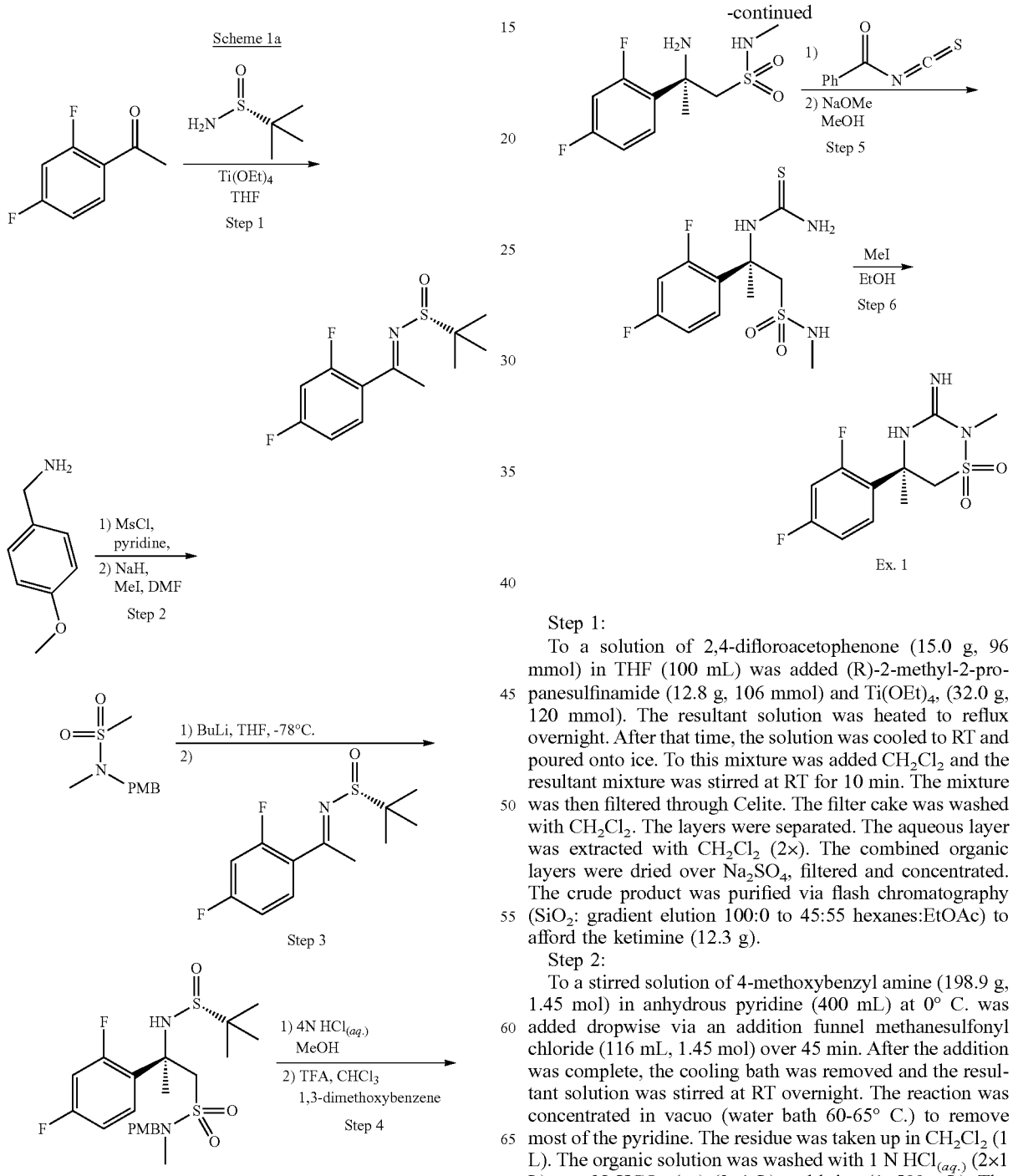

Step 1:

To a solution of 2,4-difloroacetophenone (15.0 g, 96 mmol) in THF (100 mL) was added (R)-2-methyl-2-propanesulfinamide (12.8 g, 106 mmol) and Ti(OEt)$_4$, (32.0 g, 120 mmol). The resultant solution was heated to reflux overnight. After that time, the solution was cooled to RT and poured onto ice. To this mixture was added CH$_2$Cl$_2$ and the resultant mixture was stirred at RT for 10 min. The mixture was then filtered through Celite. The filter cake was washed with CH$_2$Cl$_2$. The layers were separated. The aqueous layer was extracted with CH$_2$Cl$_2$ (2×). The combined organic layers were dried over Na$_2$SO$_4$, filtered and concentrated. The crude product was purified via flash chromatography (SiO$_2$: gradient elution 100:0 to 45:55 hexanes:EtOAc) to afford the ketimine (12.3 g).

Step 2:

To a stirred solution of 4-methoxybenzyl amine (198.9 g, 1.45 mol) in anhydrous pyridine (400 mL) at 0° C. was added dropwise via an addition funnel methanesulfonyl chloride (116 mL, 1.45 mol) over 45 min. After the addition was complete, the cooling bath was removed and the resultant solution was stirred at RT overnight. The reaction was concentrated in vacuo (water bath 60-65° C.) to remove most of the pyridine. The residue was taken up in CH$_2$Cl$_2$ (1 L). The organic solution was washed with 1 N HCl$_{(aq.)}$ (2×1 L), sat. NaHCO$_3$ (aq) (2×1 L) and brine (1×500 mL). The organic layer was dried over Na$_2$SO$_4$, filtered and concentrated to afford a crude solid. This solid was dissolved in 95% EtOH (430 mL) using a steam bath to warm the solution. The solution was allowed to cool, causing the product to precipitate from solution. The product was removed by filtration and the solid was washed with cold EtOH (3×150 mL). A second crop was obtained after allowing the mother liquor to stir at RT overnight. The overall yield of the product was 246.5 g (79% yield).

This product was dissolved in anhydrous DMF (3.0 L), cooled to 0° C. and placed under an atmosphere of N$_2$. To this solution was added in small portions sodium hydride (60% in mineral oil, 60.2 g, 1.51 mol, 1.3 eq.). After the addition was complete, the mixture was stirred for an additional 10 min. To this mixture was added dropwise via an addition funnel methyl iodide (250 g, 1.76 mol, 1.5 eq.). After the addition was complete, the cooling bath was removed and the mixture was allowed to stir at RT overnight. The mixture was then concentrated in vacuo (p=10 torr, bath temp=55-60° C.) to remove ca. 2.5 L of DMF. Some solids precipitated from the solution. The remaining mixture was partitioned between 5 L ice water, 5 L Et$_2$O and 500 mL of EtOAc. The organic layer was separated. The aqueous layer was extracted with Et$_2$O (2×1 L). The combined organic layers were washed with brine (2×1 L), dried over Na$_2$SO$_4$, filtered and concentrated. The solid was stirred with hexanes using a wire stir blade to powderize the solid. The solid was removed by filtration and washed with hexanes (2×250 mL). The solid was dissolved in hexanes/EtOAc (1:1, 450 mL) using a steam bath to warm the mixture. An off white precipitate formed on cooling and was filtered off (182 g). The remaining mother liquor was purified via flash chromatography (SiO$_2$: 1:1 hexanes:EtOAc) to afford additional product (51.8 g) for an overall yield of 233.8 g (89% yield).

Step 3:

To a solution of the sulfonamide from step 2 (4.18 g, 18.2 mmol) in anhydrous THF (50 mL) at −78° C. under an atmosphere of N$_2$ was added dropwise a solution of n-BuLi (1.6 M in hexanes, 11.4 mL, 18.2 mmol). The resultant solution was stirred at −78° C. for 30 min. After that time, a solution of the ketimine from step 1 (3.15 g, 12.1 mmol) in THF (50 mL) precooled to −78° C. in a separate round bottom flask was transferred via cannula to the solution above. The resultant solution was stirred at −78° C. for 3.5 hours. Water was added and the mixture was allowed to warm to RT. The aqueous layer was extracted with EtOAc (3×). The combined organic layers were washed with brine, dried over Na$_2$SO$_4$, filtered and concentrated. The crude product was purified via flash chromatography (SiO$_2$: gradient elution 100:0 to 40:60 hexanes:EtOAc) to afford the sulfinamide (3.95 g, 67% yield).

Step 4:

To a solution of the sulfinamide from step 3 (3.80 g, 7.6 mmol) in CH$_2$Cl$_2$/MeOH (3:1 80 mL) was added a solution of 4 M HCl$_{(dioxane)}$ (11.4 mL, 45.4 mmol). The resultant solution was stirred at RT for 1.5 hours. The solution was concentrated. The residue was re-concentrated from toluene (1×). The residue was then taken up in CHCl$_3$ and TFA (26 mL, 1:1). To this solution was added 1,3-dimethoxybenzene (6.5 mL, 50 mmol). The resultant solution was stirred at RT overnight. The resultant solution was concentrated. The resultant oil was partitioned between Et$_2$O and 1 M HCl$_{(aq.)}$. The aqueous layer was extracted with Et$_2$O (2×). The aqueous layer was then adjusted to pH 10 with the addition of sat. Na$_2$CO$_3$ $_{(aq.)}$. The aqueous layer was extracted with CH$_2$Cl$_2$ (3×). The organic layers were extracted from the basic aqueous layer, combined, dried over Na$_2$SO$_4$, filtered and concentrated to afford the amine (1.88 g, 85%).

Step 5:

To a solution of the amine from step 4 (1.80 g, 6.8 mmol) in CH$_2$Cl$_2$ (30 mL) was added benzoyl isothiocyanate (1.01 mL, 7.49 mmol). The resultant solution was stirred at RT overnight. The solution was then concentrated. The residue was redissolved in MeOH (20 mL). To this solution was added a solution of NaOMe in MeOH (25%, 3.9 mL). The resultant solution was stirred at RT for 45 min. The solution was concentrated in vacuo. The residue was then partitioned between CH$_2$Cl$_2$ and water. The pH of the aqueous layer was adjusted to ca 11 with the addition of NaHCO$_3$ (aq.). The aqueous layer was extracted with CH$_2$Cl$_2$ (3×). The combined organic layers were dried over Na$_2$SO$_4$, filtered and concentrated to afford the thiourea (1.90 g, 86%).

Step 6:

To the thiourea from step 5 (1.90 g, 5.88 mmol) in MOH (40 mL) was added methyl iodide (0.42 mL, 6.7 mmol). The resultant solution was heated to reflux for 3 hours. The solution was cooled to RT and concentrated in vacuo. The residue was partitioned between EtOAc and Na$_2$CO$_3$ $_{(aq.)}$. The aqueous layer was extracted with EtOAc (3×). The combined organic layers were washed with brine, dried over Na$_2$SO$_4$, filtered and concentrated. The crude product was purified via flash chromatography (SiO$_2$: gradient elution 100:0 to 92:8 CH$_2$Cl$_2$:MeOH) to afford Ex. 1 (1.12 g, 66% yield). LCMS (conditions D): t$_R$=1.73 min, m/e=290.2 (M+H).

TABLE I

The following sulfonamides were prepared using a procedure similar to that described in Scheme 1a step 2.

| Entry | Amine | Alkyl halide | sulfonamide |
|---|---|---|---|
| 1 | 4-methoxybenzylamine | isopropyl iodide | N-isopropyl-N-(4-methoxybenzyl)methanesulfonamide |
| 2 | 4-methoxybenzylamine | isobutyl iodide | N-isobutyl-N-(4-methoxybenzyl)methanesulfonamide |

TABLE I-continued

The following sulfonamides were prepared using a procedure similar to that described in Scheme 1a step 2.

| Entry | Amine | Alkyl halide | sulfonamide |
|---|---|---|---|
| 3* | MeO-C6H4-CH2-NH2 | CD3I | MeO-C6H4-CH2-N(CD3)-SO2Me |
| 4* | MeO-C6H4-CH2-NH2 | cyclopropyl-CH2-Br | MeO-C6H4-CH2-N(CH2-cyclopropyl)-SO2Me |

*Cesium carbonate was used as the base instead of NaH for entries 3 and 4.

Scheme 1b:

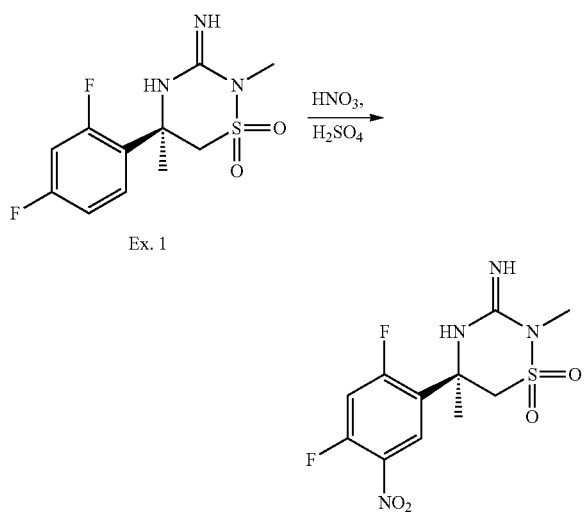

Ex. 1

Step 1:

To a mixture of Ex. 1. (8.00 g, 28.0 mmol.) and concentrated sulfuric acid (16 mL) was added fuming nitric acid (2.24 mL) at 0° C. The reaction mixture was stirred from 0° C. to room temperature over 2 h. After this time, the reaction mixture was basified with sodium carbonate to pH 10 and extracted with ethyl acetate (2×200 mL). The combined extracts were dried over anhydrous $Na_2SO_4$, filtered, and concentrated under reduced pressure to afford the nitro compound (8.81 g, 94%).

Scheme 2:

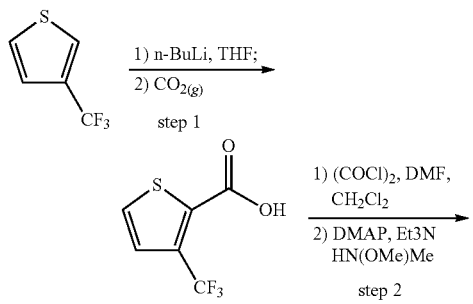

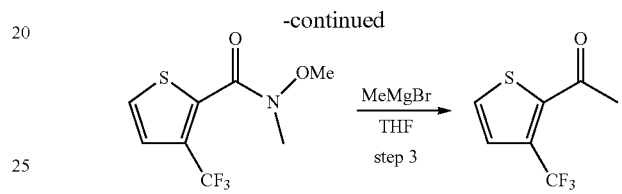

Step 1:

To a solution of 3-trifluoromethyl thiophene (3.75 g, 24.6 mmol) in anhydrous THF (60 mL) at −78° C. was added a solution of n-BuLi (2.5 M in hexanes, 13 mL, 32.5 mmol). The resultant solution was stirred at −78° C. for 10 min. To the solution was bubbled $CO_{2\,(g)}$ for 20 min at −78° C. The solution was allowed to warm to RT and stirred for an additional 40 min at RT while bubbling of $CO_{2\,(g)}$ through the solution was continued. After that time, 1 M $HCl_{(aq.)}$ was added to the solution. The aqueous layer was then extracted with EtOAc. The organic layer was washed with brine, dried over $Na_2SO_4$, filtered and concentrated. The crude product was purified via flash chromatography ($SiO_2$: 85:15:1 $CH_2Cl_2$:MeOH:AcOH) to afford the carboxylic acid (4.33 g, 90%).

Step 2:

To a solution of a portion of the acid from step 1 (465 mg, 2.37 mmol) in $CH_2Cl_2$ (12 mL) and DMF (0.20 mL) at 0° C. was added dropwise a solution of oxalyl chloride (2 M in $CH_2Cl_2$, 3.5 mL, 3 eq.). The resultant solution was stirred at 0° C. for 15 min followed by an additional 1 hour at RT. The solution was concentrated. To the residue was added N,O-dimethylhydroxylamine hydrochloride (470 mg, 2 eq.) followed by $CH_2Cl_2$ (18 mL). The resultant mixture was cooled to 0° C. To this mixture was added $Et_3N$ (1.4 mL) and DMAP (10 mg). The solution was stirred at 0° C. for 1 hour. To the solution was added 1 M $HCl_{(aq.)}$ (60 mL) and $CH_2Cl_2$ (60 mL). The layers were separated. The organic layer was washed with brine, dried and concentrated. The crude residue was purified via flash chromatography ($SiO_2$: gradient elution 100:0 to 60:40 heptane:EtOAc) to afford the amide (426 mg, 75%).

Step 3:

To a solution of the amide from step 2 (4.10 g, 17.1 mmol) in THF (70 mL) at 0° C. was slowly added a solution of methyl magnesium bromide (3 M in $Et_2O$, 7 mL). The resultant solution was stirred at 0° C. for 3 hours. After that time, 1 M $HCl_{(aq.)}$ was added. The mixture was then extracted with $Et_2O$. The organic layer was dried, filtered and concentrated. The residue was purified via flash chromatography ($SiO_2$: gradient elution 100:0 to 60:40 pentane:EtOAc) to afford the ketone (3.22 g, 97%) as a colorless oil.

TABLE Ib

The following ketones were prepared using similar procedures to that described in Scheme 2, Steps 2 and 3 using the appropriate carboxylic acids.

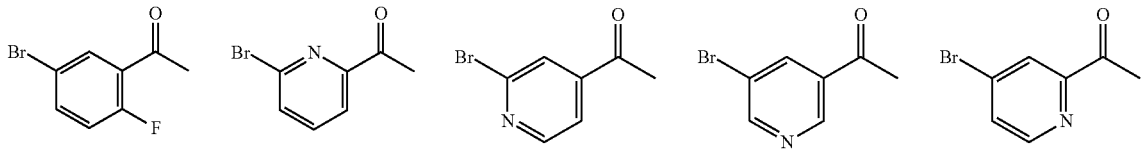

Scheme 2b:

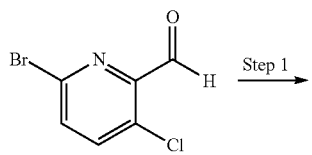

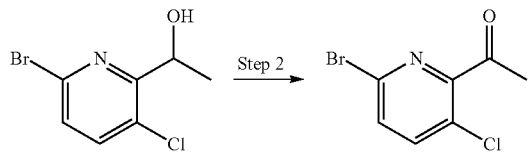

Scheme 2c:

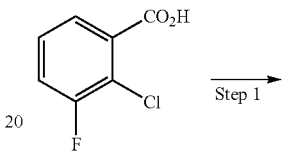

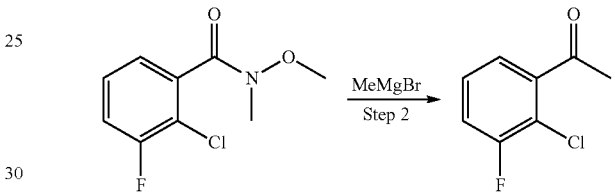

Step 1:

To a solution of 6-bromo-3-chloropicolinaldehyde (10.0 g, 45.45 mmol) in 200 mL THF stirring at −78° C. under N₂ was slowly added methylmagnesium bromide (3.0 M in diethyl ether, 16.63 mL, 50 mmol). The reaction was stirred at this temperature for 3 hours, and then saturated ammonium chloride was added. The mixture was extracted with EtOAc. The combined organic layers were dried (MgSO₄), filtered, and concentrated in vacuo. The residue was purified by silica gel chromatography (0-10% EtOAc/hexanes over 20 minutes) to provide 1-(6-bromo-3-chloropyridin-2-yl)ethanol (8.4 g, 78%).

Step 2:

The material prepared above (8.4 g, 35.5 mmol) was stirred overnight at room temperature in 100 mL DCM along with pyridinium chlorochromate (15 g, 71 mmol) and approximately 5 g celite. The reaction was filtered through celite and washed with DCM. The filtrate was concentrated to dryness in vacuo and the residue was purified by silica gel chromatography (0-10% EtOAc/hexanes over 22 minutes) to provide 1-(6-bromo-3-chloropyridin-2-yl)ethanone (6.85 g, 82%).

Step 1:

To a solution of 2-chloro-3-fluorobenzoic acid (30 g, 172 mmol) in 300 mL of DCM was added carbonyldiimidazole (CDI) (32.0 g, 198 mmol) in portions. After addition and then stirring at RT for 1 h, N,O-dimethylhydroxylamine HCl salt (18.5 g, 189 mmol) was added into the mixture followed by Et₃N (20 mL). The mixture was stirred at RT overnight. After the reaction was quenched with water, the aqueous layer was extracted with DCM (2×). The organic layers were washed with 2N HCl (aq), water, sat. NaHCO₃ (aq) and brine. The solution was dried (MgSO₄) and concentrated. The product 2-chloro-3-fluoro-N-methoxy-N-methylbenzamide (32.0 g) was obtained by silica gel chromatography (elution with 0-30% EtOAc/Hex).

Step 2:

The above material was treated according to Scheme 2, Step 3 to provide the ketone product (89% yield).

TABLE Ic

The following ketone was made using methods similar to those described in Scheme 2b:

| Entry | Aldehyde | Ketone |
|---|---|---|
| 1 | | |

TABLE II

The following examples were prepared using similar procedures to that described in Scheme 1a using the appropriate starting materials.

Examples
(LCMS data listed with each compound: observed MH+, HPLC rentention time and LCMS method)

2 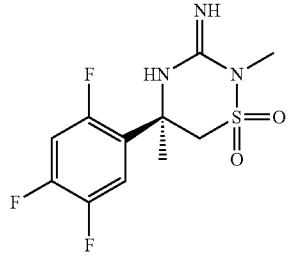

MH+: 308.2, 1.64 min, D

3 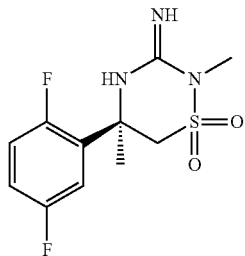 [SMILES: CN1C(=N)N[C@](C)(c2cc(F)ccc2F)CS1(=O)=O]

MH+: 290.0, 1.99 min, B

4 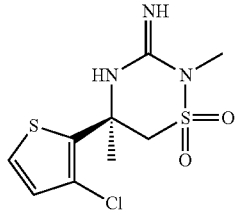 [SMILES: CN1C(=N)N[C@](C)(c2sccc2Cl)CS1(=O)=O]

MH+: 294.2, 1.43 min, A

5 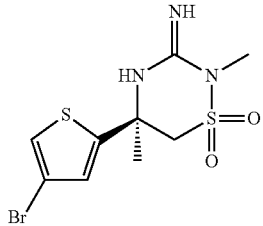 [SMILES: CN1C(=N)N[C@](C)(c2cc(Br)cs2)CS1(=O)=O]

MH+: 340.2, 2.64 min, A

6 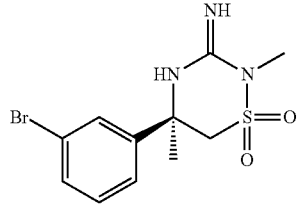 [SMILES: CN1C(=N)N[C@](C)(c2cccc(Br)c2)CS1(=O)=O]

MH+: 331.9, 1.95 min, B

TABLE II-continued

The following examples were prepared using similar procedures to that described in Scheme 1a using the appropriate starting materials.

Examples
(LCMS data listed with each compound: observed MH+, HPLC rentention time and LCMS method)

7 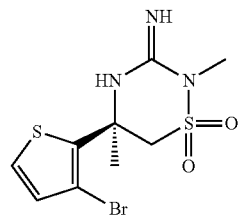 [SMILES: CN1C(=N)N[C@](C)(c2sccc2Br)CS1(=O)=O]

MH+: 340.2, 2.19 min, A

8 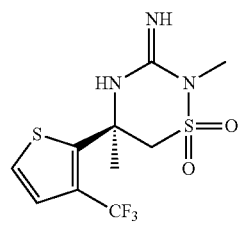 [SMILES: CN1C(=N)N[C@](C)(c2sccc2C(F)(F)F)CS1(=O)=O]

9 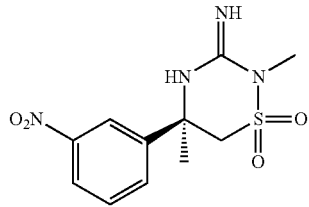 [SMILES: CN1C(=N)N[C@](C)(c2cccc([N+](=O)[O-])c2)CS1(=O)=O]

10 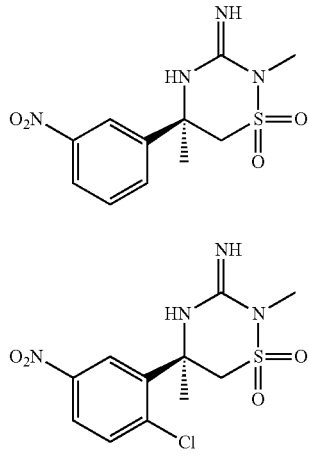

11 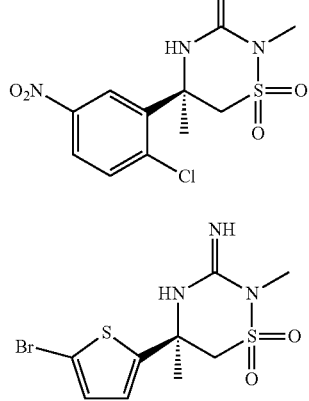

MH+: 339.8, 1.87 min, A

12 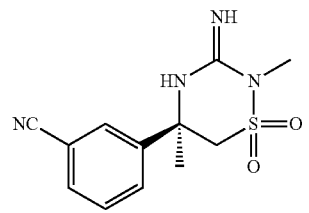 [SMILES: CN1C(=N)N[C@](C)(c2cccc(C#N)c2)CS1(=O)=O]

MH+: 278.9, 1.73 min, B

TABLE II-continued

The following examples were prepared using similar procedures to that described in Scheme 1a using the appropriate starting materials.

Examples
(LCMS data listed with each compound: observed MH+, HPLC rentention time and LCMS method)

13 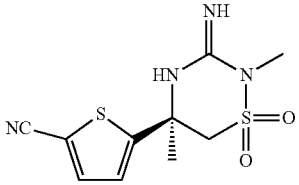 [SMILES: CN1C(=N)N[C@](C)(c2ccc(C#N)s2)CS1(=O)=O]

MH+: 285.0, 1.54 min, B

14 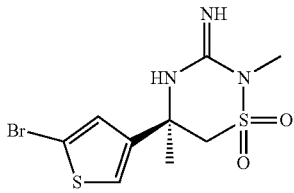 [SMILES: CN1C(=N)N[C@](C)(c2csc(Br)c2)CS1(=O)=O]

MH+: 340.2, 2.44 min, A

14a 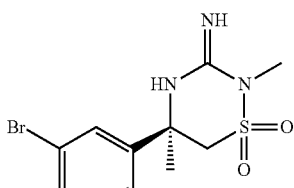

MH+: 350.0, 1.72 min, D

14b 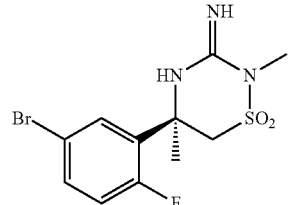

14c 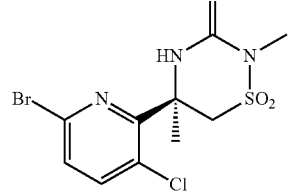

14d 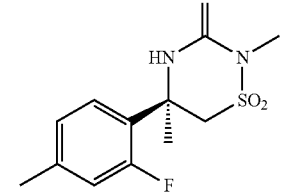

Scheme 3:

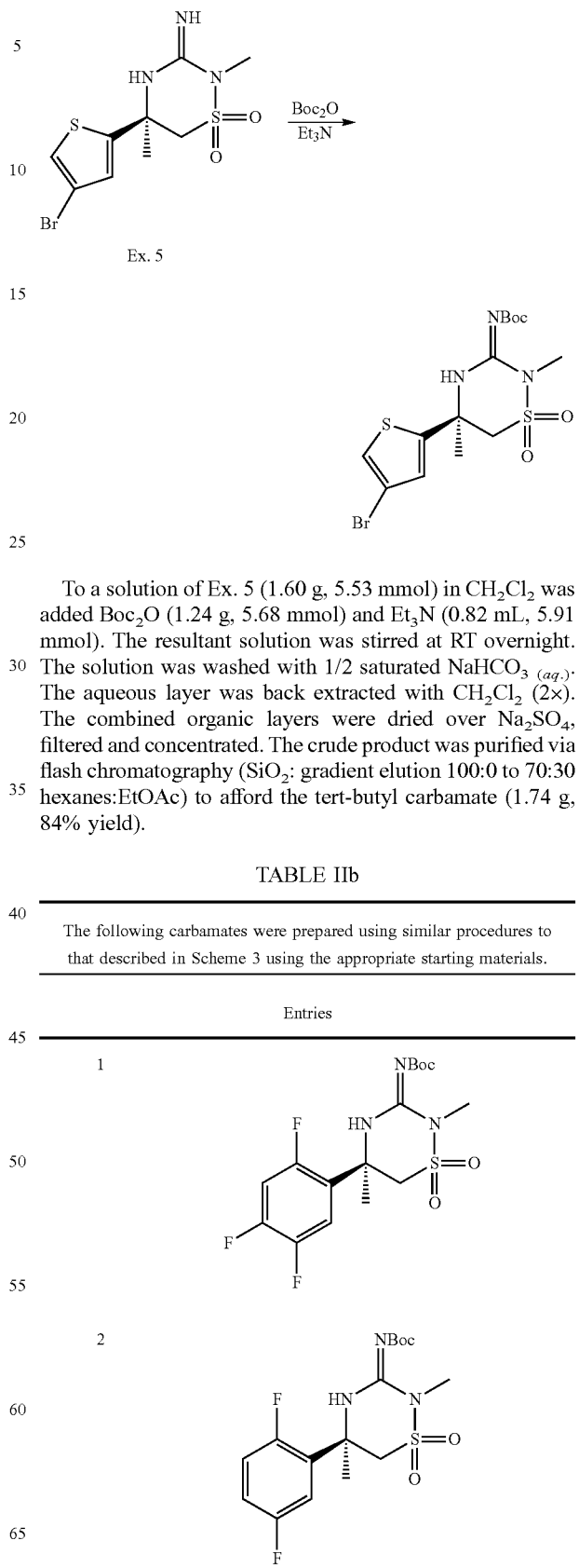

Ex. 5

To a solution of Ex. 5 (1.60 g, 5.53 mmol) in CH$_2$Cl$_2$ was added Boc$_2$O (1.24 g, 5.68 mmol) and Et$_3$N (0.82 mL, 5.91 mmol). The resultant solution was stirred at RT overnight. The solution was washed with 1/2 saturated NaHCO$_3$ $_{(aq.)}$. The aqueous layer was back extracted with CH$_2$Cl$_2$ (2×). The combined organic layers were dried over Na$_2$SO$_4$, filtered and concentrated. The crude product was purified via flash chromatography (SiO$_2$: gradient elution 100:0 to 70:30 hexanes:EtOAc) to afford the tert-butyl carbamate (1.74 g, 84% yield).

TABLE IIb

The following carbamates were prepared using similar procedures to that described in Scheme 3 using the appropriate starting materials.

Entries

1 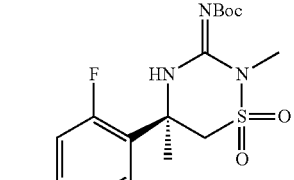

2 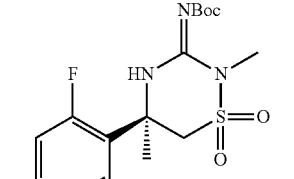

TABLE IIb-continued

The following carbamates were prepared using similar procedures to that described in Scheme 3 using the appropriate starting materials.

| Entries | |
|---|---|
| 3 | (structure: 3-chloro-thiophen-2-yl substituted thiadiazinane with NBoc, N-methyl, S(=O)₂) |
| 4 | (structure: 4-bromo-thiophen-2-yl substituted thiadiazinane with NBoc, N-methyl, S(=O)₂) |
| 5 | (structure: 3-bromophenyl substituted thiadiazinane with NBoc, N-methyl, S(=O)₂) |
| 6 | (structure: 3-bromo-thiophen-2-yl substituted thiadiazinane with NBoc, N-methyl, S(=O)₂) |
| 7 | (structure: 3-trifluoromethyl-thiophen-2-yl substituted thiadiazinane with NBoc, N-methyl, S(=O)₂) |
| 8 | (structure: 3-nitrophenyl substituted thiadiazinane with NBoc, N-methyl, S(=O)₂) |
| 9 | (structure: 2-chloro-5-nitrophenyl substituted thiadiazinane with NBoc, N-methyl, S(=O)₂) |
| 10 | (structure: 5-bromo-thiophen-2-yl substituted thiadiazinane with NBoc, N-methyl, S(=O)₂) |
| 11 | (structure: 3-cyanophenyl substituted thiadiazinane with NBoc, N-methyl, S(=O)₂) |
| 12 | (structure: 5-cyano-thiophen-2-yl substituted thiadiazinane with NBoc, N-methyl, S(=O)₂) |
| 13 | (structure: 5-bromo-thiophen-3-yl substituted thiadiazinane with NBoc, N-methyl, S(=O)₂) |

TABLE IIb-continued

The following carbamates were prepared using similar procedures to that described in Scheme 3 using the appropriate starting materials.

| Entries | |
|---|---|
| 14 | (structure: 5-bromo-2-fluorophenyl thiadiazine dioxide with NBoc) |
| 15 | (structure: 6-bromo-3-fluoropyridyl thiadiazine dioxide with NBoc) |
| 16 | (structure: 6-bromo-3-chloropyridyl thiadiazine dioxide with NBoc) |

TABLE IIc

The following example was prepared using a procedure similar to that described in Scheme 1b, using the following modified temperature profile: nitric acid addition at −40 degrees C, then warming to 0 degrees C.

| Example | Starting material | Product |
|---|---|---|
| 14e | (Example 14d structure) | (nitrated product structure) |

TABLE IId

The following thiadiazine dioxides were made according to methods similar to those in Schemes 1a and 3, with the noted exceptions:

| Entries | |
|---|---|
| 1[a,b] | (2,6-difluorophenyl thiadiazine dioxide with NBoc) |
| 2[a,b] | (2,3-difluorophenyl thiadiazine dioxide with NBoc) |
| 3[c] | (2-fluoro-3-chlorophenyl thiadiazine dioxide with NBoc) |

TABLE IId-continued

The following thiadiazine dioxides were made according to methods similar to those in Schemes 1a and 3, with the noted exceptions:

Entries

Ex. 14f[d,e]

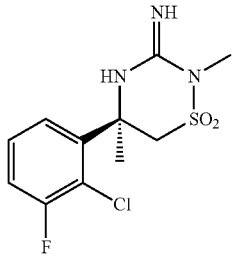 [SMILES: CN1C(=N)N[C@](C)(c2cccc(F)c2Cl)CS1(=O)=O]

[a] (S)-2-Methyl-2-propanesulfinamide was used in Step 1 Scheme 1a instead of (R)-2-methyl-2-propanesulfinamide.
[b] Re-crystallization from 95% MeOH/5% water was used to remove a diastereomeric product after silica gel purification in Step 3 Scheme 1a.
[c] SFC chromatography (TharSFC80, Chiralpak OD-H, 50 × 250 mm, 5 μm, 150 bar with 30% iPrOH, 250 g/min, 40° C.) used to remove a diastereomeric product after silica gel purification in Step 3 Scheme 1a.
[d] SFC chromatography (TharSFC80, Chiralpak OJ-H, 50 × 250 mm, 5 μm, 150 bar with 25% iPrOH, 250 g/min, 40° C.) used to remove a diastereomeric product after silica gel purification in Step 3 Scheme 1a.
[e] The product of Scheme 1a Step 4 was treated according to Scheme 3b to afford Example 14f directly, instead of employing Scheme 1a, Steps 5 and 6.

Scheme 3a:

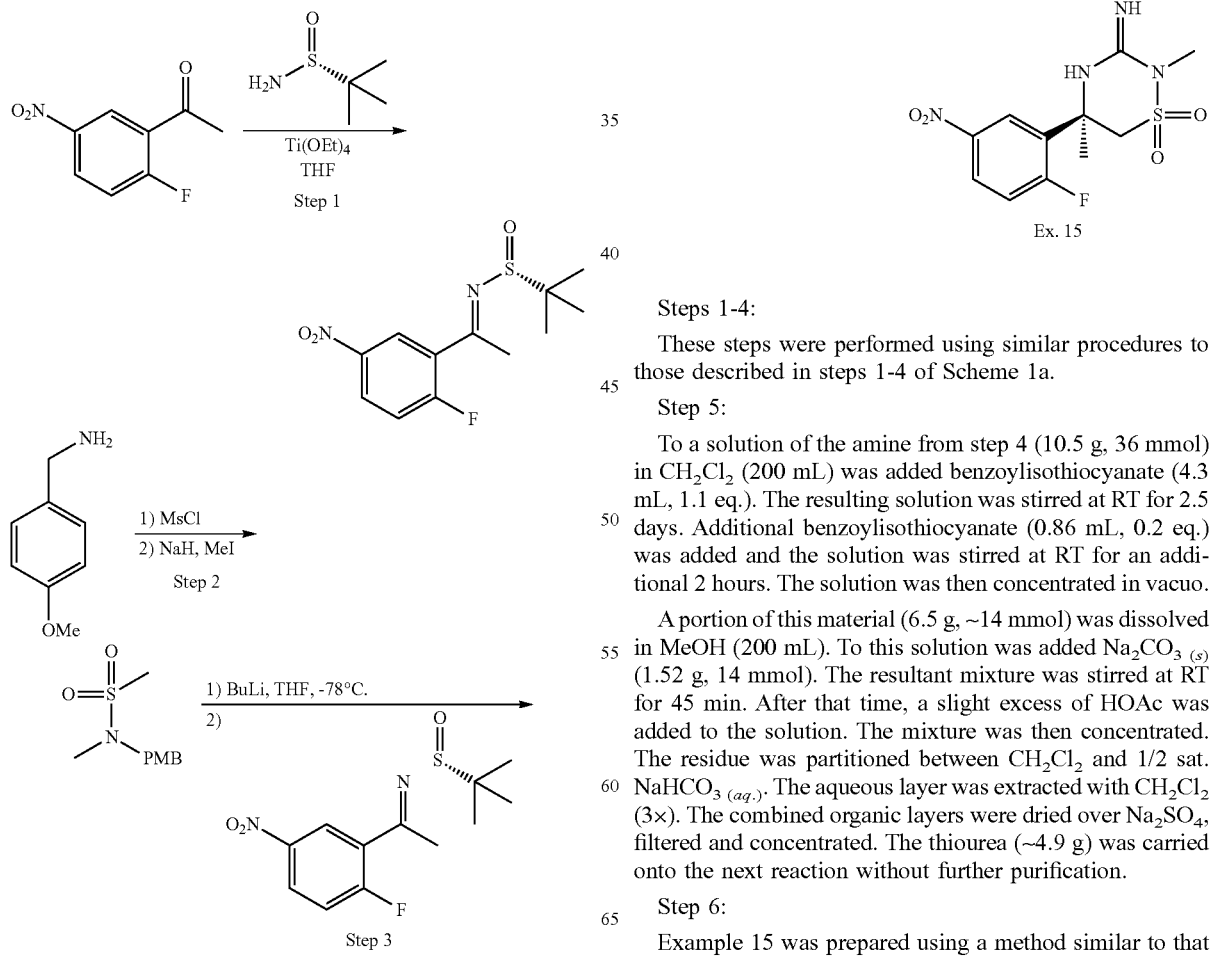

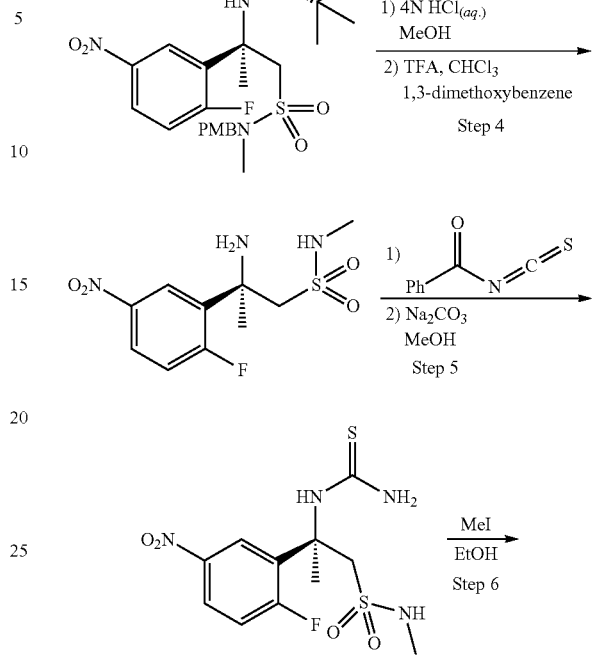

Ex. 15

Steps 1-4:

These steps were performed using similar procedures to those described in steps 1-4 of Scheme 1a.

Step 5:

To a solution of the amine from step 4 (10.5 g, 36 mmol) in CH$_2$Cl$_2$ (200 mL) was added benzoylisothiocyanate (4.3 mL, 1.1 eq.). The resulting solution was stirred at RT for 2.5 days. Additional benzoylisothiocyanate (0.86 mL, 0.2 eq.) was added and the solution was stirred at RT for an additional 2 hours. The solution was then concentrated in vacuo.

A portion of this material (6.5 g, ~14 mmol) was dissolved in MeOH (200 mL). To this solution was added Na$_2$CO$_3$ (s) (1.52 g, 14 mmol). The resultant mixture was stirred at RT for 45 min. After that time, a slight excess of HOAc was added to the solution. The mixture was then concentrated. The residue was partitioned between CH$_2$Cl$_2$ and 1/2 sat. NaHCO$_3$ (aq.). The aqueous layer was extracted with CH$_2$Cl$_2$ (3×). The combined organic layers were dried over Na$_2$SO$_4$, filtered and concentrated. The thiourea (~4.9 g) was carried onto the next reaction without further purification.

Step 6:

Example 15 was prepared using a method similar to that described in Scheme 1a step 6.

Scheme 3b:

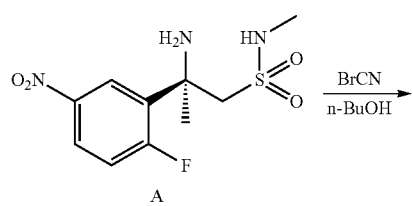

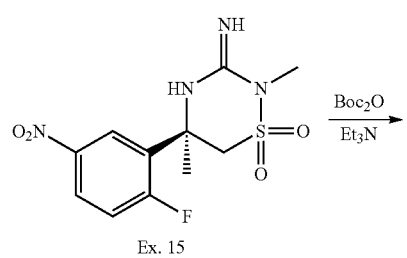

Ex. 15

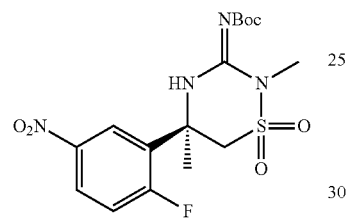

To a slurry of amine A (Scheme 3a step 4) (13.7 grams) in n-butanol (150 mL) was added a solution of cyanogen bromide (5M in MeCN). The resultant mixture was heated to reflux for 4 hours. The mixture was concentrated to ⅓ of the original volume. To the mixture was added Et₂O (200 mL). The resultant solid was removed via filtration and the solid was washed with Et₂O (2×). The solid was partitioned between EtOAc and sat. Na₂CO₃ (aq.). The aqueous layer was extracted with EtOAc (3×). The combined organic layers were washed with brine, dried over Na₂SO₄, filtered and concentrated to afford 10.6 grams of Ex. 15. This material was converted to the t-butyl carbamate using a procedure similar to that described in Scheme 3.

TABLE IIe

The following thiadiazine dioxides were prepared using procedures similar to those described in Schemes 3a (entry 1), 3b (entries 2-5) and 3 using the sulfonamides shown in Table I and Scheme 1a.

Entries

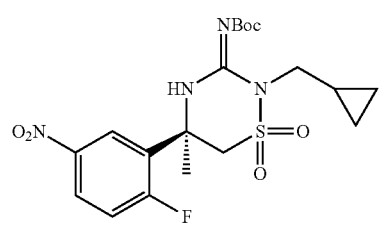

1

TABLE IIe-continued

The following thiadiazine dioxides were prepared using procedures similar to those described in Schemes 3a (entry 1), 3b (entries 2-5) and 3 using the sulfonamides shown in Table I and Scheme 1a.

Entries

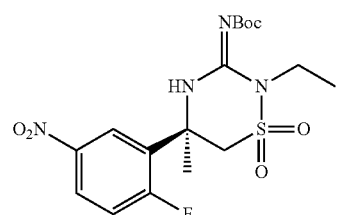

2

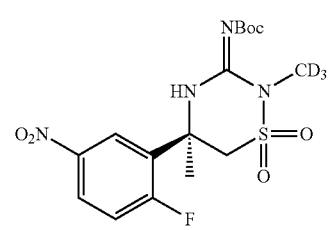

3

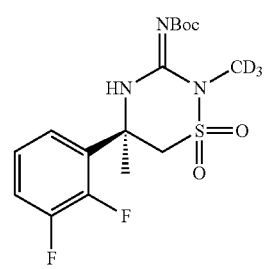

4

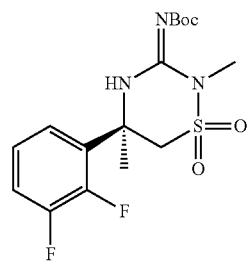

5

Scheme 4:

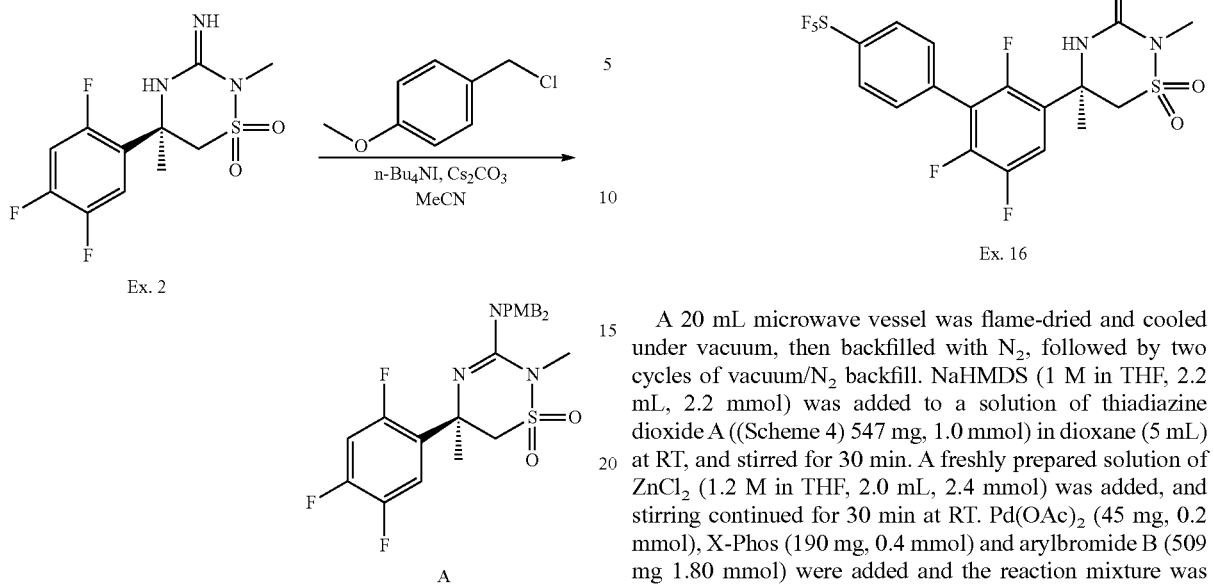

Ex. 16

To a solution of Ex. 2 (3.8 g, 12.2 mmol) in MeCN (40 mL) was added 4-methoxybenzyl chloride (4.6 g, 29 mmol), $Cs_2CO_3$ (9.9 g, 31 mmol) and n-$Bu_4$NI (450 mg, 1.2 mmol). The resultant mixture was heated to reflux for 16 hours. After that time, additional 4-methoxybenzyl chloride (1.9 g, 12 mmol) and $Cs_2CO_3$ (4.4 g, 12 mmol) were added and the mixture was heated to reflux for an additional 4 hours. The mixture was then concentrated in vacuo at RT. The residue was partitioned between water and $CH_2Cl_2$. The aqueous layer was extracted with $CH_2Cl_2$. The combined organic layers were dried over $Na_2SO_4$, filtered and concentrated. The crude residue was purified via flash chromatography ($SiO_2$: gradient elution 100:0 to 80:20 hexanes:EtOAc) to afford the bis-PMB compound A (4.9 g, 73%).

Scheme 5:

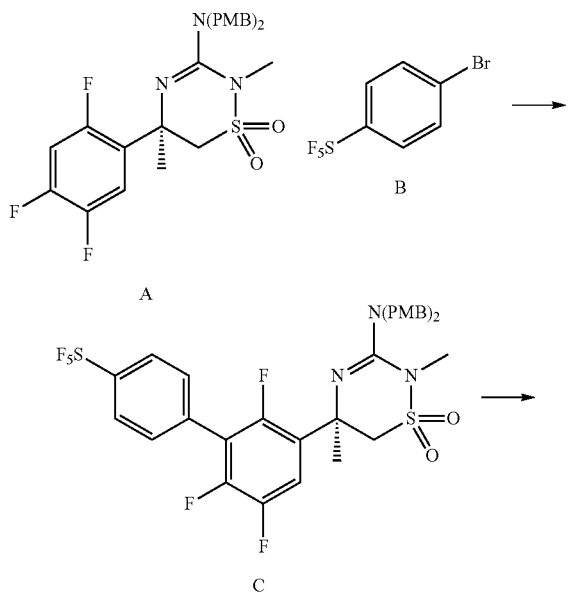

A 20 mL microwave vessel was flame-dried and cooled under vacuum, then backfilled with $N_2$, followed by two cycles of vacuum/$N_2$ backfill. NaHMDS (1 M in THF, 2.2 mL, 2.2 mmol) was added to a solution of thiadiazine dioxide A ((Scheme 4) 547 mg, 1.0 mmol) in dioxane (5 mL) at RT, and stirred for 30 min. A freshly prepared solution of $ZnCl_2$ (1.2 M in THF, 2.0 mL, 2.4 mmol) was added, and stirring continued for 30 min at RT. Pd(OAc)$_2$ (45 mg, 0.2 mmol), X-Phos (190 mg, 0.4 mmol) and arylbromide B (509 mg 1.80 mmol) were added and the reaction mixture was degassed (4× vacuum/$N_2$), capped and placed into a pre-heated 100° C. oil bath for 3 h. The crude reaction was cooled to RT, diluted with EtOAc/water, filtered through a pad of celite, and the aqueous layer extracted with EtOAc (2×). The combined organic layers were washed with brine (1×), dried over $Na_2SO_4$, filtered and concentrated under reduced pressure to give a crude residue that was subjected to silica gel chromatography (0→30% EtOAc/hexanes) followed by RP-HPLC conditions (monitoring at 220 nm) to give intermediate C (73 mg, 97 umol).

A solution of intermediate C (73 mg, 97 umol) in $CH_3CN$ (4 mL) was heated to 75° C., and a solution of $K_2HPO_4$ (26 mg, 147 umol), $KH_2PO_4$ (20 mg, 147 umol) and $K_2S_2O_8$ (158 mg, 588 umol) in water (2 mL) was added via pipette. After 60 min at 75° C., the reaction mixture was cooled to RT and concentrated under vacuum. The residue was subjected to RP-HPLC conditions to give Ex. 16 (TFA salt, 26 mg). LCMS data: (method D): $t_R$=2.17 min, m/e=510.0 (M+H).

Scheme 6a:

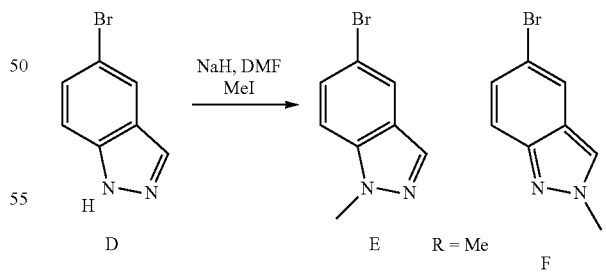

Sodium hydride (60% in oil, 1.5 g, 37.5 mmol) was added to a solution of 5-bromoindazole D (6 g, 30.6 mmol) in DMF (60 mL) at RT. After stirring for 30 min, methyl iodide (2.83 mL, 45.9 mmol) was added and the reaction stirred for another 2 h at RT. The reaction was quenched with sat. $NaHCO_3$ (aq), extracted with EtOAc (1×), dried over $MgSO_4$, filtered, and concentrated under reduced pressure to give a mixture of N-1 and N-2 methylated 5-bromoindazoles E and F, which were separated by silica-gel chromatography using 0→30% EtOAc/hexanes.

Scheme 6b:

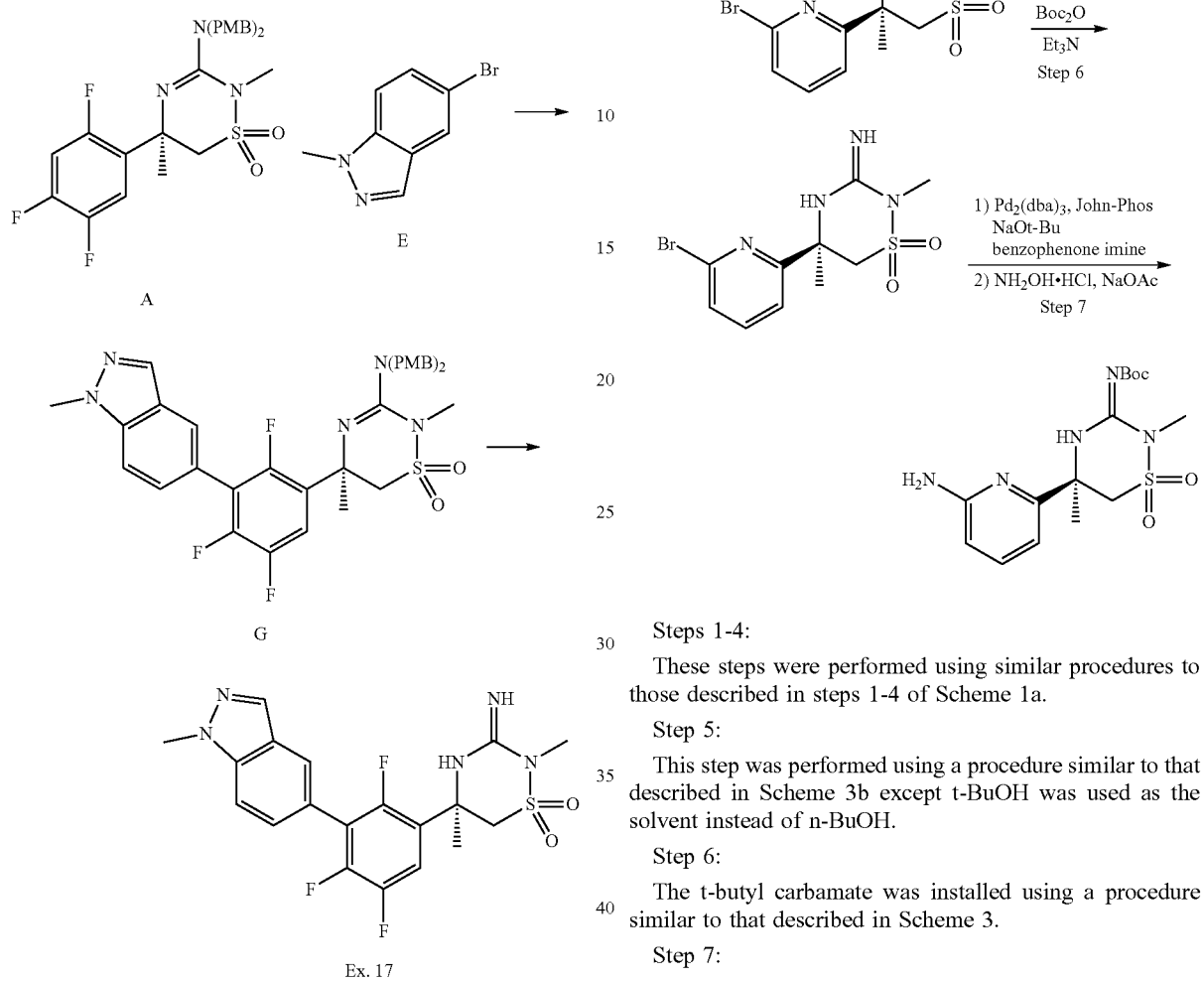

Example 17 was prepared as described for Example 16 in Scheme 5, substituting arylbromide E for B. LCMS data: (method C): $t_R$=3.12 min, m/e=438.2 (M+H).

Scheme 7a:

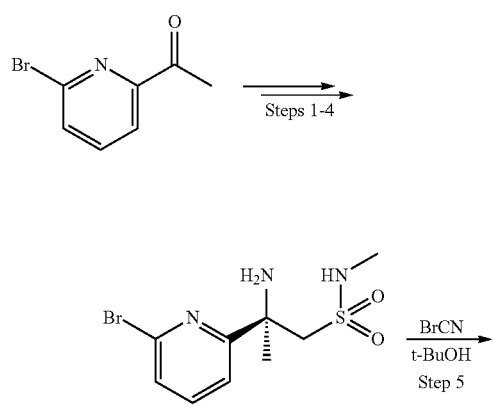

Steps 1-4:

These steps were performed using similar procedures to those described in steps 1-4 of Scheme 1a.

Step 5:

This step was performed using a procedure similar to that described in Scheme 3b except t-BuOH was used as the solvent instead of n-BuOH.

Step 6:

The t-butyl carbamate was installed using a procedure similar to that described in Scheme 3.

Step 7:

A mixture of the bromide (3.00 g, 6.92 mmol), benzophenone imine (1.39 mL, 830 mmol), Pd$_2$(dba)$_3$ (0.634 g, 0.692 mmol), John-Phos (0.413 g, 1.38 mmol), sodium tert-butoxide (2.13 g, 22.1 mmol), and toluene (51 mL) was degassed (vacuum/N$_2$). The mixture was then stirred at 65° C. under nitrogen for 3 h. After this time, the reaction mixture was cooled to room temperature and filtered through a pad of Celite and rinsed with ethyl acetate (100 mL). The filtrate was concentrated under reduced pressure. The residue was then dissolved in methanol (76 mL) and the resulting solution was charged with hydroxylamine hydrochloride (2.16 g, 31.1 mmol) and sodium acetate (2.55 g, 31.1 mmol). The reaction mixture was stirred at room temperature for 40 min. After this time, the reaction mixture was concentrated under reduced pressure. The resulting residue was dissolved in ethyl acetate (200 mL) and washed with saturated aqueous sodium bicarbonate (100 mL), water (100 mL), and brine (100 mL). The organic layer was then dried over anhydrous sodium sulfate, filtered, and concentrated under reduced pressure. The residue was purified by column chromatography (silica, 0-100% ethyl acetate/heptane) to afford the amino pyridine (0.880 g, 34%).

Scheme 7b:

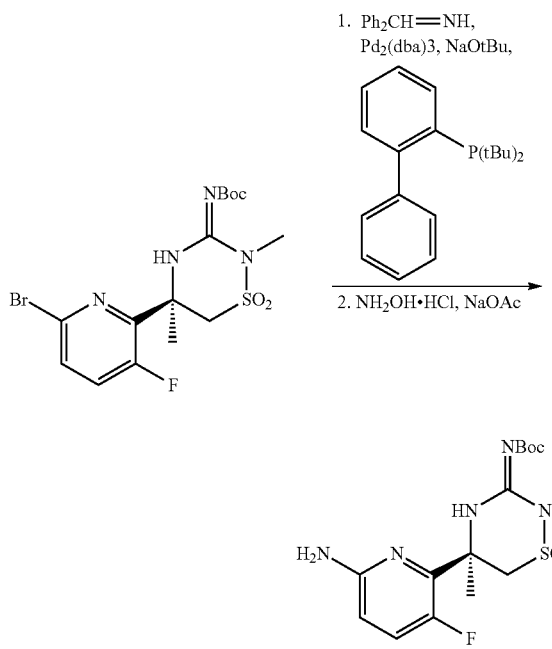

To a flame-dried flask was added a pyridyl bromide (Table IIb, Entry 15, 1.5 g, 3.3 mmol), Pd₂(dba)₃ (305 mg, 0.3 mmol), (2-biphenyl)di-tert-butylphosphine (200 mg, 0.7 mmol), sodium tert-butoxide (1.02 g, 0.011 mmol), benzophenone imine (670 ul, 4 mmol), and toluene (21 mL). The mixture was evacuated under vacuum and back-filled with N₂ (3×). The mixture was stirred at 60° C. for 1 h. After filtration through celite, the filtrate was concentrated. The crude residue was dissolved in 36 mL of methanol, and hydroxylamine hydrochloride (458 mg, 6.6 mmol) and sodium acetate (541 mg, 6.6 mmol) were added. The reaction was stirred for 35 min and then quenched with saturated aqueous sodium bicarbonate. The mixture was extracted with ethyl acetate, and the combined organic portions were dried over magnesium sulfate and concentrated. The crude residue was purified by a flash silica column (50% ethyl acetate/hexane) to get an aminopyridine product (730 mg, 68%).

TABLE IIIa

The following amino-pyridines were prepared using similar procedures to those described in Scheme 7a using the appropriate ketones from Table Ib.

Entries

1

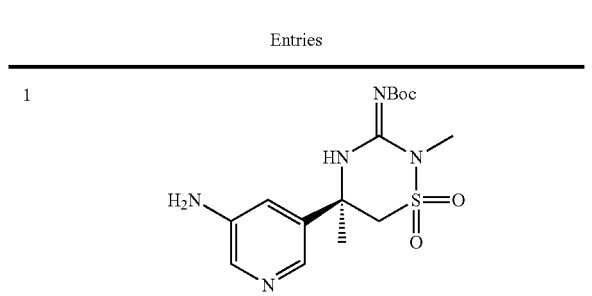

TABLE IIIa-continued

The following amino-pyridines were prepared using similar procedures to those described in Scheme 7a using the appropriate ketones from Table Ib.

Entries

2

3

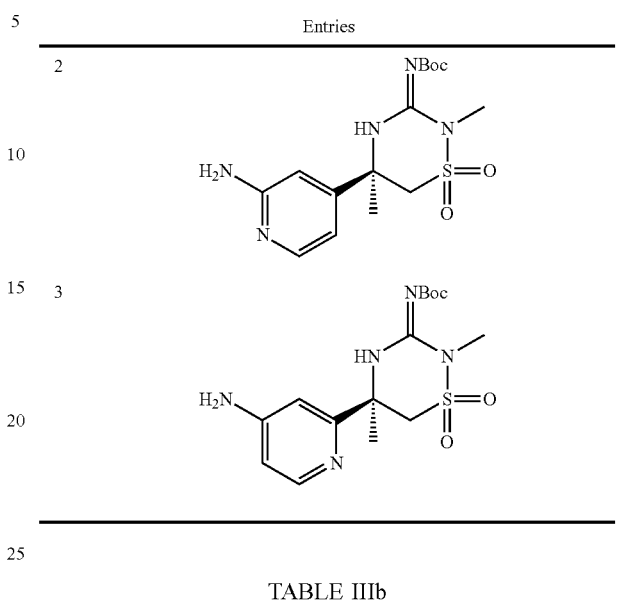

TABLE IIIb

The following compound was prepared from the bromide (Table IIb entry 16) using methods similar to those described in Scheme 7b:

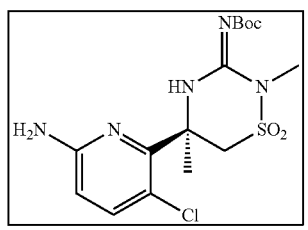

Scheme 7c:

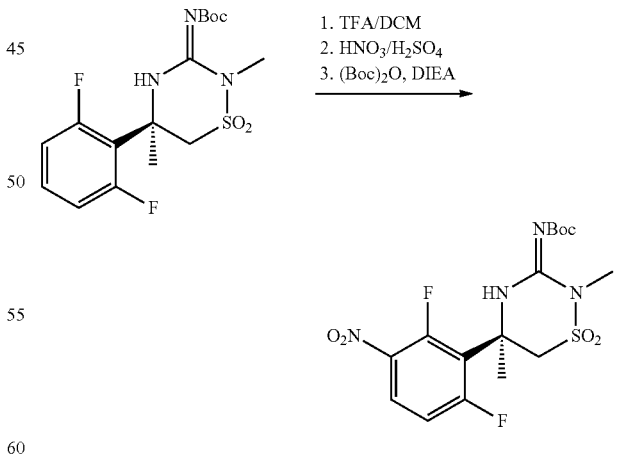

To a solution of a halophenyl thiadiazine (Table IId, entry 1: 2.31 g, 5.9 mmol) in 5 mL of DCM was added 1 mL of TFA. The mixture was stirred for 4 h and then concentrated. At 0° C., to a solution of this crude residue in 4 mL of sulfuric acid was carefully added a mixture of 0.5 mL of fuming nitric acid and 1.2 mL of sulfuric acid. The mixture was stirred at 0° C. for 2 h and then poured into 150 mL of ice. The mixture was neutralized by carefully adding saturated sodium bicarbonate solution and solid sodium hydroxide. The resulting mixture was extracted with ethyl acetate, and the combined organic layers were dried over magnesium sulfate and concentrated. This crude residue was dissolved in 20 mL of DCM, and (Boc)₂O (1.29 g, 5.9 mmol), and DIEA (2.56 mL, 14.75 mmol) were added. The reaction was stirred overnight, and then quenched with 1N HCl. The mixture was extracted with DCM, the organic portions were combined, dried over magnesium sulfate, and concentrated. The crude residue was purified by a flash silica column (25% ethyl acetate/hexane) to give a nitrophenyl thiadiazine product (1.93 g, 76% yield).

TABLE IIIc

The following compounds were made using methods similar to those described 7c starting from the appropriate starting materials shown in Table IIb:

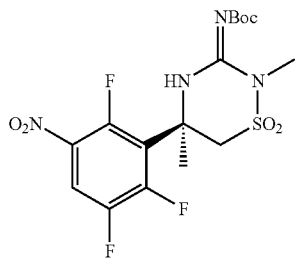

1

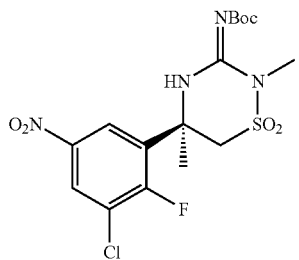

2

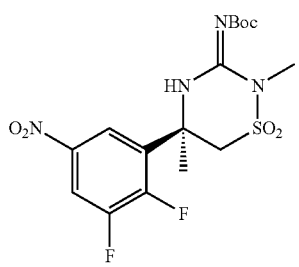

3

TABLE IIIc-continued

The following compounds were made using methods similar to those described 7c starting from the appropriate starting materials shown in Table IIb:

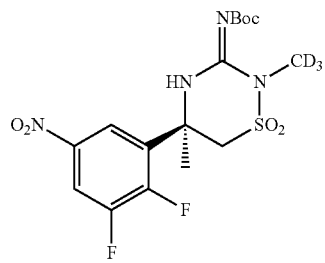

4

TABLE IIId

The following compound was made from Ex. 14f using methods similar to those described in Scheme 7c, omitting the initial treatment with TFA:

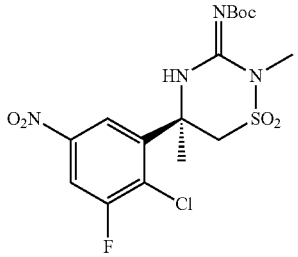

Scheme 8:

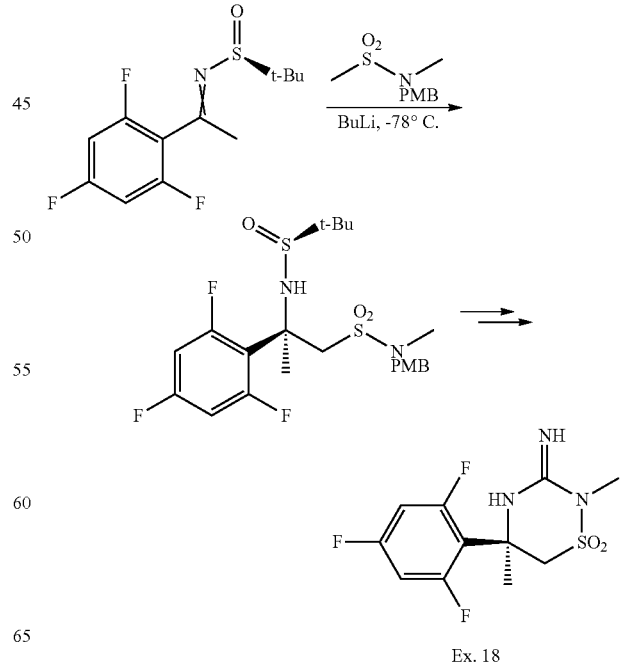

Ex. 18

To a solution of N-(4-methoxybenzyl)-N-methylmethane-sulfonamide (26.8 g, 117 mmol) in THF (200 mL) at −78° C. was added n-butyllithium (2.5 M in hexanes, 47 mL, 118 mmol) over 10 minutes. After the addition was complete, the mixture was allowed to stir at −78° C. for 1 h.

To this mixture was then added a solution of (S)-2-methyl-N-(1-(2,4,6-trifluorophenyl)ethylidene)propane-2-sulfinamide (21.6 g, 77.9 mmol, prepared from 2,4,6-trifluoroacetophenone and (S)-2-methyl-2-propanesulfinamide according to Scheme 1a, Step 1) in THF (150 mL) at −78° C. The resulting mixture was allowed to stir at −78° C. for 4 h. At that time, the reaction was quenched by rapid dilution with water (~400 mL). The mixture was then warmed to RT, further diluted with EtOAc and brine. The phases were separated, and the aqueous layer was extracted with EtOAc (4×). The organic portions were combined, washed with brine, dried over MgSO$_4$, filtered and concentrated. This crude residue was subjected to column chromatography (600 g silica, 100 mL/min, 0% to 60% EtOAc/hexanes) to give (R)-2-((S)-1,1-dimethylethylsulfinamido)-N-(4-methoxybenzyl)-N-methyl-2-(2,4,6-trifluorophenyl)propane-1-sulfonamide as a 4:1 mixture with its diastereomer (14.5 g total mass, 37%).

This material was further subjected to SFC chromatography (TharSFC80, Chiralpak OJ-H, 21×250 mm, 5 μm, 200 bar with 5% MeOH, 55 g/min, 35° C.) to give (R)-2-((S)-1,1-dimethylethylsulfinamido)-N-(4-methoxybenzyl)-N-methyl-2-(2,4,6-trifluorophenyl)propane-1-sulfonamide).

The above material was treated according to Scheme 1a, Steps 4-6 to afford Example 18, dihydro-2,5(R)-dimethyl-5-(2,4,6-trifluorophenyl)-2H-1,2,4-thiadiazin-3(4H)-imine-1,1-dioxide. LCMS (conditions A): $t_R$=1.45 min, m/e=308.2 (M+H).

Scheme 9:

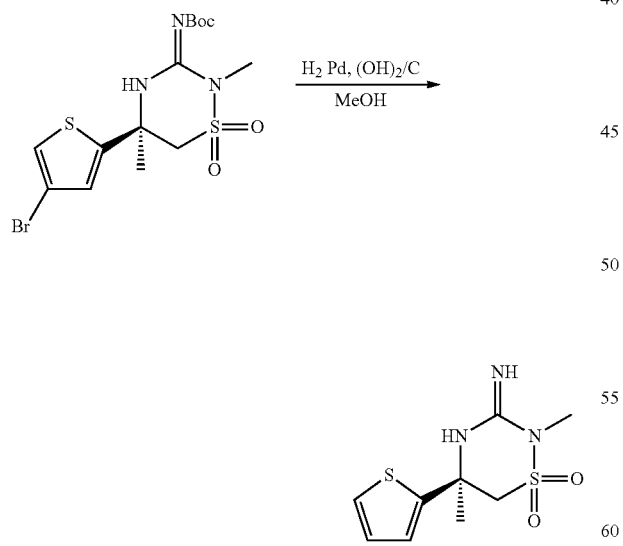

To a degassed solution the tert-butyl carbamate (Scheme 3) (348 mg, 0.794 mmol) in MeOH (10 mL) was added 20% Pd(OH)$_2$/C (50% water) (52 mg, 0.074 mmol). The flask was purged with H$_2$ and allowed to stir at RT under a balloon of H$_2$ for 2.75 hours. The mixture was purged with N$_2$, filtered through Celite and concentrated. The crude product was purified via flash chromatography (SiO$_2$: gradient elution 100:0 to 95:5 CH$_2$Cl$_2$:MeOH) to afford Ex. 19 (69 mg). LCMS (conditions A): $t_R$=2.00 min, m/e=260.1 (M+H).

Scheme 9a:

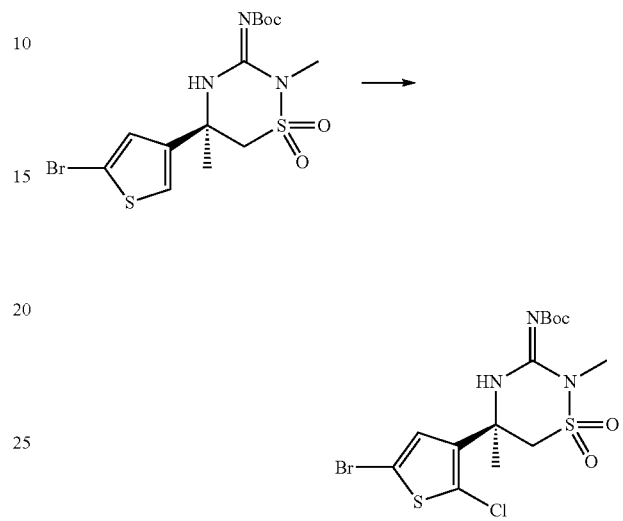

To the bromide (Table IIb, entry 13) (0.8 g, 1.8 mmol) in DMF (6 mL) was added N-chlorosuccinimide (0.7 g, 5.5 mmol). The reaction was warmed to 60° C. and stirred for 5 h. Ethyl acetate was added and the mixture was washed with saturated NaHCO$_3$ (aq), water, and brine. The organic layer was dried (MgSO$_4$), filtered, and concentrated in vacuo. The residue was purified by silica gel chromatography (0-30% EtOAc/hex over 30 minutes) to provide a white foam that was further purified by reverse phase chromatography (C18: gradient elution, 90:10:0.1 to 0:100:0.1 water:MeCN:formic acid) to afford the chlorothiophene (0.63 g, 1.3 mmol).

Scheme 10:

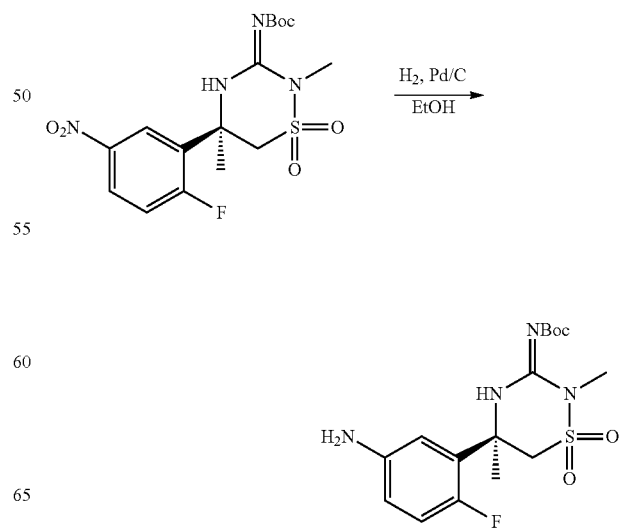

A solution of the nitro compound (Scheme 3b) (2.50 g, 6.0 mmol) in EtOH (150 mL) was degassed by bubbling $N_2$ through the solution for 3 min. To this solution was added Pd/C (10% w/w, 50% $H_2O$, 698 mg.). The mixture was placed under an atmosphere of $N_2$. The atmosphere was evacuated and back-filled with $H_2$ (3×). The resulting mixture was stirred at RT under a $H_2$ balloon for 2 h. The mixture was purged by bubbling $N_2$ through it, filtered through Celite and concentrated. The product was purified by filtering through a small plug of silica gel column eluting with EtOAc to afford the aniline (2.2 g, 97%).

TABLE IV

The following anilines were prepared from the corresponding nitro compounds using a procedure similar to that described in Scheme 10.

Entries

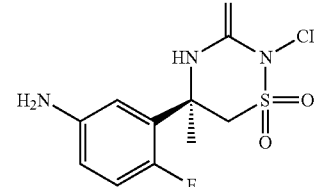

1

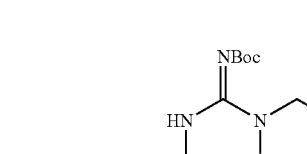

2

TABLE IV-continued

The following anilines were prepared from the corresponding nitro compounds using a procedure similar to that described in Scheme 10.

Entries

3

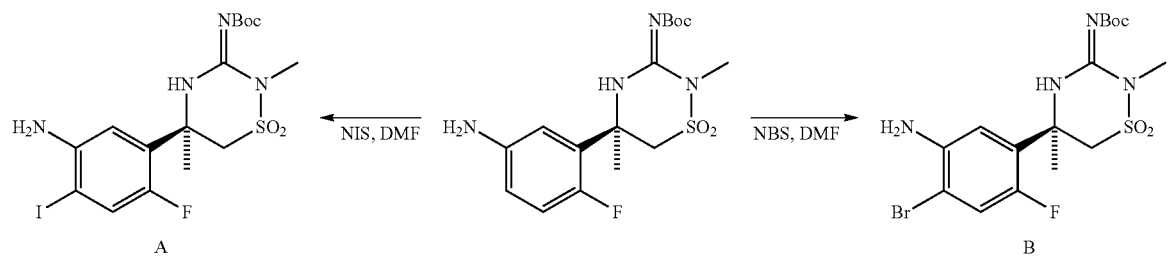

4

5

Scheme 10a:

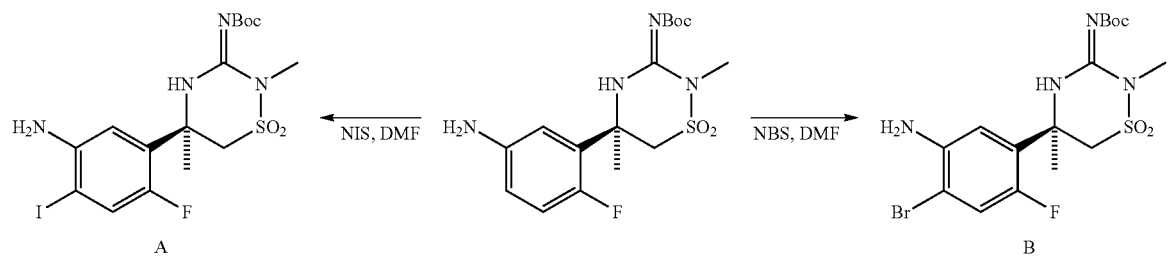

Iodoaniline a Preparation:

NIS (2.52 g, 11.2 mmol) was added at 0° C. to a solution of the aniline (3.6 g, 9.31 mmol, Scheme 10) in DMF (40 mL). After 60 minutes at 0° C. and 60 min at RT, the reaction was quenched with saturated aq. NaHCO$_3$ (aq), extracted with EtOAc (3×), and the combined organic layers dried over Na$_2$SO$_4$. After removal of the volatiles under reduced pressure, the residue was subjected to silica gel chromatography (gradient elution 100:0 to 70:30 hexanes:EtOAc) to give the iodoaniline (3.2 g, 67%).

Bromoaniline B Preparation:

NBS (1.05 g, 6.21 mmol) was added at RT to a solution of the aniline (2.0 g, 5.17 mmol, Scheme 10) in DMF (21 mL). After 30 minutes, the reaction was quenched with 10% aq. Na$_2$SO$_3$ (aq), diluted with EtOAc, and the organic layer was washed with saturated aq. NaHCO$_3$ (2×), brine (1×) and dried over Na$_2$SO$_4$. After removal of the volatiles under reduced pressure, the residue (2.57 g) was subjected to silica gel chromatography (gradient elution 100:0 to 50:50 hexanes:EtOAc) to give the bromoaniline (2.065 g, 86%).

Scheme 11a:

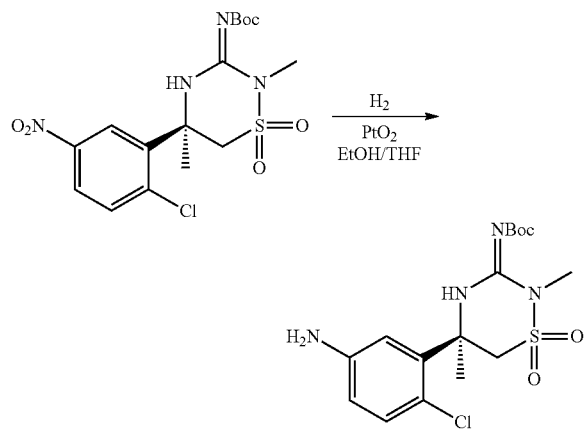

A solution of the nitro compound (Entry 9, Table IIb) (515 mg, 1.19 mmol) in 1:1 EtOH:THF (24 mL) in a pressure vessel was degassed by bubbling N$_2$ through it for 5 min. To this solution was added PtO$_2$ (27 mg, 0.12 mmol). The vessel was sealed. The vessel was then evacuated and backfilled with N$_2$ (3×). The vessel was then evacuated and purged with H$_2$ (3×). The vessel was pressurized to 60 psi with H$_2$ and shaken at RT overnight. After that time, the vessel was purged with. N$_2$. The mixture was then filtered through Celite. The solvent was removed in vacuo to afford the aniline (500 mg, 100%).

TABLE IVa

The following compound was prepared from the corresponding nitro compound (Table IIId) according the methods described in Scheme 11a:

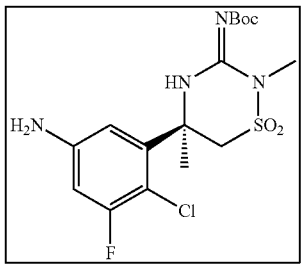

Scheme 11b:

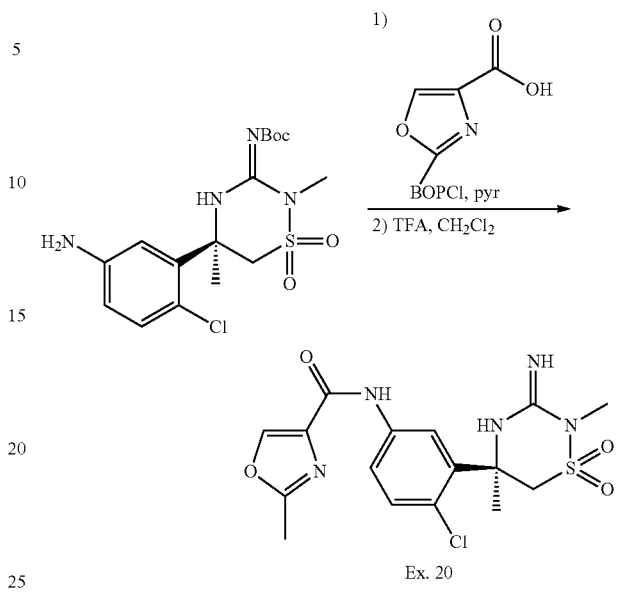

Step 1:

To a flask containing the aniline (Scheme 11a) (100 mg, 0.25 mmol) and 2-methyl-1,3-oxazole-4-carboxylic acid (47 mg, 0.37 mmol) was added BOPCl (145 mg, 0.57 mmol). The flask was sealed and purged with N$_2$. To the flask was added pyridine (1.0 mL). The resultant solution was stirred at RT for 1 hour. After that time, the solution was partitioned between EtOAc and water. The mixture was filtered through Celite to remove the solids. The aqueous layer was extracted with EtOAc (3×). The combined organic layers were washed with brine, dried over Na$_2$SO$_4$, filtered and concentrated. The crude product was purified via flash chromatography (SiO$_2$: gradient elution 100:0 to 65:35 hexanes:EtOAc) to afford the amide (81 mg, 64%).

Step 2:

To a solution of the amide from step 1 (81 mg, 0.16 mmol) in CH$_2$Cl$_2$ (1.5 mL) was added TFA (1.5 mL). The resultant solution was stirred at RT for 2 hours. The solution was concentrated in vacuo to afford Ex. 20 (83 mg) as the trifluoroacetate salt. LCMS data: (method D): t$_R$=1.75 min, m/e 412.0 (M+H).

Scheme 11c:

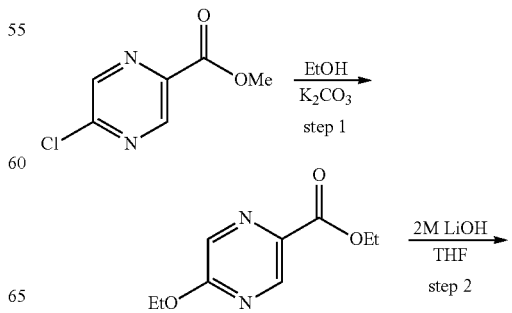

-continued

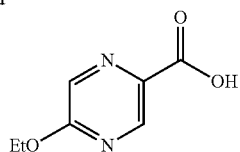

Step 1:
To a slurry of methyl 5-chloropyrazine-2-carboxylate (250 mg, 1.45 mmol) in EtOH (5 mL) was added potassium carbonate (300 mg, 2.18 mmol). The resultant solution was stirred at RT for 2 hours. The mixture was concentrated. The residue was partitioned between water and CH$_2$Cl$_2$. The aqueous layer was extracted with CH$_2$Cl$_2$ (3×). The combined organic layers were dried over Na$_2$SO$_4$, filtered and concentrated to afford ethyl 5-ethoxypyrazine-2-carboxylate (110 mg, 39%) as a yellow solid.

Step 2:
To a solution of the material from step 1 (110 mg, 0.60 mmol) in THF (3 mL) was added a solution of LiOH (2M in water, 0.90 mL, 1.8 mmol). The solution was stirred at RT for 1 h. The solution was adjusted to pH 1 using 1M HCl (aq.). The aqueous layer was extracted with EtOAc (3×). The combined organic layers were dried over Na$_2$SO$_4$, filtered and concentrated to afford the acid (75 mg, 74%).

TABLE IVb

The following pyrazine carboxylic acids were prepared using a procedure similar to that described in Scheme 11c using the appropriate alcohol in step 1. Modifications for specific examples are listed below the table.

| Entries | |
|---|---|
| 1 | ![structure: F3CCH2O-pyrazine-COOH] |
| 2[a] | ![structure: MeOCH2CH2O-pyrazine-COOH] |
| 3[b] | ![structure: BnOCH2CH2O-pyrazine-COOH] |
| 4[a] | ![structure: propyl-O-pyrazine-COOH] |
| 5[b] | ![structure: cyclopropylmethyl-O-pyrazine-COOH] |
| 6[c] | ![structure: isobutyl-O-pyrazine-COOH] |
| 7 | ![structure: D3C-O-pyrazine-COOH] |

[a]Step 1 modification: the ether was purified via flash chromatography (SiO$_2$ gradient elution 100:0 to 70:30 hexanes:EtOAc).
[b]Step 1 modification: the ether was purified via flash chromatography (C$_{18}$ gradient elution 90:10:0.1 to 0:100:0.1 water:MeCN:formic acid).
[c]Step 2 modification: the pyrazine acid was purified via flash chromatography (C$_{18}$ gradient elution 90:10:0.1 to 0:100:0.1 water:MeCN:formic acid).

Scheme 11d:

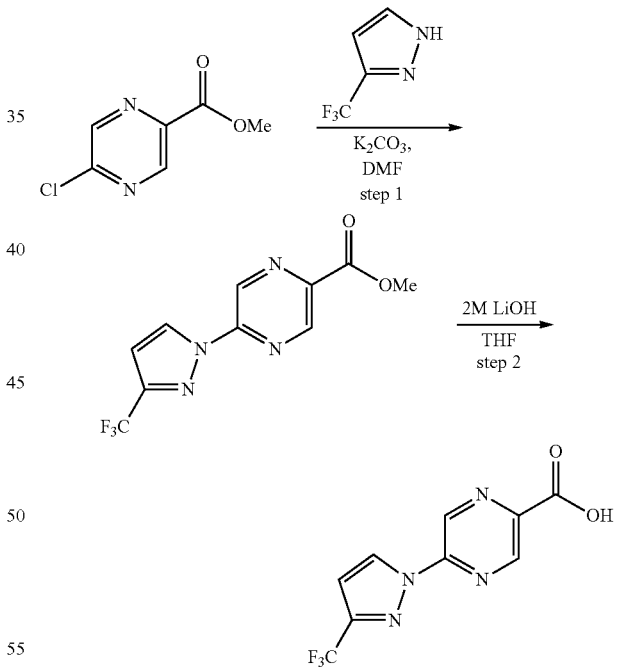

Step 1:
To a solution of methyl 5-chloropyrazine-2-carboxylate (500 mg, 2.90 mmol) and 3-(trifluoromethyl)-1H-pyrazole (591 mg, 4.35 mmol) in DMF (7 mL) was added potassium carbonate (591 mg, 4.35 mmol). The resultant solution was stirred at RT overnight. The mixture was partitioned between water and EtOAc and separated. The organic layer was dried over Na$_2$SO$_4$, filtered and concentrated to afford the biaryl ester (560 mg, 71%).

Step 2:

The acid was formed using a procedure similar to that described in Scheme 11c step 2.

TABLE IVc

The following pyrazine carboxylic acids were prepared using a procedure similar to that described in Scheme 11d using the appropriate pyrazole.

Entries

Scheme 11e:

extracted with $CH_2Cl_2$ (3×). The combined organic layers were dried over $Na_2SO_4$, filtered and concentrated. The residue was purified via flash chromatography ($SiO_2$ gradient elution 100:0 to 10:90 hexanes:EtOAc) to afford the biaryl ester (560 mg, 88%).

Step 2:

The acid was formed using a procedure similar to that described in Scheme 11c step 2.

Scheme 11f:

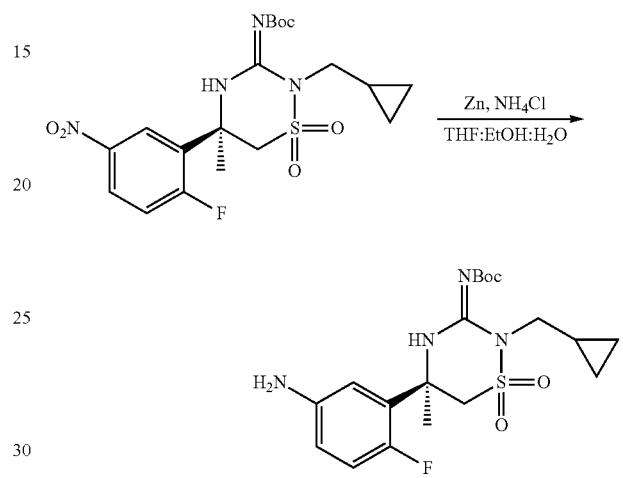

A solution of the nitro compound (Table IIe, entry 1, 1.70 grams, 3.7 mmol) in THF:EtOH:$H_2O$ (30 mL, 3:1:0.3) was degassed by bubbling $N_2$ through the solution for 3 min. To the solution was added Zn (2.4 g, 37 mmol) and $NH_4Cl$ (996 mg, 18 mmol). The resultant mixture was heated to reflux under an atmosphere of $N_2$ for 3 hours. The mixture was filtered through celite and concentrated. The residue was purified via reverse phase flash chromatography ($C_{18}$, gradient elution 90:10:0.1 to 0:100:0.1 $H_2O$:MeCN:formic acid). The resultant formate salt was partitioned between EtOAc and sat $NaHCO_3$ (aq.). The aqueous layer was extracted with EtOAc (3×). The combined organic layers were dried over $Na_2SO_4$, filtered and concentrated to afford the aniline (847 mg, 54%).

TABLE IVd

The following compounds were prepared according the methods described in Scheme 11f except they were purified via $SiO_2$ flash chromatography:

Entries

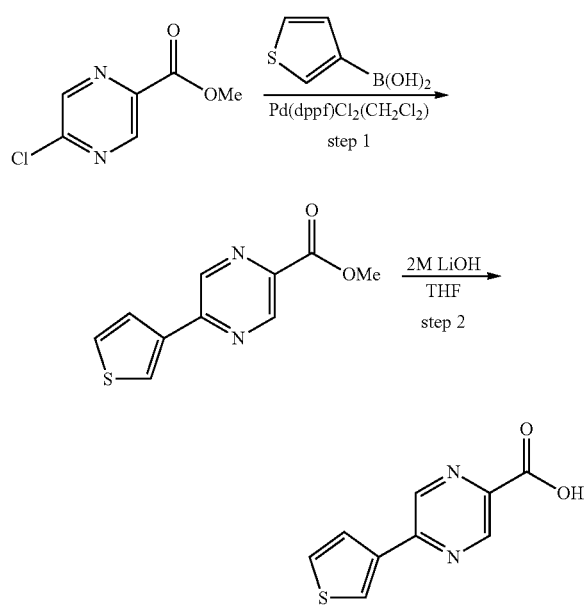

Step 1:

A degassed mixture of 5-chloropyrazine-2-carboxylate (500 mg, 2.90 mmol), $Cs_2CO_3$ (1.1 g, 3.5 mmol), Pd(dppf)$Cl_2.CH_2Cl_2$ (237 mg, 0.29 mmol) and thiophen-3-ylboronic acid (445 mg, 3.5 mmol) in dioxane (10 mL) was heated to reflux for 2 hours. The mixture was concentrated. The residue was partitioned between water and $CH_2Cl_2$ and filtered through Celite. The aqueous layer of the filtrate was

TABLE IVd-continued

The following compounds were prepared according the methods described in Scheme 11f except they were purified via SiO₂ flash chromatography:

| Entries |
| --- |
| 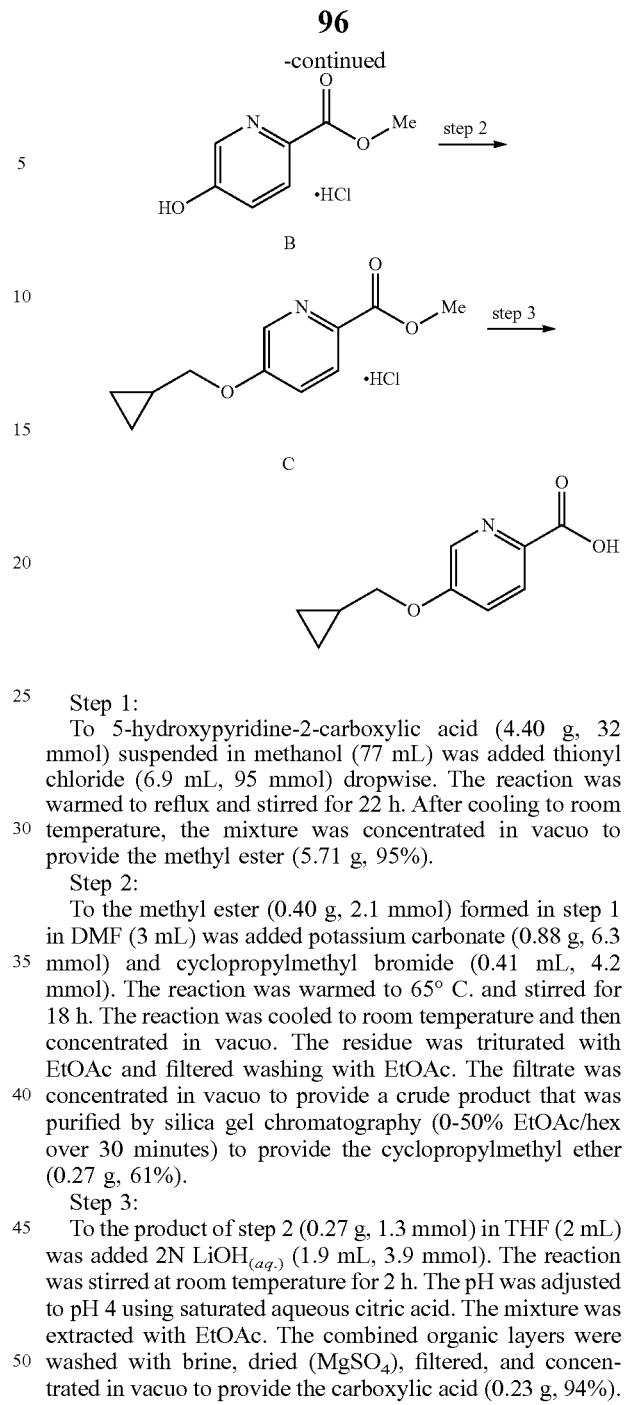 2 |
| 3 |
| 4 |
| 5 |

Scheme 11g:

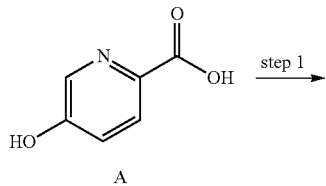

A

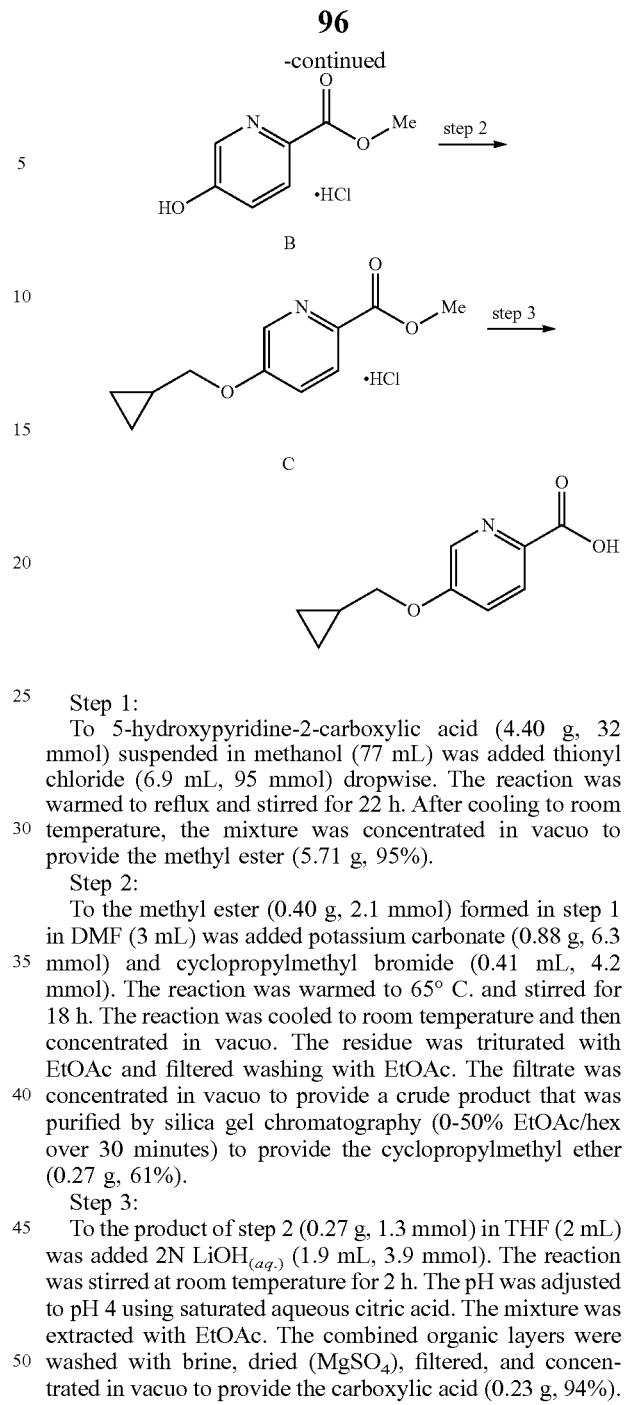

B

C

Step 1:
To 5-hydroxypyridine-2-carboxylic acid (4.40 g, 32 mmol) suspended in methanol (77 mL) was added thionyl chloride (6.9 mL, 95 mmol) dropwise. The reaction was warmed to reflux and stirred for 22 h. After cooling to room temperature, the mixture was concentrated in vacuo to provide the methyl ester (5.71 g, 95%).

Step 2:
To the methyl ester (0.40 g, 2.1 mmol) formed in step 1 in DMF (3 mL) was added potassium carbonate (0.88 g, 6.3 mmol) and cyclopropylmethyl bromide (0.41 mL, 4.2 mmol). The reaction was warmed to 65° C. and stirred for 18 h. The reaction was cooled to room temperature and then concentrated in vacuo. The residue was triturated with EtOAc and filtered washing with EtOAc. The filtrate was concentrated in vacuo to provide a crude product that was purified by silica gel chromatography (0-50% EtOAc/hex over 30 minutes) to provide the cyclopropylmethyl ether (0.27 g, 61%).

Step 3:
To the product of step 2 (0.27 g, 1.3 mmol) in THF (2 mL) was added 2N LiOH$_{(aq.)}$ (1.9 mL, 3.9 mmol). The reaction was stirred at room temperature for 2 h. The pH was adjusted to pH 4 using saturated aqueous citric acid. The mixture was extracted with EtOAc. The combined organic layers were washed with brine, dried (MgSO₄), filtered, and concentrated in vacuo to provide the carboxylic acid (0.23 g, 94%).

Scheme 11h:

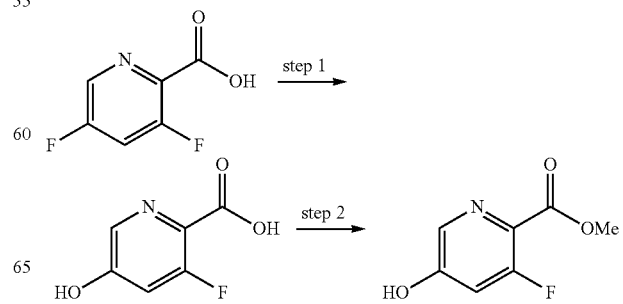

Step 1:

To 3,5-difluoropyridine-2-carboxylic acid (3.0 g, 19 mmol) in THF (30 mL) in a glass tube reaction vessel was added 2N LiOH$_{(aq)}$. The reaction mixture was capped and warmed to 100° C. The reaction was stirred for 18 h and then cooled to room temperature. TFA (5 mL) was added and the reaction was concentrated in vacuo. The residue was purified by reverse phase chromatography [C18 (360 g) 0.1% formic acid/water for 20 minutes followed by 0-100% 0.1% formic acid/acetonitrile/0.1% formic acid/water] to provide the hydroxy pyridine (2.1 g) as a ~1:1 mixture of starting material and product. The mixture was carried on directly.

Step 2:

To the hydroxy pyridine prepared in the previous step (2.1 g) in methanol (20 mL) was added thionyl chloride (2.2 mL, 31 mmol). The reaction was warmed to 70° C. and stirred for 18 h. The reaction was cooled to room temperature and concentrated in vacuo. The residue was purified by reverse phase chromatography [C18 (205 g), 0-100% over 20 minutes 0.1% formic acid/acetonitrile/0.1% formic acid/water] to provide the methyl ester (1.0 g, 31% over 2 steps).

Scheme 11i

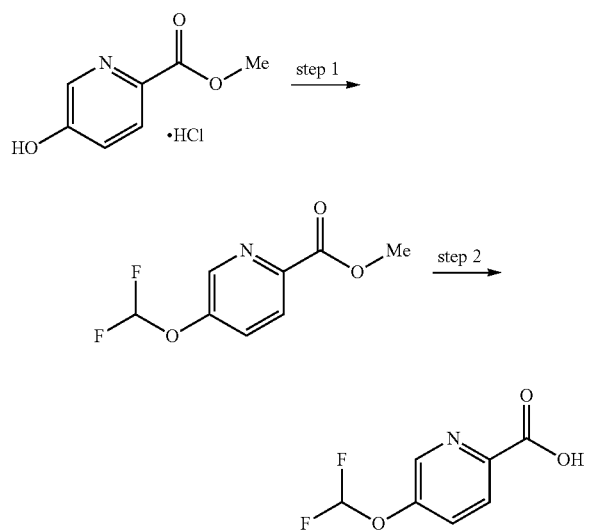

Step 1:

To the methyl 5-hydroxypicolinate hydrochloride prepared in step 1 of Scheme 11g (0.21 g, 1.1 mmol) in a glass tube reactor in acetonitrile (4 mL) was added water (4 mL), potassium carbonate (5.5 g, 40 mmol) and 2-chloro-2,2-difluoroacetophenone (1.0 g, 5.5 mmol). The reaction vessel was capped and warmed to 80° C. The reaction was stirred at 80° C. for 3 h and cooled to room temperature. The mixture was filtered washing with ether. The filtrate was washed with ether. The ether washes were combined and washed with water and brine, dried (MgSO$_4$), filtered, and concentrated in vacuo to provide a tan oil. The oil was purified by silica gel chromatography (0-40% EtOAc/hex over 30 minutes) to provide the ether (0.13 g, 60%).

Step 2:

Using the procedure described in step 3 of Scheme 11g, the product of step 1 was converted to the carboxylic acid.

Scheme 11j:

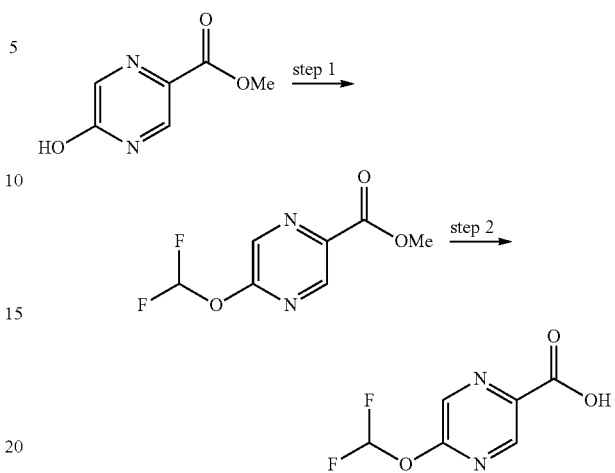

Step 1:

To 5-hydroxypyrazine-2-carboxylic acid methyl ester (2.0 g, 13 mmol) in a glass tube reaction vessel in DMF (26 mL) was added potassium carbonate (5.3 g, 39 mmol) and sodium 2-chloro-2,2-difluoroacetate (4.0 g, 26 mmol). The reaction vessel was capped and warmed to 100° C. The reaction was stirred for 30 minutes and cooled to room temperature. The reaction was filtered washing with EtOAc. The filtrate was concentrated in vacuo. The residue was taken up into EtOAc and washed with brine. The organic layer was dried (MgSO$_4$), filtered, and concentrated in vacuo. The residue was purified by silica gel chromatography (0-40% EtOAc/hex) to give methyl-5-(difluoromethoxy)pyrazine-2-carboxylate (0.09 g, 0.46 mmol) (0.40 g, 20%).

Step 2:

To the product of step 1 (0.09 g, 0.46 mmol) was added 3N HCl$_{(aq)}$. The reaction was heated in a sealed microwave reactor vial to 100° C. for 2 h. The reaction was concentrated in vacuo to provide the carboxylic acid (0.88 g, 100%).

TABLE IVf

The following pyridine carboxylic acids were prepared from either intermediate B, Scheme 11g or the hydroxypyridine from Scheme 11h using conditions similar to those described in Scheme 11g steps 2 and 3. Modifications of the experimental conditions are noted below the table.

| Entry | |
|---|---|
| 1[a] | ![structure] |
| 2[b] | ![structure] |

TABLE IVf-continued

The following pyridine carboxylic acids were prepared from either intermediate B, Scheme 11g or the hydroxypyridine from Scheme 11h using conditions similar to those described in Scheme 11g steps 2 and 3. Modifications of the experimental conditions are noted below the table.

| Entry | |
|---|---|
| 3[b] | 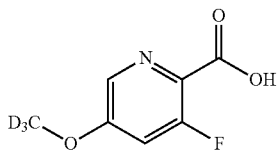 [SMILES: [2H]C([2H])([2H])Oc1cnc(C(=O)O)c(F)c1] |
| 4[b] | 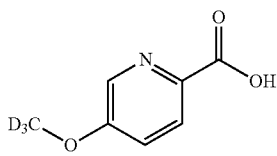 [SMILES: [2H]C([2H])([2H])Oc1ccc(C(=O)O)nc1] |
| 5[c,g] | 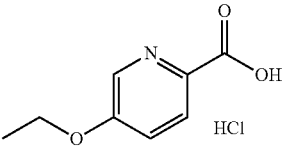 |
| 6[c,g] | 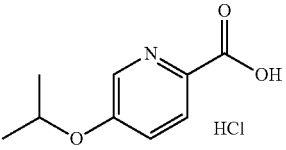 |
| 7[f] | 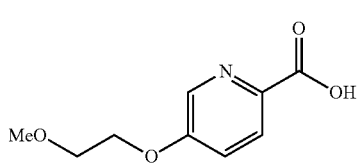 [SMILES: COCCOc1ccc(C(=O)O)nc1] |
| 8[d] | 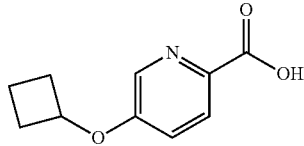 [SMILES: O=C(O)c1ccc(OC2CCC2)cn1] |
| 9[e] | 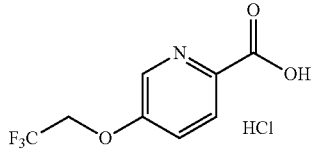 |

Alkylation conditions:
[a] $Cs_2CO_3$, NaI, 150° C., 7 h;
[b] rt;
[c] 45° C.;
[d] 100° C.;
[e] 130° C., microwave, 1 h;
[f] 70° C.
Hydrolysis conditions: g: See Scheme 11j, step 2.

Scheme 11k:

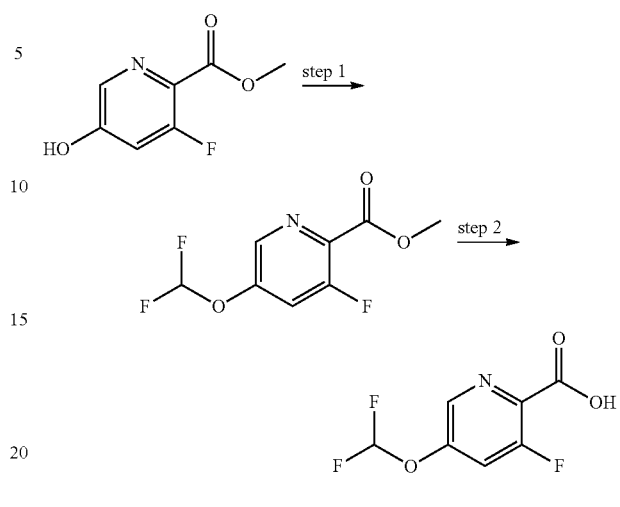

Step 1:

To the hydroxypyridine prepared in Scheme 11h (0.19 g, 1.1 mmol) in acetonitrile (4 mL) and water (4 mL) was added potassium carbonate (5.5 g, 40 mmol) and 2-chloro-2,2-difluoroacetophenone. The glass reaction tube was sealed and warmed to 80° C. After 3.5 h, the reaction was cooled to room temperature and filtered washing with EtOAc. The filtrate was extracted with ether. The combined ether layers were washed with water and brine, dried ($MgSO_4$), filtered, and concentrated in vacuo. The residue was purified by silica gel chromatography (0-30% EtOAc/hex over 30 minutes) to provide product (0.15 g, 60%).

Step 2:

The product of step 1 was converted to the carboxylic acid using the conditions found in step 3 of Scheme 11g.

Scheme 11l:

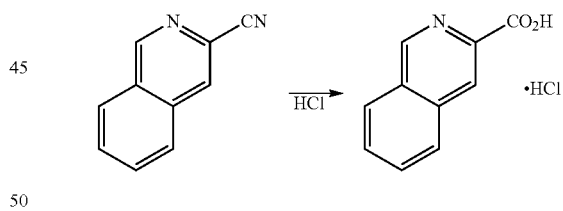

3-Cyanoisoquinoline (1.047 g, 6.79 mmol) was suspended in 6 M HCl (aq) (50 mL) and refluxed at 95° C. for 18 h. The reaction was cooled to RT, and the volatiles removed under vacuum to provide the carboxylic acid (2.07 g) that was used as is.

Scheme 11m:

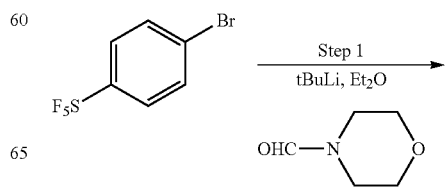

-continued

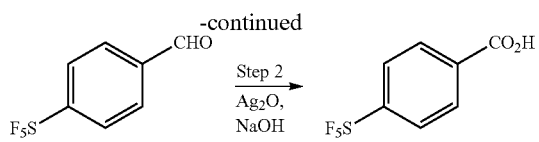

4-Pentafluorosulfur benzoic acid was obtained in two steps from 4-bromophenyl sulfurpentafluoride according to the literature procedure by Zarantonello et al., *J. Fluor. Chem.* 2007, 128, 1449-1453.

Scheme 11n:

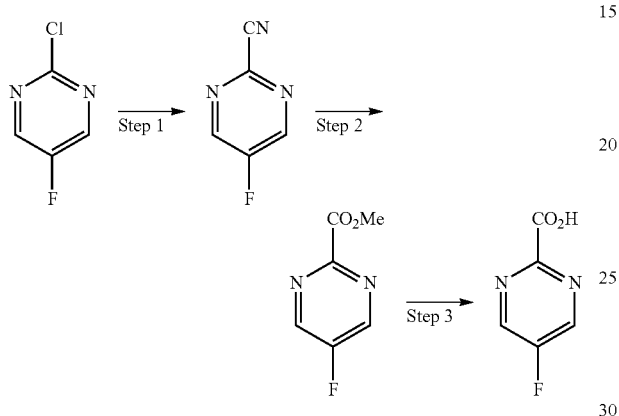

Step 1:

To 2-chloro-5-fluoropyrimidine (2 g, 15 mmol) in a 250-mL round bottom flask was added DMA (8 mL), tris(dibenzylideneacetone)dipalladium (0.544 g, 0.6 mmol), 1,1'-bis(diphenylphosphino)ferrocene (0.67 g, 1.2 mmol), zinc cyanide (1.15 g, 9.8 mmol), and zinc dust (0.237 g, 3.62 mmol). The flask was capped, flushed with nitrogen, and stirred for 2.5 h at 100° C. The reaction was cooled to room temperature, filtered through celite, and washed with DCM. The filtrate was poured into water and extracted with DCM. The combined organic layers were dried (MgSO$_4$), filtered, and concentrated in vacuo. The residue was purified by silica gel chromatography (0-10% EtOAc/hexanes over 20 minutes) to provide the nitrile compound (0.58 g, 31%).

Step 2:

To the nitrile compound prepared in Step 1 (0.51 g, 4.14 mmol) stirring in 5 mL MeOH was added 5 mL conc. HCl. The reaction was fitted with a reflux condenser and heated at 80° C. for 2 hours, then cooled to room temperature. Saturated aqueous sodium bicarbonate was added and stirred for 1 hour at room temperature. The mixture was acidified to pH 4 using 1 N HCl(aq) and extracted with EtOAc. The combined organic layers were dried (MgSO$_4$), filtered, and concentrated in vacuo to provide the methyl ester (0.256 g, 40%).

Step 3:

To the methyl ester compound prepared in Step 2 (0.256 g, 1.64 mmol) in 6 mL 1:1:1 THF:H$_2$O:MeOH was added LiOH hydrate (0.272 g, 4.04 mmol), and the mixture stirred at room temperature for 1 hour. The reaction was acidified to pH 4 using 1 N HCl (ac$_t$) and extracted with EtOAc. The combined organic layers were dried (MgSO$_4$), filtered, and concentrated in vacuo to provide the carboxylic acid (0.136 g, 58%).

TABLE IVg

The following acids were made using methods similar to those described in Scheme 11n using the appropriate aryl chloride (entries 1-3) or bromide (entries 4 and 5):

| Entries | |
|---|---|
| 1 | pyrimidine-2-CO$_2$H, 4-CF$_3$ |
| 2 | pyrimidine-2-CO$_2$H, 5-Cl |
| 3 | pyrimidine-2-CO$_2$H, 5-OMe |
| 4 | pyrazine-CO$_2$H, 5-cyclopropyl |
| 5 | pyridine-2-CO$_2$H, 5-CD$_3$ |

TABLE IVh

The following acid was made using methods similar to those described in Scheme 11n, Step 3:

| Entry | Starting material | Acid |
|---|---|---|
| 1 | 4-cyclopropyl-thiazole-2-CO$_2$Et | 4-cyclopropyl-thiazole-2-CO$_2$H |

TABLE IVi

The following acid was made according to methods similar to those described in Scheme 11n, using Step 1 and then Step 3, omitting Step 2:

| Entry | Starting material | Acid |
|---|---|---|
| 1 | CO₂Me, Br, OMe (structure) | CO₂H, CN, OMe (structure) |

Scheme 11o:

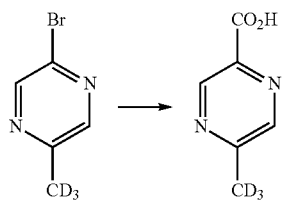

To 2-bromo-5-(methyl-D₃)-pyrazine (400 mg, 2.27 mmol) stirring in 8 mL anhydrous THF at −78° C. under N₂ atmosphere was slowly added n-BuLi (2.5 M in hexanes, 1.14 mL, 2.85 mmol). The reaction was stirred for 30 minutes at this temperature, upon which carbon dioxide was bubbled through the solution for 15 minutes via cannulating needle. The cold bath was removed and the reaction allowed to come to room temperature slowly over 1 hour. Water was then added and the reaction was extracted with ethyl acetate. The organics were combined, dried (MgSO₄), and concentrated in vacuo to provide an oil (120 mg, 38%) that was used without further purification.

3-Fluoro-5-(trifluoromethyl)picolinic acid was prepared from 2-bromo-3-fluoro-5-(trifluoromethyl)pyridine using a procedure similar to that described above in Scheme 11o.

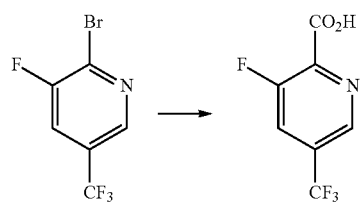 [SMILES: Fc1cc(C(F)(F)F)cnc1Br ; O=C(O)c1ncc(C(F)(F)F)cc1F]

Scheme 11p:

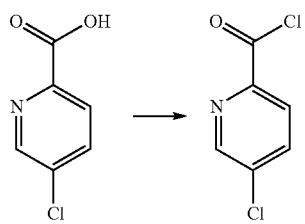

To 5-chloropicolinic acid (0.3 g, 1.9 mmol) stirring at room temperature in 6 mL THF and 1 drop of DMF was slowly added dropwise oxalyl chloride (0.48 mL, 5.7 mmol). Vigourous outgassing was observed. The reaction was stirred at room temperature for 1.5 hours, then concentrated to dryness in vacuo and the product used without further purification.

TABLE IVj

The following acid chlorides were made using methods similar to those described in Scheme 11p from the appropriate carboxylic acid.

Entries 1  (CO₂Cl pyrazine with OMe structure)

2  (CO₂Cl pyridine with CF₃ structure)

Scheme 11q:

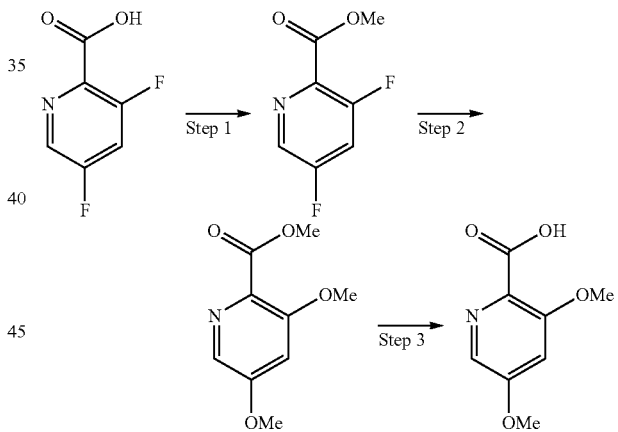

Step 1:

To 3,5-difluoropyridine-2-carboxylic acid (2 g, 12.6 mmol) stirring in 20 mL 4:1 toluene:MeOH at room temperature was slowly added dropwise trimethylsilyldiazomethane (2.0 M in hexanes, 15.1 mmol, 7.5 mL). The reaction was allowed to stir for 30 minutes, and then was concentrated to dryness in vacuo and used without further purification.

Step 2:

To the methyl ester prepared in step 1 (1.09 g, 6.3 mmol) stirring at room temperature in 20 mL MeOH in a 350-mL sealed vessel was added 25 weight % sodium methoxide in methanol (3.4 g sodium methoxide, 13.6 g solution, 63 mmol). The reaction was flushed with nitrogen, sealed, and stirred 16 hours in a 100° C. oil bath. The next day the reaction was cooled to room temperature and acidified to pH 4 using 1 N HCl. The solution was extracted with 1:1

EtOAc:THF (250 mL). The organic layer was dried (MgSO$_4$), filtered, and concentrated in vacuo. The residue was purified by silica gel chromatography (0-60% EtOAc/hexanes over 20 minutes) to provide the desired bis-methoxy compound (0.53 g, 43%).

Step 3:

The methyl ester was converted to the carboxylic acid using methods similar to those described in Scheme 11n, Step 3.

TABLE IVk

The following acids were made using methods similar to those described in Scheme 11q using the appropriate aryl chloride:

| Entries | |
|---|---|
| 1 | CO$_2$H, OMe, OMe pyrazine |
| 2 | CO$_2$H, CF$_3$, OMe pyridine |

Scheme 11r:

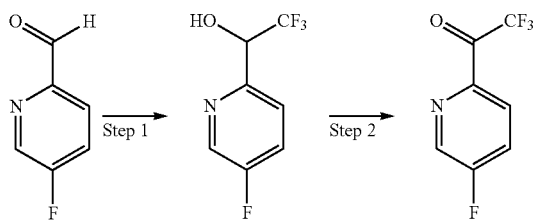

Step 1:

To 2-fluoro-5-formylpyridine (1.57 g, 12.55 mmol) stirring in anhydrous THF (20 mL) at 0° C. under a nitrogen atmosphere was slowly added (trifluoromethyl)-trimethylsilane (2.67 g, 18.78 mmol). The mixture was stirred at 0° C. for 15 minutes, and then tetrabutylammonium fluoride (1.0 M in THF, 31.38 mL, 31.38 mmol) was slowly added dropwise, upon which the ice bath was removed, and the reaction was allowed to stir at room temperature overnight (total reaction time 16 hours). The reaction was then poured into water and extracted with EtOAc. The combined organic layers were dried (MgSO$_4$), filtered, and concentrated in vacuo. The residue was purified by silica gel chromatography (0-20% EtOAc/hexanes over 20 minutes) to provide the trifluoromethyl alcohol product (2.01 g, 82%).

Step 2:

To the trifluoromethyl alcohol prepared in step 1 (1 g, 5.12 mmol) stirring in anhydrous DCM (20 mL) was added Dess-Martin periodinane (2.63 g, 6.14 mmol). The reaction was stirred at room temperature overnight (total reaction time 16 hours). Hexanes were added upon which a precipitate formed. The solid was filtered off and washed with DCM. The filtrate was taken and poured into saturated aqueous sodium bicarbonate and extracted with DCM. The combined organic layers were dried (MgSO$_4$), filtered, and concentrated in vacuo. The residue was purified by silica gel chromatography (0-20% EtOAc/hexanes over 20 minutes) to provide the trifluoromethyl ketone product (0.453 g, 46%).

Scheme 11s:

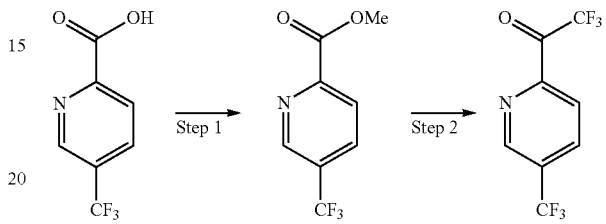

Step 1:

The carboxylic acid (1.5 g, 7.84 mmol) was converted to the methyl ester using methods similar to those described in Scheme 11q, Step 1. The crude reaction was evaporated to dryness in vacuo, and purified by silica gel chromatography (0-30% EtOAc/hexanes over 20 minutes, 30-40% EtOAc/hexane from 20-30 minutes) to provide the methyl ester product as a solid (1.02 g, 63%).

Step 2:

To a mixture of methyl 5-(trifluoromethyl)pyridine-2-carboxylate prepared above (0.2 g, 0.97 mmol) and (trifluoromethyl)trimethylsilane (0.173 g, 1.22 mmol) stirring at −78° C. in pentane (3 mL) under a nitrogen atmosphere was slowly added tetrabutylammonium fluoride (1.0 M in THF, 25 µL, 0.024 mmol). The reaction was allowed to come to room temperature and stirred overnight (total reaction time 16 hours). At that time, 2 N HCl was added, and the mixture was stirred vigorously at room temperature for 2 hours. The solution was extracted with DCM. The combined organic layers were dried (MgSO$_4$), filtered, and concentrated in vacuo. The residue was purified by silica gel chromatography (0-20% EtOAc/hexanes over 20 minutes) to provide the trifluoromethyl ketone product (0.084 g, 35%).

TABLE IVl

The following pyrazine carboxylic acid was prepared using a procedure similar to that described in Scheme 11e.

| Entry 1 | |
|---|---|
| | 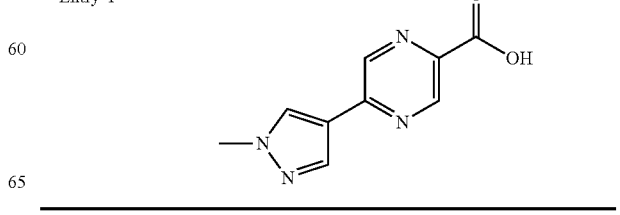 |

Scheme 11t:

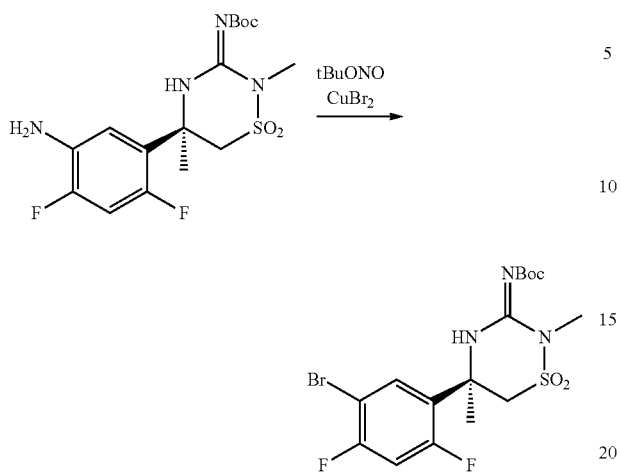

A large microwave tube was charged sequentially with MeCN (9 mL), tert-butyl nitrite (0.15 mL, 1.2 mmol), and copper(II) bromide (0.331 g, 1.48 mmol). The tube was crimp sealed and immersed in an oil bath at 60° C. To the resulting black-green mixture was added a solution of 1,1-dimethylethyl[5(R)-(5-amino-2,4-difluorophenyl)dihydro-2,5-dimethyl-1,1-dioxido-2H-1,2,4-thiadiazin-3(4H)-ylidene]carbamate (Table IV, Entry 2, 500 mg, 1.24 mmol) in MeCN (3 mL) via syringe over ~2 min. After the addition was complete, the reaction was stirred at 60° C. for 20 min. At that time, the reaction was cooled, diluted with EtOAc, and filtered through Celite. The filtrate was diluted with water and EtOAc. The phases were separated and the aqueous layer was extracted 2× with EtOAc. The organic portions were combined, washed with sat. aq. NaHCO$_3$ and brine, dried over MgSO$_4$, filtered, and concentrated. This crude sample was subjected to column chromatography (80 g silica, 60 mL/min, 0% to 50% EtOAc/hexanes) to give product 1,1-dimethylethyl[5(R)-(5-bromo-2,4-difluorophenyl)dihydro-2,5-dimethyl-1,1-dioxido-2H-1,2,4-thiadiazin-3(4H)-ylidene]carbamate (0.30 g, 52%).

Scheme 11u:

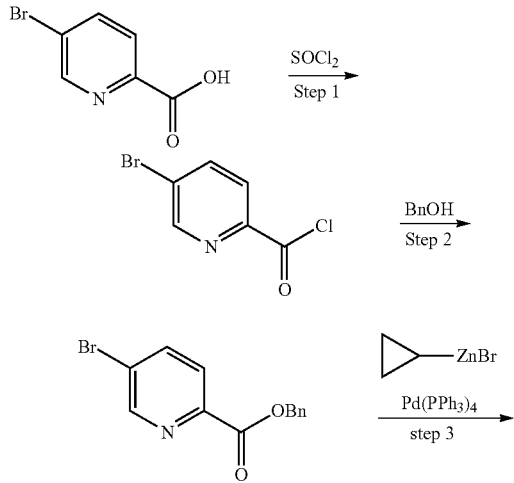

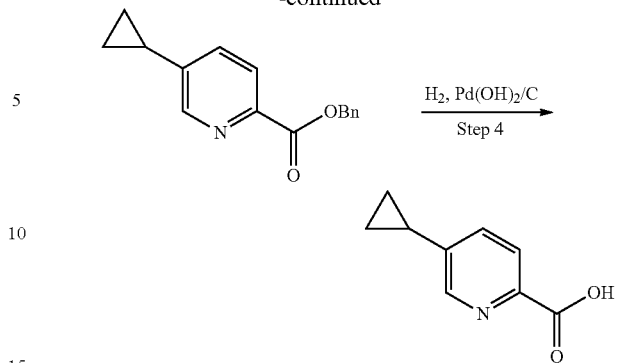

Step 1:

To a suspension of 5-bromopicolinic acid (20.2 g, 100 mmol) in 200 mL of toluene was added thionyl chloride (11 mL, 150 mmol). The mixture was stirred at room temperature for 20 min and then heated to reflux for 30 min. The resulting solution was cooled to room temperature and concentrated to dryness. The crude product 5-bromopicolinoyl chloride was used directly in the next step.

Step 2:

After addition of THF (200 mL) and Et$_3$N (42 mL) to the above residue, the mixture was cooled in an ice-water bath. Benzyl alcohol (31.1 mL, 300 mmol) was added slowly. The mixture was warmed up to room temperature and stirred overnight.

The reaction mixture was diluted with ether, washed with sat, NaHCO$_{3(aq.)}$, H$_2$O, brine and then dried (MgSO$_4$). After concentration and crystallization, the desired product benzyl 5-bromopicolinate (20.6 g) was obtained.

Step 3:

To a solution of benzyl 5-bromopicolinate (876 mg, 3.0 mmol) in THF (10 mL) was added Pd(PPh$_3$)$_4$ (173 mg, 0.15 mmol) under N$_2$. After addition of a solution of cyclopropylzinc bromide in THF (0.5 M, 10 mL), the mixture was heated at 80° C. for 3 hours and then cooled to room temperature. The reaction mixture was quenched with sat. NH$_4$Cl (aq) and extracted with EtOAc (3×). The organic layer was washed with sat. NaHCO$_{3(aq.)}$, brine, and dried (MgSO$_4$). The product benzyl 5-cyclopropylpicolinate (510 mg) was obtained by silica gel chromatography (elution with 0-15% EtOAc/Hex, then 15% EtOAc/Hex).

Step 4:

To a solution of benzyl 5-cyclopropylpicolinate in MeOH (15 mL) was added 20% Pd(OH)$_2$/C (100 mg). The hydrogenolysis with H$_2$ was carried out at room temperature under a H$_2$ balloon. The desired product 5-cyclopropylpicolinic acid (305 mg) was obtained after filtration and concentration.

Scheme 11v:

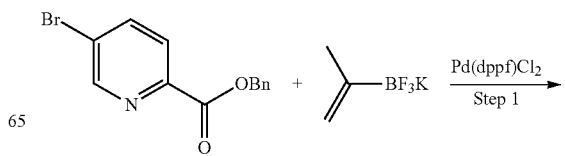

-continued

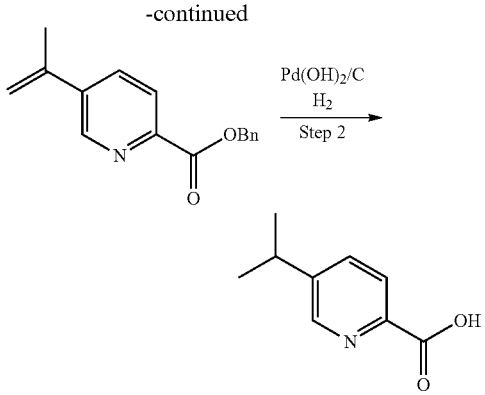

Step 1:
A mixture of benzyl 5-bromopicolinate (2.92 g, 10 mmol), potassium isopropenyl trifluoroborate (3.05 g, 21 mmol), Pd(dppf)Cl$_2$ (445 mg, 0.54 mmol), and Et$_3$N (1.4 mL) in isopropyl alcohol (20 mL) was degassed with N$_2$ and heated at 80° C. for 7 h. The mixture was cooled to room temperature and diluted with EtOAc. The organic layer was washed with H$_2$O, 5% citric acid, sat.NaHCO$_{3(aq.)}$ and brine, then dried (MgSO$_4$) and concentrated. The product benzyl 5-isopropenylpicolinate (1.27 g) was obtained by silica gel chromatography (elution with 0-16% EtOAc/Hex).

Step 2:
A solution of benzyl 5-isopropenylpicolinate (1.27 g, 5 mmol) in MeOH (25 mL) was subjected to hydrogenation with 20% Pd(OH)$_2$/C (200 mg) with a H$_2$ balloon for 2 h. The product 5-isopropenylpicolinic acid (780 mg) was obtained by filtration and concentration.

Scheme 11w:

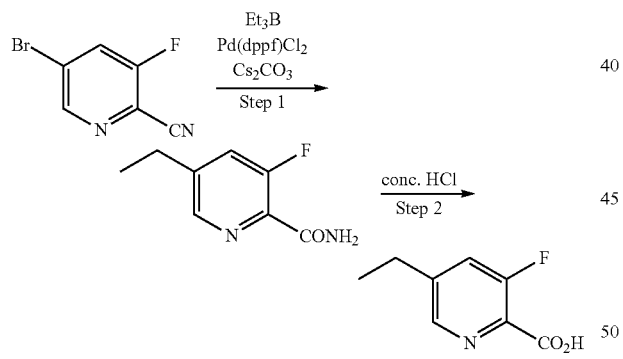

Step 1:
A mixture of 5-bromo-3-fluoropicolinonitrile (1.0 g, 5 mmol), Pd(dppf)Cl$_2$ (82 mg, 0.1 mmol) and cesium carbonate (3.26, 10 mmol) in THF (20 mL) was degassed with N$_2$. After addition of a solution of triethylborane (1.0 M THF, 10 mL), the mixture was heated at 65° C. for 5 h. The mixture was cooled down to room temperature, and then further cooled down in an ice bath. Into the mixture was added a solution of NaOH (1.2 g) in 20 mL of H$_2$O, followed by H$_2$O$_2$ (30% aqueous 7 mL). The mixture was stirred at 0° C. for 30 min and extracted with ether (4×). The organic layer was washed with brine and dried (MgSO$_4$), and concentrated. The product 5-ethyl-3-fluoropicolinamide (370 mg) was obtained from silica gel chromatography (elution with 0-40% EtOAc/Hex).

Step 2:
A mixture of amide (475 mg, 2.8 mmol) in 10 mL of conc. HCl was heated at reflux for 5 h. The mixture was concentrated and dried in vacuo to give the product 5-ethyl-3-fluoropicolinic acid.

Scheme 11x:

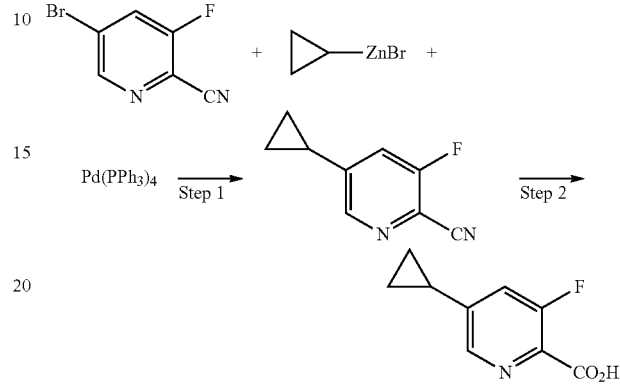

Step 1:
To solution of 5-bromo-3-fluoropicolinonitrile (603 mg, 3.0 mmol) and Pd(PPh$_3$)$_4$ (173 mg, 0.15 mmol) in 10 mL of THF was added cyclopropyl zinc bromide (0.5 M, 10 mL) under N$_2$. After being heated 80° C. for 4 h, the mixture was cooled to room temperature and quenched with sat. NH$_4$Cl (aq). The mixture was extracted with EtOAc (3×) and the combined organic layers were washed with sat. NaHCO$_{3\ (aq.)}$ and brine, dried (MgSO$_4$), and concentrated. The crude product was purified by silica gel chromatography (elution with 0-8% EtOAc/Hex) to afford 5-cyclopropyl-3-fluoropicolinonitrile (406 mg).

Step 2:
The product of step 1 was heated at reflux in 10 mL of conc. HCl overnight. After concentration, the solid product 5-cyclopropyl-3-fluoropicolinic acid (400 mg) was washed with cold water and dried in vacuo.

Scheme 11y:

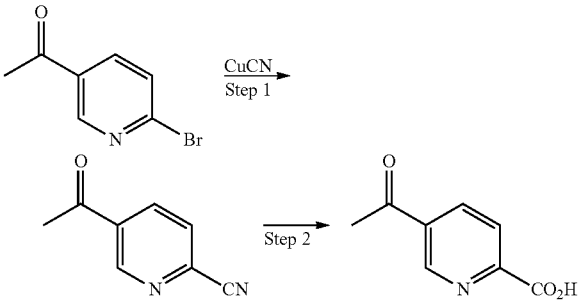

Step 1:
A mixture of 1-(6-bromopyridin-3-yl)ethanone (200 mg, 1.0 mmol) and CuCN (179 mg, 2.0 mmol) in anhydrous DMF (5 mL) was heated at 110° C. for 18 h under N$_2$. The mixture was cooled to room temperature and diluted with water. After addition of EtOAc and filtration, the aqueous layer was extracted with EtOAc. The organic layer was washed with sat. NaHCO$_3$ (aq), brine, and then dried (MgSO$_4$) and concentrated. The product 5-acetylpicolinonitrile (120 mg) was obtained by silica gel chromatography (elution with 0-20% EtOAc/Hex).

Step 2:

5-Acetylpicolinonitrile (146 mg, 1.0 mmol) in 5 mL of conc. HCl was heated at reflux for 2.5 h. The mixture was concentrated and dried in vacuo. The crude product 5-acetylpicolinic acid was used without further purification.

Scheme 11z:

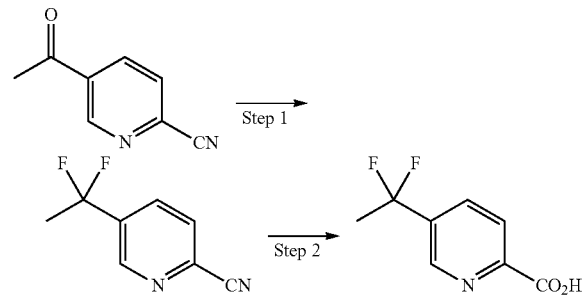

Step 1:

A mixture of 5-acetylpicolinonitrile (146 mg, 1.0 mmol) and Deoxo-Fluor™ (1.0 mL, 50% in toluene) was heated at 80° C. for 3 h under N$_2$. The mixture was cooled to room temperature and diluted with DCM. The organic layer was washed with sat. NaHCO$_3$ $_{(aq.)}$, and brine, dried (MgSO$_4$) and concentrated. The residue was purified by silica gel chromatography (elution with 0-15% EtOAc/Hex) to afford 5-(1,1-difluoroethyl)picolinonitrile (120 mg).

Step 2:

5-(1,1-Difluoroethyl)picolinonitrile (120 mg, 0.71 mmol) in 9 mL of conc. HCl was heated at 110° C. for 5 h. The mixture was concentrated. To the residue was added diisopropylethylamine (2 mL) and the mixture was concentrated. The residue was dried in vacuo and used without further purification.

Scheme 11aa:

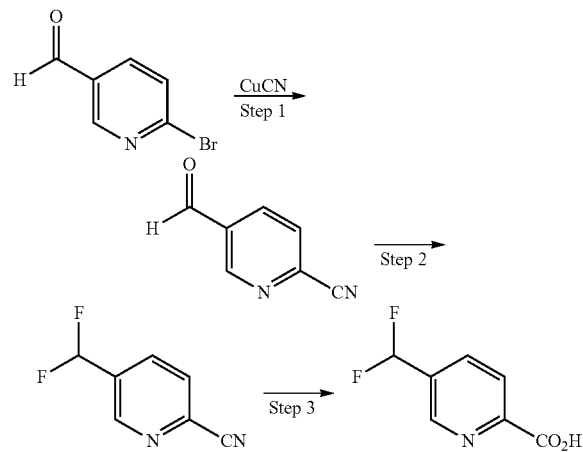

Step 1:

A mixture of 6-bromonicotinaldehyde (11.2 g, 60 mmol) and CuCN (8.06 g, 90 mmol) in DMF (100 mL) was heated at 120° C. for 3 h under N$_2$. The mixture was cooled to rt and diluted with EtOAc and filtered through a pad of celite. The organic layer was washed with water and brine and then dried (MgSO$_4$) and concentrated. The product 5-formylpicolinonitrile (4.55 g) was obtained by silica gel chromatography (elution with 0-20% EtOAc/Hex).

Step 2:

A mixture of 5-formylpicolinonitrile (132 mg, 1.0 mmol) and Deoxo-Fluor® (1.0 mL, 50% in toluene) was stirred at room temperature 16 h. After dilution with DCM, the solution was washed with sat. NaHCO$_3$, brine, then dried (MgSO$_4$) and concentrated. The product 5-(difluoromethyl)picolinonitrile (118 mg) was obtained by silica gel chromatography (elution with 0-10% EtOAc/Hex).

Step 3:

5-(Difluoromethyl)picolinonitrile (118 mg, 0.75 mmol) in 9 mL of conc. HCl was heated at 110° C. for 2.5 h. The mixture was cooled, concentrated and treated with diisopropylethylamine (2 mL). The mixture was re-concentrated and dried in vacuo to give 5-(difluoromethyl)picolinic acid that was used without purification.

Scheme 11ab:

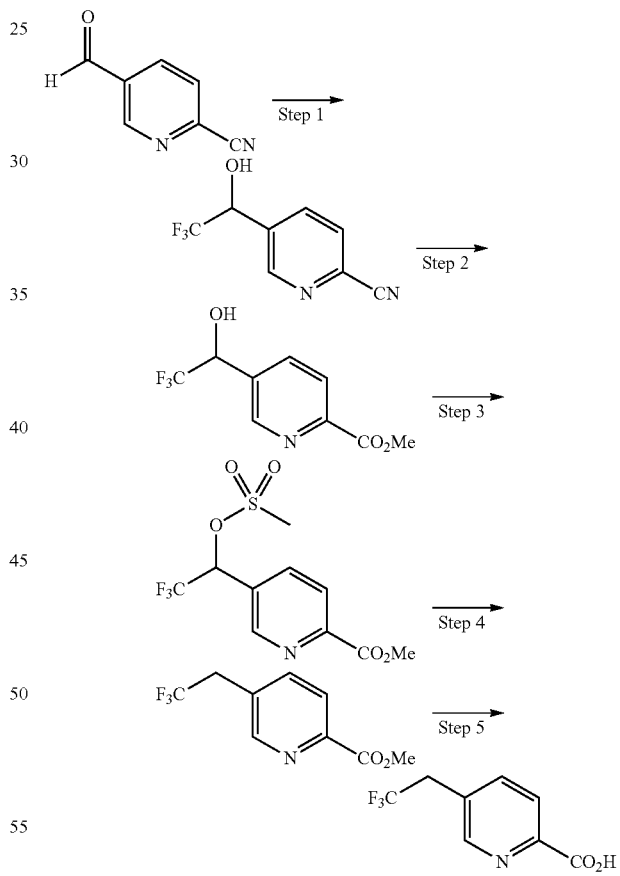

Step 1:

To a −78° C. solution of 5-formylpicolinonitrile (1.0 g, 7.58 mmol) and tetrabutylammonium triphenyldifluorosilicate (4.9 g, 9.10 mmol) in 60 mL of THF was added a solution of trimethyl(trifluoromethyl)silane (1.62 g, 114 mmol). The mixture was stirred for 20 min at −78° C. Then the cooling bath was changed to an ice bath. After stirring for another 30 min, the reaction was quenched with sat. NH$_4$Cl$_{(aq.)}$. The mixture was extracted with EtOAc (3×). The organic layer was washed with sat. NaHCO$_{3(aq.)}$, brine, then dried (MgSO$_4$) and concentrated. The product 5-(2,2,2-trifluoro-1-hydroxyethyl)picolinonitrile (600 mg) was obtained by silica gel chromatography (elution with 0-40% EtOAc/Hex).

Step 2:

A mixture of 5-(2,2,2-trifluoro-1-hydroxyethyl)picolinonitrile (202 mg, 1.0 mmol), conc. HCl (0.5 mL) and conc. H$_2$SO$_4$ (0.25 mL) in 10 mL of anhydrous MeOH was heated at reflux for 19 h. The solution was concentrated and neutralized with sat. NaHCO$_{3(aq.)}$. Extraction with EtOAc followed by concentration of the organic layer and purification of the residue by silica gel chromatography (elution with 0-45% EtOAc/Hex) afforded methyl 5-(2,2,2-trifluoro-1-hydroxyethyl)picolinate (76 mg).

Step 3:

To a solution of methyl 5-(2,2,2-trifluoro-1-hydroxyethyl)picolinate (76 mg, 0.32 mmol) in 3 mL of DCM was added triethylamine (0.22 mL), followed by a solution of methanesulfonyl chloride (45 mg, 0.39 mmol) in 1 mL of DCM. The mixture was stirred at room temperature for 7 h and then diluted with DCM. The solution was washed with 5% citric acid and sat. NaHCO$_{3(aq.)}$ dried (MgSO$_4$), and concentrated. The product methyl 5-(2,2,2-trifluoro-1-(methylsulfonyloxy)ethyl)picolinate (95 mg) was purified by chromatography.

Step 4:

To a solution of methyl 5-(2,2,2-trifluoro-1-(methylsulfonyloxy)ethyl)picolinate (95 mg, 0.3 mmol) in 5 mL of MeOH was added 10% Pd/C (45 mg). Hydrogenation with 1 atm H$_2$ was carried out at room temperature for 2 h. After the catalyst was removed by filtration, the filtrated was concentrated. The residue was dissolved in DCM and washed with sat. NaHCO$_3$ (aq,), and brine. The solution was dried (MgSO$_4$) and concentrated to give methyl 5-(2,2,2-trifluoroethyl)picolinate that was used without purification.

Step 5:

A mixture of methyl 5-(2,2,2-trifluoroethyl)picolinate (57 mg, 0.26 mmol) and LiOH (12.5 mg, 0.52 mmol) in 6 mL MeOH/water (5:1) was stirred at room temperature for 3.5 h. The reaction mixture was acidified with 5% citric acid, and then concentrated. The residue was extracted with DCM (4×). The organic layer was washed with brine and dried (Na$_2$SO$_4$). After concentration, the product 5-(2,2,2-trifluoroethyl)picolinic acid was dried in vacuo and used without further purification.

Scheme 11ac:

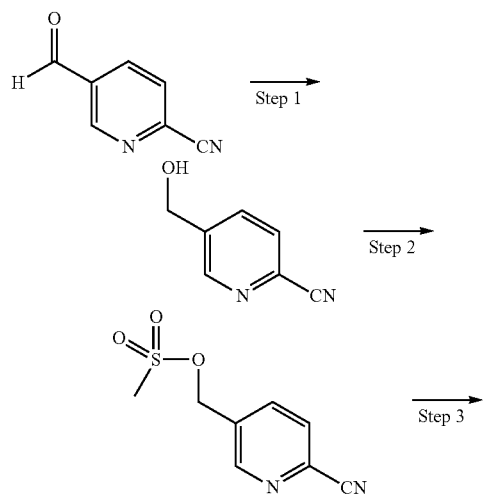

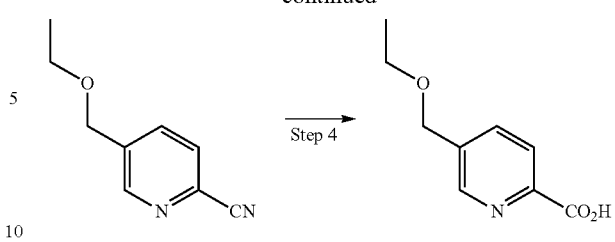

Step 1:

To a 0° C. solution of 5-formylpicolinonitrile (490 mg, 3.71 mmol) in 15 mL of MeOH was added NaBH$_4$ (140 mg, 3.71 mmol). The reaction mixture was stirred at 0° C. for 1 h and quenched with 5% citric acid. After most MeOH was removed by concentration, the residue was partitioned between DCM and sat. NaHCO$_3$ $_{(aq.)}$. The aqueous layer was extracted with DCM (10×). The organic layer was washed with brine and dried (Na$_2$SO$_4$). The product 5-(hydroxymethyl)picolinonitrile (431 mg) was obtained by concentration under vacuum.

Step 2:

To a solution of 5-(hydroxymethyl)picolinonitrile (1.59 g, 11.9 mmol) in 80 mL of DCM was added diisopropylethylamine (3.2 mL), followed by a solution of methanesulfonyl chloride (1.49 g, 13.0 mmol) in 20 mL of DCM at 0° C. The solution was stirred at 0° C. for 40 min and washed with 5% citric acid, sat. NaHCO$_{3(aq.)}$ and brine. After concentration, the residue was purified by silica gel chromatography (elution with 0-30% EtOAc/Hex) to afford (6-cyanopyridin-3-yl)methyl methanesulfonate (2.33 g).

Step 3:

(6-Cyanopyridin-3-yl)methyl methanesulfonate (199 mg, 0.94 mmol) in 2 mL anhydrous EtOH was heated at 85° C. in a sealed tube for 3.5 h. The mixture was concentrated and purified by silica gel chromatography (elution with 0-25% EtOAc/Hex) to afford 5-(ethoxymethyl)picolinonitrile (104 mg).

Step 4:

A solution of 5-(ethoxymethyl)picolinonitrile (104 mg) in 10 ml. of conc. HCl was heated at reflux for 3.5 h. After concentration, diisopropylethylamine (3 mL) was added into the residue. The mixture was concentrated and dried in vacuo. The product 5-(ethoxymethyl)picolinic acid was used without further purification.

TABLE IVm

The following acids were prepared using similar procedures described in Scheme 11ac, substituting the appropriate alcohol in Step 3.

| | Entries |
|---|---|
| 1 |  |

TABLE IVm-continued

The following acids were prepared using similar procedures described in Scheme 11ac, substituting the appropriate alcohol in Step 3.

| | Entries |
|---|---|
| 2 | 5-(isopropoxymethyl)pyridine-2-carboxylic acid |
| 3 | 5-(methoxymethyl)pyridine-2-carboxylic acid |

TABLE V

The following examples were prepared using a procedure similar to that described in Scheme 11b using the appropriate aryl amines and carboxylic acids.

Examples (LCMS data listed with each compound: observed MH+, HPLC retention time and LCMS method)

| | |
|---|---|
| 21 | MH+: 442, 1.89 min, D |
| 22 | MH+: 392, 1.76 min, D |
| 23 | MH+: 378, 1.64 min, D |
| 24 | MH+: 396.0, 1.69 min, D |
| 25 | MH+: 410.0, 1.79 min, D |
| 26 | MH+: 460.0, 1.90 min, D |
| 27 | MH+: 407, 1.86 min, D |
| 28 | MH+: 392, 1.76 min, D |

TABLE V-continued

The following examples were prepared using a procedure similar to that described in Scheme 11b using the appropriate aryl amines and carboxylic acids.
Examples (LCMS data listed with each compound: observed MH$^+$, HPLC retention time and LCMS method)

29
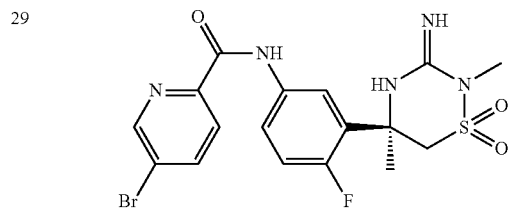
MH$^+$: 470.0, 1.87 min, D

30
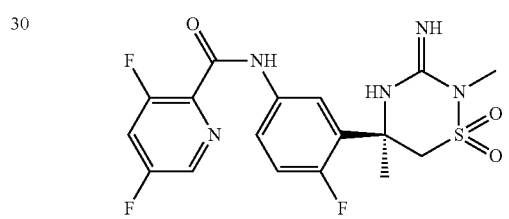
MH$^+$: 428, 1.76 min, D

31
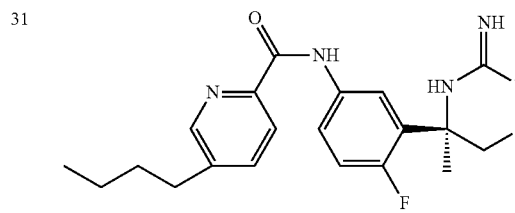
MH$^+$: 448.2, 2.02 min, D

32
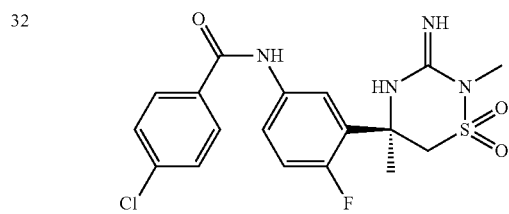
MH$^+$: 426, 1.88 min, D

33
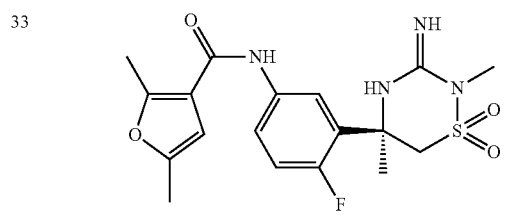
MH$^+$: 409.2, 1.68 min, D

TABLE V-continued

The following examples were prepared using a procedure similar to that described in Scheme 11b using the appropriate aryl amines and carboxylic acids.
Examples (LCMS data listed with each compound: observed MH$^+$, HPLC retention time and LCMS method)

34
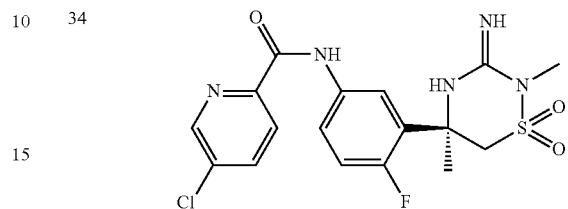
MH$^+$: 426.2, 3.25 min, A

35
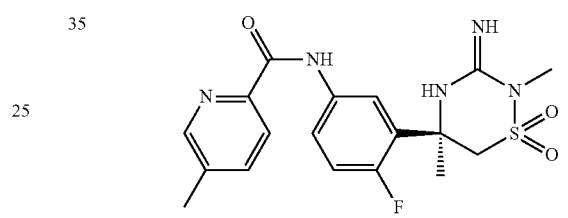
MH$^+$: 406.2, 1.8 min, D

36
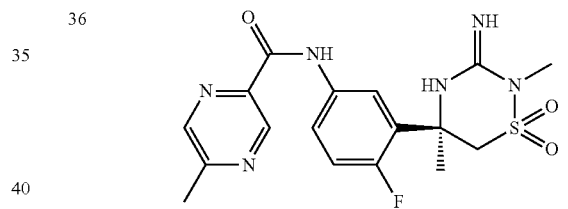
MH$^+$: 407.2, 1.71 min, D

37
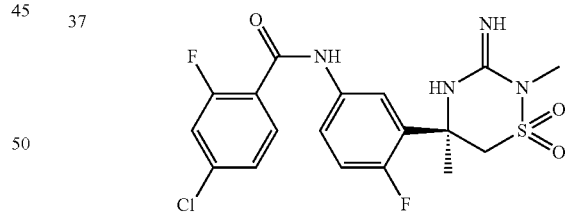
MH$^+$: 444, 1.86 min, D

38
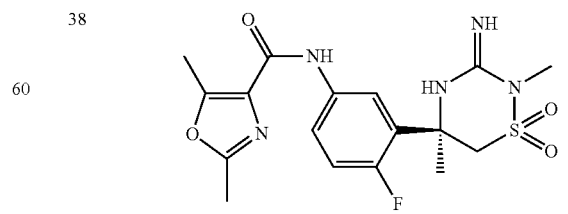
MH$^+$: 410.2, 1.78 min, D

TABLE V-continued
The following examples were prepared using a procedure similar to that described in Scheme 11b using the appropriate aryl amines and carboxylic acids.
Examples (LCMS data listed with each compound: observed MH+, HPLC retention time and LCMS method)
39
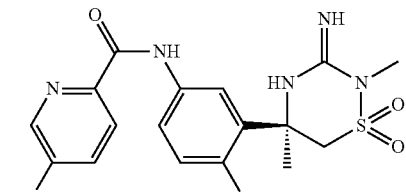
MH+: 476.0, 1.91 min, D
40
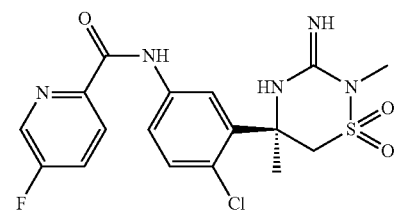
MH+: 426.0, 1.83 min, D
40a
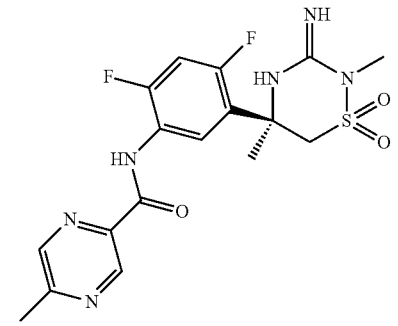
MH+: 425.1, 1.91 min, B
40b
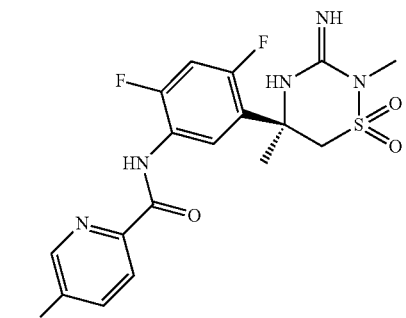
MH+: 478, 2.25 min, B
40c
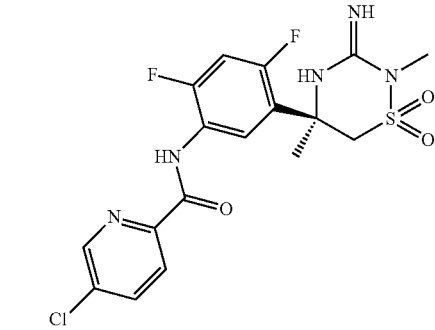
MH+: 443.9, 2.18 min, B
40d
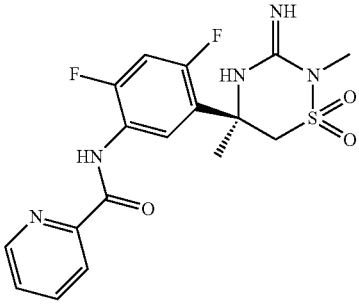
MH+: 410.2, 2.02 min, B
40e
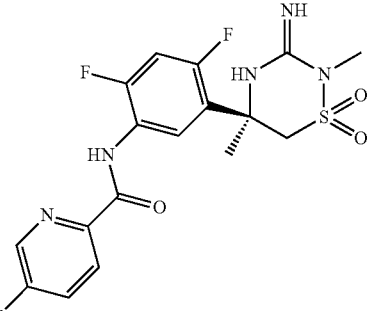
MH+: 428, 2.06 min, B
40f
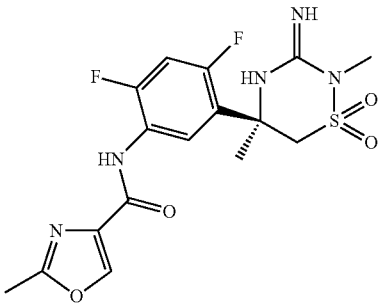
MH+: 414.1, 1.86 min, B TABLE V-continued
The following examples were prepared using a procedure similar to that described in Scheme 11b using the appropriate aryl amines and carboxylic acids.
Examples (LCMS data listed with each compound: observed MH+, HPLC retention time and LCMS method)
40g
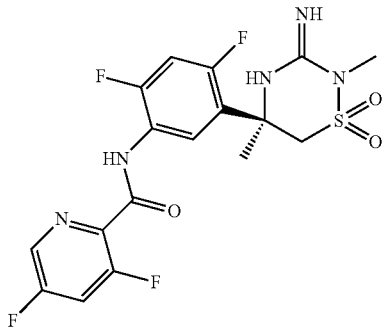
MH+: 446.0, 2.01 min, B
40h
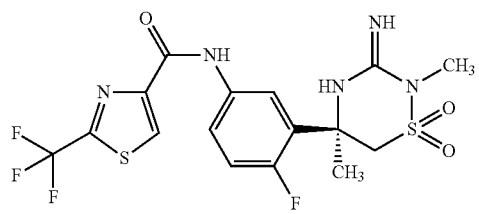
MH+: 466.2, 1.84 min, D
40i
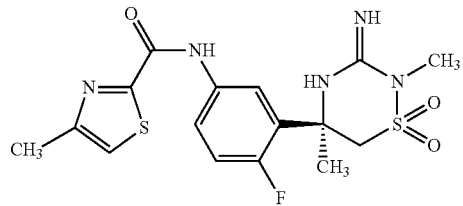
MH+: 412.2, 1.77 min, D
40j
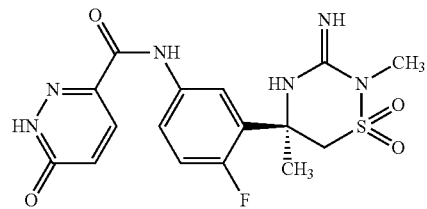
MH+: 409.3, 1.55 min, D
40k
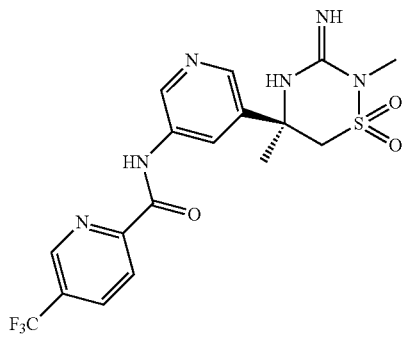
MH+: 443.1, 1.94 min, B
40l
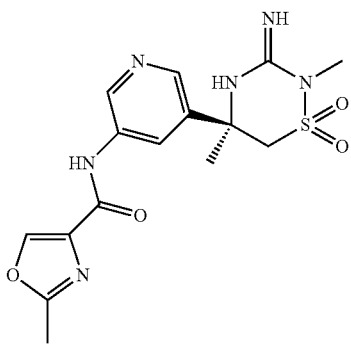
MH+: 379.1, 1.49 min, B
40m
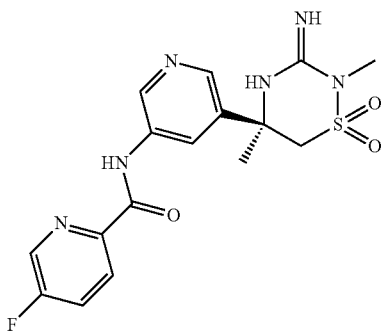
MH+: 393, 1.73 min, B
40n
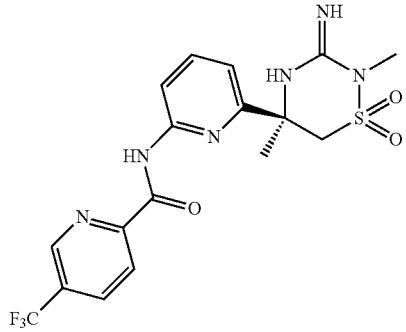
MH+: 443.1, 2.07 min, B
40o
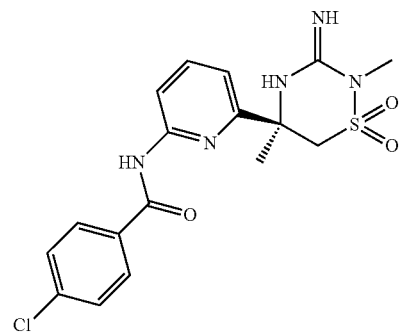
MH+: 408.1, 2.03 min, B TABLE V-continued The following examples were prepared using a procedure similar to that described in Scheme 11b using the appropriate aryl amines and carboxylic acids.
Examples (LCMS data listed with each compound: observed MH+, HPLC retention time and LCMS method)

40p

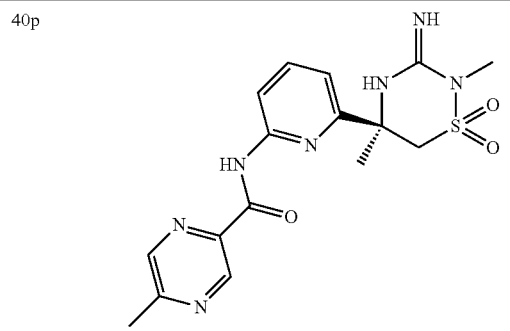

MH+: 390.2, 1.66 min, B

40q

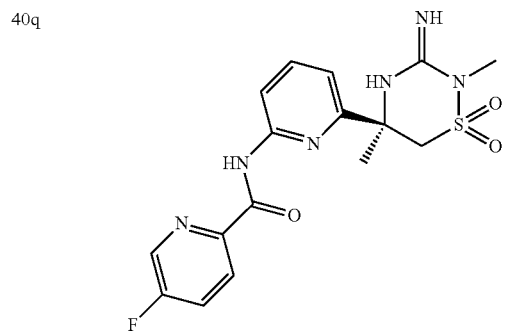

MH+: 393.1, 1.86 min, B

40r

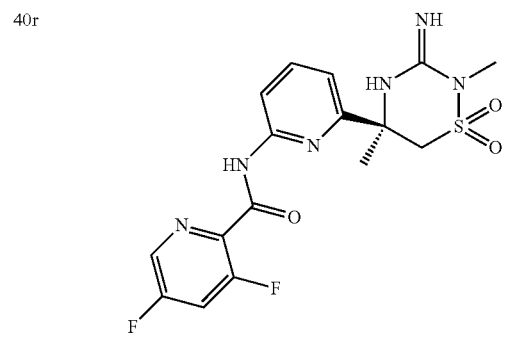

MH+: 411.1, 1.79 min, B

40s

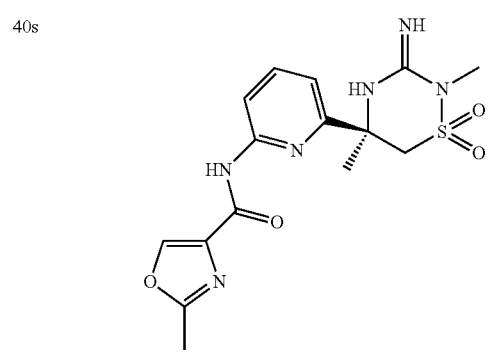

MH+: 379.2, 1.64 min, B

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40t

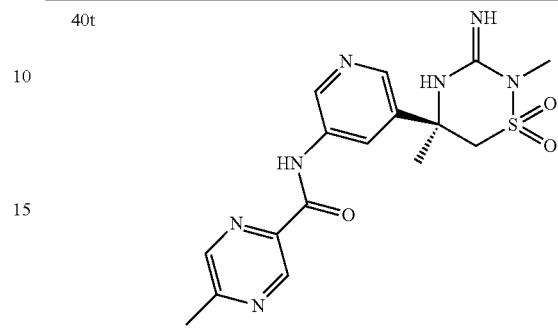

MH+: 390.1, 1.46 min, B

40u

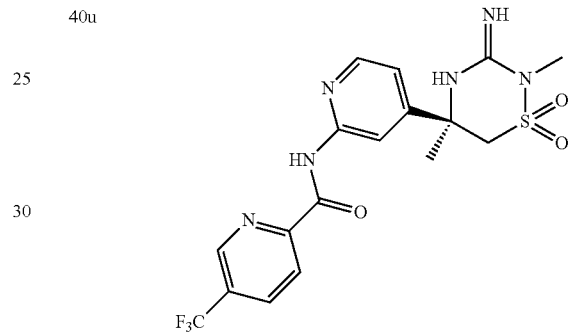

MH+: 443.0, 1.94 min, B

40v

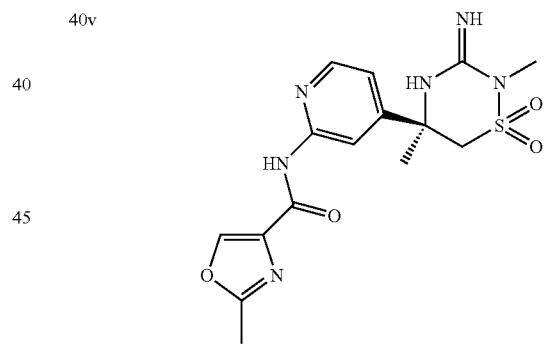

MH+: 379.1, 1.55 min, B

40w

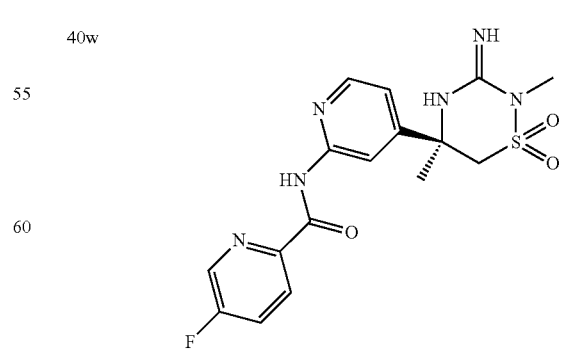

MH+: 393.1, 1.77 min, D

TABLE V-continued
The following examples were prepared using a procedure similar to that described in Scheme 11b using the appropriate aryl amines and carboxylic acids.
Examples (LCMS data listed with each compound: observed MH+, HPLC retention time and LCMS method)
40x
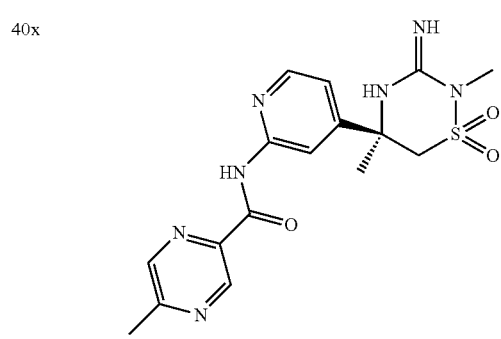
MH+: 390.2, 1.53 min, B
40y
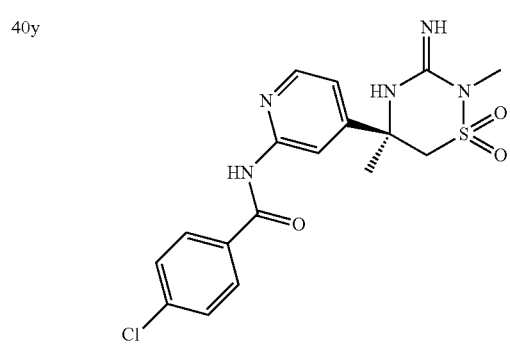
MH+: 408.0, 1.85 min, B
40z
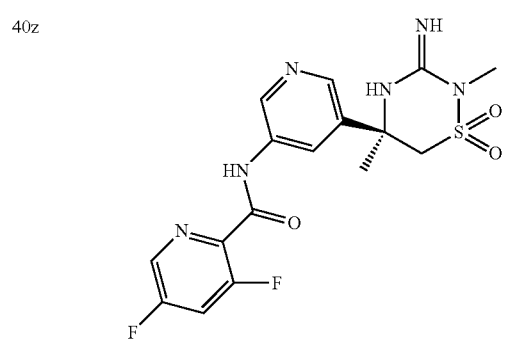
MH+: 411.0, 1.69 min, B
40aa
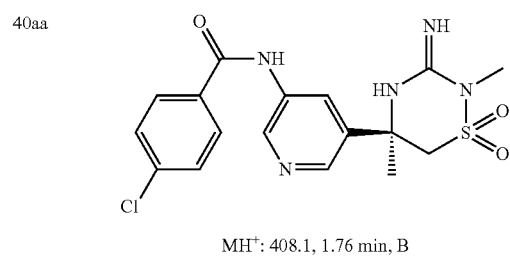
MH+: 408.1, 1.76 min, B
40ab
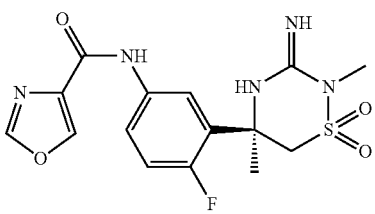
MH+: 382.2, 1.61 min, D
40ac
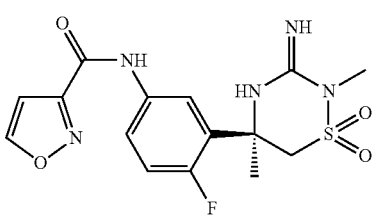
MH+: 382.2, 1.65 min, D
40ad
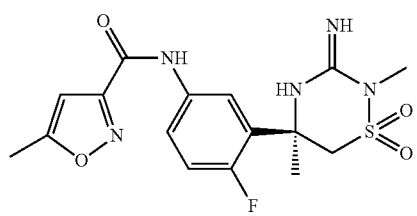
MH+: 396.1, 1.49 min, F
40ae
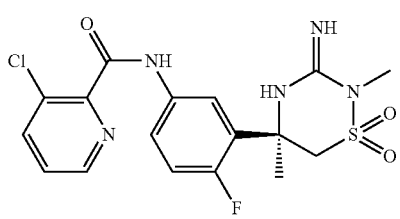
MH+: 426.2, 1.73 min, D
40af
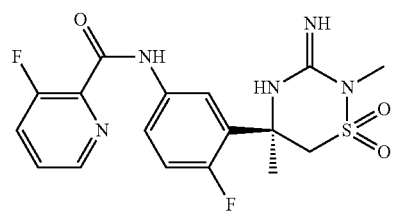
MH+: 410.2, 1.71 min, D TABLE V-continued The following examples were prepared using a procedure similar to that described in Scheme 11b using the appropriate aryl amines and carboxylic acids.
Examples (LCMS data listed with each compound: observed MH+, HPLC retention time and LCMS method)

40ag
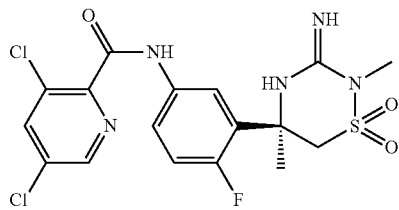
MH+: 460.2, 1.82 min, D

40ah
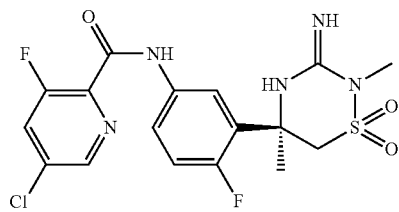
MH+: 444.2, 1.78 min, D

40ai
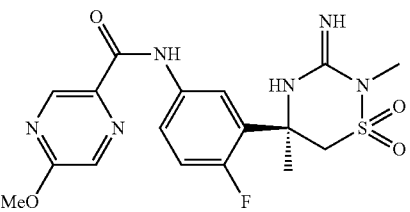
MH+: 423.2, 1.76 min, D

40aj
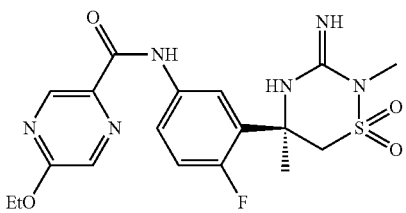
MH+: 437.2, 1.85 min, D

40ak
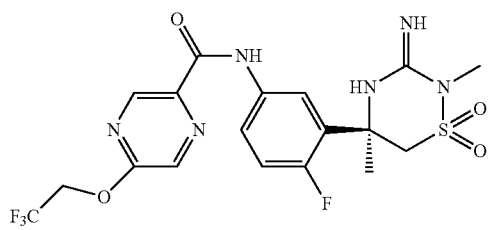
MH+: 491.2, 1.91 min, D

40al
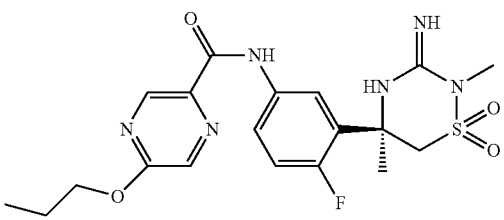
MH+: 451.3, 1.93 min, D

40am
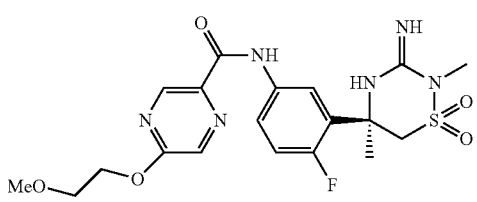
MH+: 467.2, 1.79 min, D

40an
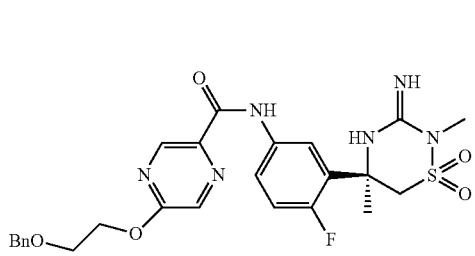
MH+: 543.1, 2.01 min, D

40ao
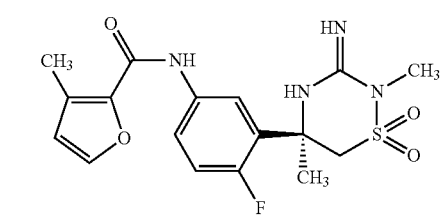
MH+: 395.2, 1.81 min, D

40ap
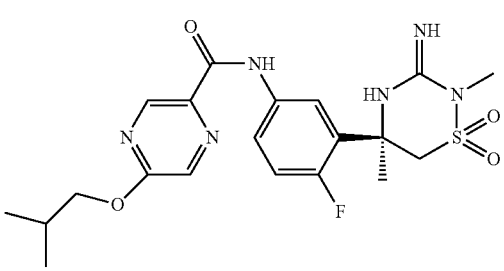
MH+: 465.2, 1.99 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40aq
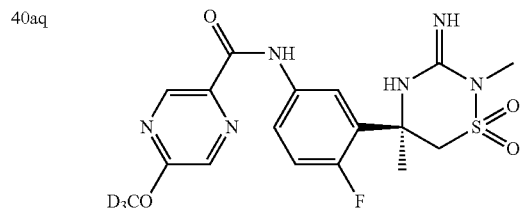
MH+: 426.0, 1.75 min, D

40ar
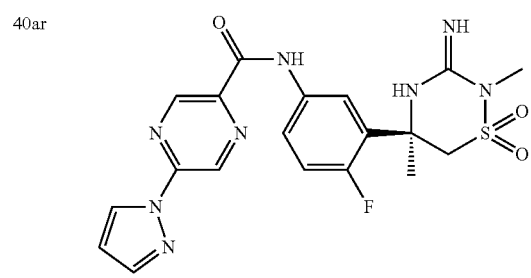
MH+: 459.0, 1.86 min, D

40as
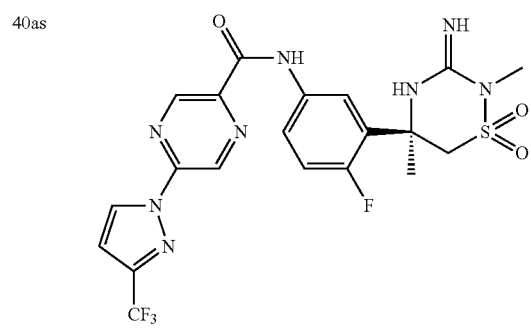
MH+: 527.0, 2.01 min, D

40at
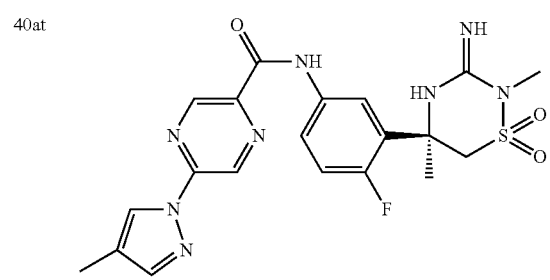
MH+: 473.0, 1.93 min, D

40au
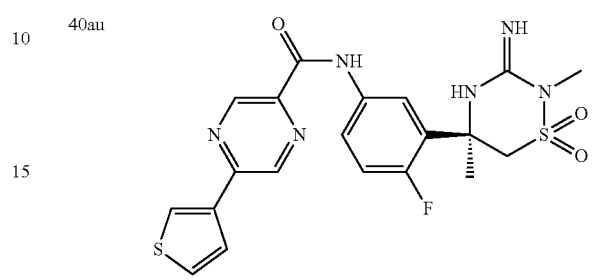
MH+: 475.0, 1.93 min, D

40av
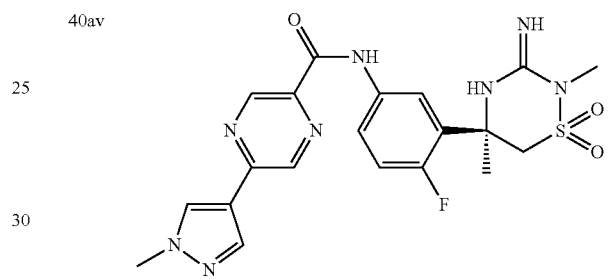
MH+: 473.0, 1.78 min, D

40aw
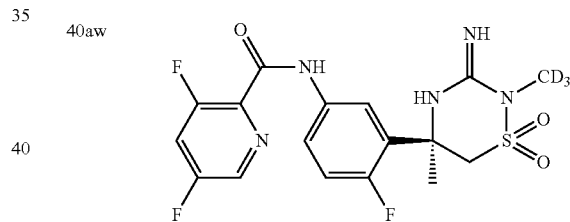
MH+: 431.2, 1.75 min, D

40ax
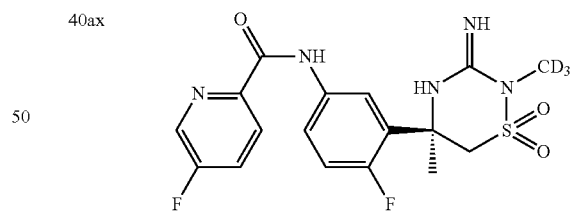
MH+: 413.0, 1.81 min, D

40ay
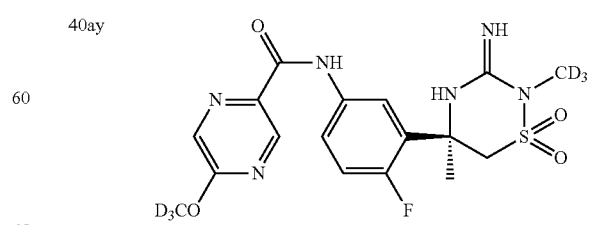
MH+: 429.0, 1.78 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40az
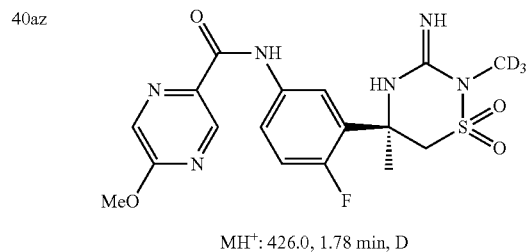
MH+: 426.0, 1.78 min, D

40ba
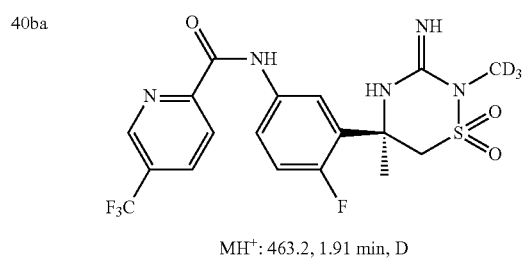
MH+: 463.2, 1.91 min, D

40bb
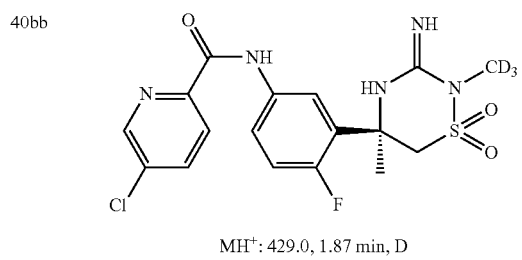
MH+: 429.0, 1.87 min, D

40bc
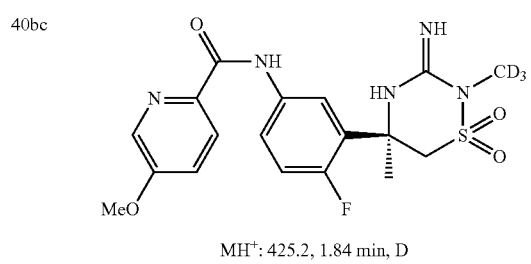
MH+: 425.2, 1.84 min, D

40bd
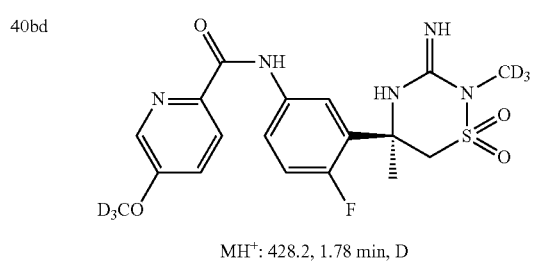
MH+: 428.2, 1.78 min, D

40be
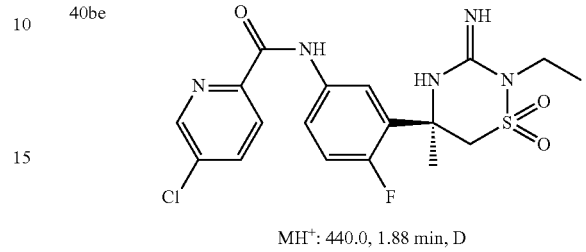
MH+: 440.0, 1.88 min, D

40bf
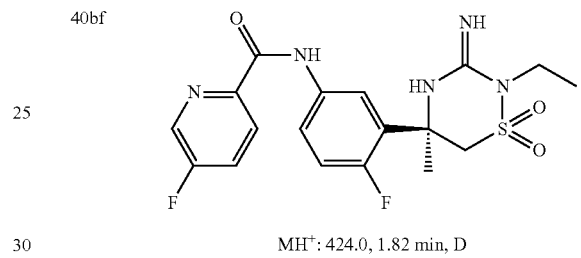
MH+: 424.0, 1.82 min, D

40bg
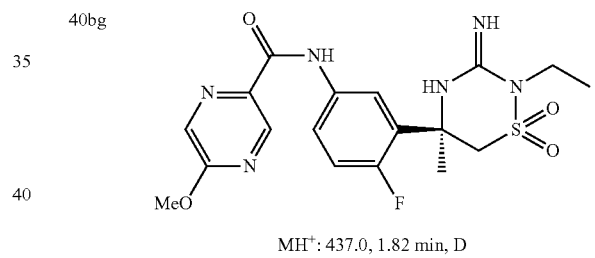
MH+: 437.0, 1.82 min, D

40bh
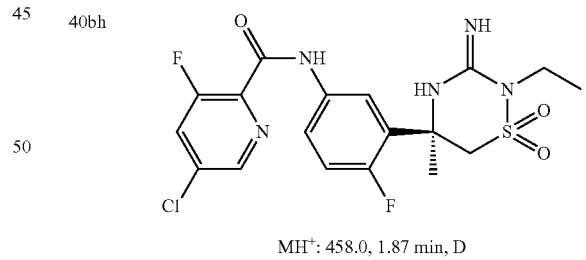
MH+: 458.0, 1.87 min, D

40bi
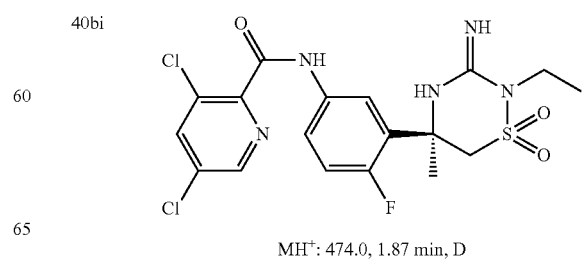
MH+: 474.0, 1.87 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40bj
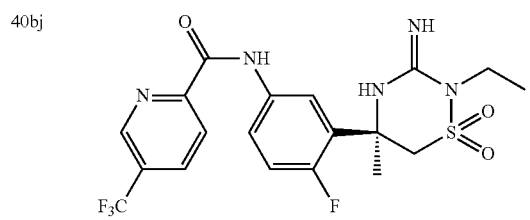
MH+: 474.2, 1.95 min, D

40bk
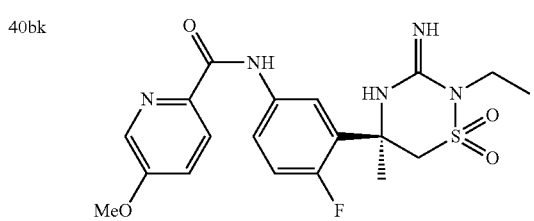
MH+: 436.0, 1.85 min, D

40bl
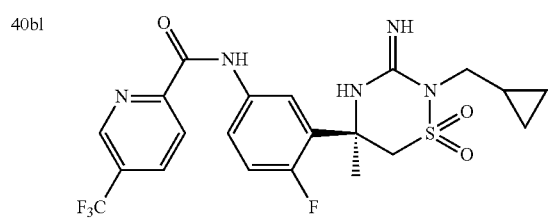
MH+: 500.0, 1.98 min, D

40bm
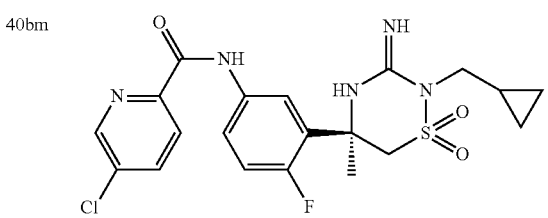
MH+: 466.0, 1.95 min, D

40bn
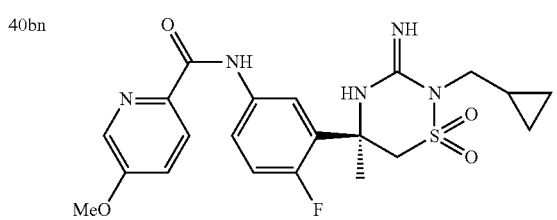
MH+: 462.0, 1.92 min, D

40bo
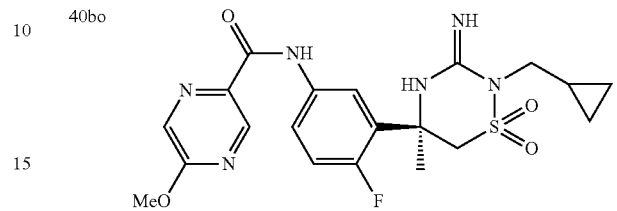
MH+: 463.0, 1.90 min, D

40bp
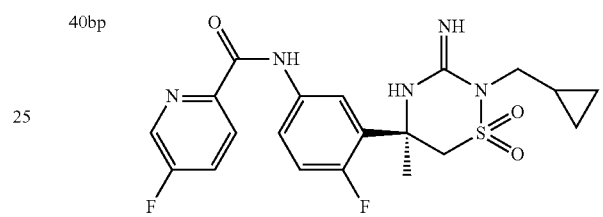
MH+: 450.0, 1.91 min, D

40bq
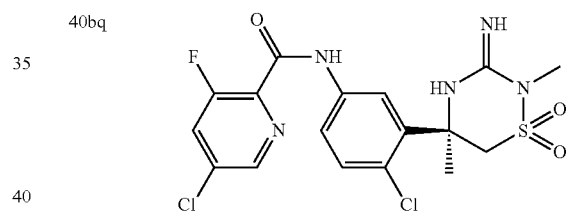
MH+: 460.0, 1.87 min, D

40br
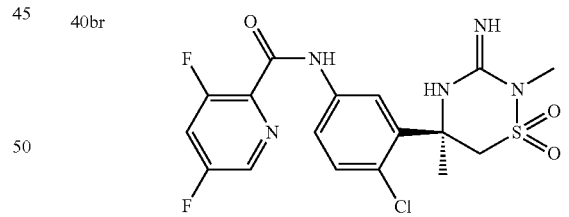
MH+: 444.0, 1.81 min, D

40bs
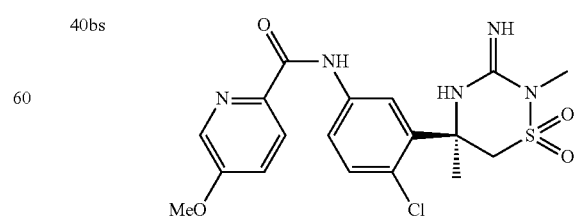
MH+: 438.0, 1.86 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40bt
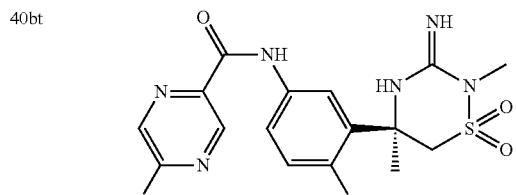
MH+: 439.0, 1.83 min, D

40bu
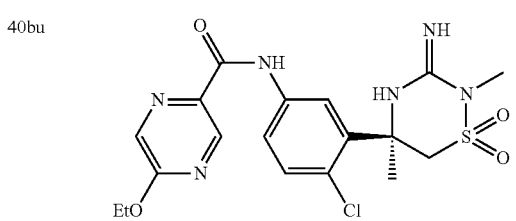
MH+: 453.0, 1.92 min, D

40bv
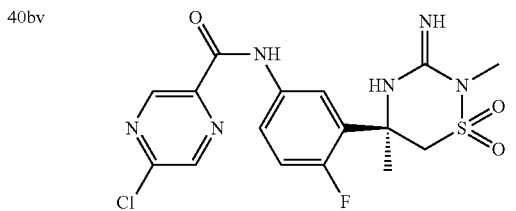
MH+: 427.0, 1.79 min, D

40bw
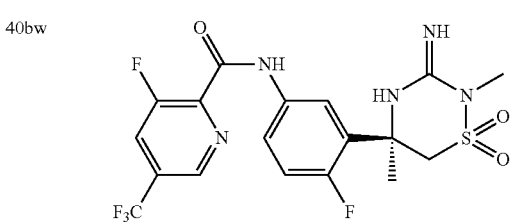
MH+: 478.0, 1.87 min, D

40bx
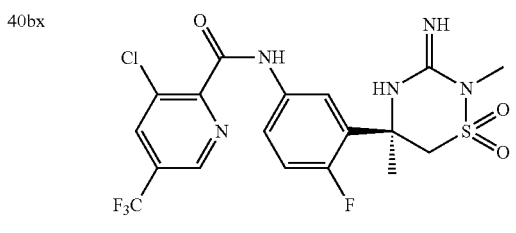
MH+: 494.2, 1.81 min, D

40by
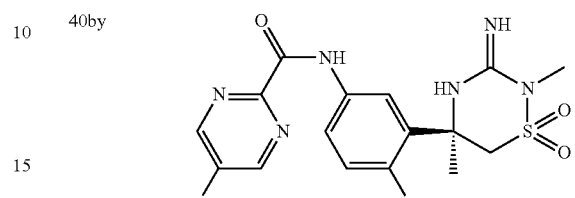
MH+: 461.2, 1.73 min, D

40bz
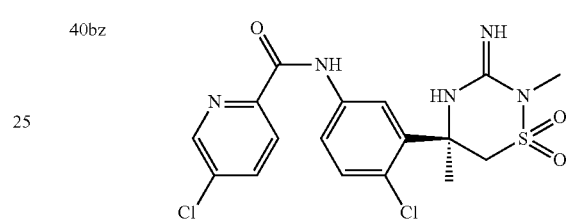
MH+: 442.0, 1.86 min, D

40ca
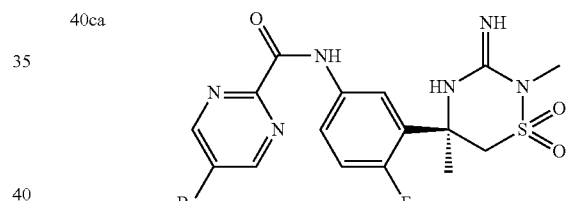
MH+: 473.0, 1.71 min, D

40cb
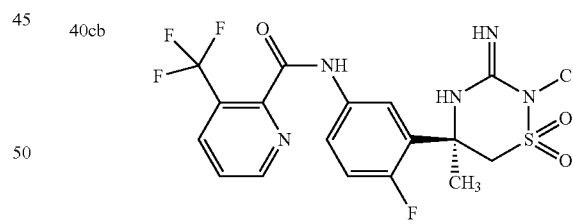
MH+: 460.2, 1.78 min, D

40cc
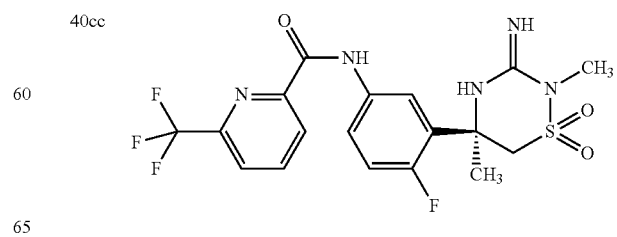
MH+: 460.2, 1.87 min, D

TABLE V-continued
The following examples were prepared using a procedure similar to that described in Scheme 11b using the appropriate aryl amines and carboxylic acids.
Examples (LCMS data listed with each compound: observed MH+, HPLC retention time and LCMS method)
40cd
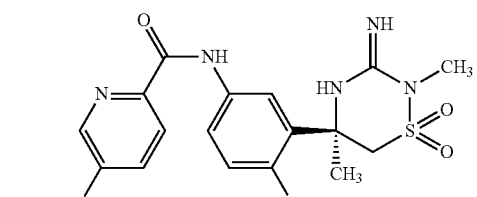
MH+: 422.2, 1.79 min, D
40ce
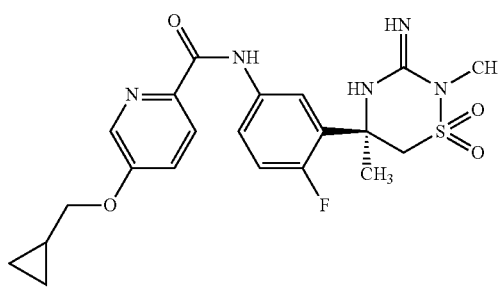
MH+: 484.2, 1.90 min, D
40cf
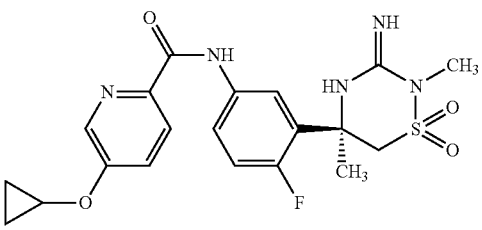
MH+: 448.0, 1.88 min, D
40cg
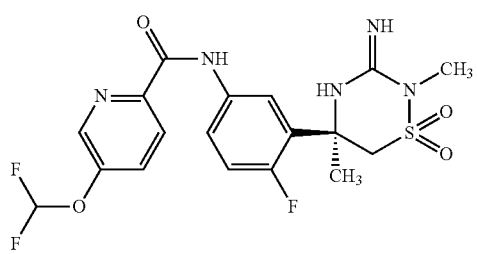
MH+: 458.0, 1.59 min, F
40ch
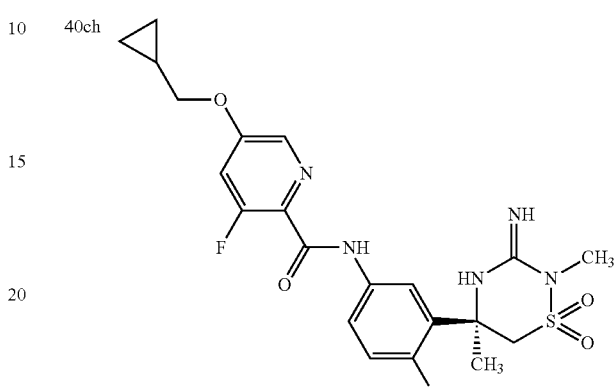
MH+: 480.0, 1.92 min, D
40ci
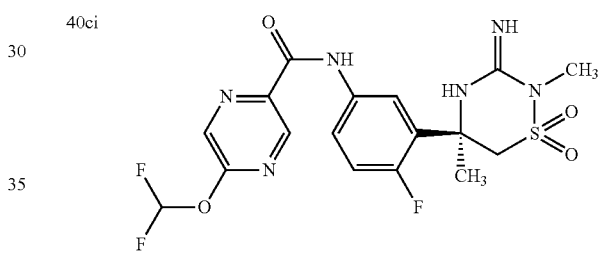
MH+: 459.2, 1.73 min, D
40cj
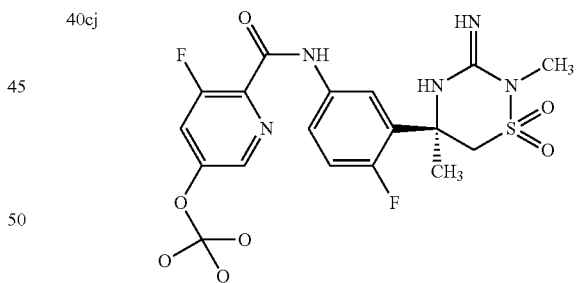
MH+: 443.0, 1.79 min, D
40ck
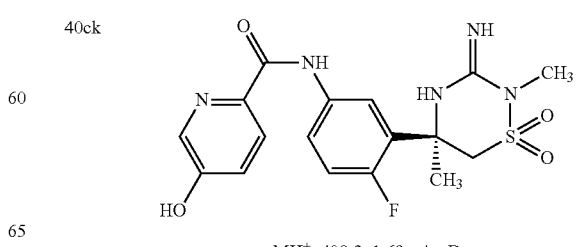
MH+: 408.2, 1.69 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40cl
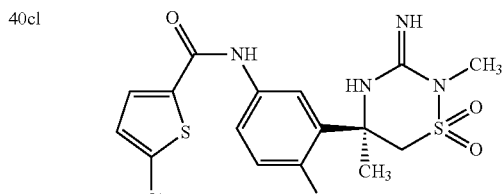
MH+: 431.0, 1.85 min, D

40cm
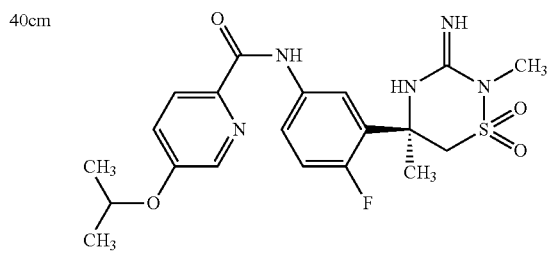
MH+: 450.2, 1.88 min, D

40cn
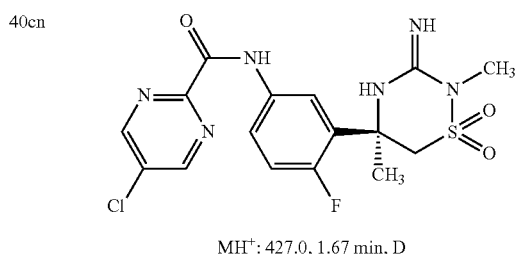
MH+: 427.0, 1.67 min, D

40co
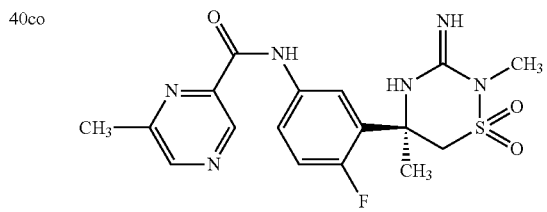
MH+: 407.0, 1.72 min, D

40cp
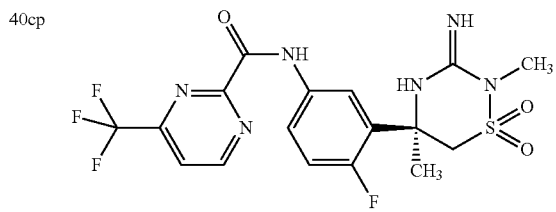
MH+: 461.0, 1.75 min, D

40cq
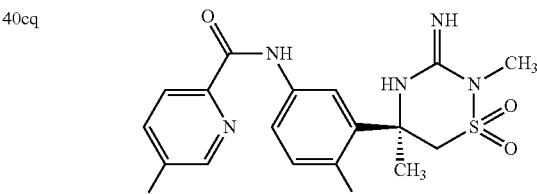
MH+: 436.2, 1.84 min, D

40cr
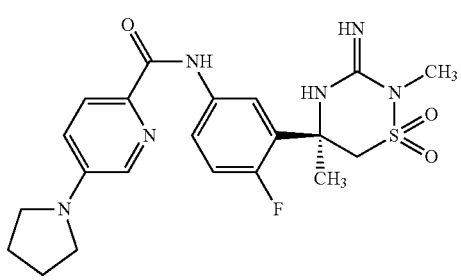
MH+: 461.4, 1.83 min, D

40cs
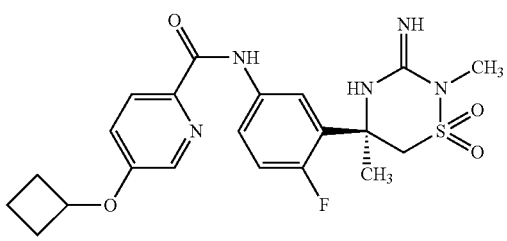
MH+: 462.0, 1.92 min, D

40ct
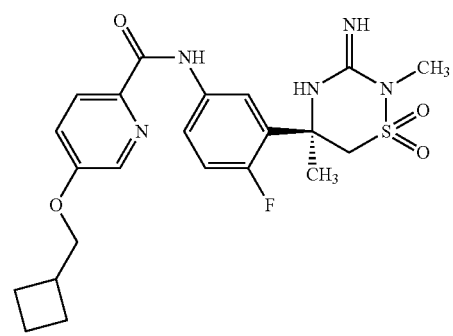
MH+: 476.2, 1.97 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40cu
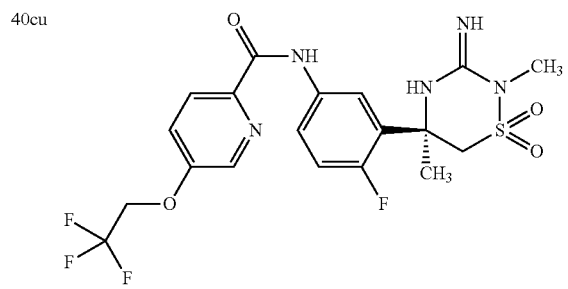
MH+: 490.0, 1.92 min, D

40cv
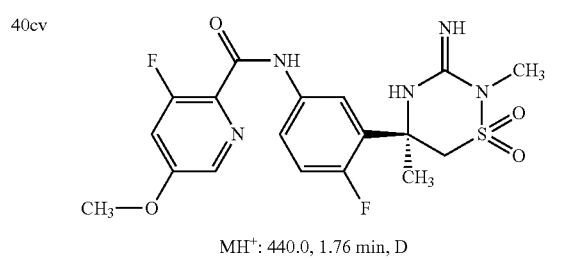
MH+: 440.0, 1.76 min, D

40cw
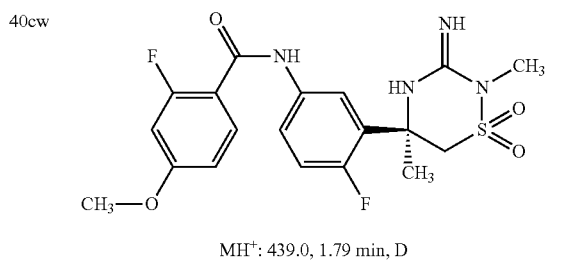
MH+: 439.0, 1.79 min, D

40cx
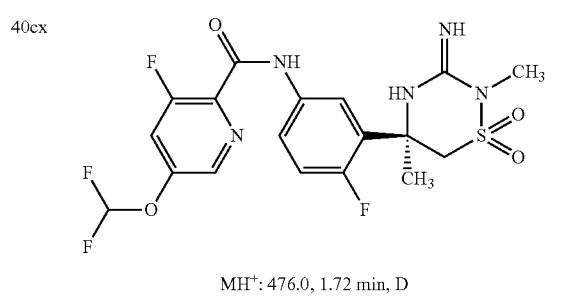
MH+: 476.0, 1.72 min, D

40cy
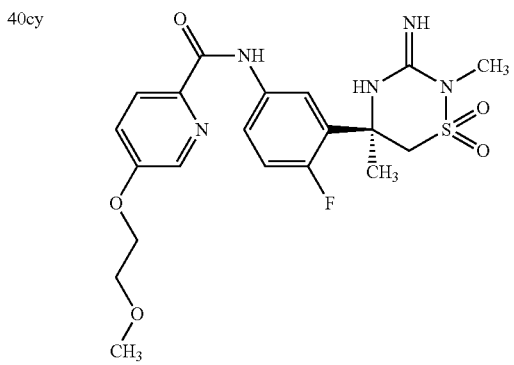
MH+: 466.0, 1.82 min, D

40cz
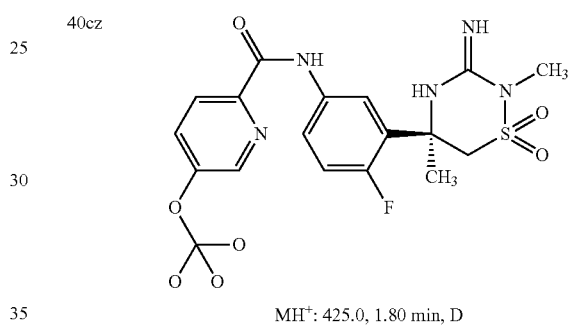
MH+: 425.0, 1.80 min, D

40da
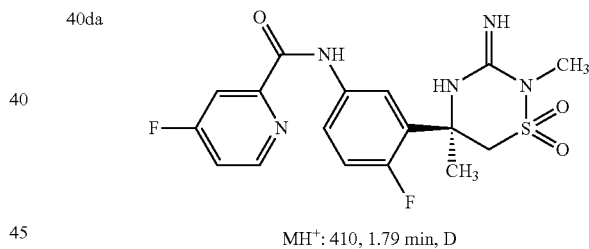
MH+: 410, 1.79 min, D

40db
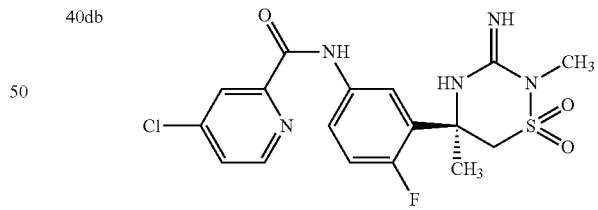
MH+: 426.0, 1.83 min, D

40dc
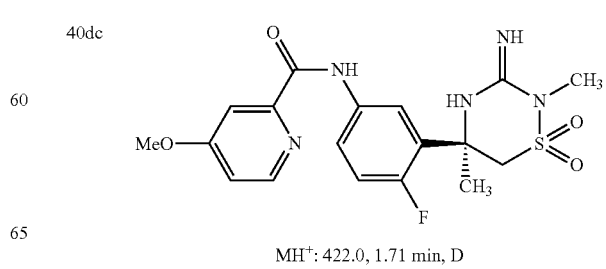
MH+: 422.0, 1.71 min, D

TABLE V-continued
The following examples were prepared using a procedure similar to that described in Scheme 11b using the appropriate aryl amines and carboxylic acids.
Examples (LCMS data listed with each compound: observed MH+, HPLC retention time and LCMS method)
40dd
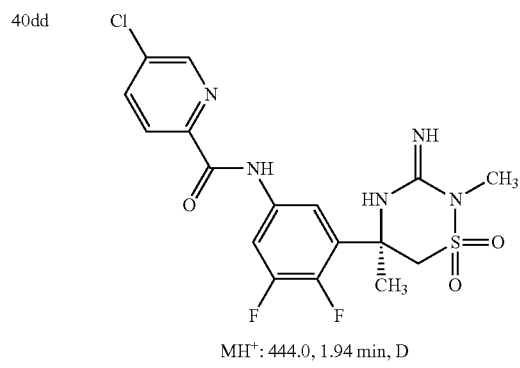
MH+: 444.0, 1.94 min, D
40de
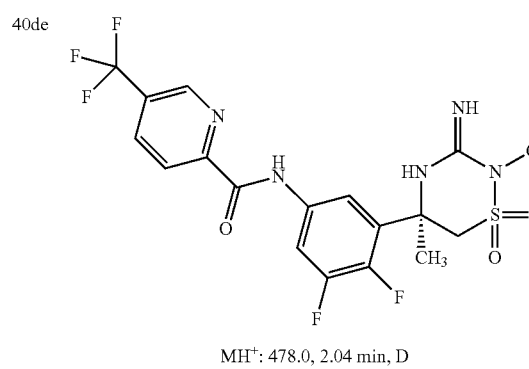
MH+: 478.0, 2.04 min, D
40df
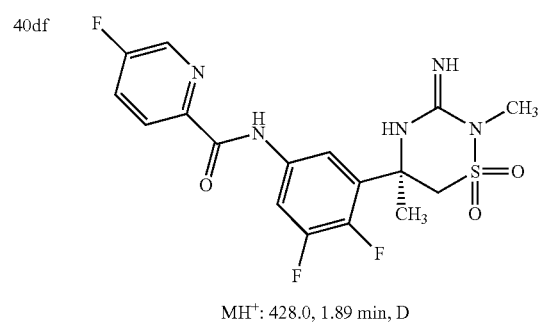
MH+: 428.0, 1.89 min, D
40dg
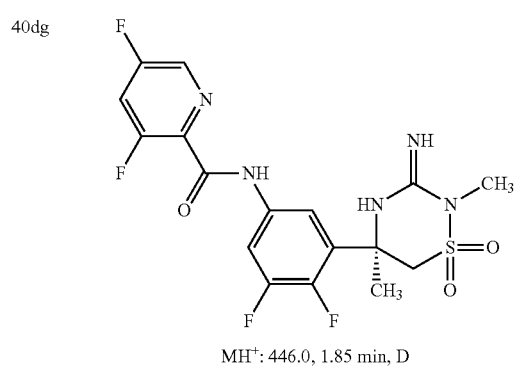
MH+: 446.0, 1.85 min, D
40dh
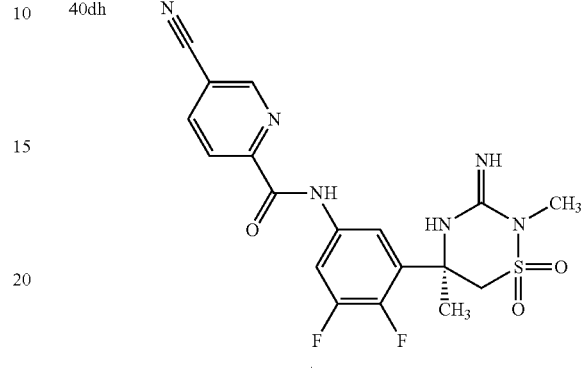
MH+: 435.0, 1.87 min, D
40di
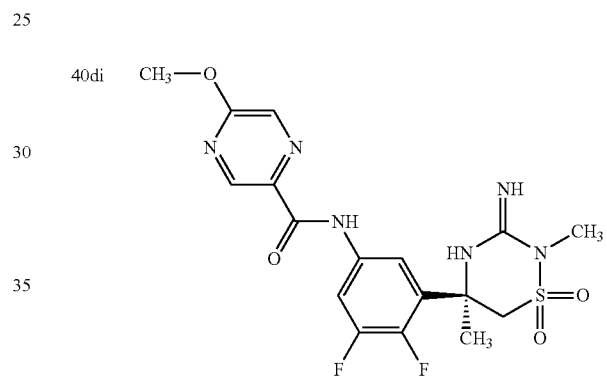
MH+: 441.0, 1.85 min, D
40dj
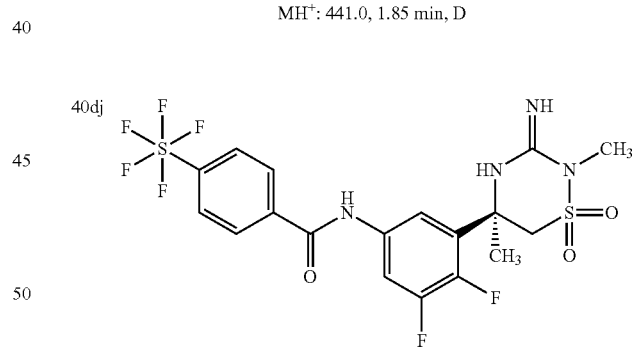
MH+: 534.8, 2.04 min, D
40dk
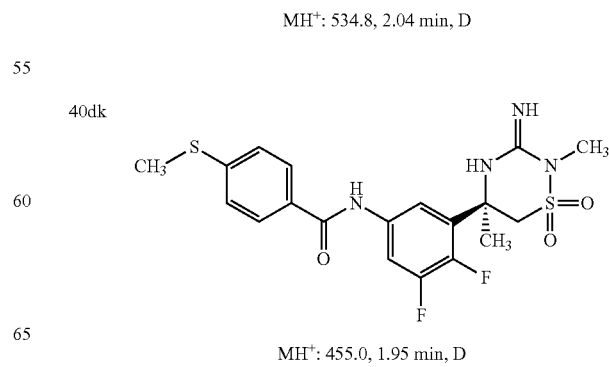
MH+: 455.0, 1.95 min, D TABLE V-continued The following examples were prepared using a procedure similar to that described in Scheme 11b using the appropriate aryl amines and carboxylic acids.
Examples (LCMS data listed with each compound: observed MH+, HPLC retention time and LCMS method)

40dl

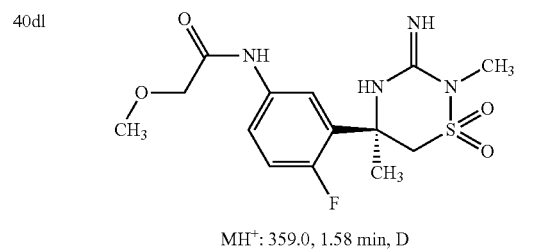

MH+: 359.0, 1.58 min, D

40dm

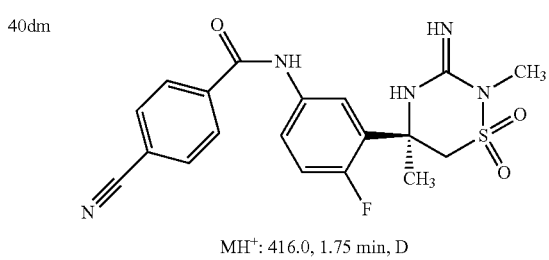

MH+: 416.0, 1.75 min, D

40dn

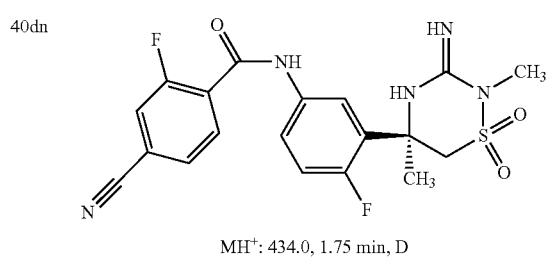

MH+: 434.0, 1.75 min, D

40do

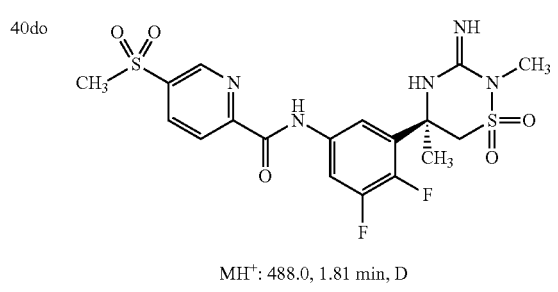

MH+: 488.0, 1.81 min, D

40dp

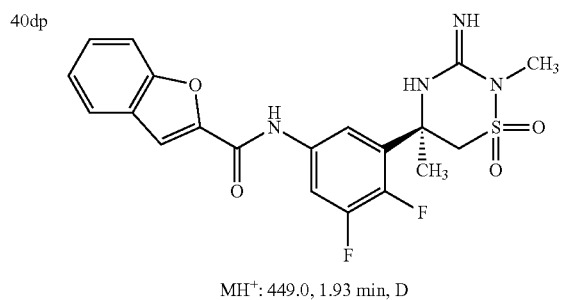

MH+: 449.0, 1.93 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40dq

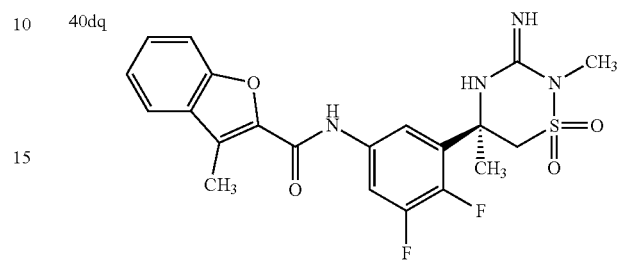

MH+: 463.0, 2.02 min, D

40dr

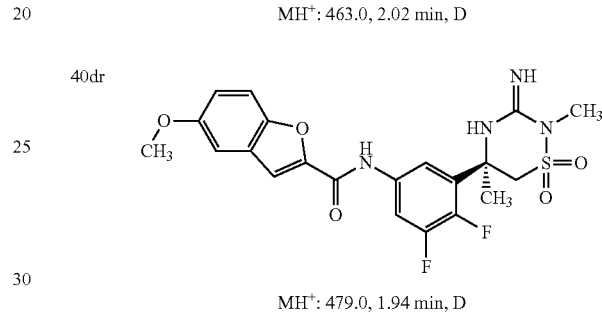

MH+: 479.0, 1.94 min, D

40ds

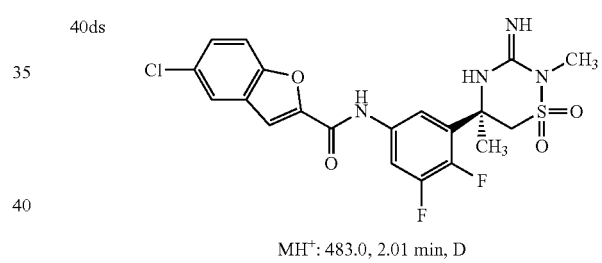

MH+: 483.0, 2.01 min, D

40dt

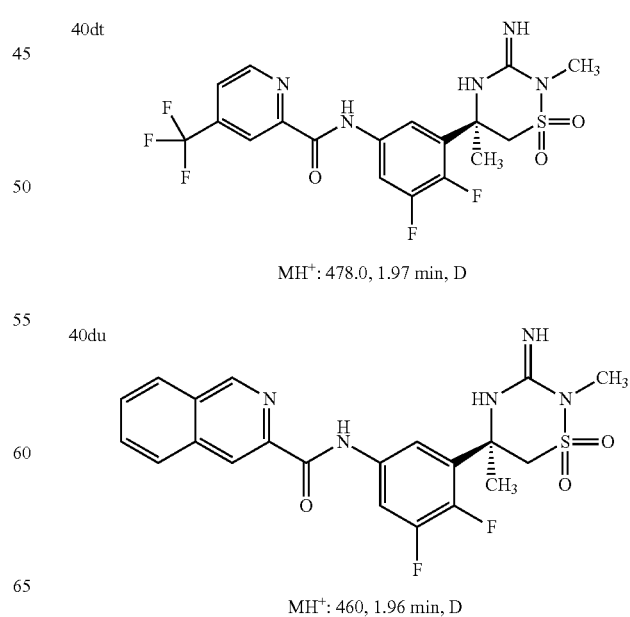

MH+: 478.0, 1.97 min, D

40du

MH+: 460, 1.96 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40dv

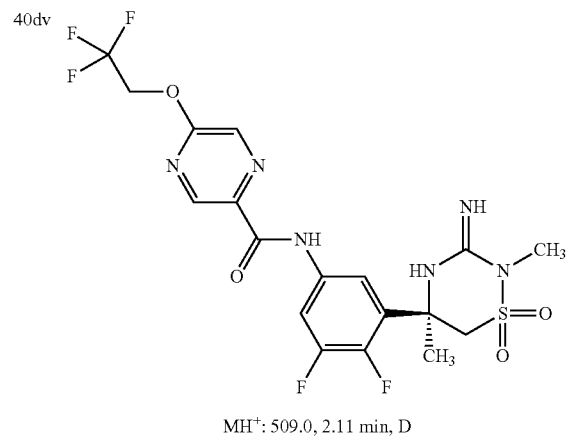

MH+: 509.0, 2.11 min, D

40dw

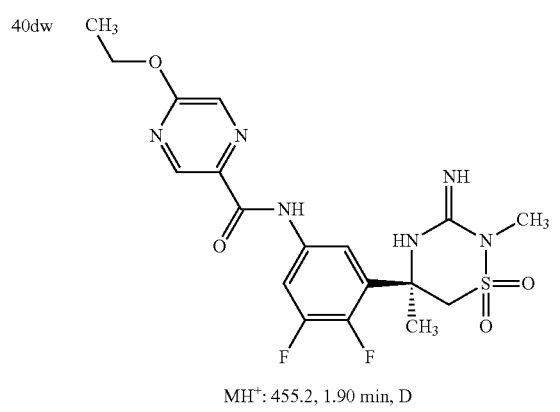

MH+: 455.2, 1.90 min, D

40dx

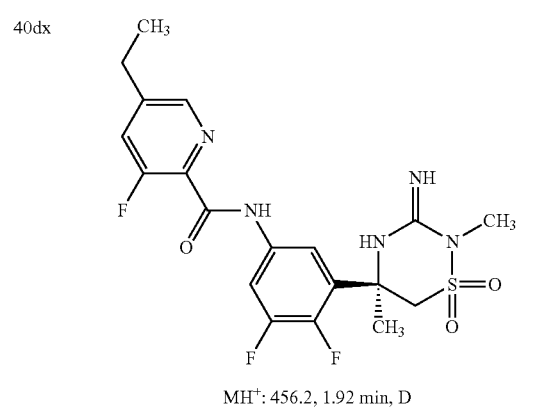

MH+: 456.2, 1.92 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40dy

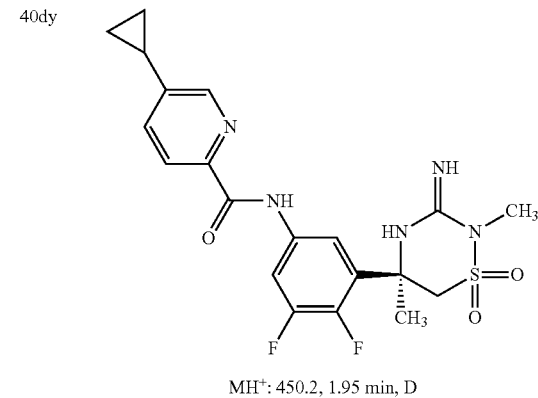

MH+: 450.2, 1.95 min, D

40dz

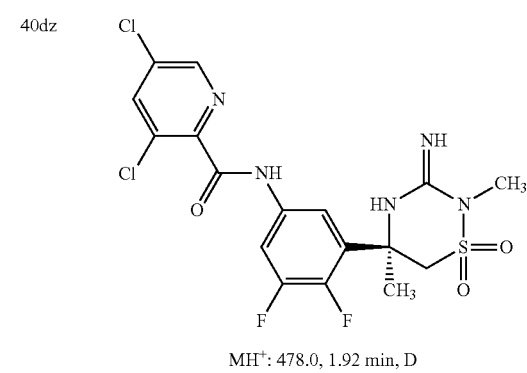

MH+: 478.0, 1.92 min, D

40ea

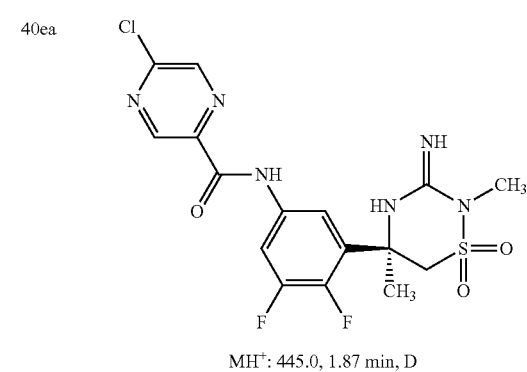

MH+: 445.0, 1.87 min, D

40eb

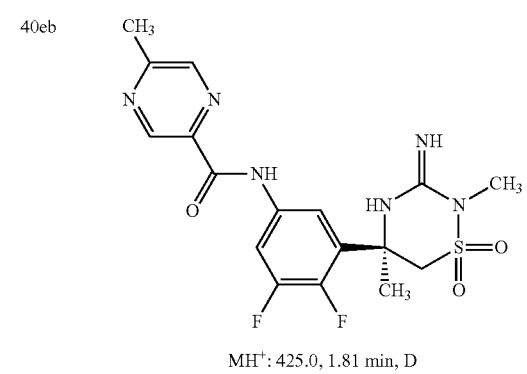

MH+: 425.0, 1.81 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40ec

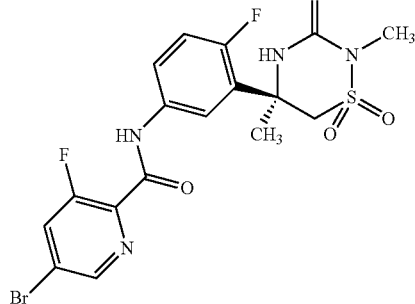

MH+: 490.0, 1.90 min, D

40ed

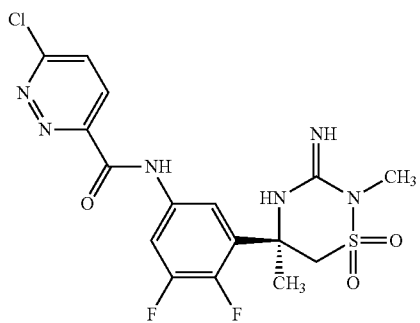

MH+: 445.0, 1.84 min, D

40ee

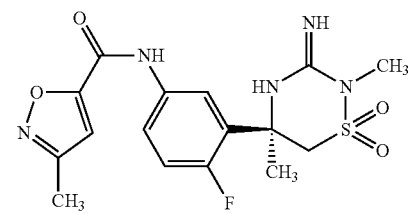

MH+: 396.2, 1.67 min, D

40ef

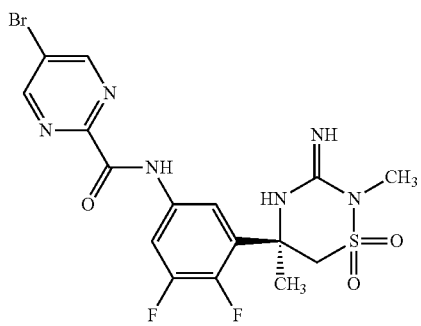

MH+: 488.8, 1.80 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40eg

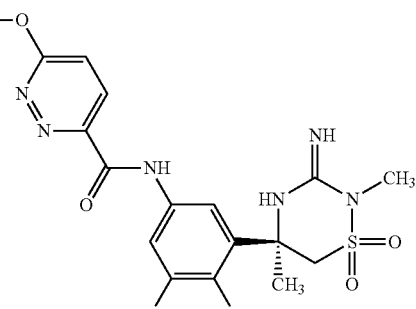

MH+: 441.0, 1.84 min, D

40eh

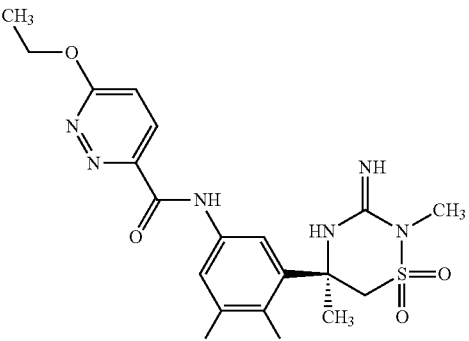

MH+: 455.0, 1.91 min, D

40ei

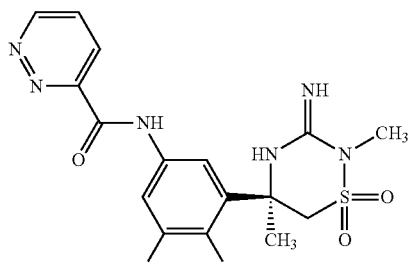

MH+: 411.0, 1.76 min, D

40ej

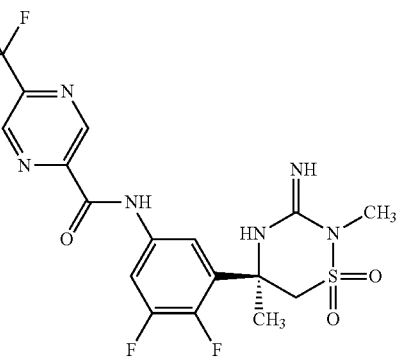

MH+: 479.0, 1.95 min, D

TABLE V-continued
The following examples were prepared using a procedure similar to that described in Scheme 11b using the appropriate aryl amines and carboxylic acids.
Examples (LCMS data listed with each compound: observed MH+, HPLC retention time and LCMS method)
40ek
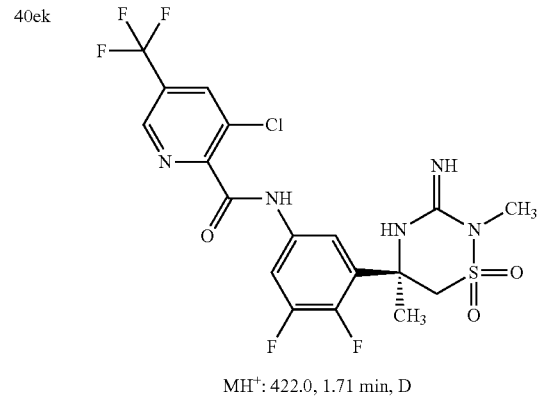
MH+: 422.0, 1.71 min, D
40el
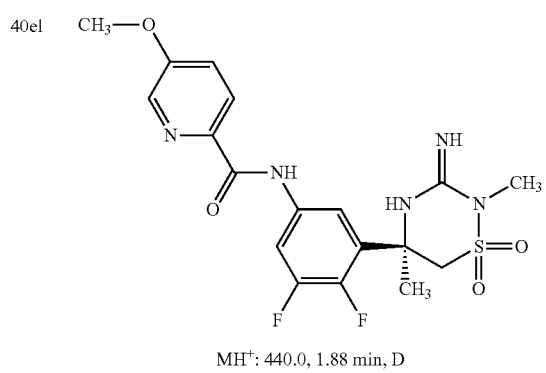
MH+: 440.0, 1.88 min, D
40em
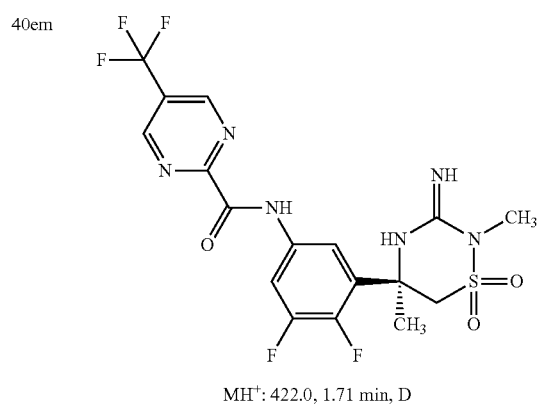
MH+: 422.0, 1.71 min, D
40en
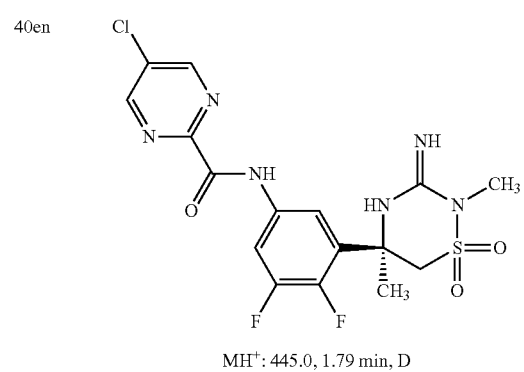
MH+: 445.0, 1.79 min, D
40eo
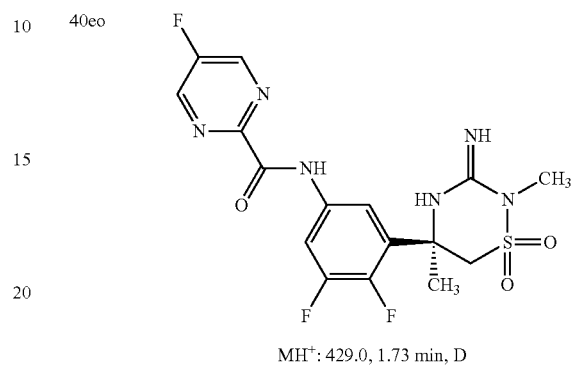
MH+: 429.0, 1.73 min, D
40ep
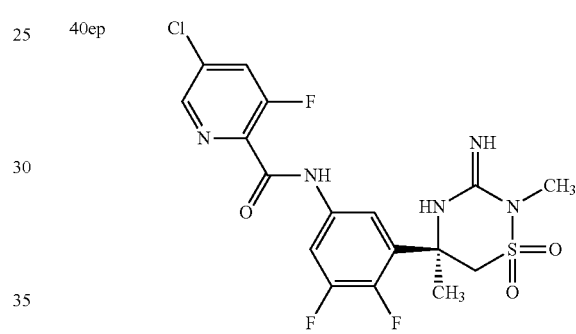
MH+: 462.0, 1.90 min, D
40eq
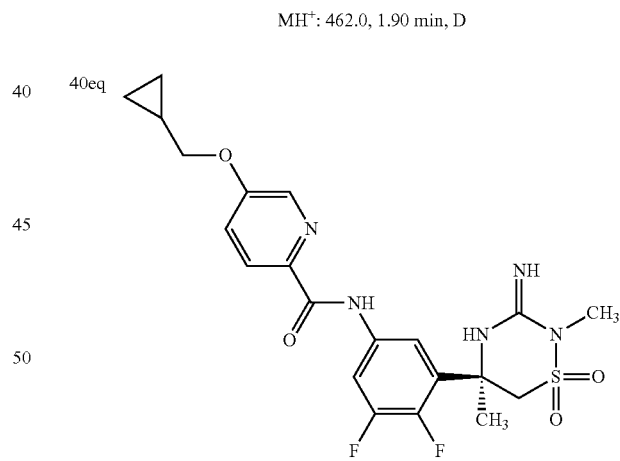
MH+: 480.0, 1.98 min, D
40er
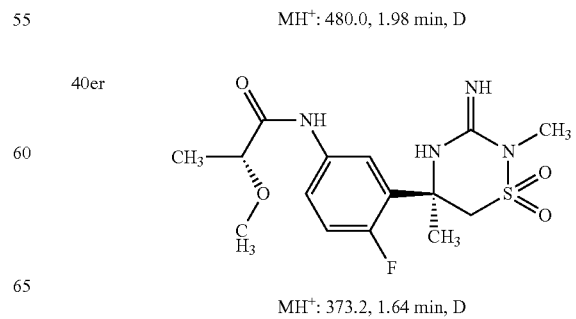
MH+: 373.2, 1.64 min, D TABLE V-continued
The following examples were prepared using a procedure similar to that described in Scheme 11b using the appropriate aryl amines and carboxylic acids.
Examples (LCMS data listed with each compound: observed MH+, HPLC retention time and LCMS method)
40es
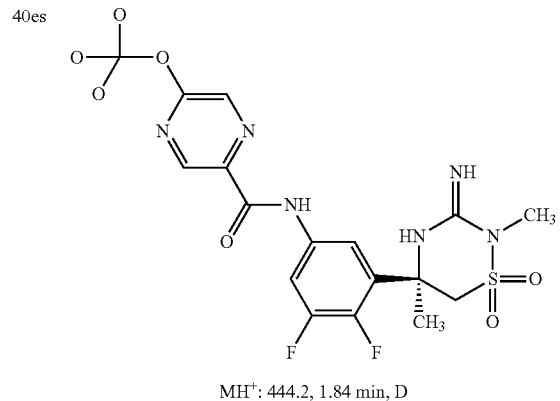
MH+: 444.2, 1.84 min, D
40et
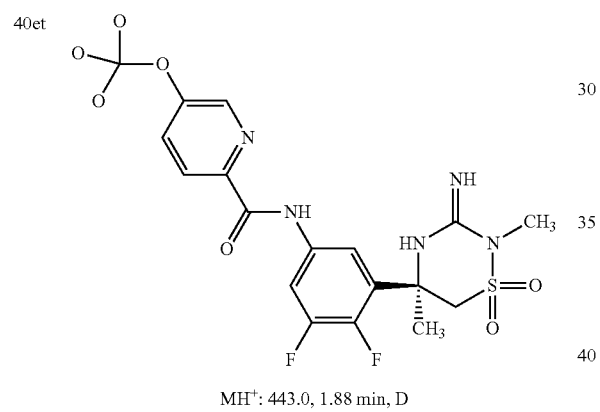
MH+: 443.0, 1.88 min, D
40eu
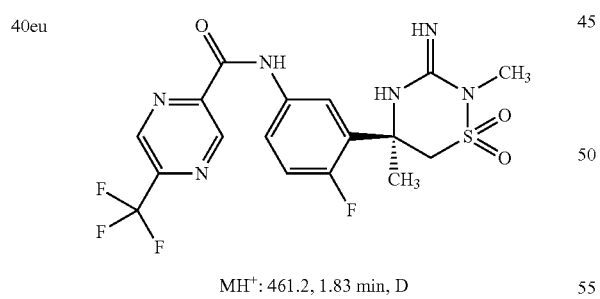
MH+: 461.2, 1.83 min, D
40ev
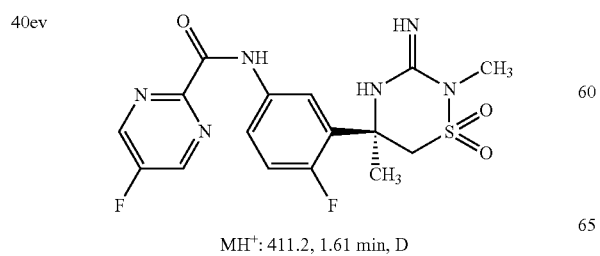
MH+: 411.2, 1.61 min, D
40ew
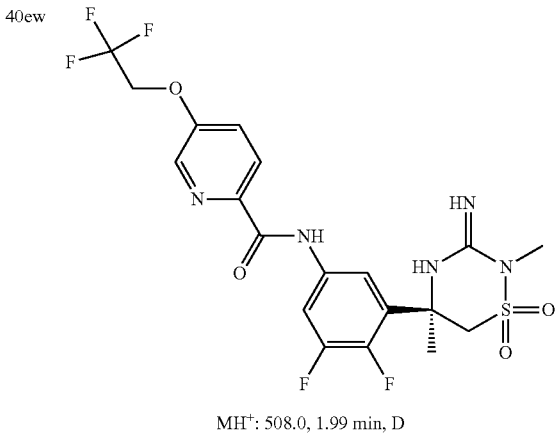
MH+: 508.0, 1.99 min, D
40ex
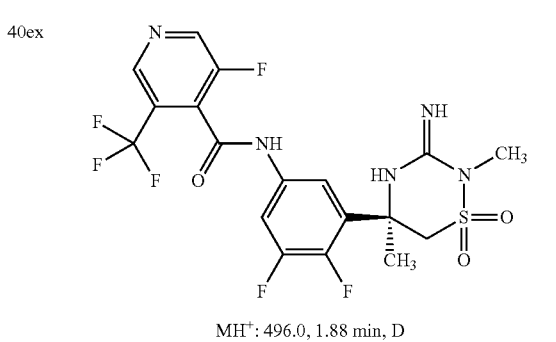
MH+: 496.0, 1.88 min, D
40ez
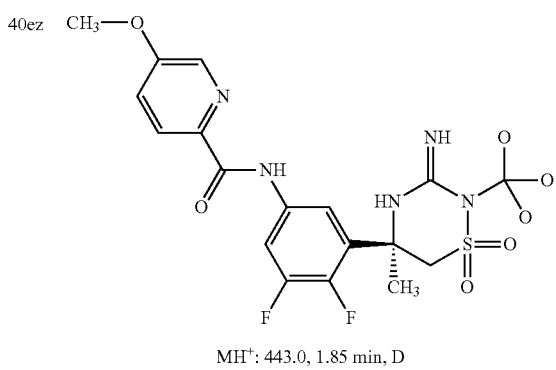
MH+: 443.0, 1.85 min, D
40fa
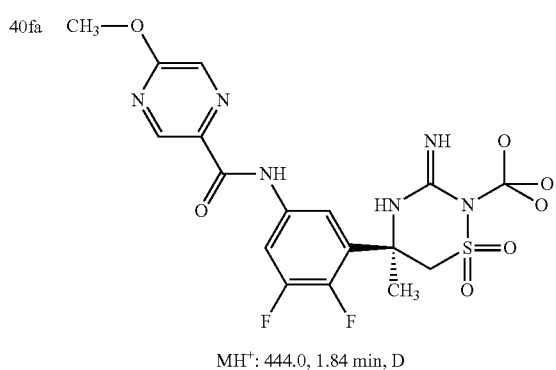
MH+: 444.0, 1.84 min, D

TABLE V-continued
The following examples were prepared using a procedure similar to that described in Scheme 11b using the appropriate aryl amines and carboxylic acids.
Examples (LCMS data listed with each compound: observed MH+, HPLC retention time and LCMS method)
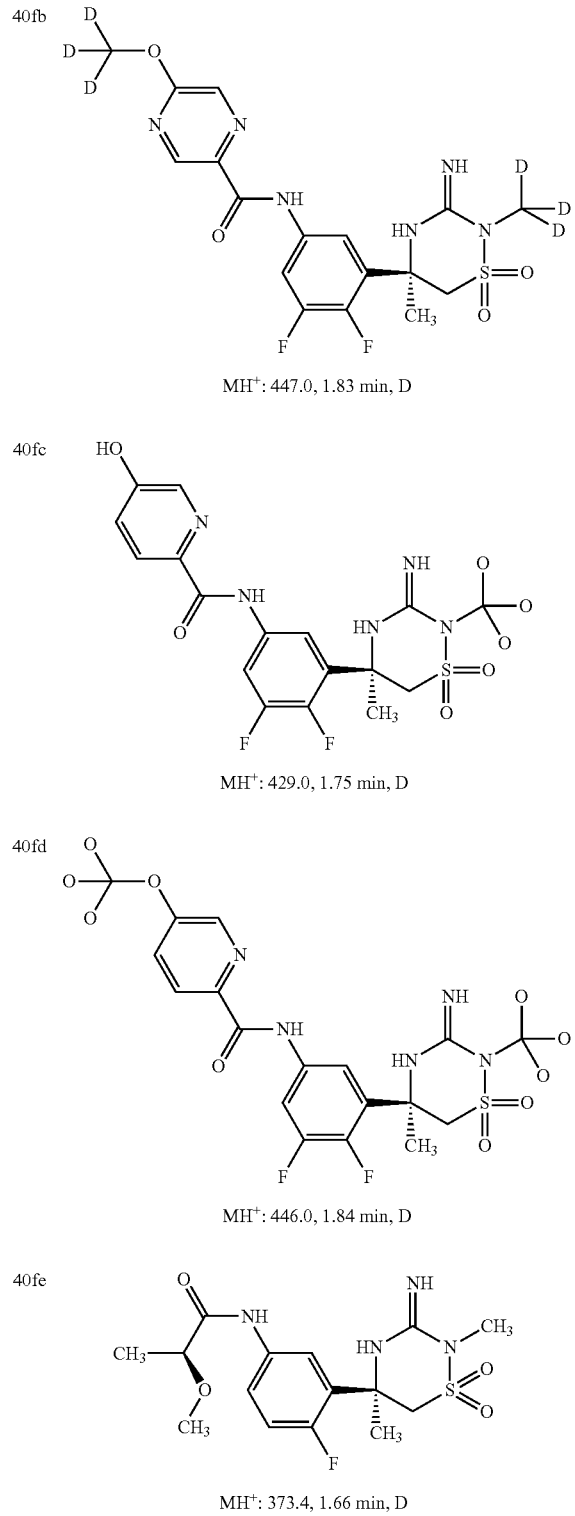
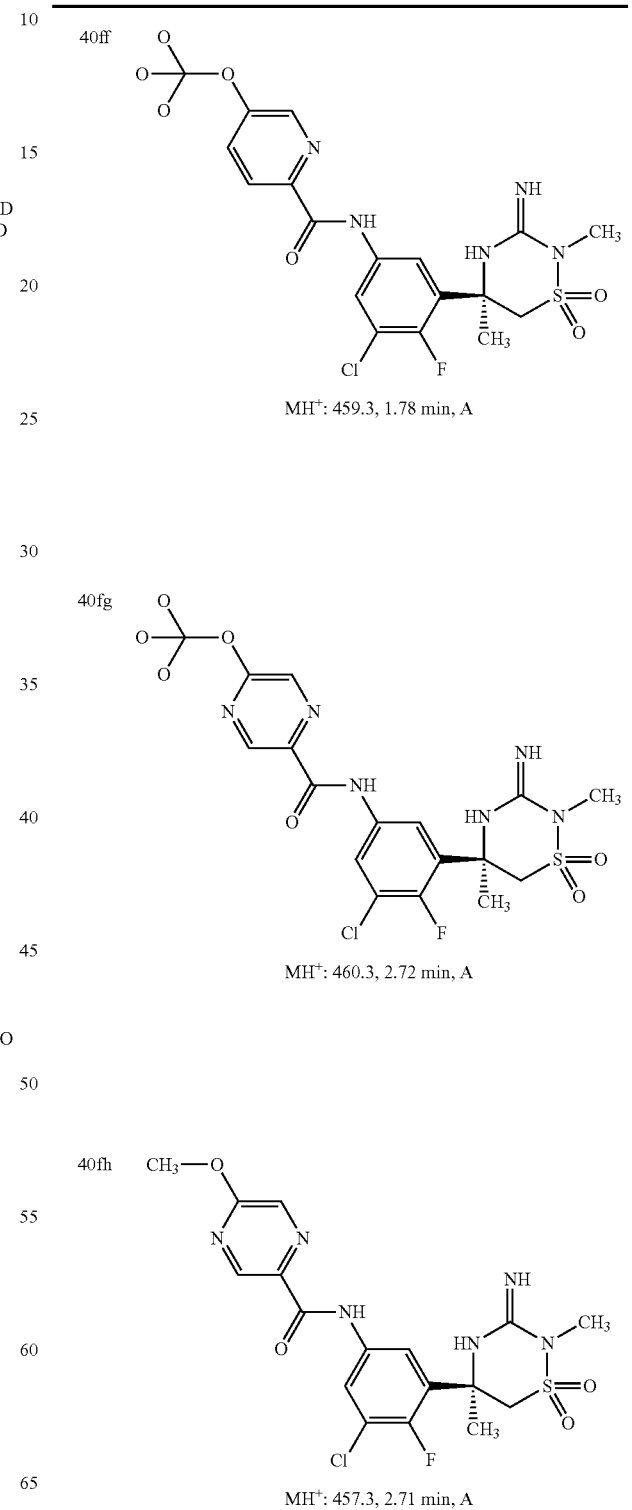

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40fi

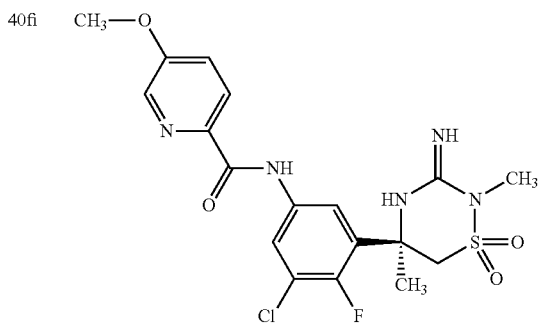

MH+: 456.3, 2.76 min, A

40fj

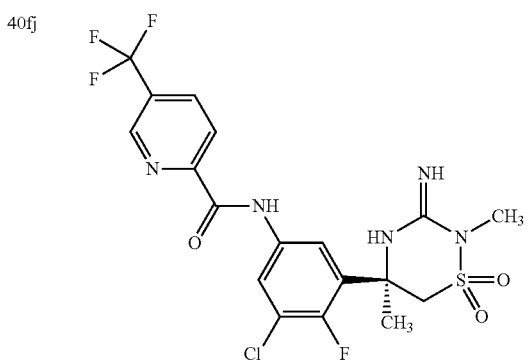

MH+: 494.3, 3.08 min, A

40fk

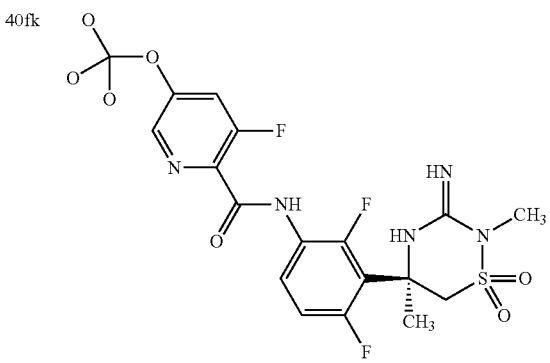

MH+: 461.3, 2.83 min, A

40fl

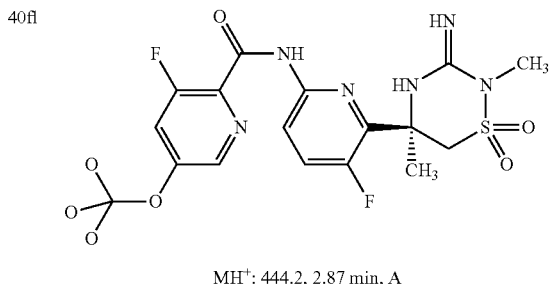

MH+: 444.2, 2.87 min, A

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40fm

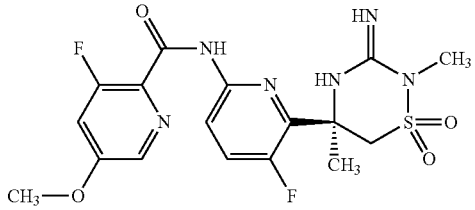

MH+: 441.2, 2.80 min, A

40fn

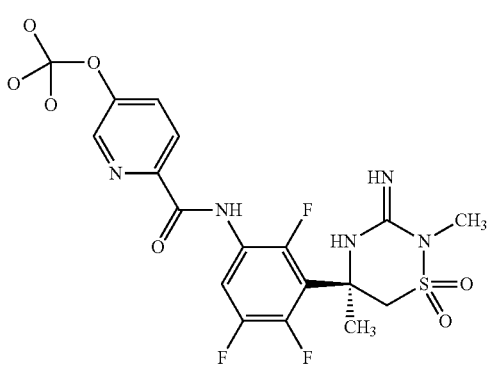

MH+: 461.3, 2.88 min, A

40fo

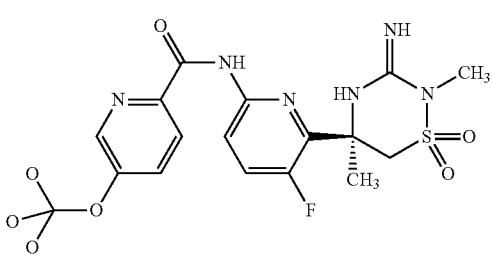

MH+: 426.2, 2.68 min, A

40fp

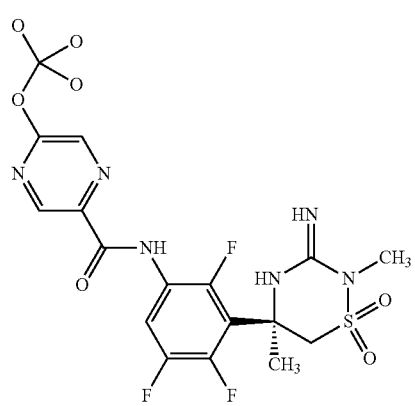

MH+: 462.3, 3.09 min, A

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40fq

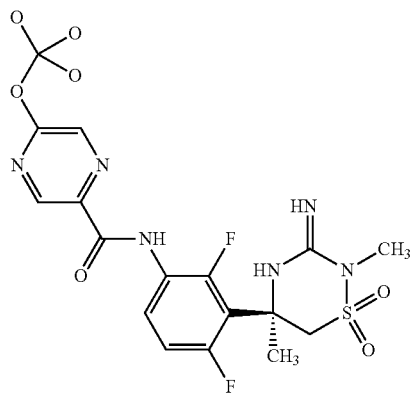

MH+: 444.2, 2.82 min, A

40fr

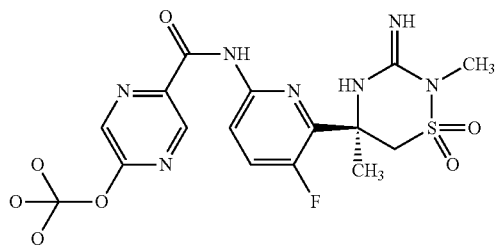

MH+: 427.2, 2.85 min, A

40fs

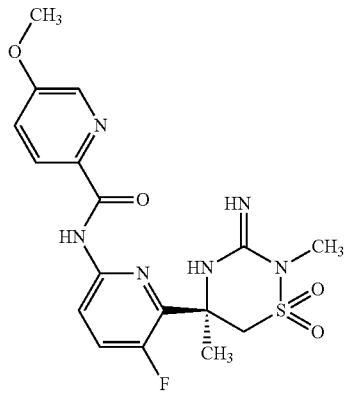

MH+: 423.2, 2.46 min, A

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40ft

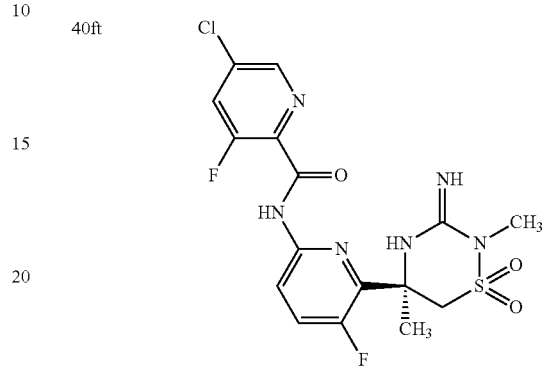

MH+: 445.2, 3.04 min, A

40fu

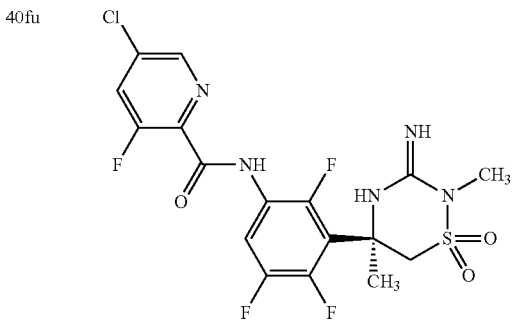

MH+: 480.3, 2.68 min, A

40fv

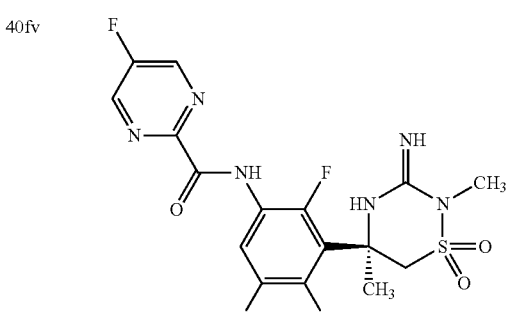

MH+: 447.2, 2.04 min, A

TABLE V-continued
The following examples were prepared using a procedure similar to that described in Scheme 11b using the appropriate aryl amines and carboxylic acids.
Examples (LCMS data listed with each compound: observed MH+, HPLC retention time and LCMS method)
40fw
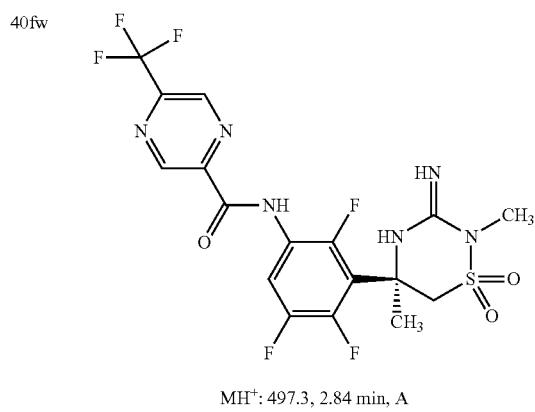
MH+: 497.3, 2.84 min, A
40fx
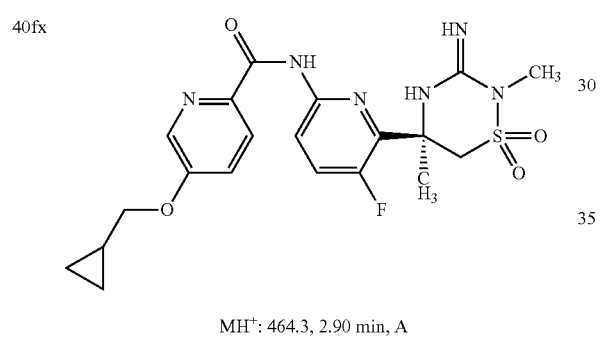
MH+: 464.3, 2.90 min, A
40fy
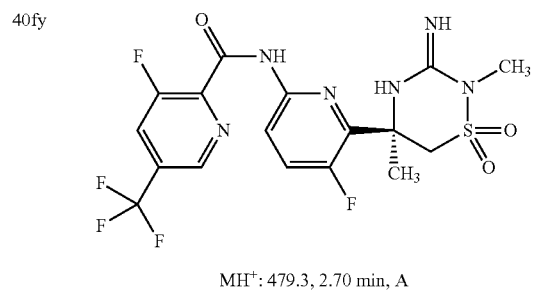
MH+: 479.3, 2.70 min, A
40fz
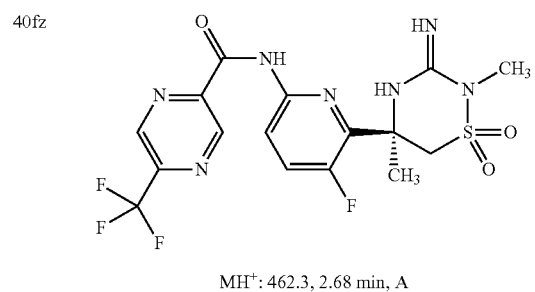
MH+: 462.3, 2.68 min, A
40ga
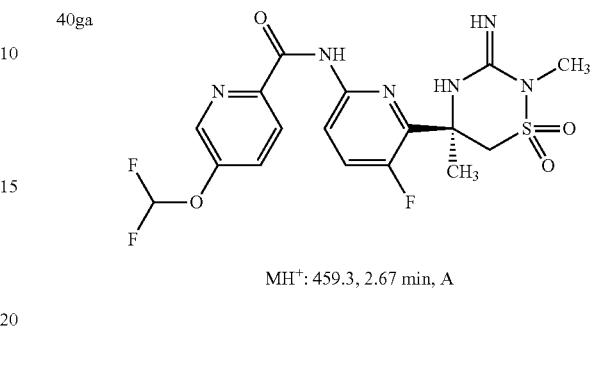
MH+: 459.3, 2.67 min, A
40gb
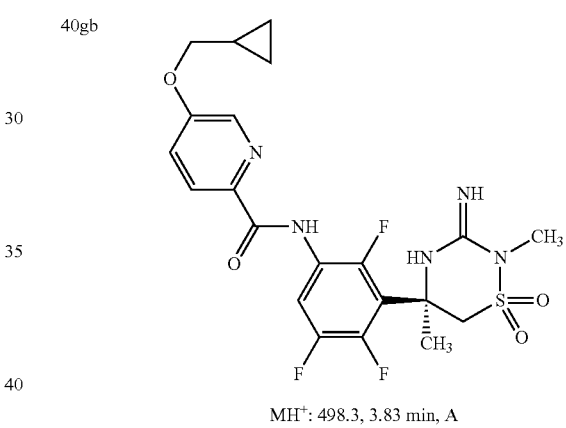
MH+: 498.3, 3.83 min, A
40gc
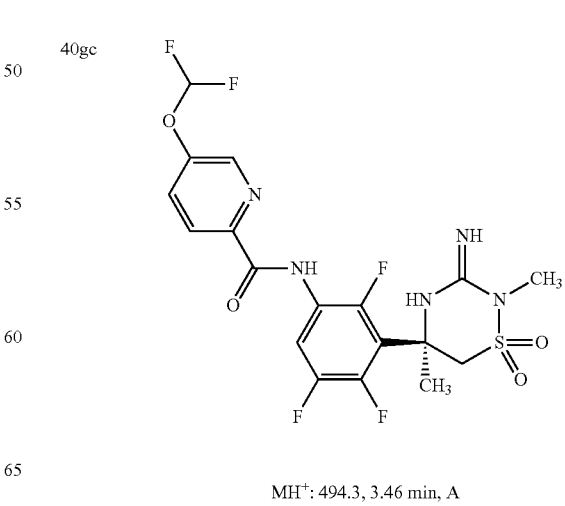
MH+: 494.3, 3.46 min, A TABLE V-continued
The following examples were prepared using a procedure similar to that described in Scheme 11b using the appropriate aryl amines and carboxylic acids.
Examples (LCMS data listed with each compound: observed MH+, HPLC retention time and LCMS method)
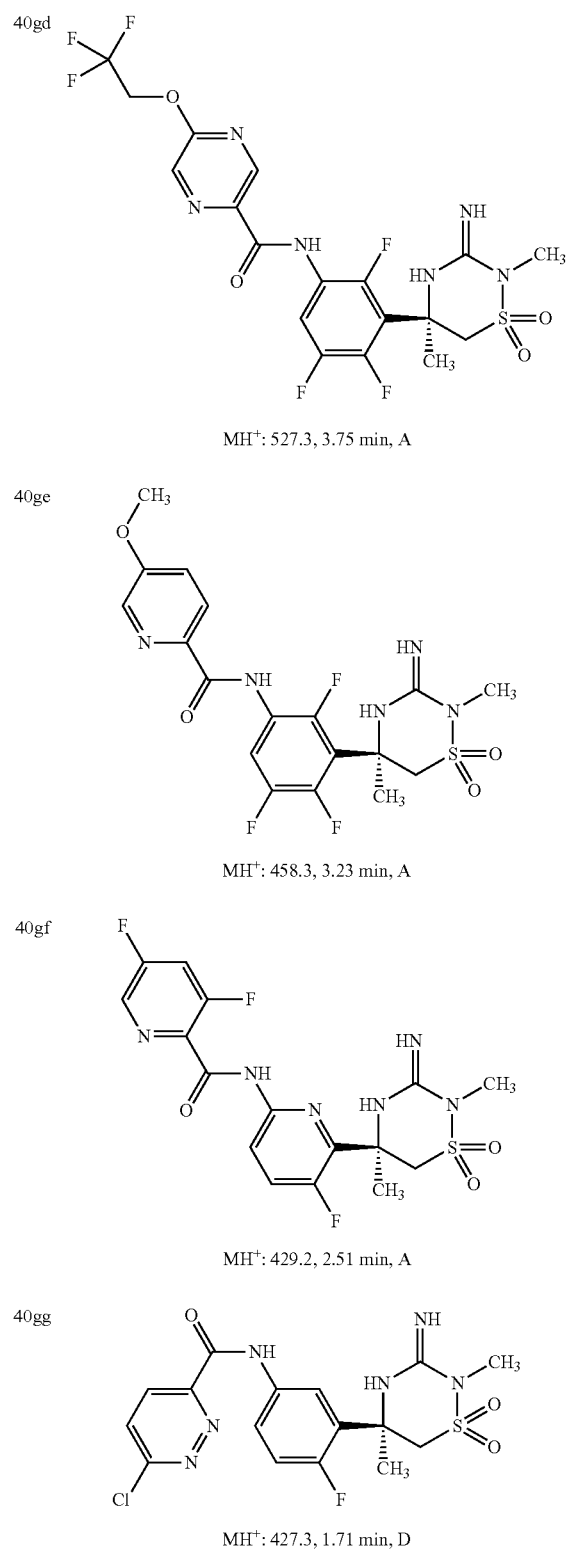
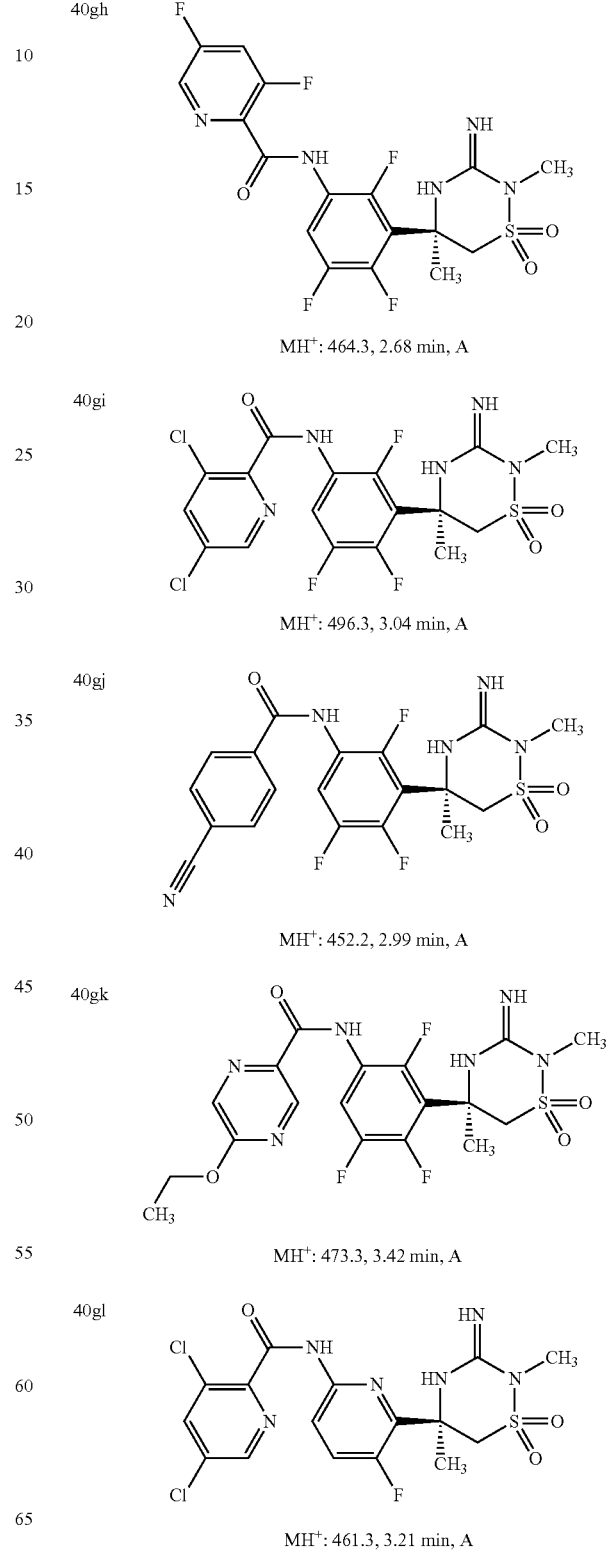

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40gm
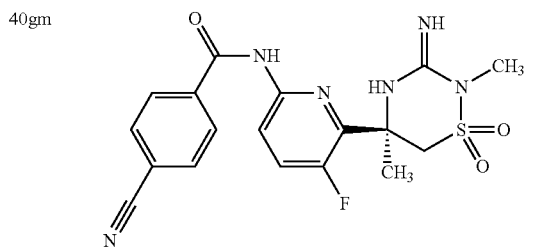
MH+: 417.2, 2.48 min, A

40gn
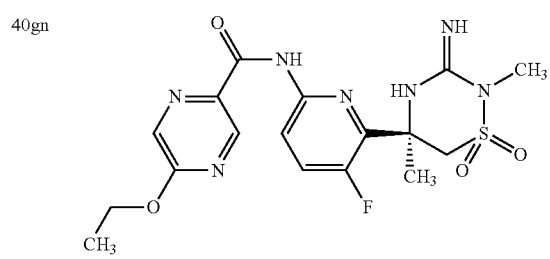
MH+: 438.2, 2.64 min, A

40go
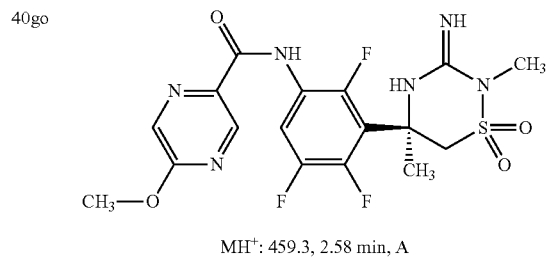
MH+: 459.3, 2.58 min, A

40gp
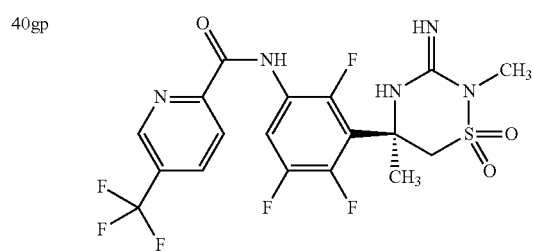
MH+: 496.3, 2.96 min, A

40gq
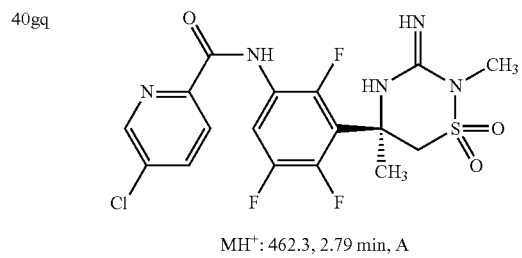
MH+: 462.3, 2.79 min, A

40gr
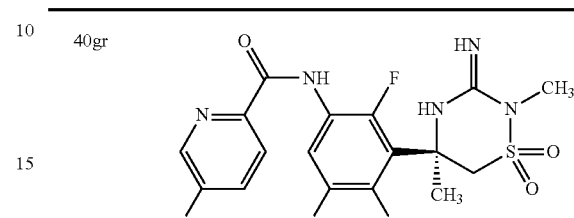
MH+: 446.2, 2.60 min, A

40gs
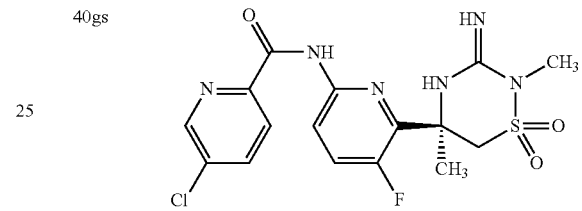
MH+: 427.2, 2.74 min, A

40gt
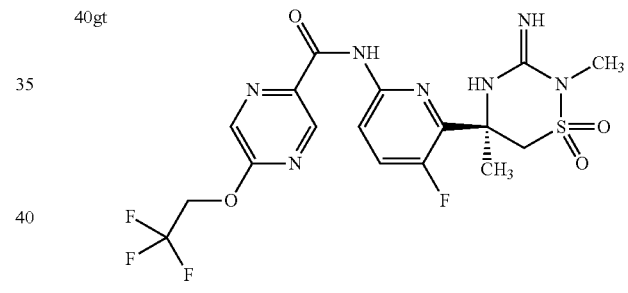
MH+: 492.3, 2.99 min, A

40gu
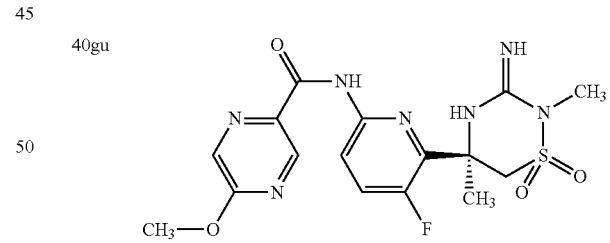
MH+: 424.2, 2.92 min, A

40gv
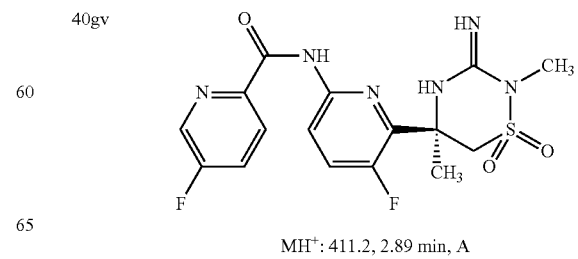
MH+: 411.2, 2.89 min, A

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40gw
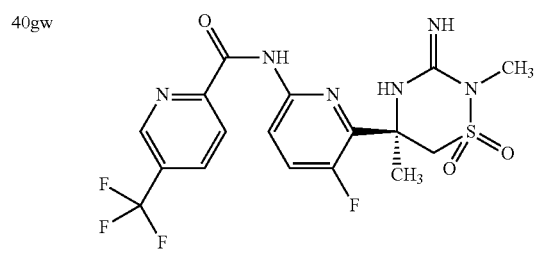
MH+: 461.3, 3.40 min, A

40gx
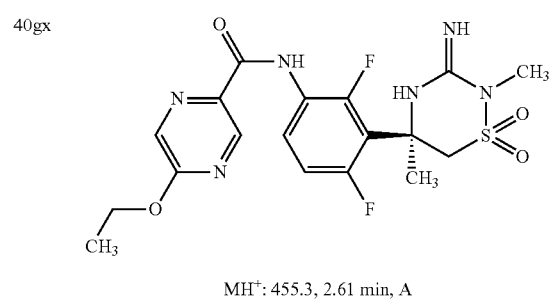
MH+: 455.3, 2.61 min, A

40gy
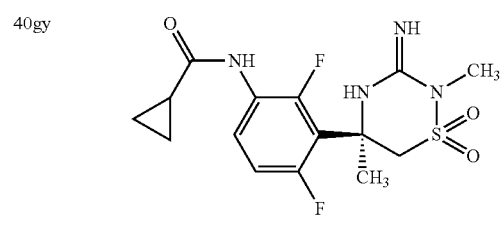
MH+: 373.2, 2.24 min, A

40gz
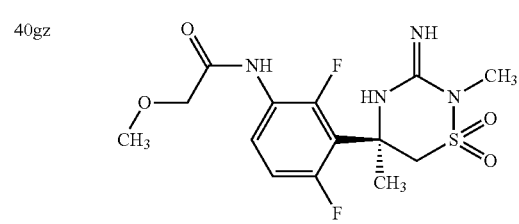
MH+: 377.2, 1.96 min, A

40ha
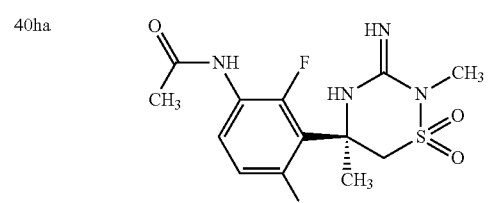
MH+: 347.2, 1.76 min, A

40hb
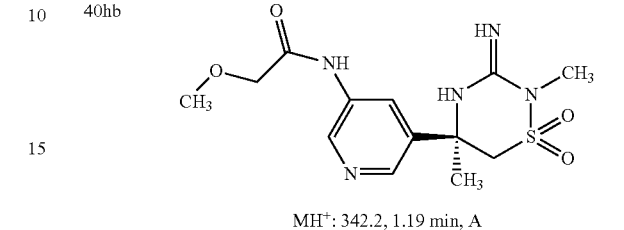
MH+: 342.2, 1.19 min, A

40hc
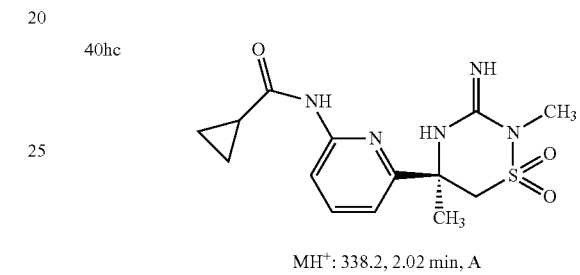
MH+: 338.2, 2.02 min, A

40hd
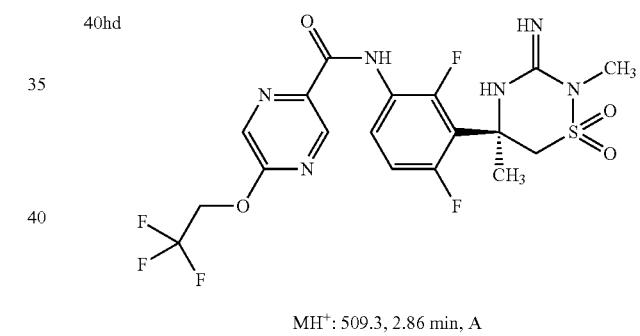
MH+: 509.3, 2.86 min, A

40he
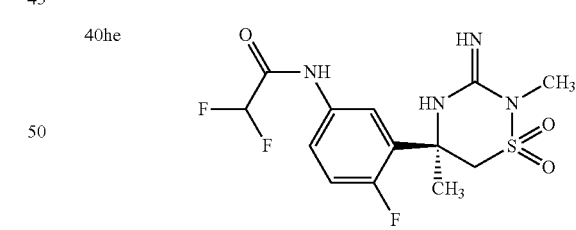
MH+: 365.0, 1.62 min, D

40hf
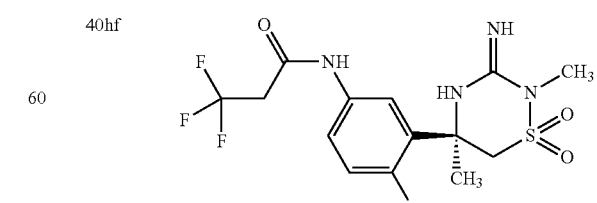
MH+: 397.0, 1.71 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

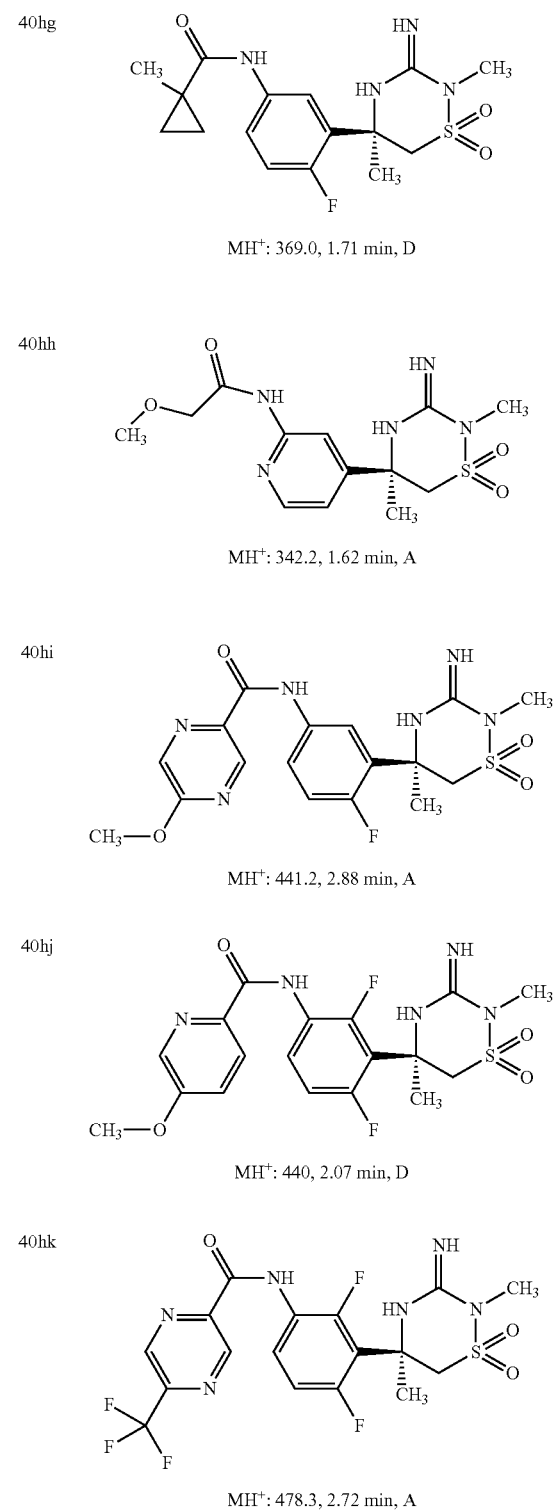

40hg MH+: 369.0, 1.71 min, D

40hh MH+: 342.2, 1.62 min, A

40hi MH+: 441.2, 2.88 min, A

40hj MH+: 440, 2.07 min, D

40hk MH+: 478.3, 2.72 min, A

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

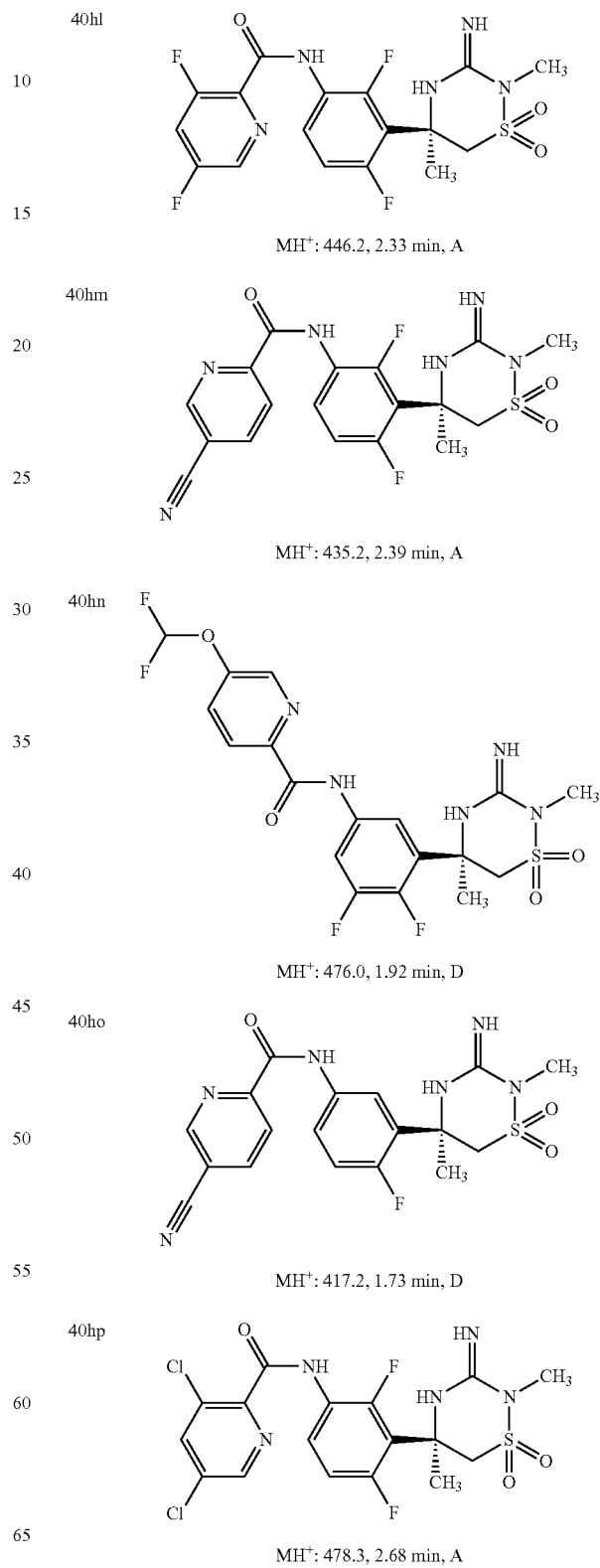

40hl MH+: 446.2, 2.33 min, A

40hm MH+: 435.2, 2.39 min, A

40hn MH+: 476.0, 1.92 min, D

40ho MH+: 417.2, 1.73 min, D

40hp MH+: 478.3, 2.68 min, A

TABLE V-continued
The following examples were prepared using a procedure similar to that described in Scheme 11b using the appropriate aryl amines and carboxylic acids.
Examples (LCMS data listed with each compound: observed MH+, HPLC retention time and LCMS method)
40hq
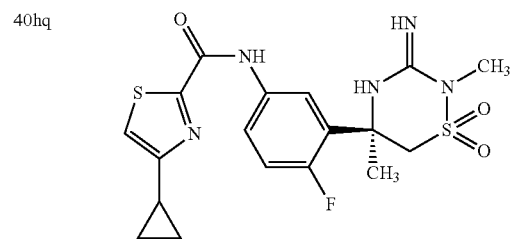
MH+: 438.0, 1.89 min, D
40hr
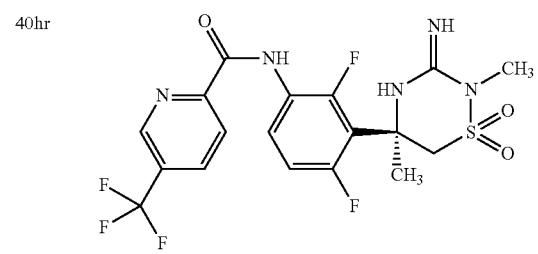
MH+: 478.3, 1.99 min, A
40hs
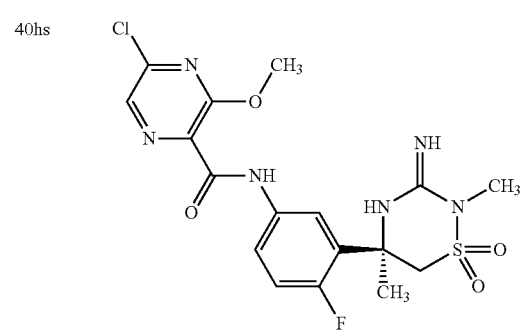
MH+: 457.0, 1.79 min, D
40ht
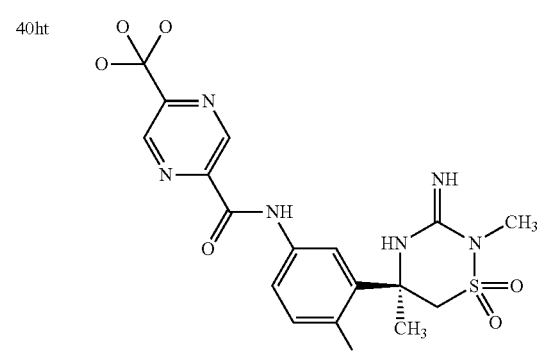
MH+: 410.0, 1.71 min, D
40hu
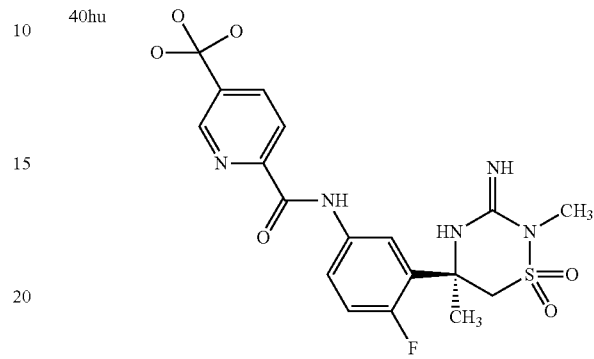
MH+: 409.2, 1.79 min, D
40hv
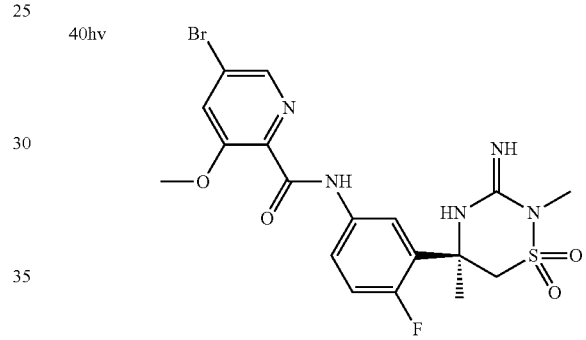
MH+: 500.0, 1.81 min, D
40hw
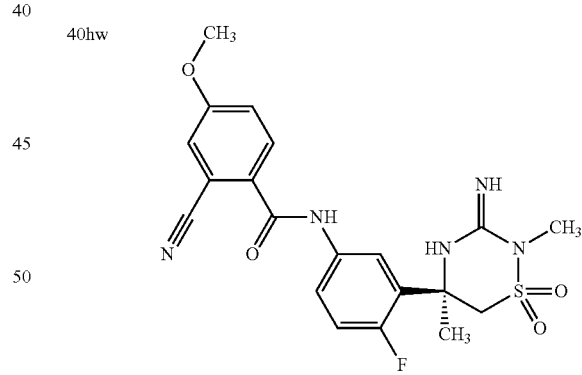
MH+: 446.0, 1.79 min, D
40hx
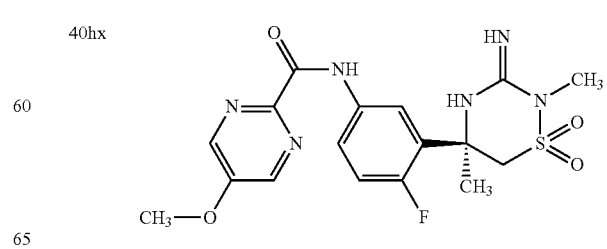
MH+: 423.0, 1.68 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40hy
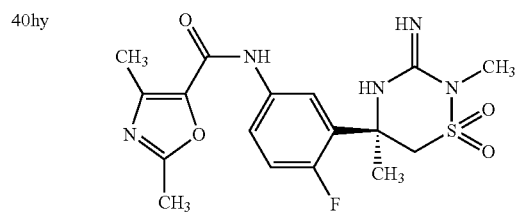
MH+: 410.2, 1.69 min, D

40hz
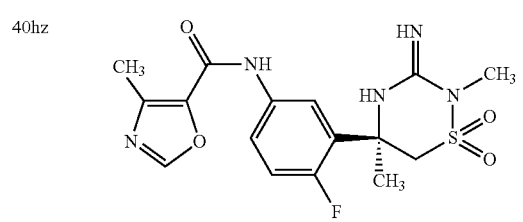
MH+: 396.2, 1.65 min, D

40ia
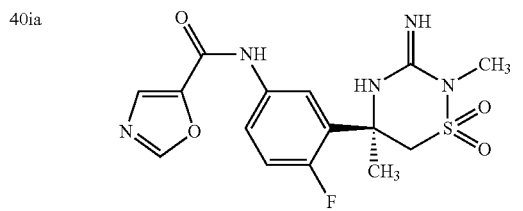
MH+: 382.2, 1.58 min, D

40ib*
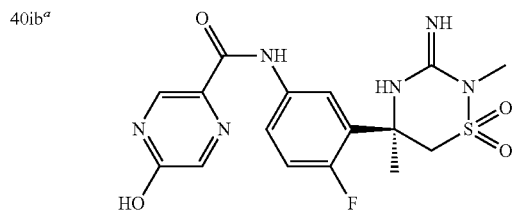
MH+: 409.0, 1.58 min, D

40ic*
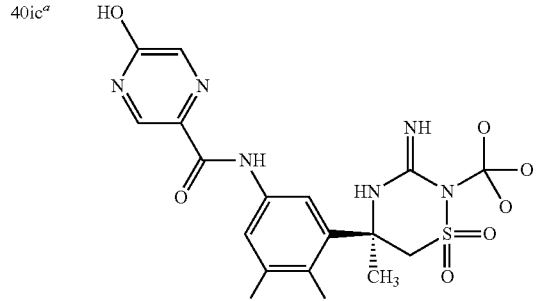
MH+: 430.0, 1.66 min, D

40id*
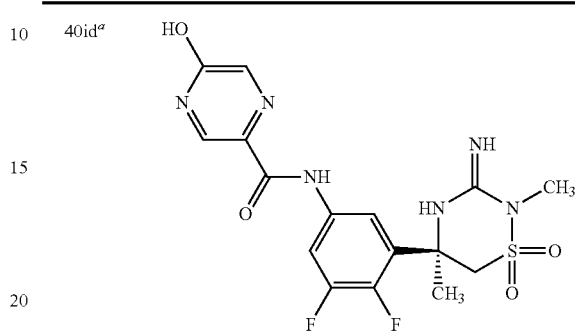
MH+: 427.0, 1.68 min, D

40ie
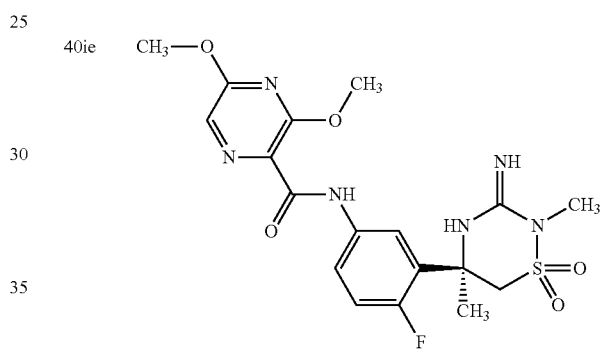
MH+: 453.2, 1.60 min, D

40if
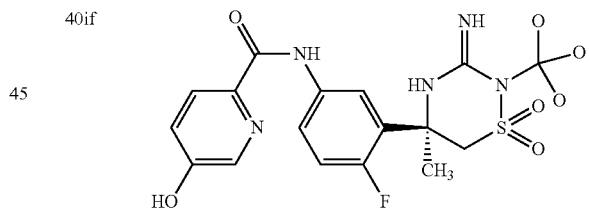
MH+: 411.0, 1.83 min, D

40ig
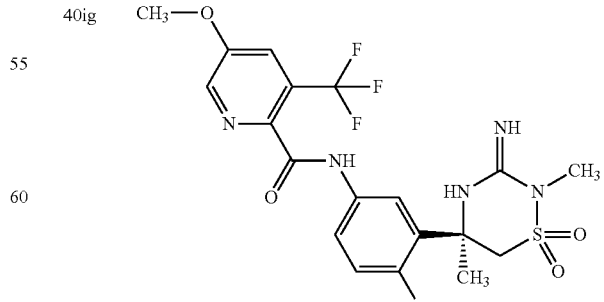
MH+: 490.0, 1.96 min, D

TABLE V-continued

The following examples were prepared using a procedure similar to that described in Scheme 11b using the appropriate aryl amines and carboxylic acids.
Examples (LCMS data listed with each compound: observed MH+, HPLC retention time and LCMS method)

40ih[a]

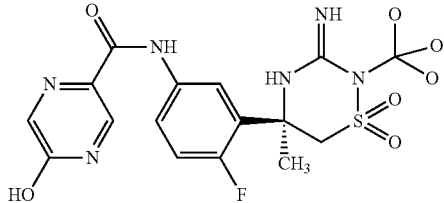

MH+: 412.0, 1.72 min, D

40ii

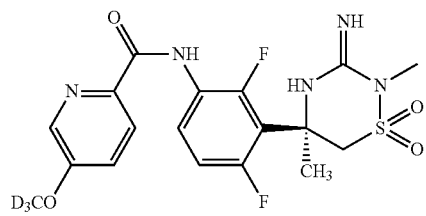

MH+: 443.2, 2.57 min, A

40ij

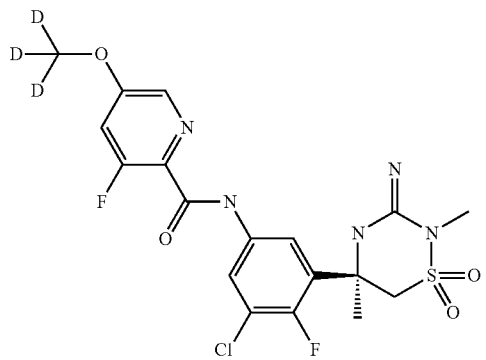

MH+: 477.3, 2.95 min, A

[a]The hydroxypyrazine amides were formed using the cyclopropylmethylether pyrazine acid (Entry 5, Table IVb) instead of 1,3-oxazole-4-carboxylic acid in step 1 of Scheme 11b.

Scheme 12:

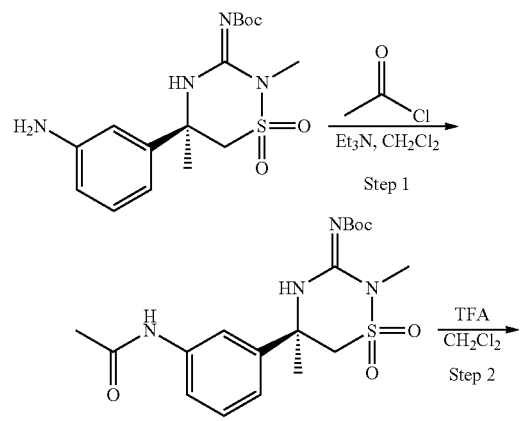

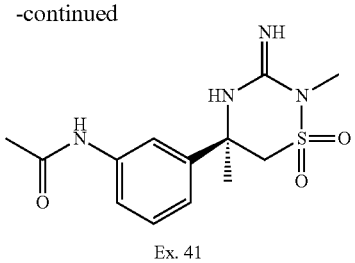

Ex. 41

Step 1:
To a solution of the aniline from Table IV entry 1 (80 mg) and Et₃N (50 μL) in CH₂Cl₂ (2 mL) was added acetyl chloride (1.2 eq.). The resulting solution was stirred at RT for 2 hours. Water was added and the aqueous layer was extracted with CH₂Cl₂, dried over Na₂SO₄, filtered and concentrated. The crude residue was purified via flash chromatography (SiO₂: 0 to 60% EtoAc in hex).

Step 2:
Example 41 was prepared as the TFA salt from the product of step 1 using a method similar to that described in Scheme 11b step 2. LCMS data: (method D): $t_R$=0.91 min, m/e=311 (M+H).

Scheme 12b:

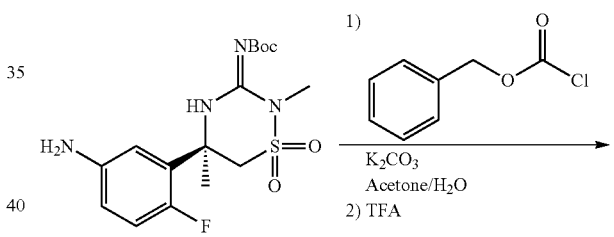

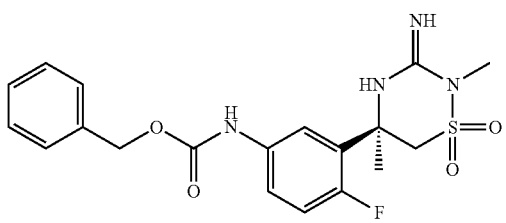

Ex. 41b

To a mixture of the aniline from Scheme 10 (50 mg, 0.13 mmol) and potassium carbonate (18 mg, 0.13 mmol) in 1:1 acetone:water (4 mL) was added benzyl chloroformate (0.028 mL, 0.19 mmol). The mixture was stirred at RT for 30 min. Water was added and the mixture was extracted with CH₂Cl₂ (3×). The combined organic layers were dried over Na₂SO₄, filtered and concentrated. The crude product was purified via flash chromatography (SiO₂: gradient elution 100:0 to 70:30 hexanes:EtOAc) to afford the carbamate.

Example 41b was prepared as its TFA salt from the above carbamate using a method similar to that described in Scheme 11b step 2. LCMS data: (method D): $t_R$=1.88 min, m/e=421.0 (M+H).

Scheme 12c:

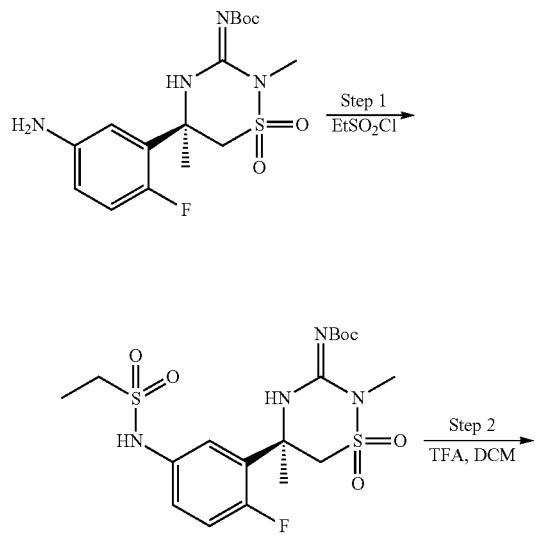

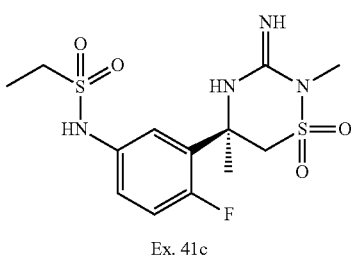

Ex. 41c

Step 1:

To a mixture of the aniline (200 mg, 0.517 mmol, Scheme 10) and DIEA (0.36 mL, 2.07 mmol) in $CH_2Cl_2$ (2 mL) at RT was added dropwise ethylsulfonyl chloride (0.074 mL, 0.775 mmol). After 18 h, the reaction was quenched with 1 M HCl and the aqueous layer was extracted with DCM. The combined organic layers were dried over $MgSO_4$ and concentrated under reduced pressure.

Step 2:

Example 41c was prepared from the above material using a method similar to that described in Scheme 11b step 2. After deprotection, the resulting residue was purified by reverse phase chromatography (C18: gradient elution, 90:10:0.1 to 0:100:0.1 water:MeCN:TFA) to provide Example 41c as its TFA salt. LCMS (conditions D): $t_R$=1.64 min, m/e=379.0 (M+H).

TABLE Va

The following examples were prepared using a method similar to that described in Scheme 12c.
Examples (LCMS data listed with each compound: observed MH+, HPLC retention time and LCMS method)

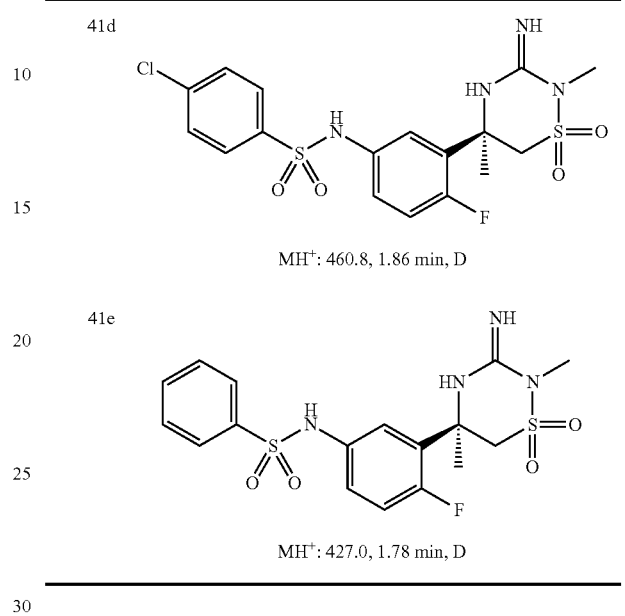

Scheme 12d:

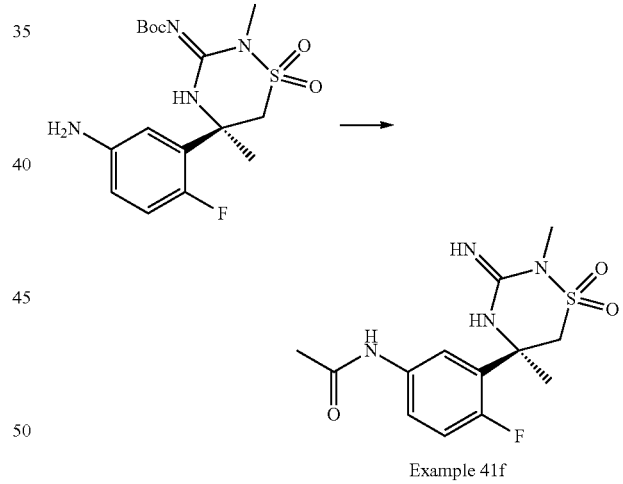

Example 41f

To the aniline (Scheme 10, 70 mg, 0.18 mmol) in 2 mL DCM was added acetic anhydride (19 μL, 0.2 mmol) and triethylamine (29 μL, 0.2 mmol). The reaction was stirred for 3 hours at room temperature, then poured into water. The mixture was extracted with DCM. The combined organic layers were dried (MgSO₄), filtered, and concentrated in vacuo. The residue was purified by silica gel chromatography (0-50% EtOAc/hexanes over 30 minutes) to provide a methyl amide product. This material was stirred in 2 mL 20% TFA/DCM for 1 hr and then concentrated in vacuo to provide Example 41f as a trifluoroacetate salt (0.041 g, 69%). LCMS data: (method A): $t_R$=2.96 min, m/e=379.2 (M+H).

TABLE VI

The following examples were prepared using a method similar to that described in Scheme 12 using the appropriate acid chlorides and aryl amines.
Examples (LCMS data listed with each compound: observed MH+, HPLC retention time and LCMS method)

42

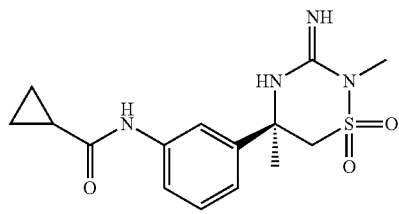

MH+: 337, 1.57 min, D

42a

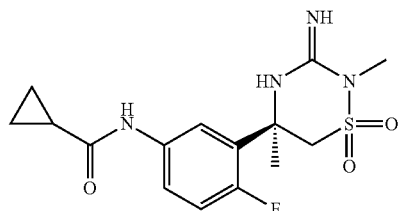

MH+: 335.0, 1.66 min, D

Scheme 12e:

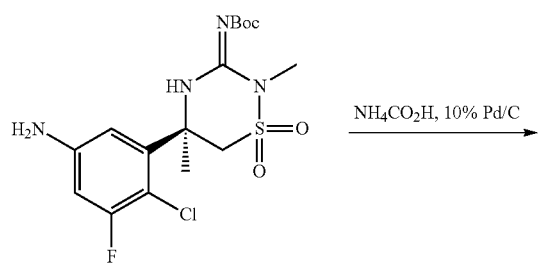

A mixture of 2-chloro-3-fluoro aniline (252 mg, 0.60 mmol), ammonium formate (5.0 g, 79 mmol) in 25 mL of isopropanol was heated at 70° C. overnight. After filtration and concentration, the residue was purified by silica gel chromatography (elution with 0-30% EtOAc/Hex) to afford the 3-fluoro aniline product (150 mg).

Scheme 12f:

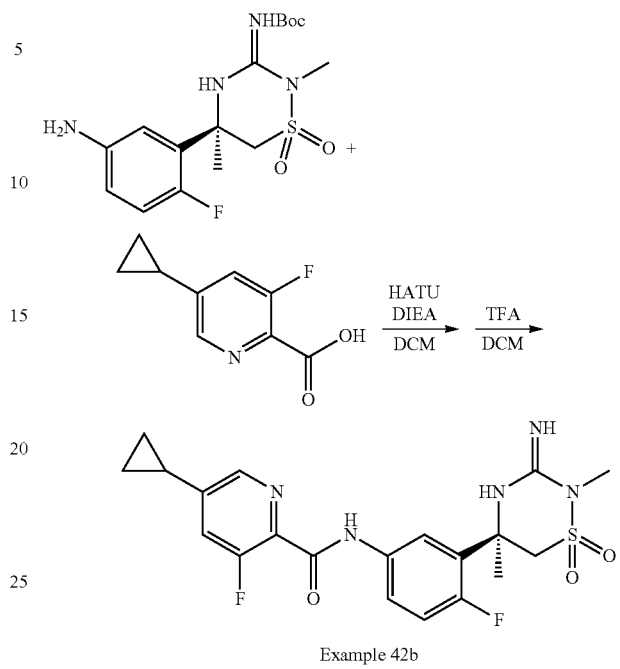

Example 42b

A mixture of aniline (96 mg, 0.25 mmol, Scheme 10), the acid (Scheme 11x, 81 mg, 0.45 mmol), HATU (230 mg, 0.60 mmol), and DMEA (0.36 mL, 2.0 mmol) in 5 mL of DCM was stirred at room temperature overnight. The reaction mixture was diluted with DCM, washed with 5% citric acid, sat. NaHCO$_3$, and brine. After drying (MgSO$_4$) and concentration, the residue was subjected to silica gel chromatograpy (elution with 0-25% EtOAc/Hex). The resulting product was dissolved in 6 mL of 25% of TFA/DCM and stirred at room temperature for 1 h. Concentration and drying in vacuo provided Example 42b (143 mg) as a TFA salt. LCMS (conditions D): $t_R$=1.91 min, m/e=450.2 (M±H).

TABLE VIb

The following examples were prepared from the corresponding aniline and carboxylic acid using a procedure similar to that described in Scheme 12f.
Examples (LCMS data listed with each compound: observed MH+, HPLV rentention time and LCMS method)

42c

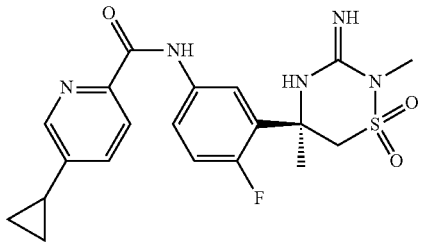

MH+: 432.2, 1.95 min, D

TABLE VIb-continued

The following examples were prepared from the corresponding aniline and carboxylic acid using a procedure similar to that described in Scheme 12f. Examples (LCMS data listed with each compound: observed MH+, HPLV rentention time and LCMS method)

42d
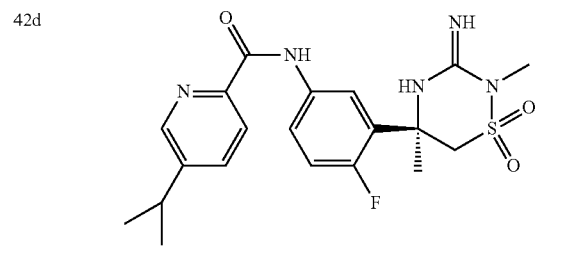
MH+: 434.2, 1.99 min, D

42e
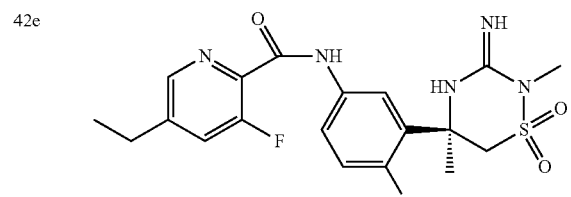
MH+: 438.2, 1.91 min, D

42f
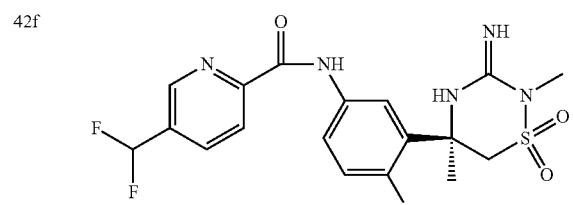
MH+: 442.2, 0.81 min, E

42g
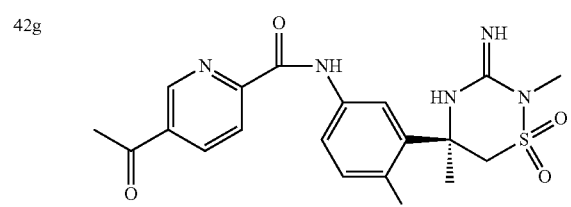
MH+: 434.2, 0.76 min, E

42h
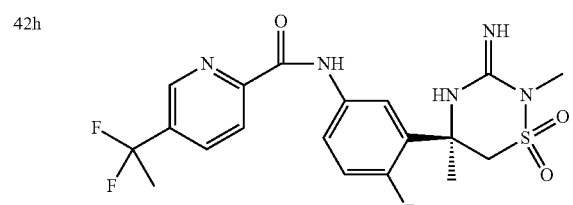
MH+: 432.2, 1.95 min, D

42i
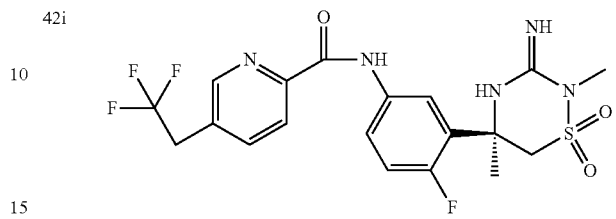
MH+: 474.0, 0.84 min, E

42j
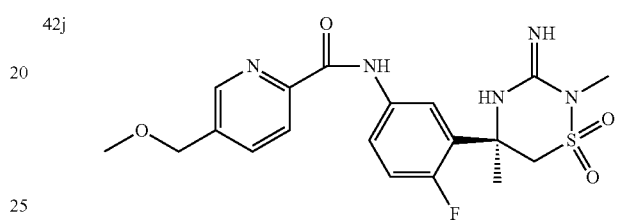
MH+: 436.0, 0.77 min, E

42k
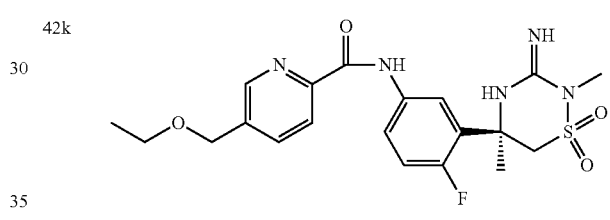
MH+: 450.0, 0.84 min, E

42l
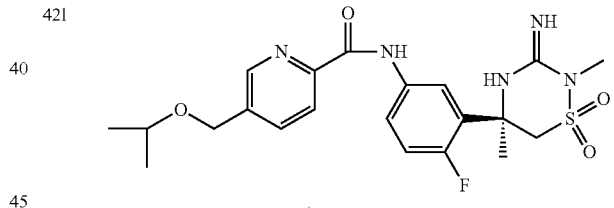
MH+: 464.0, 0.88 min, E

42m
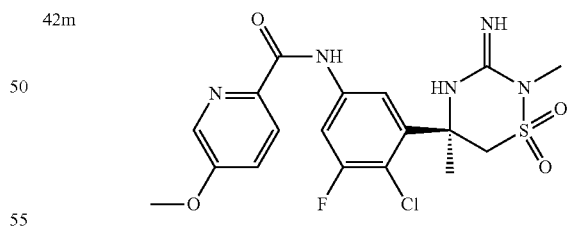
MH+: 456.0, 1.87 min, D

42n
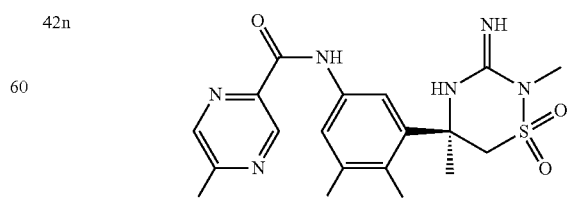
MH+: 457.0, 0.84 min, E

TABLE VIb-continued

The following examples were prepared from the corresponding aniline and carboxylic acid using a procedure similar to that described in Scheme 12f. Examples (LCMS data listed with each compound: observed MH+, HPLV retention time and LCMS method)

42o MH+: 459.0, 0.84 min, E

42p MH+: 460.0, 0.84 min, E

42q MH+: 493.9, 0.88 min, E

42r MH+: 444.0, 0.82 min, E

42s MH+: 459.9, 0.88 min, E

42t MH+: 468.0, 0.79 min, E

42u MH+: 432.0, 0.78 min, E

42v MH+: 410.0, 0.79 min, E

Scheme 13:

To a solution of the thiophene from Table IIb Entry 3 (12 g, 5.6 mmol) in DMF in an aluminum foil wrapped round bottom flask under an atmosphere of $N_2$ was added NBS (2.7 g, 15 mmol). The resultant solution was heated to 50° C. with stirring for 8 hours. The solution was cooled to RT. To the solution was added an aqueous solution of $NaHCO_3$ and $Na_2S_2O_5$. The aqueous layer was extracted with EtOAc. The organic layer was washed with sat $NaHCO_{3\ (aq.)}$ (2×). The organic layer was dried over Na$_2$SO$_4$, filtered and concentrated. The crude product was purified via flash chromatography (SiO$_2$: gradient elution 100:0 to 83:17 hexanes:EtOAc) to afford the bromothiophene (1.7 g, 63% yield).

TABLE VII

The following compounds were prepared using a procedure similar to that described in Scheme 13 using the appropriate starting material.

| Entry | 2-bromothiophene |
|---|---|
| 1 | (structure with NBoc, HN, S, SO$_2$, CF$_3$, Br) |
| 2 | (structure with NBoc, HN, S, SO$_2$, Br, Br) |

Scheme 14:

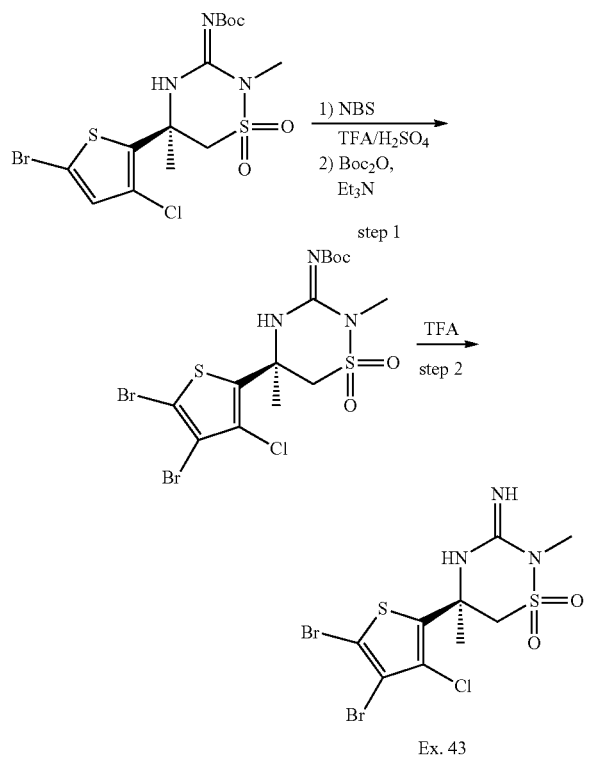

Ex. 43

Step 1:
To a solution of the thiophene from Scheme 13 (100 mg, 0.21 mmol) in TFA (ca. 2 mL) was added NBS (94 mg, 0.53 mmol) and H$_2$SO$_4$ (4 drops). The solution was allowed to stir at RT for 30 min. After that time, additional NBS (80 mg) was added and the solution was stirred for an additional 30 min. The mixture was then quenched with sat. NaHCO$_3$ $_{(aq.)}$ and Na$_2$S$_2$O$_5$ $_{(s)}$. The aqueous layer was extracted with EtOAc. The organic layer was washed with sat. NaHCO$_3$ $_{(aq.)}$ (2×), dried over Na$_2$SO$_4$, filtered and concentrated. The crude product was slurried in CH$_2$Cl$_2$. To this mixture was added di-tert-butyldicarbonate (96 mg, 0.21 mmol) and Et$_3$N (25 mg, 0.23 mmol). The resultant mixture was stirred at RT overnight. The solution was then concentrated and the crude residue was purified via prep TLC (SiO$_2$: 3:1 hexanes:EtOAc) to afford the dibromothiophene (49 mg).

Step 2:
Example 43 was prepared using a method similar to that described in Scheme 11b
Step 2. LCMS (conditions A): $t_R$=3.07 min, m/e=452.2 (M+H).

Scheme 15:

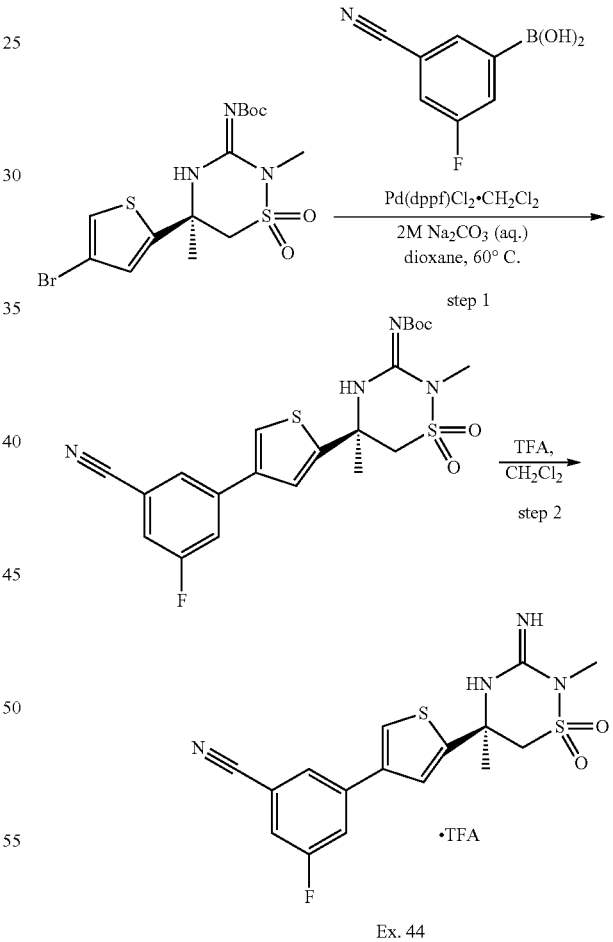

Ex. 44

Step 1:
To a microwave vial containing the thiophene bromide (Scheme 3) (149 mg, 0.34 mmol) was added 3-cyano-5-fluorophenyl boronic acid (146 mg, 0.88 mmol), 2 M Na$_2$CO$_3$ $_{(aq.)}$ (0.31 mL) and dioxane (2.5 mL). The mixture was degassed by bubbling N$_2$ through it for 5 min. To this mixture was added [1,1'-bis(diphenylphosphino)ferrocene]

dichloropalladium(II) complex with $CH_2Cl_2$ (60 mg, 0.074 mmol). The vial was capped and the atmosphere was purged with nitrogen. The mixture was heated to 60° C. with stirring for 2 hours. The mixture was cooled to RT and diluted with EtOAc. The mixture was then filtered through Celite. The organic layer was washed with brine. The aqueous layer was hack extracted with EtOAc (3×). The combined organic layers were dried over $Na_2SO_4$, filtered and concentrated. The crude product was purified via preperative TLC ($SiO_2$: 3:1 hexanes:EtOAc) to afford the biaryl compound (105 mg).

Step 2:

To a solution of the biaryl compound from step 1 in $CH_2Cl_2$ (1.0 mL) was added TFA (1.0 mL). The resultant solution was stirred at RT for 1.5 hours. The solvent was removed in vacuo to afford Example 44 as the trifluoroacetate salt. LCMS data: (method A): $t_R$=2.96 min, m/e=379.2 (M+H).

TABLE VIII

The following examples were prepared using a procedure similar to that described in Scheme 15 using the appropriate aryl bromide and boronic acid/ester.
Examples
(LCMS data listed with each compound: observed $MH^+$, HPLC retention time and LCMS method)

45

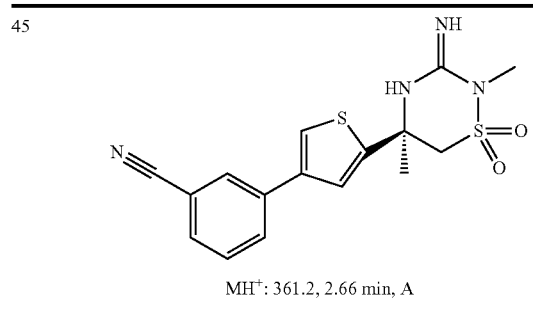

$MH^+$: 361.2, 2.66 min, A

46

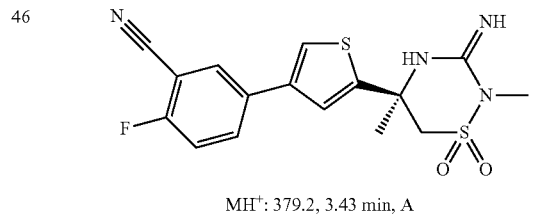

$MH^+$: 379.2, 3.43 min, A

47

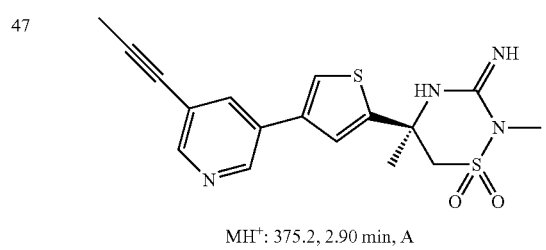

$MH^+$: 375.2, 2.90 min, A

48

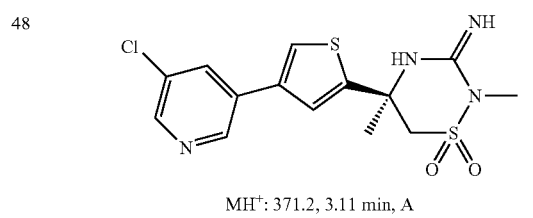

$MH^+$: 371.2, 3.11 min, A

TABLE VIII-continued

The following examples were prepared using a procedure similar to that described in Scheme 15 using the appropriate aryl bromide and boronic acid/ester.
Examples
(LCMS data listed with each compound: observed $MH^+$, HPLC retention time and LCMS method)

49

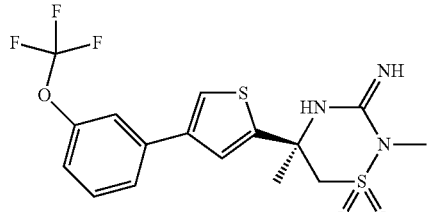

$MH^+$: 420.2, 3.33 min, A

50

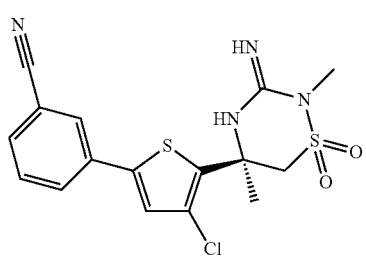

$MH^+$: 395.2, 2.99 min, A

51

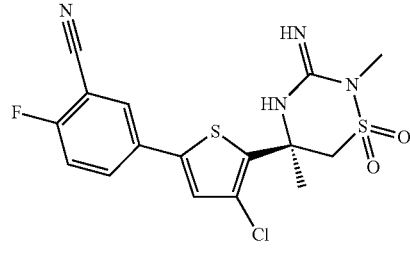

$MH^+$: 413.2, 3.11 min, A

52

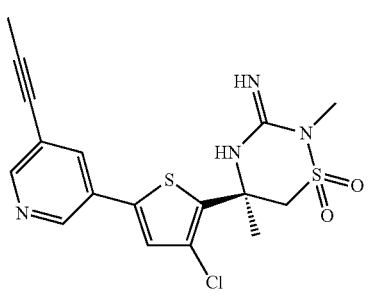

$MH^+$: 409.2, 2.83 min, A

53

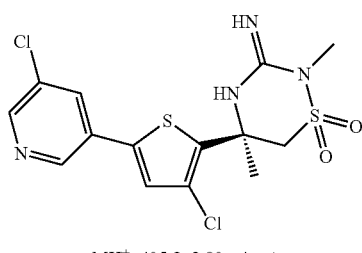

$MH^+$: 405.2, 2.80 min, A

TABLE VIII-continued

The following examples were prepared using a procedure similar to that described in Scheme 15 using the appropriate aryl bromide and boronic acid/ester.
Examples
(LCMS data listed with each compound: observed MH⁺, HPLC retention time and LCMS method)

54

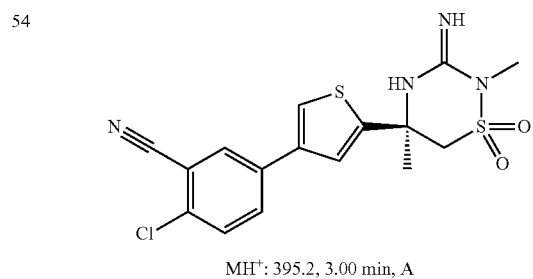

MH⁺: 395.2, 3.00 min, A

55

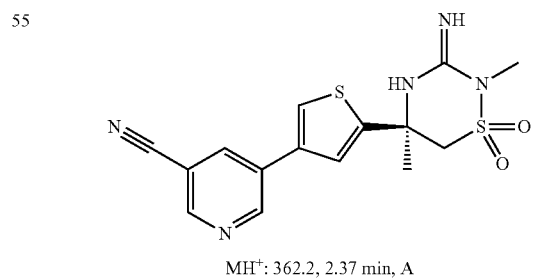

MH⁺: 362.2, 2.37 min, A

56

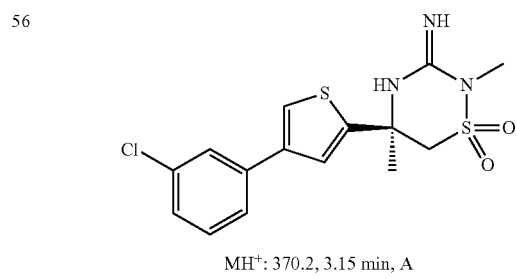

MH⁺: 370.2, 3.15 min, A

57

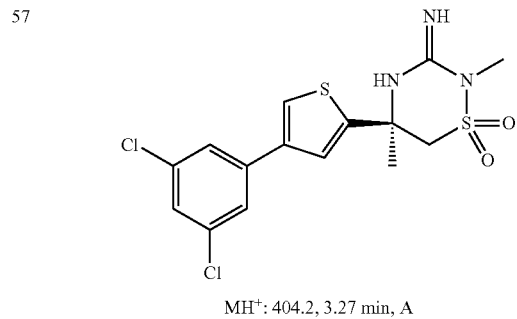

MH⁺: 404.2, 3.27 min, A

58

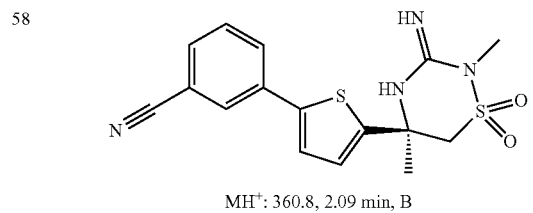

MH⁺: 360.8, 2.09 min, B

TABLE VIII-continued

The following examples were prepared using a procedure similar to that described in Scheme 15 using the appropriate aryl bromide and boronic acid/ester.
Examples
(LCMS data listed with each compound: observed MH⁺, HPLC retention time and LCMS method)

59

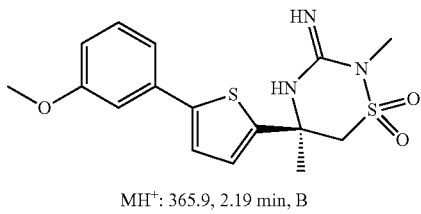 [SMILES: COc1cccc(-c2ccc([C@]3(C)CS(=O)(=O)N(C)C(=N)N3)s2)c1]

MH⁺: 365.9, 2.19 min, B

60

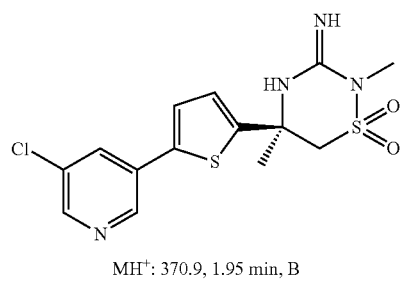 [SMILES: CN1C(=N)N[C@](C)(c2ccc(-c3cncc(Cl)c3)s2)CS1(=O)=O]

MH⁺: 370.9, 1.95 min, B

61

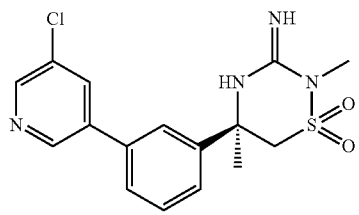

MH⁺: 364.9, 1.98 min, B

62

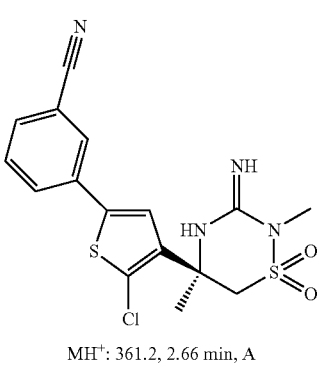 [SMILES: CN1C(=N)N[C@](C)(c2cc(-c3cccc(C#N)c3)sc2Cl)CS1(=O)=O]

MH⁺: 361.2, 2.66 min, A

63

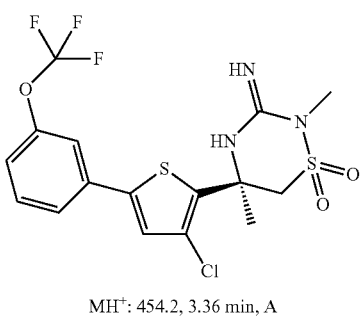 [SMILES: CN1C(=N)N[C@](C)(c2sc(-c3cccc(OC(F)(F)F)c3)cc2Cl)CS1(=O)=O]

MH⁺: 454.2, 3.36 min, A

TABLE VIII-continued
The following examples were prepared using a procedure similar to that described in Scheme 15 using the appropriate aryl bromide and boronic acid/ester.
Examples
(LCMS data listed with each compound: observed MH+, HPLC retention time and LCMS method)
64 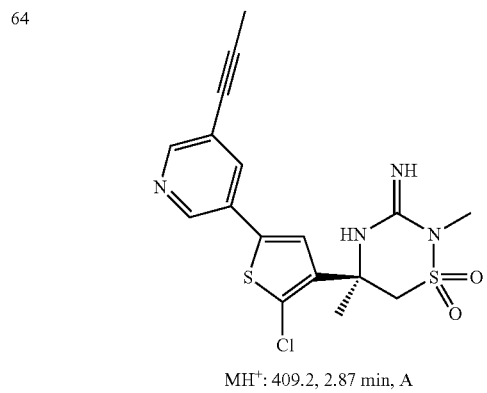
MH+: 409.2, 2.87 min, A
65 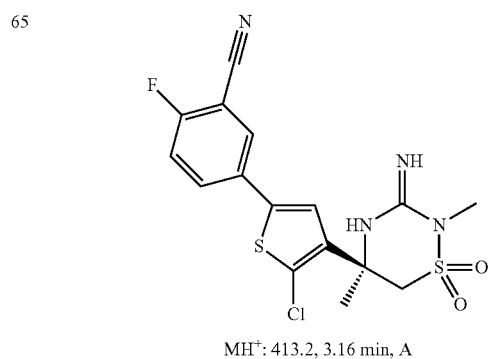
MH+: 413.2, 3.16 min, A
66 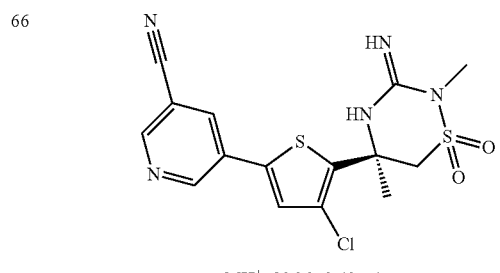
MH+: 396.2, 2.49 min, A
67 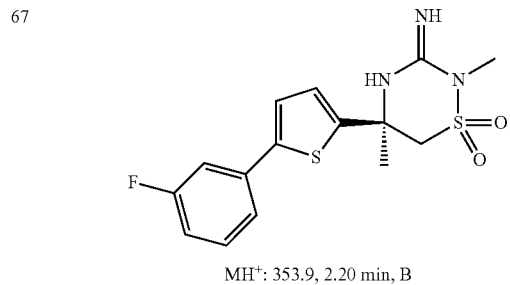
MH+: 353.9, 2.20 min, B
68 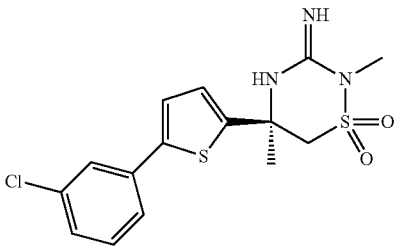
MH+: 369.9, 2.27 min, B
69 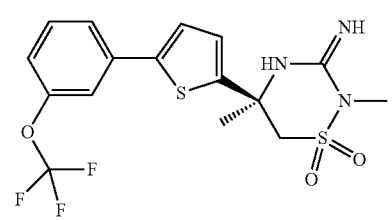
MH+: 419.9, 2.36 min, B
70 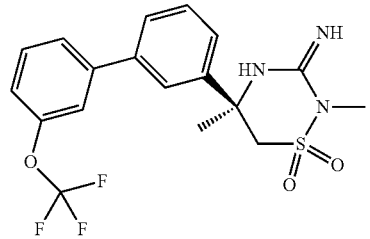
MH+: 413.9, 2.42 min, B
71 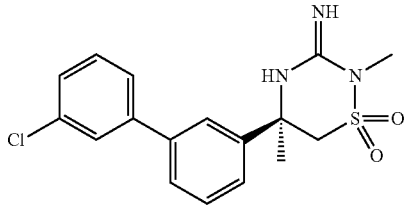
MH+: 363.9, 2.28 min, B
72 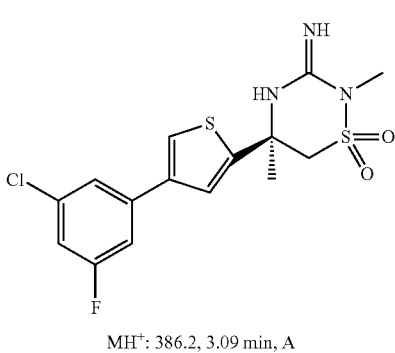 [SMILES: CN1C(=N)N[C@](C)(c2cc(-c3cc(F)cc(Cl)c3)cs2)CS1(=O)=O]
MH+: 386.2, 3.09 min, A

TABLE VIII-continued

The following examples were prepared using a procedure similar to that described in Scheme 15 using the appropriate aryl bromide and boronic acid/ester.
Examples
(LCMS data listed with each compound: observed MH+, HPLC retention time and LCMS method)

73
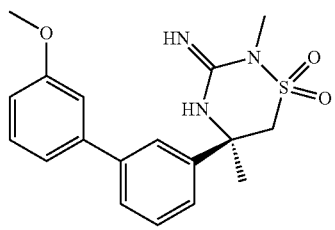
MH+: 359.2, 2.17 min, B

74
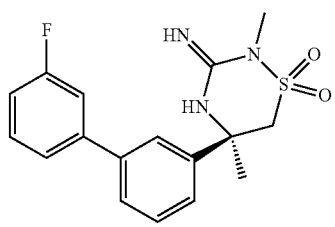
MH+: 348.0, 2.38 min, B

75
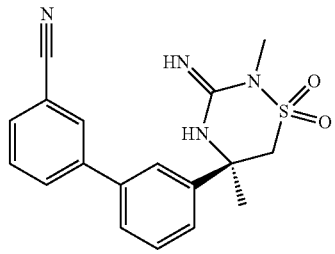 [SMILES: CC1[C@@](C)(c2cccc(-c3cccc(C#N)c3)c2)NC(=N)N(C)S1(=O)=O]
MH+: 355.0, 2.30 min, B

76
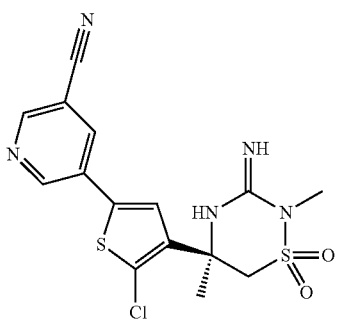
MH+: 396.2, 2.56 min, A

TABLE VIII-continued

The following examples were prepared using a procedure similar to that described in Scheme 15 using the appropriate aryl bromide and boronic acid/ester.
Examples
(LCMS data listed with each compound: observed MH+, HPLC retention time and LCMS method)

77
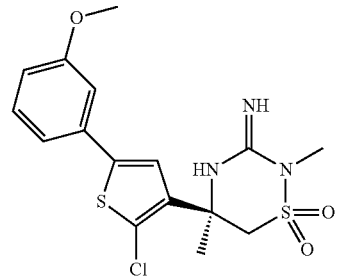
MH+: 400.2, 3.10 min, A

78
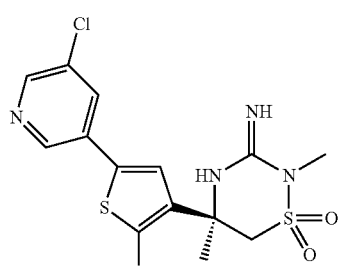
MH+: 406.2, 2.88 min, A

79
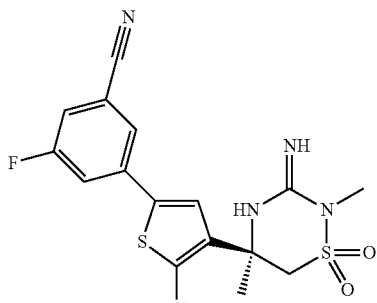
MH+: 413.2, 3.17 min, A

80
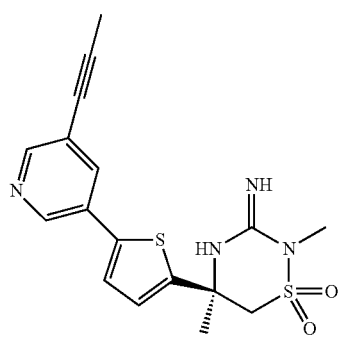
MH+: 375.0, 1.94 min, B

TABLE VIII-continued
The following examples were prepared using a procedure similar to that described in Scheme 15 using the appropriate aryl bromide and boronic acid/ester. Examples (LCMS data listed with each compound: observed MH+, HPLC retention time and LCMS method)
81
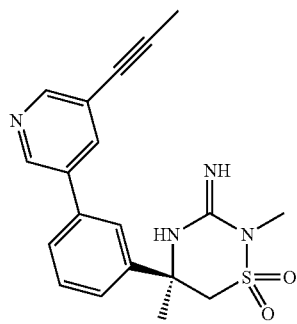
MH+: 369.0, 1.95 min, B
82
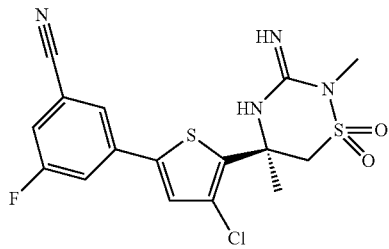
MH+: 413.2, 2.96 min, A
83
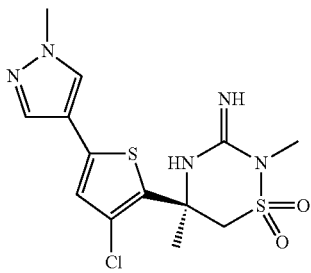
MH+: 374.2, 2.59 min, A
84
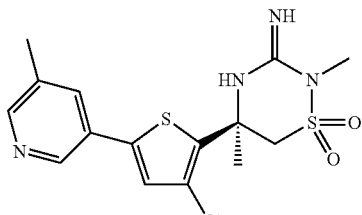
MH+: 385.2, 1.92 min, A
85
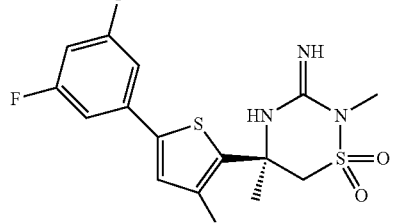
MH+: 406.2, 3.22 min, A
86
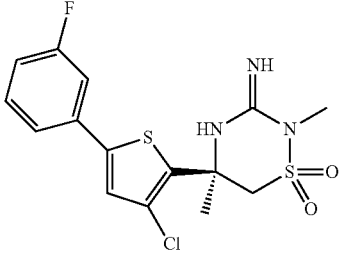
MH+: 388.2, 3.15 min, A
87
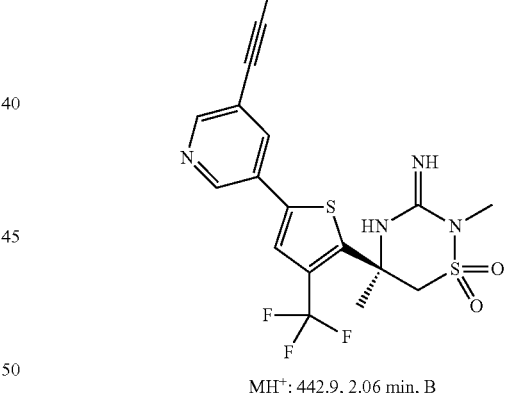
MH+: 442.9, 2.06 min, B
88
MH+: 455.3, 2.99 min, A

TABLE VIII-continued
The following examples were prepared using a procedure similar to that described in Scheme 15 using the appropriate aryl bromide and boronic acid/ester.
Examples
(LCMS data listed with each compound: observed MH+, HPLC retention time and LCMS method)
89
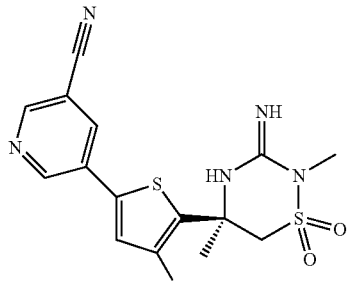
MH+: 440.2, 2.77 min, A
90
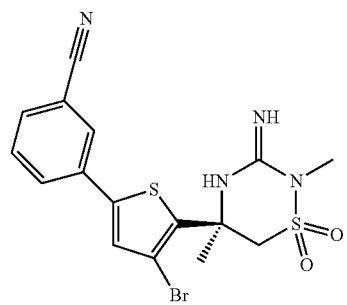
MH+: 441.2, 3.10 min, A
91
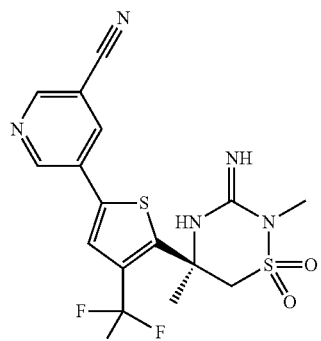
MH+: 361.2, 2.66 min, B
92
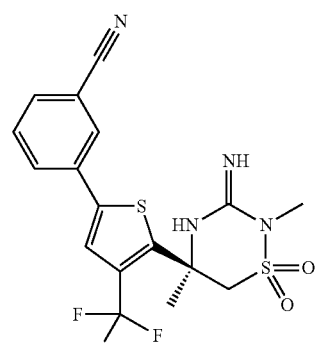
MH+: 428.9, 2.34 min, B
93
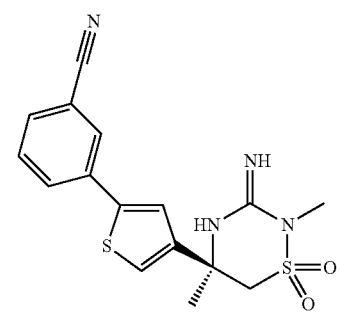
MH+: 361.2, 2.80 min, A
94
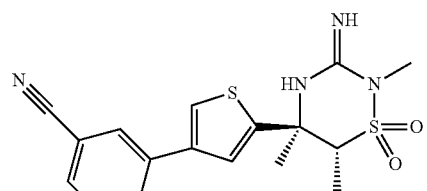
MH+: 375.2, 2.84 min, A
95
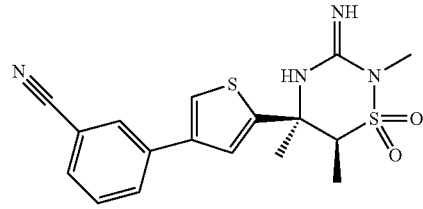
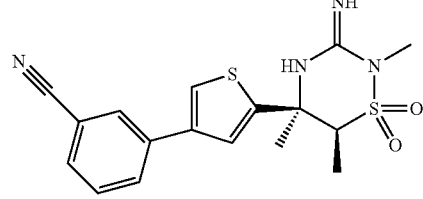
MH+: 375.2, 2.94 min, A
95a
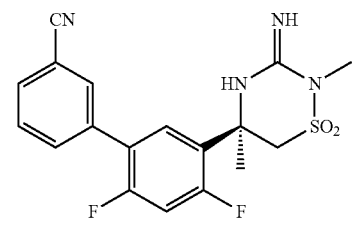
MH+: 391.0, 3.09 min, C
95b
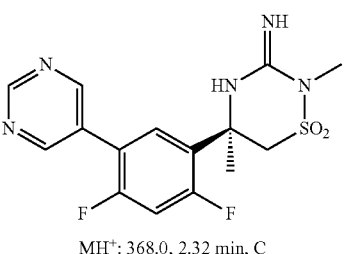
MH+: 368.0, 2.32 min, C TABLE VIII-continued The following examples were prepared
using a procedure similar to that
described in Scheme 15 using the appropriate
aryl bromide and boronic acid/ester.
Examples
(LCMS data listed with each compound: observed
MH+, HPLC retention time and LCMS method)

95c 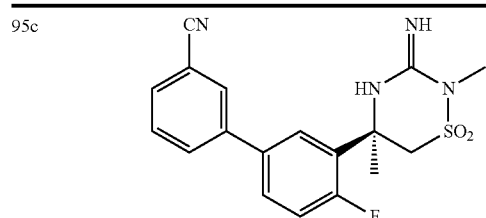

MH+: 373.0, 2.98 min, C

95d 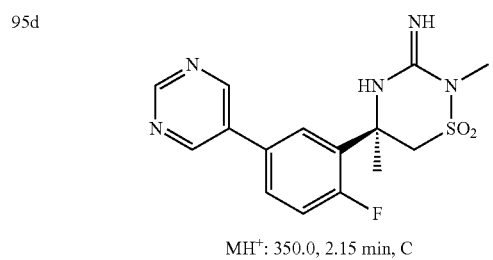

MH+: 350.0, 2.15 min, C

95e 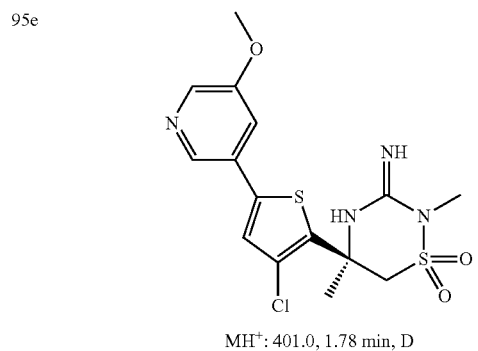

MH+: 401.0, 1.78 min, D

95f 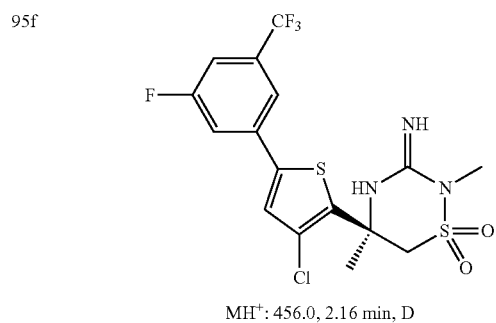

MH+: 456.0, 2.16 min, D

95g 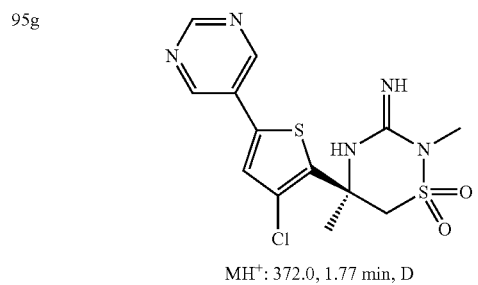

MH+: 372.0, 1.77 min, D

TABLE VIII-continued

The following examples were prepared
using a procedure similar to that
described in Scheme 15 using the appropriate
aryl bromide and boronic acid/ester.
Examples
(LCMS data listed with each compound: observed
MH+, HPLC retention time and LCMS method)

95h 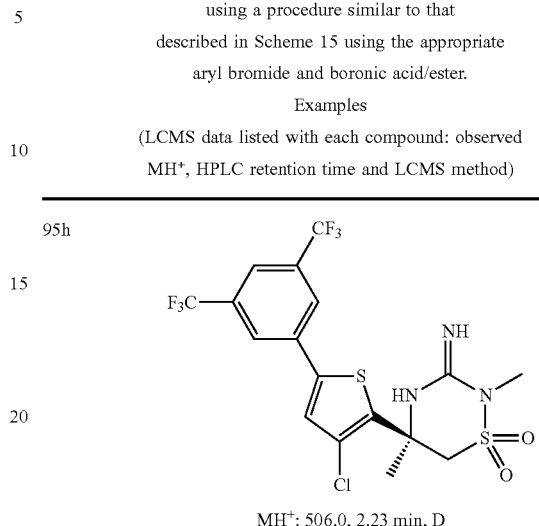

MH+: 506.0, 2.23 min, D

95i 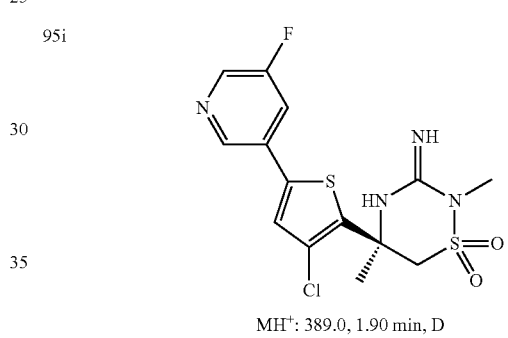

MH+: 389.0, 1.90 min, D

Scheme 16:

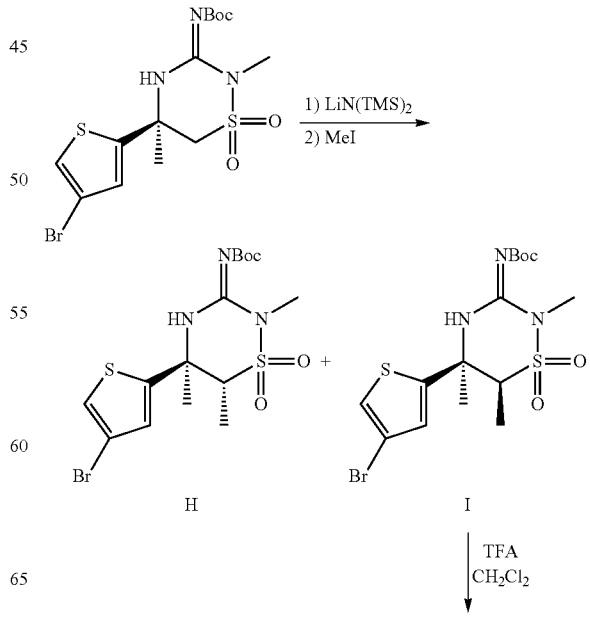

-continued

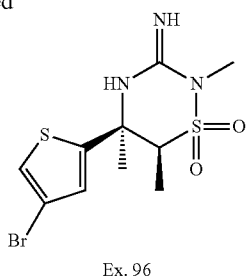

Ex. 96

Step 1:
To a solution of the thiophene (Scheme 3) (238 mg, 0.54 mmol) in anhydrous THF (2.5 mL) at −78° C. was added a solution of LHMDS (1.0 M in THF, 1.63 mL). The resultant solution was stirred at −78° C. for 1 hour. To this solution was added methyl iodide (0.086 mL, 1.36 mmol). The resultant solution was stirred at −78° C. for an additional 1.25 hours. After that time, water was added and the mixture was allowed to warm to RT. The aqueous layer was then extracted with EtOAc (3×). The combined organic layers were washed with brine, dried over $Na_2SO_4$, filtered and concentrated. The crude product was purified via flash chromatography ($SiO_2$: gradient elution 100:0 to 80:20 hexanes:EtOAc) to afford the faster eluting trans isomer H (20 mg, 8.1%) and the slower eluting cis isomer I (168 mg, 68%).

Step 2:
To a solution of I (16 mg, 0.035 mmol) in $CH_2Cl_2$ (1 mL) was added TFA (1 mL). The resultant solution was stirred at AT for 1.5 hours. The solution was concentrated to afford Example 96 (15 mg) as the trifluoroacetate salt. LCMS data: (method A): $t_R$=2.79 min, m/e=354.2 (M+H).

TABLE IX

The following examples were prepared using a method similar to that described in Scheme 16 except NaHMDS was used instead of LHMDS in step 1.

| Core | Alkyl halide | Examples | | LCMS Obser. MH⁺ | LCMS Ret time (min) | lcms method |
|---|---|---|---|---|---|---|
| [structure] | [EtI] | 97 | [structure] | 318.1 | 2.02 | B |
| | | 98 | [structure] | 318.0 | 2.44 | B |
| [structure] | MeI | 99 | [structure] | 304.0 | 1.77 | B |

TABLE IX-continued

The following examples were prepared using a method similar to that described in Scheme 16 except NaHMDS was used instead of LHMDS in step 1.

| Core | Alkyl halide | Examples | LCMS Obser. MH+ | LCMS Ret time (min) | lcms method |
|---|---|---|---|---|---|
| (structure) | Br~~~O~ | 100 (structure) | 348.1 | 2.12 | B |
| (structure) | MeI | 101 (structure) | 369.0 | 2.16 | B |

Scheme 17:

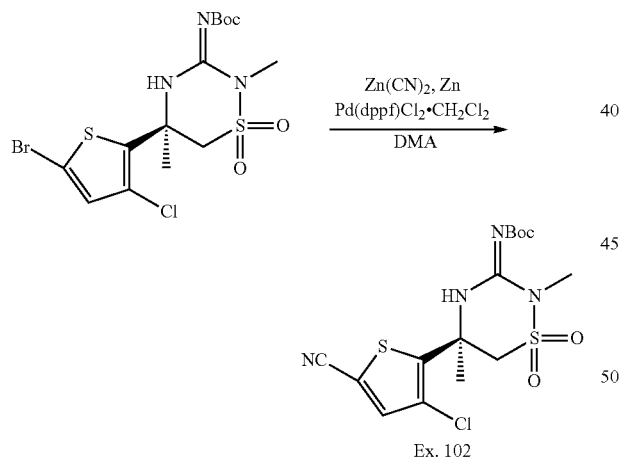

Ex. 102

A sealed microwave vial containing a slurry of the thiophene from Scheme 13 (74 mg, 0.16 mmol), Pd(dppf)Cl₂·CH₂Cl₂ (19 mg, 0.023 mmol), zinc (8.2 mg, 0.12 mmol), zinc cyanide (11 mg, 0.094 mmol) in N,N-dimethylacetamide (2.0 mL) was degassed by bubbling N₂ through the mixture for 5 min. The mixture was then heated to 85° C. with stirring for 2 hours. The mixture was cooled to RT and diluted with Et₂O. The organic layer was washed with water (2×), dried over Na₂SO₄, filtered and concentrated. The crude residue was purified by preperative TLC (SiO₂: 95:5 CH₂Cl₂:MeOH) to afford Example 102 (15 mg). LCMS data: (method A): $t_R$=2.22 min, m/e 319.2 (M+H).

Scheme 18:

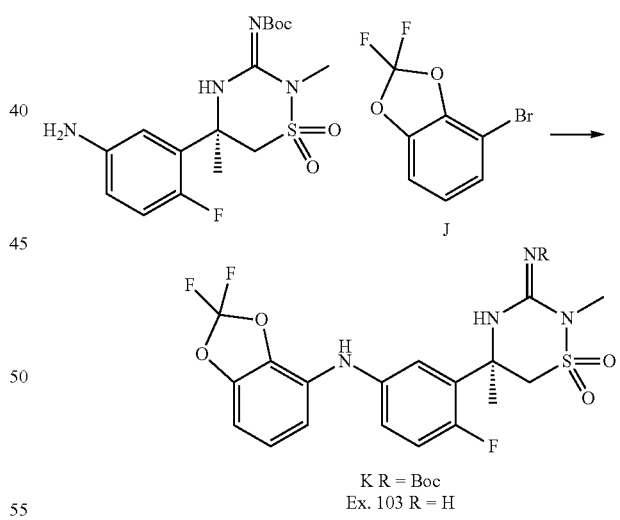

K R = Boc
Ex. 103 R = H

A 20 mL microwave vessel was flame-dried and cooled under vacuum, then backfilled with N₂, followed by two cycles of vacuum/N₂ backfill. The aniline (Scheme 10) (55 mg, 142 mmol), Pd₂dba₃·CHCl₃ (17 mg, 19 μmol), di-tert-butylphosphinyl-2-biphenyl (15 mg, 50 μmol), sodium tert-butoxide (31 mg, 322 mmol) and 4-bromo-2,2-difluorobenzo[d][1,3]dioxole J (48 mg, 202 mmol) were suspended in anhydrous toluene (2 mL), the microwave vial was sealed and placed in a preheated 65° C. oil bath. After stirring for 18 h, the reaction mixture was diluted with EtOAc, washed with sat. aqueous NaHCO₃ (1×), dried over MgSO₄, filtered, and concentrated under reduced pressure to give a yellow oil, which was subjected to silica-gel chromatography using 0→0.20% EtOAc/hexanes as eluent to give intermediate K as a film (39 mg). This intermediate was deprotected with TFA (2 mL) in CH$_2$Cl$_2$ (3 mL) at RT, then diluted with toluene (5 mL), concentrated under reduced pressure, and subjected to RP-HPLC (C18, 30 ml/min, 10%-100% MeCN/H$_2$O) with 0.1% TFA) to give Example 103 in 32% yield (24.9 mg, TPA salt). LCMS (conditions C): t$_R$=3.44 min, m/e 443.2 (M+H).

Step 1:
To a microwave vial containing 3 mL toluene/water (3:1) was added the bromothiophene from Scheme 13 (50 mg, 0.11 mmol), Pd(OAc)$_2$ (5 mg, 0.02 mmol), RuPhos (21 mg, 0.04 mmol.), potassium cyclopropyl trifluoroborate (17 mg, 0.12 mmol) and Cs$_2$CO$_3$ (108 mg, 0.33 mmol). The vial was sealed and the vial was purged with N$_2$. The mixture was then heated at 70° C. for 12 hours. Additional Pd(OAc)$_2$ (5 mg, 0.02 mmol), RuPhos (21 mg, 0.04 mmol), potassium cyclopropyl trifluoroborate (17 mg, 0.12 mmol) were added and the mixture was heated under an atmosphere of N$_2$ to 70° C. for an additional 12 hours. The mixture was cooled to RT, filtered through celite and extracted with CH$_2$Cl$_2$. The aqueous layer was dried over Na$_2$SO$_4$, filtered and concentrated. The crude mixture was then dissolved in CH$_2$Cl$_2$. To this solution was added Boc$_2$O (24 mg, 0.11 mmol) and Et$_3$N (13 mg, 0.13 mmol). The resultant solution was stirred overnight at RT. The solution was concentrated and the crude product was purified via preparative TLC (SiO$_2$; 70:30 hexanes:EtOAc).

Step 2:
Example 104 was prepared from the above material using a method similar to that described in Scheme 11b step 2. LCMS data: (method A): t$_R$=2.85 min, m/e=334.2 (M+H).

Scheme 20:

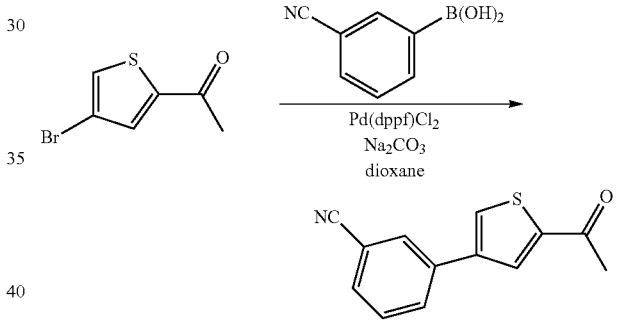

The biaryl ketone was formed using a method similar to that described in Scheme 15 step 1.

TABLE IXa

The following Examples were made using methods described in Scheme 18, with the following modification: The coupling reaction was run at 80° C.:
Examples
(LCMS data: observed MH$^+$,
HPLC retention time and LCMS method)

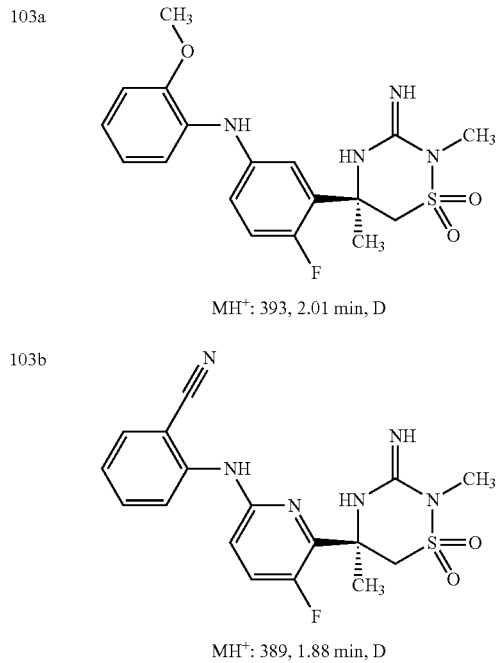

103a MH$^+$: 393, 2.01 min, D

103b MH$^+$: 389, 1.88 min, D

Scheme 19:

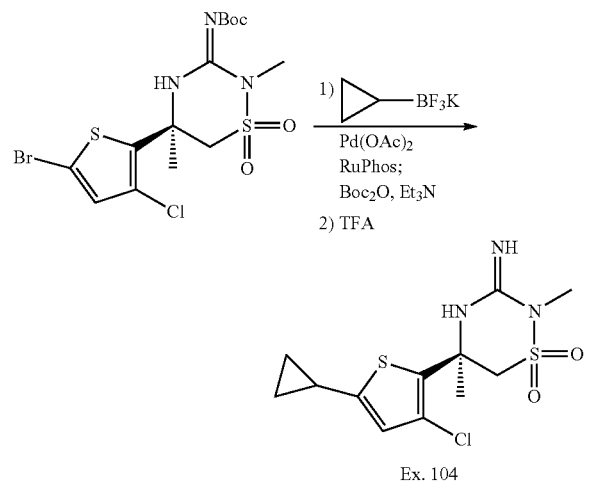

Ex. 104

TABLE X

The following examples were formed using methods similar to that described in Scheme 1a starting from the ketone in Scheme 20 and the appropriate sulfonamide from Table I.
Examples
(LCMS data: observed MH$^+$,
HPLC retention time and LCMS method)

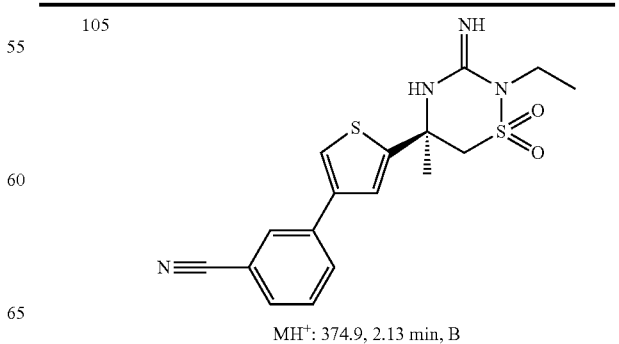

105 MH$^+$: 374.9, 2.13 min, B

TABLE X-continued

The following examples were formed using methods similar to that described in Scheme 1a starting from the ketone in Scheme 20 and the appropriate sulfonamide from Table I. Examples (LCMS data: observed MH+, HPLC retention time and LCMS method)

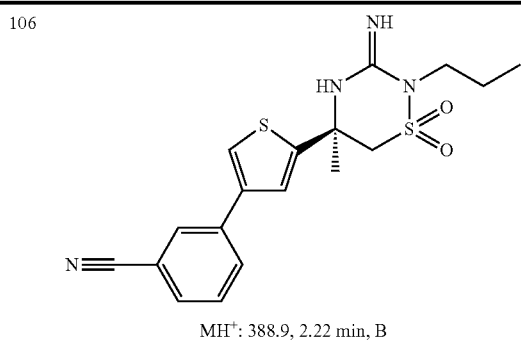

106

MH+: 388.9, 2.22 min, B

TABLE XI

The following examples were prepared using a method similar to that described in Scheme 11b step 2.

| Carbamate | | Examples | LCMS Obser. MH+ | LCMS Ret. time (min) | LCMS method |
|---|---|---|---|---|---|
| (structure, Br-thiophene-Cl) | 107 | (structure, Br-thiophene-Cl) | 374.2 | 2.81 | A |
| (structure, Br-thiophene-Cl) | 108 | (structure, Br-thiophene-Cl) | 374.2 | 2.69 | A |

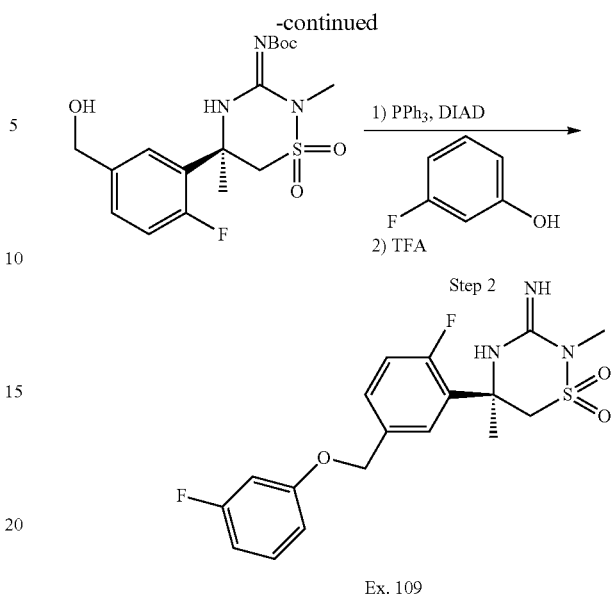

Ex. 109

Scheme 21:

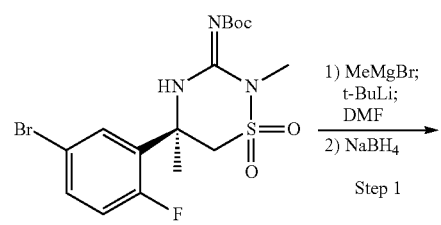

Step 1:
To a solution of the bromide (Table IIb, entry 14) (500 mg, 1.11 mmol) in THF (7 mL) at −20° C. was added a solution of MeMgBr (3 M in Et₂O, 0.48 mL, 1.4 mmol). The solution was stirred for 30 min at −20° C. The solution was then cooled to −78° C. To the solution was added t-BuLi (1.7 M in pentane, 1.6 mL, 2.8 mmol). The solution was stirred for 2 h at −78° C. To the solution was added DMF (0.13 mL, 1.7 mmol). The solution was allowed to slowly warm to RT over 2.5 hours. To the solution was then added sat. NH₄Cl (aq.) (20 mL) and the mixture was extracted with EtOAc (3×). The combined organic layers were dried over Na₂SO₄, filtered and concentrated. The crude product was purified via flash chromatography (SiO$_2$: 3:1 heptane:EtOAc) to afford the aldehyde (237 mg, 54%).

To a solution of the aldehyde (1.04 g, 2.60 mmol) in MeOH (10 mL) at 0° C. was added portionwise over 3 min NaBH$_4$ (197 mg, 5.21 mmol). The resultant mixture was stirred for 20 min. To the solution was then added sat. NH$_4$Cl(aq.) (30 mL) and the mixture was extracted with CH$_2$Cl$_2$ (3×). The combined organic layers were dried over Na$_2$SO$_4$, filtered and concentrated. The crude product was purified via flash chromatography (SiO$_2$: 1:1 heptane:EtOAc) to afford the alcohol (949 mg, 91%).

Step 2:

To a solution of the alcohol from step 1 (105 mg, 0.26 mmol) and triphenylphosphine (102 mg, 0.39 mmol) in THF (3 mL) was added 3-fluorophenol (0.030 mL, 0.33 mmol). To this solution was added dropwise DIAD (0.075 mL, 0.39 mmol) and the resultant solution was stirred for 2 hours. The reaction was loaded onto a SiO$_2$ flash column and purified (gradient elution 100:0 to 0:100 heptane:EtOAc) to afford the ether (73 mg, 56%).

Ex. 109 was prepared from the above material using a method similar to that described in Scheme 11b step 2. LCMS (conditions B): t$_R$=2.10 min, m/e=396.0 (M+H).

TABLE XII

The following examples were prepared from the benzylic alcohol described in Scheme 21 step 1 using a method similar to that described in Scheme 21 step 2 using the appropriate aryl alcohol.
Examples
(LCMS data listed with each compound: observed MH$^+$, HPLC retention time and LCMS method)

110

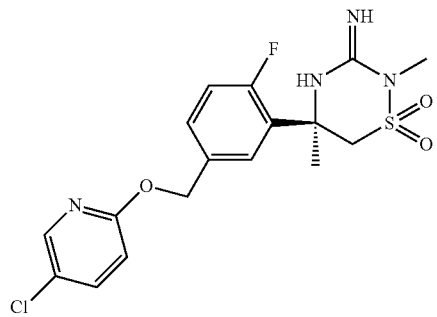

MH$^+$: 412.0, 2.17 min, B

111

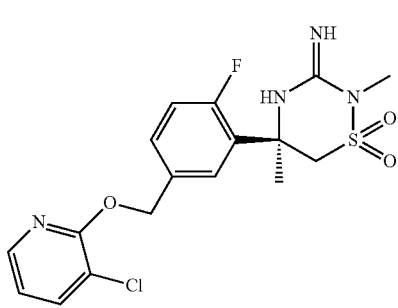

MH$^+$: 413.0, 2.02 min, B

TABLE XII-continued

The following examples were prepared from the benzylic alcohol described in Scheme 21 step 1 using a method similar to that described in Scheme 21 step 2 using the appropriate aryl alcohol.
Examples
(LCMS data listed with each compound: observed MH$^+$, HPLC retention time and LCMS method)

112

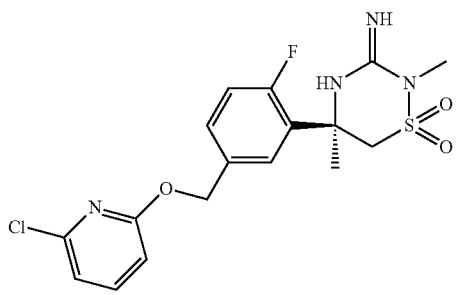

MH$^+$: 397.0, 1.99 min, B

113

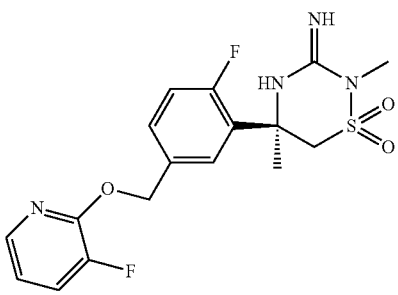

MH$^+$: 396.0, 2.06 min, B

114

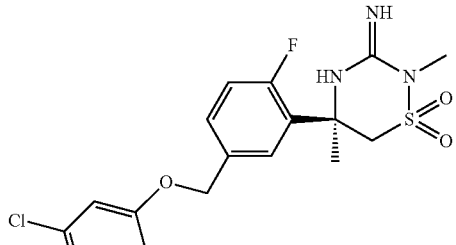

MH$^+$: 397.1, 1.96 min, B

115

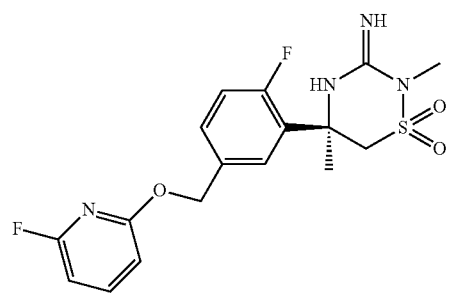

MH$^+$: 412.9, 2.08 min, B

Scheme 22:

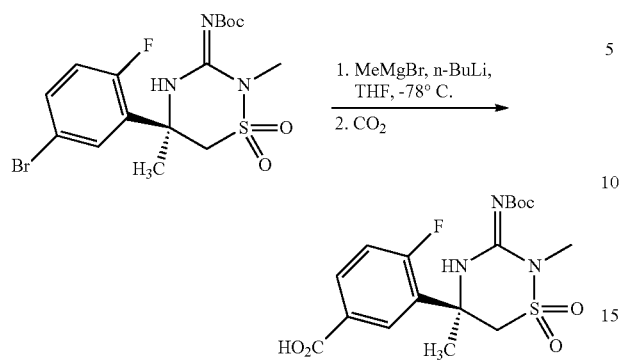

To a stirred solution of the bromide (Table IIb, entry 14, 2.55 g, 5.66 mmol) in anhydrous THF (45 mL) was added a MeMgBr solution (3 M in Et$_2$O, 2.4 mL, 7.20 mmol) at −78° C. under nitrogen. After addition was completed, the reaction mixture was stirred for 20 min. After that time, a solution of n-BuLi solution (2.5 M in hexanes, 5.1 mL, 12.8 mmol) was added dropwise over 5 min. The reaction mixture was then stirred for 50 min at −78° C. and the cooling bath was removed. CO$_2$ gas was bubbled into the reaction mixture for 50 min. After this time, the reaction was quenched with saturated aqueous NH$_4$Cl (50 mL) and 1 N hydrochloric acid (aq) (100 mL). The resulting mixture was extracted with EtOAc (3×100 mL). The combined extracts were washed with brine (100 mL), dried over anhydrous sodium sulfate, filtered, and concentrated under reduced pressure. The residue was purified by column chromatography (silica, 10% methanol/methylene chloride) to afford the carboxylic acid (1.49 g, 53%).

TABLE XIII

The following examples were prepared using a procedure similar to that described in Scheme 11b using the acid from Scheme 22 and the appropriate aryl amine. The molar ratios used for the acid, amine and BOPCl were 1:1.3:1.5 respectively.
Examples
(LCMS data: observed MH$^+$, HPLC retention time and LCMS method)

116

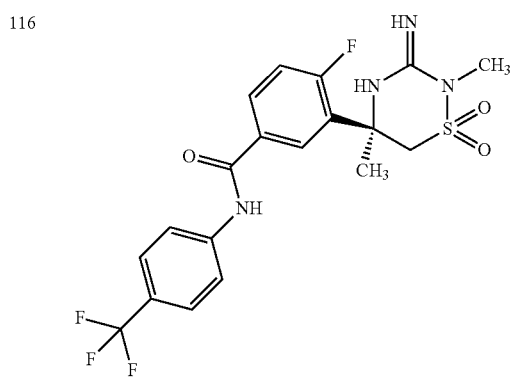

MH$^+$: 459.0, 2.35 min, B

TABLE XIII-continued

The following examples were prepared using a procedure similar to that described in Scheme 11b using the acid from Scheme 22 and the appropriate aryl amine. The molar ratios used for the acid, amine and BOPCl were 1:1.3:1.5 respectively.
Examples
(LCMS data: observed MH$^+$, HPLC retention time and LCMS method)

117

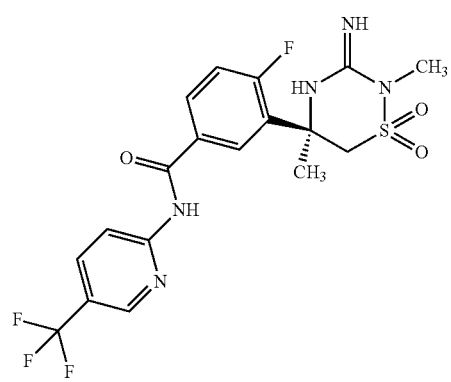

MH$^+$: 460.1, 2.02 min, B

118

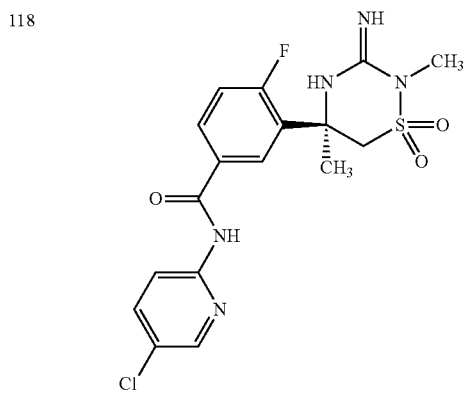

MH$^+$: 426.1, 1.86 min, B

119

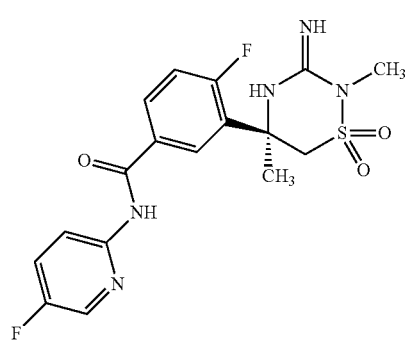

MH$^+$: 410.1, 1.74 min, B

Scheme 23:

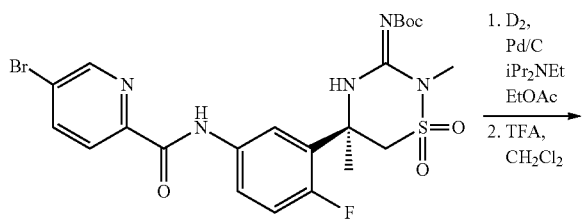

was added iPr₂NEt (22 μL, 0.13 mmol) and 10% Pd/C, Degussa type (9.0 mg, 0.0042 mmol). The flask was evacuated and backfilled with D₂ (3×). The mixture was stirred under an atmosphere of D₂ for 4.5 hours. The mixture was purged with N₂, filtered and concentrated. The residue was partitioned between EtOAc and 1/2 sat. NaHCO₃ (aq.). The aqueous layer was extracted with EtOAc (3×). The combined organic layers were washed with brine, dried over Na₂SO₄, filtered and concentrated to afford the deuterate (38 mg, 92%) as a white solid.

Example 120 was prepared as its TPA salt from the above material using a procedure similar to that described in Scheme 11b step 2. LCMS data: (method D): $t_R$=1.76 min, m/e=393.0 (M+H).

Scheme 24:

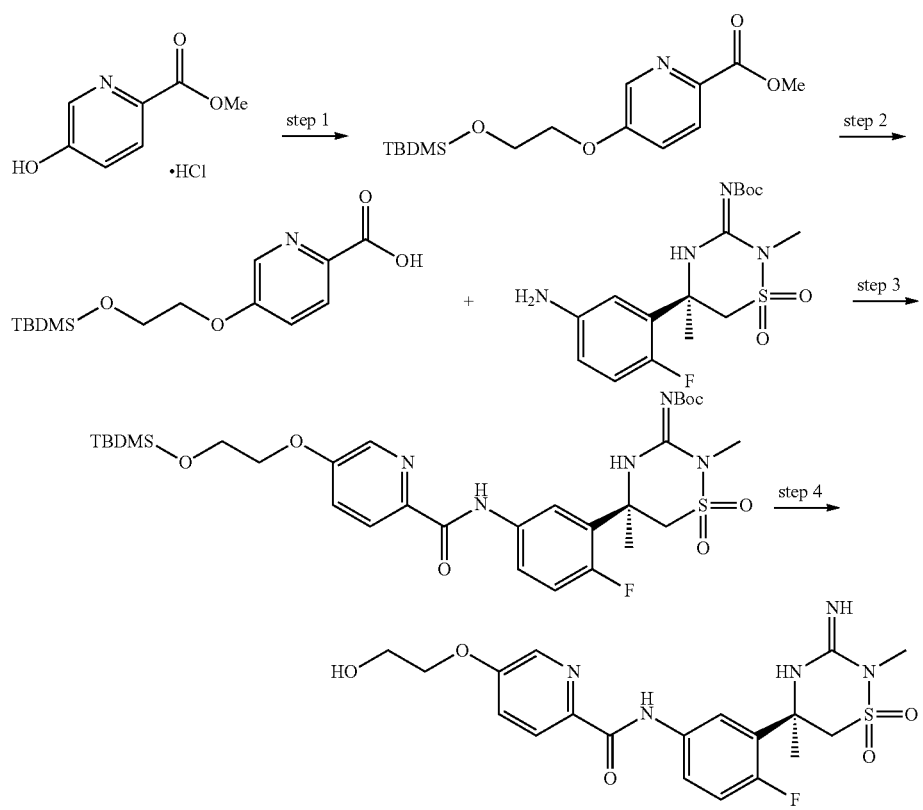

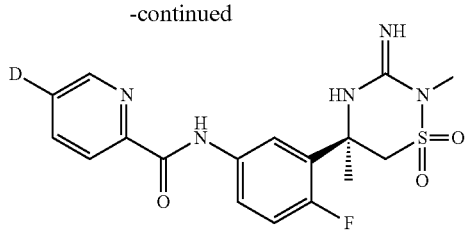

To a sealed round bottom flask containing a solution of the bromide (Table V: Hoc intermediate for Ex. 29) (48 mg, 0.084 mmol) in EtOAc (4 mL) under an atmosphere of N₂

Step 1:
To the methyl 5-hydroxypicolinate hydrochloride prepared in scheme 11h (0.40 g, 2.1 mmol) in DMF (1 mL) was added potassium carbonate (0.88 g, 6.3 mmol) and (2-bromoethoxy)-tert-butyldimethylsilane (0.68 mL, 3.2 mmol). The reaction was warmed to 70° C. and stirred for 18 h. Another equivalent of (2-bromoethoxy)-tert-butyldimethylsilane was added and the reaction stirred for an additional 1.5 h at 90° C. The reaction was cooled to room temperature and water was added. The mixture was extracted with EtOAc. The combined organic layers were washed with water and brine, dried (MgSO₄), filtered, and concentrated in vacuo. The residue was purified by silica gel chromatography (0-30% EtOAc/hex) over 30 minutes to provide product (0.31 g, 47%).

Step 2:

To the compound prepared in step 1 (0.31 g, 1.0 mmol) in THF (1.5 mL) was added 2N LiOH (1.5 mL, 3 mmol). The reaction was stirred at room temperature for 4 h. The reaction pH was adjusted to pH~4 using saturated aqueous citric acid. The mixture was extracted with EtOAc. The combined organic layers were washed with water and brine, dried (MgSO$_4$), filtered, and concentrated in vacuo to provide the carboxylic acid (0.18 g, 60%).

Step 3:

To the aniline prepared in scheme 10 (0.15 g, 0.39 mmol) in pyridine (1.5 mL) was added the carboxylic acid prepared in step 2 (0.17 g, 0.58 mmol) followed by BOP Cl (0.23 g, 0.89 mmol). The reaction was stirred at room temperature for 4.5 h. The reaction was then concentrated in vacuo and the residue was taken up into EtOAc and washed with water and brine, dried (MgSO$_4$), filtered, and concentrated in vacuo. The residue was purified by silica gel chromatography (0-30% EtOAc/hex over 30 minutes) to provide the amide product (0.14 g, 54%).

Step 4:

To the product from step 3 (0.20 g, 0.30 mmol) in THF (1 mL) was added TBAF (1.0 M in THF, 0.33 mL, 0.33 mmol). The reaction was stirred at room temperature for 24 h. EtOAc was added to the reaction mixture and the mixture was washed with water and brine, dried (MgSO$_4$), filtered, and concentrated in vacuo. The residue was purified by silica gel chromatography (0-70% EtOAc/hex over 30 minutes) to yield the alcohol (0.14 g, 85%). To that product (0.14 g, 0.25 mmol) in DCM (2 mL) was added TFA (2 mL). The reaction was stirred at room temperature for 1 h and concentrated in vacuo. The reaction was then stirred for 1 h with methanol (1 mL) and 7N NH$_3$/MeOH (0.5 mL). The reaction was then concentrated in vacuo and taken up into EtOAc. The mixture was washed with saturated NaHCO$_3$, water and brine, dried (MgSO$_4$), filtered, and concentrated in vacuo to provide Example 121 (0.10 g, 88%). LCMS data: (method D): t$_R$=1.68 min, m/e=452.0 (M+H).

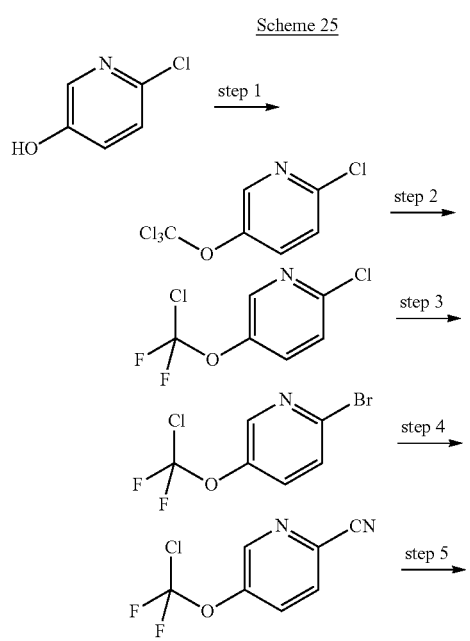

Scheme 25

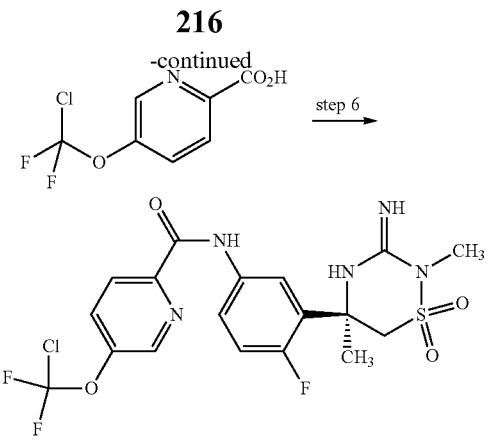

Ex. 122

Step 1:

To 2-chloro-5-hydroxypyridine (10 g, 80 mmol) in 1.5 M NaOH$_{(aq)}$ (67 mL) at 0° C. was added thiophosgene (6.0 mL, 79 mmol) in chloroform (46 mL) dropwise. After addition, the reaction was stirred for 2 h. The mixture was then extracted with CHCl$_3$. The combined CHCl$_3$ layers were washed with 1N HCl (aq) and water, dried (MgSO$_4$), and filtered. Into this solution was bubbled Cl$_2$ gas until the reaction became warm (~1 minute). The reaction was stirred at room temperature for 2 h and then Cl$_2$ gas was bubbled through the mixture again. The reaction was then stirred for 18 h. Nitrogen gas was then bubbled through the reaction mixture to remove residual Cl$_2$ gas. The reaction was then concentrated in vacuo. The residue was purified by reverse phase chromatography [C18 (800 g) 5% (2 column volumes (CV), 5-100% (10 CV), 100 (2 CV); 0.1% formic acid/water/0.1% formic acid/acetonitrile] to provide the trichloromethyl ether (4.0 g, 21%).

Step 2:

To antimony trifluoride (4.1 g, 22.7 mmol) and antimony pentachloride (0.22 mL, 1.7 mmol) at 120° C. was added the trichloromethylether prepared in step 1 (2.8 g, 11.3 mmol). The mixture was warmed to 150° C., stirred for 1 h and then cooled to room temperature. DCM and saturated NaHCO$_3$ (aq) were added and the aqueous laywer was extracted with DCM. The combination was washed with 20% KF$_{(a)}$, water and brine, dried (MgSO$_4$), filtered, and concentrated in vacuo to provide product (2.0 g, 83%).

Step 3:

To the chlorodifluoromethylether prepared in step 2 (2.0 g, 9.3 mmol) in propanenitrile (11 mL) was added bromotrimethylsilane (2.8 mL, 21 mmol). The reaction was warmed to 100° C. and stirred for 6.5 h. The reaction was cooled to room temperature and saturated NaHCO$_3$ was added. The mixture was extracted with EtOAc. The combined organics were washed with water and brine, dried (MgSO$_4$), filtered, and concentrated in vacuo to provide a product (2.1 g) which was used in the next step without further purification.

Step 4:

To the bromopyridine prepared in step 3 (0.33 g, 1.3 mmol) in DMF (2.7 mL) in a microwave reaction vial was bubbled N$_2$ gas for 5 minutes. Zn(CN)$_2$ (0.22 g, 1.9 mmol) was added and nitrogen was bubbled through the reaction mixture for 5 minutes. Pd(PPh$_3$)$_4$ (0.078 g, 0.07 mmol) was added and nitrogen was bubbled through the reaction for 5 minutes. The reaction vessel was capped and warmed to 100° C., then stirred for 2.5 h and cooled to room temperature. Water and EtOAc were added and the combination was then filtered through a pad of Celite washing with EtOAc. The filtrate was then extracted with EtOAc. The organics were then combined and washed with water and brine, dried (MgSO₄), filtered, and concentrated in vacuo, then purified by silica gel chromatography (0-8% EtOAc/hex over 30 minutes) to provide product (0.21 g, 81%).

Step 5:

To the nitrile prepared in step 4 (0.21 g, 1.0 mmol) in ethanol (2 mL) was added 2N LiOH$_{(aq)}$ (2.7 mL). The reaction was warmed to 100° C. and stirred for 2 h. The reaction was cooled to room temperature and the ethanol removed in vacuo. The pH of the aqueous was adjusted to pH~4 using saturated aqueous citric acid. Solid sodium chloride was added and the mixture was extracted with EtOAc. The combined organic layers were washed with brine, dried (MgSO₄), filtered, and concentrated in vacuo to provide a white solid (0.14 g, 62%).

Step 6:

To the aniline prepared in scheme 10 (0.20 g, 0.52 mmol) in THF (0.84 mL) at 0° C. was added the carboxylic acid prepared in step 5 (0.14 g, 0.63 mmol), diisopropylethylamine (0.27 mL, 1.6 mmol), and 50% 1-propanephosphonic acid cyclic anhydride in ethyl acetate (0.42 mL, 0.71 mmol), respectively. The reaction mixture was then stirred for 1 h at 0° C. and then another hour at room temperature. Water was added to the reaction and the mixture was stirred vigorously for 20 minutes. The mixture was then extracted with EtOAc. The combined organic layers were washed with water and brine, dried (MgSO₄), filtered, and concentrated in vacuo. The residue was purified by silica gel chromatography (0-30% EtOAc/hex over 30 minutes) to provide the amide (0.26 g, 84%). To the amide (0.26 g, 0.44 mmol) in DCM (1 mL) at room temperature was added TFA (0.68 mL, 8.8 mmol). The reaction was stirred for 18 h and then concentrated in vacuo. The residue was taken up into DCM and stirred with saturated NaHCO₃ (aq). The mixture was extracted with DCM. The combined DCM layers were washed with water and brine, dried (MgSO₄), filtered, and concentrated in vacuo to provide Example 122. LCMS data: (method D): t$_R$=2.06 min, m/e=492 (M+H).

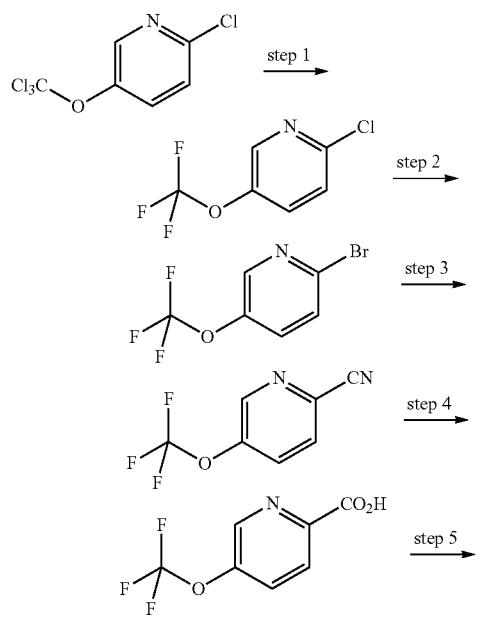

Scheme 26

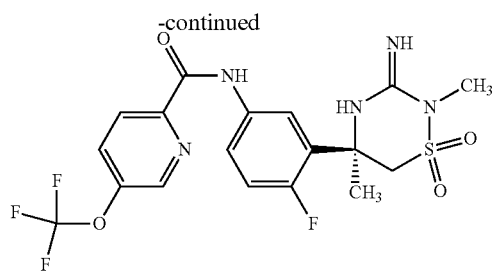

Ex. 123

Step 1:

To antimony trifluoride (4.05 g, 23 mmol) and antimony pentachloride (0.22 mL, 1.7 mmol) at 120° C. was added the trichloromethyl ether prepared in step 1 of scheme 25 (2.80 g, 11 mmol). The reaction was warmed to 165° C. under nitrogen and stirred for 14 h and then warmed to 175° C. and stirred for an additional 4 h. The reaction was cooled to room temperature. The resulting solid mass was stirred vigorously with saturated NaHCO₃$_{(aq.)}$ [Gas evolution!] and EtOAc. The mixture was filtered through a plug of Celite washing with EtOAc. The filtrate was extracted with EtOAc. The combined organic layers were washed with water and brine, dried (MgSO₄), filtered, and concentrated in vacuo. The residue was purified by silica gel chromatography (0-10% EtOAc/hex over 30 minutes) (0.90 g, 40%).

Step 2:

The trifluoromethylether prepared in step 1 was converted to the bromopyridine according to the procedure in step 3 of scheme 25.

Step 3:

The bromopyridine prepared in step 2 was converted to the cyanopyridine according to the procedure in step 4 of scheme 25.

Step 4:

The cyanopyridine prepared in step 3 was converted to the pyridylcarboxylic acid according to the procedure in step 5 of scheme 25.

Step 5:

The pyridylcarboxylic acid prepared in step 4 was converted to Ex. 123 according to the procedures in step 6 of scheme 25. LCMS (conditions D): t$_R$=2.04 min, m/e=476.0 (M+H).

Scheme 27

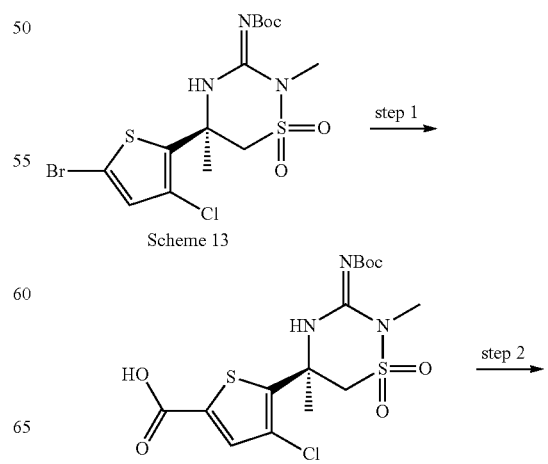

219
-continued

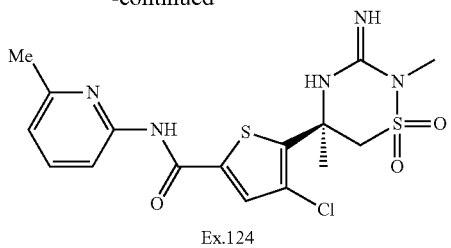

Ex.124

Step 1:
To the bromothiophene prepared in scheme 13 (1.34 g, 2.83 mmol) in THF (9.2 mL) at 0° C. was added methylmagnesium chloride (3.0 M in THF, 1.18 mL, 3.54 mmol). The reaction was stirred for 30 minutes at 0° C. and then cooled to −78° C. n-Butyllithium (2.5 M in hexanes, 2.55 mL, 6.38 mmol) was added over 10 minutes. The reaction was stirred for 1 hour at −78° and then $CO_2$ gas was bubbled through the reaction. The cold bath was taken away and the reaction allowed to warm to room temperature while continuing to bubble $CO_2$ gas through the mixture. To the mixture was added 1N $HCl_{(aq.)}$ and the mixture was extracted with EtOAc. The combined organic layers were washed with water and brine, dried ($MgSO_4$), filtered, and concentrated in vacuo. The residue was purified by silica gel chromatography (0-80% EtOAc/hex over 30 minutes) to provide the carboxylic acid (0.97 g, 78%).

Step 2:
To the carboxylic acid prepared in step 1 (0.027 g, 0.06 mmol) in pyridine (0.25 mL) was added 2-amino-6-methylpyridine (0.013 g, 0.12 mmol) and bis(2-oxo-3-oxazolidinyl)phosphinic chloride (0.024 g, 0.09 mmol). The reaction was stirred for 18 h at room temperature and then concentrated in vacuo. Water was added and the mixture was extracted with EtOAc. The combined organic layers were washed with brine, dried ($MgSO_4$), filtered, and concentrated in vacuo. The residue was purified by preparative silica gel TLC (1000 μm $SiO_2$, 30% EtOAc/hexane) to provide product (13 mg, 40%). To the amide (0.065 g, 0.14 mmol) in DCM (0.4 mL) was added TFA (0.2 mL). The reaction was stirred for 20 h at RT and then concentrated in vacuo to provide Ex. 124 as the TFA salt. LCMS data: (method. D): $t_R$=1.59 min, m/e=428.0 (M+H).

TABLE XIV

The following examples were prepared using procedures similar to those described in Scheme 27 using the appropriate aryl amines.
Examples
(LCMS data: observed MH+, HPLC retention time and LCMS method)

125

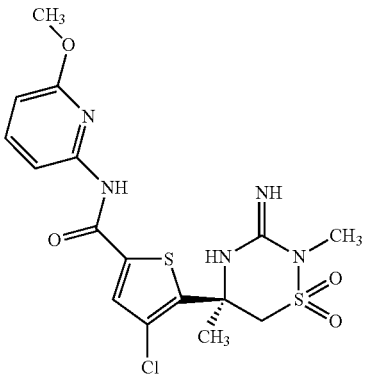

MH+: 466.0, 1.82 min, D

TABLE XIV-continued

The following examples were prepared using procedures similar to those described in Scheme 27 using the appropriate aryl amines.
Examples
(LCMS data: observed MH+, HPLC retention time and LCMS method)

126

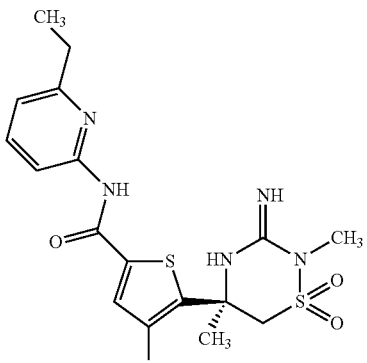

MH+: 482.0, 2.21 min, D

127

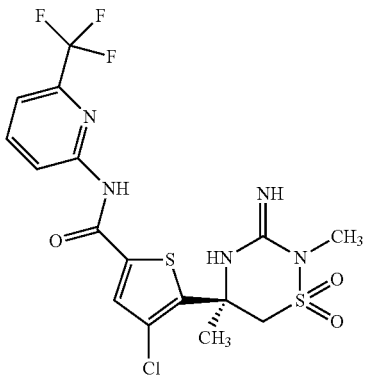

MH+: 442.0, 1.70 min, D

128

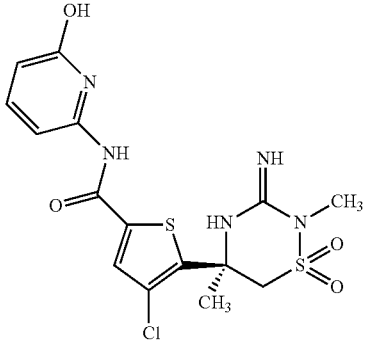

MH+: 430.0, 1.74 min, D

TABLE XIV-continued

The following examples were prepared using procedures similar to those described in Scheme 27 using the appropriate aryl amines.
Examples
(LCMS data: observed MH+, HPLC retention time and LCMS method)

129
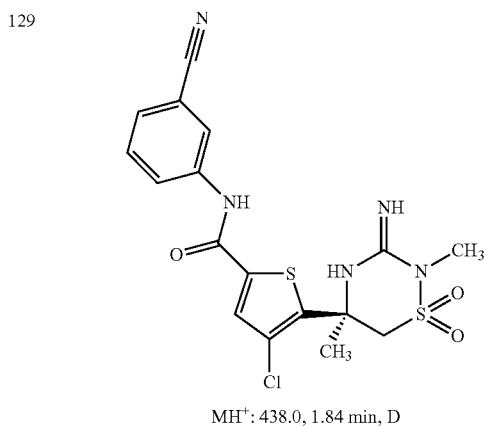
MH+: 438.0, 1.84 min, D

130
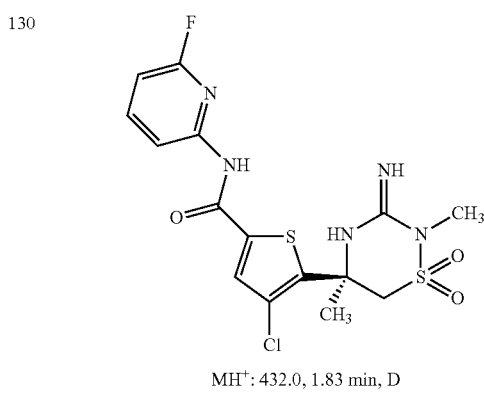
MH+: 432.0, 1.83 min, D

130a
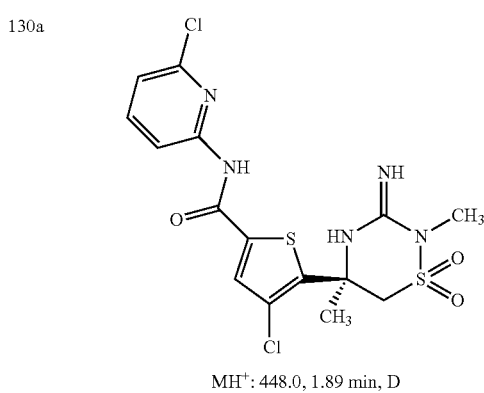
MH+: 448.0, 1.89 min, D

TABLE XIV-continued

The following examples were prepared using procedures similar to those described in Scheme 27 using the appropriate aryl amines.
Examples
(LCMS data: observed MH+, HPLC retention time and LCMS method)

130b
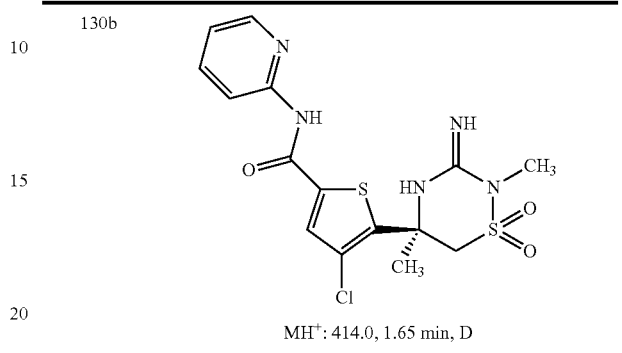
MH+: 414.0, 1.65 min, D

Scheme 28

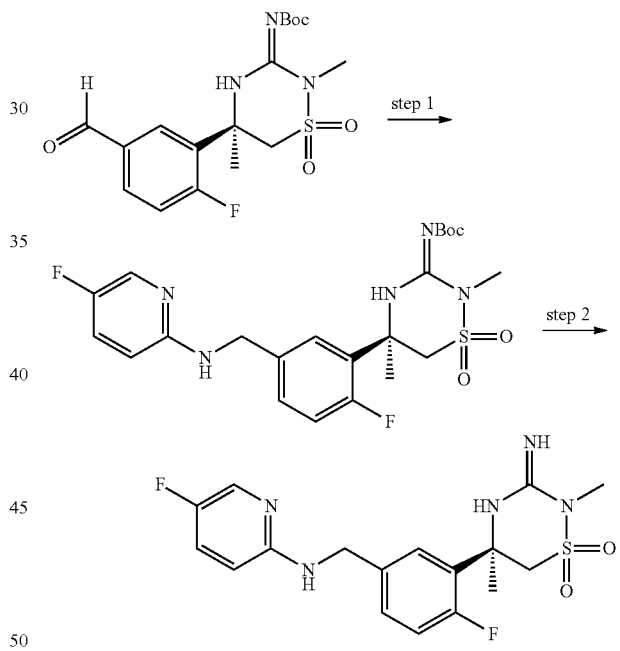

Ex. 131

Step 1:

To the aldehyde (intermediate from scheme 21 step 1 prior to treatment with NaBH$_4$) (0.10 g, 0.2 mmol) in methanol (1.5 mL) and pyridine (0.5 mL) was added 4 Å mol sieves (100 mg), 2-amino-5-fluoropyridine (0.056 g, 0.5 mmol), and acetic acid (0.02 mL, 0.35 mmol). The reaction was warmed to 50° C. and stirred for 18 h. After cooling to room temperature, saturated sodium bicarbonate (0.5 mL) was added and the mixture was stirred for 10 minutes. The mixture was then filtered and the filtrate was concentrated in vacuo. The residue was purified by silica gel chromatography (0-35% EtOAc/hex over 30 minutes) to provide product (0.077 g, 78%).

223

Step 2:

To the material prepared in step 1 (0.077 g, 0.16 mmol) in DCM (0.4 mL) was added TFA (0.24 mL, 3.1 mmol). The reaction was stirred at room temperature for 2 h and then concentrated in vacuo. The residue was taken up into DCM and washed with saturated NaHCO₃ (aq) water, and brine. The DCM layer was dried (MgSO₄), filtered, and concentrated in vacuo. The residue was then taken up into DCM and excess 2N HCl/ether was added. The mixture was concentrated to provide Ex. 131 (57 mg) as the HCl salt. LCMS data: (method D): $t_R$=1.56 min, m/e=396.2 (M+H).

Scheme 29:

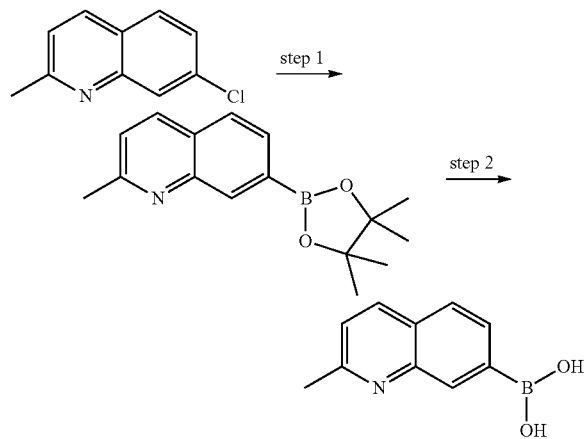

Step 1:

To 7-chloroquinaldine (1.2 g, 6.5 mmol) in THF (80 mL) was added bis(pinacolato)diboron (1.9 g, 7.6 mmol), 1,3-bis(2,6-diisopropylphenyl)imidazol-2-ylidene hydrochloride (0.17 g, 0.4 mmol), and potassium acetate (1.6 g, 16 mmol). Nitrogen was bubbled through the reaction for 10 minutes. Palladium acetate (0.044 g, 0.20 mmol) was added and the reaction was warmed to reflux and stirred for 6 hours. The reaction was filtered through a plug of silica gel washing with EtOAc. The filtrate was concentrated in vacuo. The filtrate was purified by silica gel chromatography (0-30% EtOAc/hex over 30 minutes) to provide the boronic ester (0.97 g, 55%).

Step 2:

To the boronic ester prepared in step 1 (0.78 g, 2.9 mmol) in THF (6 mL) was added water (24 mL) and sodium metaperiodate (0.93 g, 4.4 mmol). The reaction was stirred for 1 h and then 3M HCl$_{(aq)}$ (19 mL) were added. The mixture was stirred for 45 minutes and then extracted with EtOAc. The aqueous layer was then basified with saturated NaHCO₃$_{(aq)}$ and extracted with EtOAc. The organic layer was washed with water and brine, dried (MgSO₄), filtered, and concentrated in vacuo to provide the boronic acid (0.34 g, 63%).

Scheme 30:

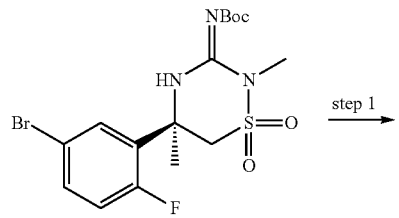

224

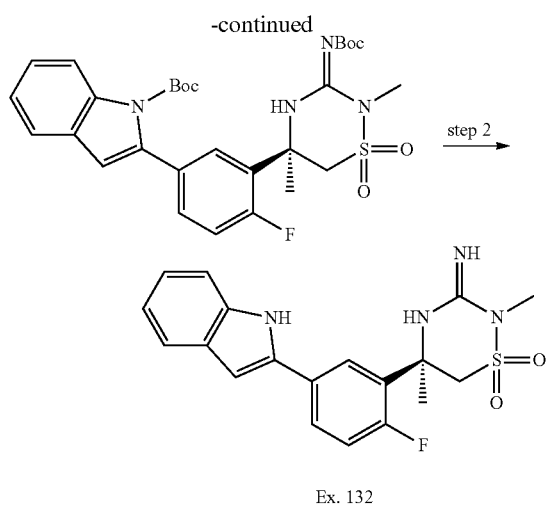

Ex. 132

Step 1:

To the bromide (Table IIb, entry 14) (0.15 g, 0.33 mmol) in a microwave reaction vial was added t-butanol (1.5 mL), 1-(t-butoxycarbonyl)-indole-2-boronic acid (0.16 g, 0.60 mmol) and aqueous potassium carbonate (2M, 0.25 mL, 0.50 mmol). Nitrogen was bubbled through the reaction mixture for 10 minutes. PdCl₂ (dppf) (0.054 g, 0.066 mmol) was added and nitrogen was bubbled through the reaction for 5 minutes. The reaction vessel was capped, warmed to 65° C., and stirred for 3 h. The reaction was cooled to room temperature and EtOAc was added. The mixture was washed with water and brine, dried (MgSO₄), filtered, and concentrated in vacuo. The residue was purified by silica gel chromatography (0-20% EtOAc/hex over 30 minutes) to provide the biaryl product (0.12 g, 60%).

Step 2:

To the product prepared in step 1 (0.12 g, 0.20 mmol) in DCM (2 mL) was added TFA (2 mL). The reaction was stirred at room temperature for 1 h and then concentrated in vacuo to provide Ex. 132 as a TFA salt (0.078 g, 78%). LCMS data: (method D): $t_R$=1.96 min, m/e=387.0 (M+H). The residue was further purified as needed by reverse phase chromatography [C18 5% (2 column volumes (CV), 5-100% (10 CV), 100 (2 CV); 0.1% formic acid/water/0.1% formic acid/acetonitrile].

TABLE XV

The following examples were prepared using procedures similar to those described in Scheme 30 using the appropriate aryl bromides and boronic acids. Examples (LCMS data: observed MH⁺, HPLC retention time and LCMS method)

| | |
|---|---|
| 133 | 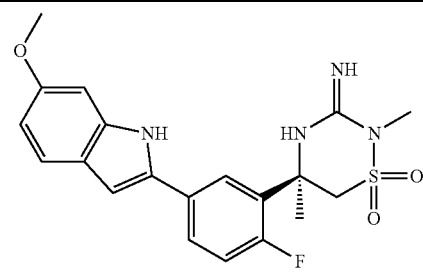 <br> MH⁺: 417.0, 1.93 min, D |

TABLE XV-continued

The following examples were prepared using procedures similar to those described in Scheme 30 using the appropriate aryl bromides and boronic acids. Examples (LCMS data: observed MH+, HPLC retention time and LCMS method)

134 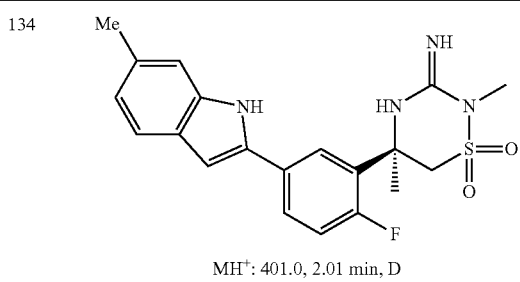

MH+: 401.0, 2.01 min, D

135 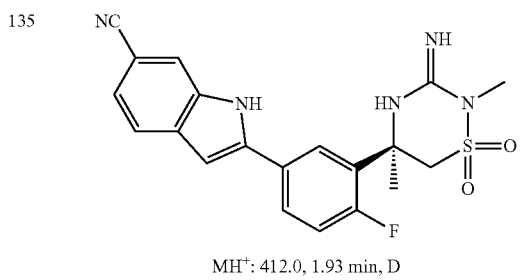

MH+: 412.0, 1.93 min, D

136 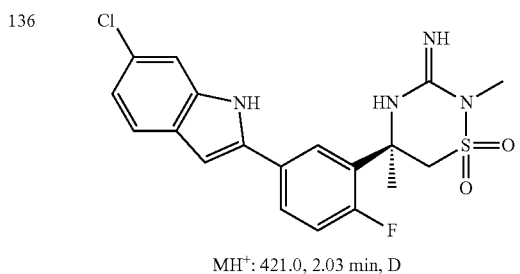

MH+: 421.0, 2.03 min, D

137 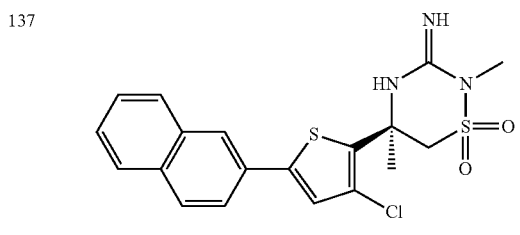

MH+: 420.0, 2.07 min, D

138 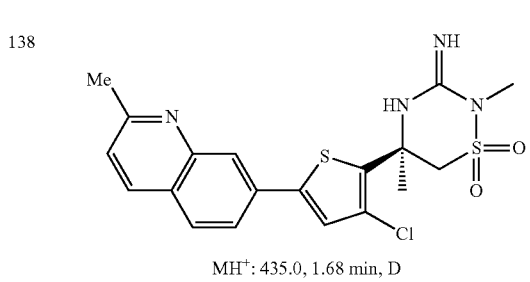

MH+: 435.0, 1.68 min, D

TABLE XV-continued

The following examples were prepared using procedures similar to those described in Scheme 30 using the appropriate aryl bromides and boronic acids. Examples (LCMS data: observed MH+, HPLC retention time and LCMS method)

139 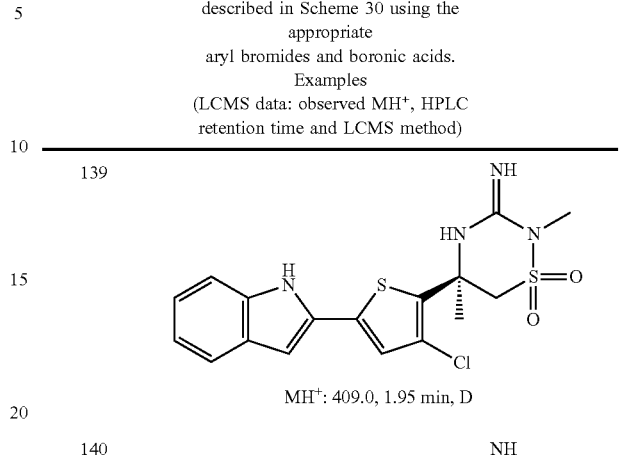

MH+: 409.0, 1.95 min, D

140

MH+: 428.0, 1.99 min, D

141 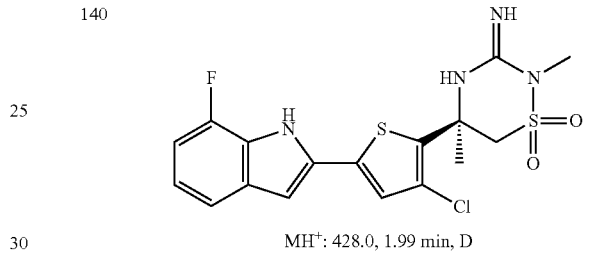

MH+: 439.0, 1.96 min, D

141a 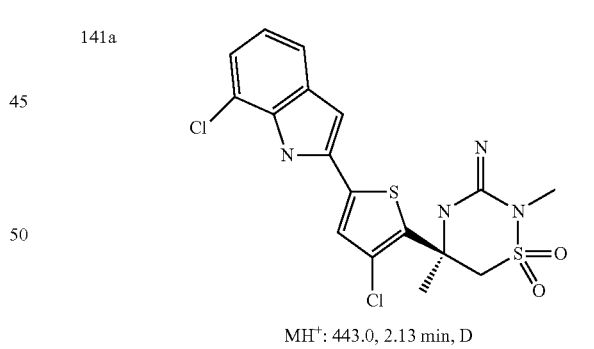

MH+: 443.0, 2.13 min, D

\*\*  \*\*
\*\*  \*\*

Scheme 31: 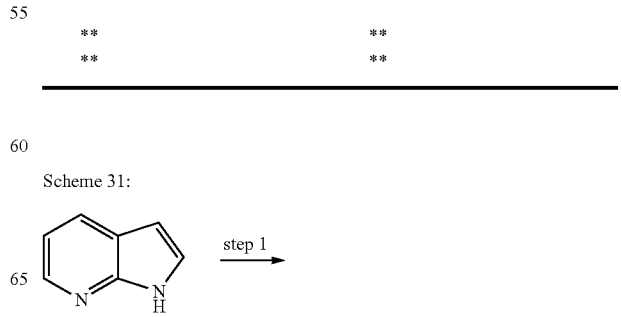

step 1

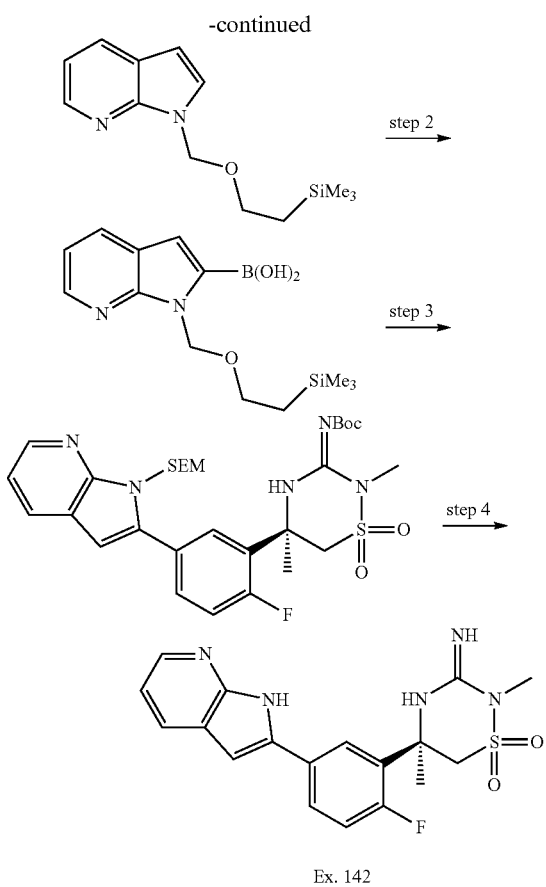

Ex. 142

K$_2$CO$_3$ $_{(aq)}$ (0.34 mL, 0.68 mmol). Nitrogen was bubbled through the reaction for 10 minutes. PdCl$_2$(dppf) (0.075 g, 0.092 mmol) was added and the reaction was sealed and heated to 65° C. After 3 h, the reaction was cooled to room temperature and EtOAc was added. The mixture was washed with water and brine (MgSO$_4$), filtered, and concentrated in vacuo. The residue was purified by silica gel chromatography (0-20% EtOAc/hex over 30 minutes) to provide the coupling product (0.21 g, 74%).

Step 4:

To the coupling product prepared in step 3 (0.086 g, 0.14 mmol) was added 4M HCl in ethanol (6 mL). The reaction was warmed to 60° C. and stirred for 20 h. The reaction was concentrated in vacuo and then purified by reverse phase chromatography (C18: gradient elution, 90:10:0.1 to 0:100:0.1 water:MeCN:formic acid) to provide Ex. 142 (0.030 g). LCMS data: (method D): t$_R$=1.67 min, m/e=388.0 (M+H).

Scheme 32:

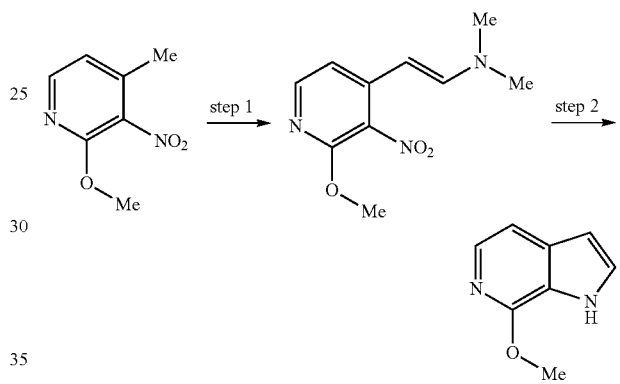

Step 1:

To the nitropyridine (5.1 g, 30 ml) in DMF (5 mL) was added 1,1-methoxy-N,N-dimethylmethanamine (15 mL, 110 mmol). The reaction was warmed to 130° C. and stirred for 16 h. The reaction was cooled to room temperature and then added to a beaker of ice. The resulting solid was isolated by filtration to give product (5.9 g, 88%).

Step 2:

To the enamine prepared in step 1 (5.9 g, 26 mmol) in ethanol (275 mL) was added 10% palladium on carbon, Degussa type (1.5 g). The reaction mixture was shaken under a hydrogen atmosphere (15 psi) for 15 minutes. The reaction was filtered through a bed of celite washing with DCM. The filtrate was concentrated in vacuo to provide the indole (4.3 g, 61%).

Step 1:

To 7-azaindole (1.5 g, 12.7 mmol) in DMF (30 mL) at 0° C. was added NaH (60% dispersion in mineral oil, 0.56 g, 14 mmol). The reaction was stirred for 15 minutes at room temperature then cooled to −40° C. (EtOAc/CO$_2$ cooling bath). (2-(Chloromethoxy)ethyl) trimethylsilane (2.5 mL, 14 mmol) was then added and the reaction allowed to warm to room temperature. The reaction was stirred at room temperature for 18 h. EtOAc was added and the mixture was washed with water and brine, dried (MgSO$_4$), filtered, and concentrated in vacuo. The residue was purified by silica gel chromatography (0-10% EtOAc/hex over 30 minutes) to provide the SEM-protected indole (2.9 g, 91%).

Step 2:

To the SEM-protected indole prepared in step 1 (0.99 g, 4.0 mmol) in THF (10 mL) at −40° C. was added n-BuLi (2.5 M in hexanes, 1.9 mL, 4.8 mmol). The mixture was stirred at −40° C. for 1 h and then triisopropyl borate (1.2 mL, 5.2 mmol) was added. The mixture was allowed to warm to room temperature while stirring for 18 h. To the reaction mixture was added 1N HCl (aq). The mixture was stirred at room temperature for 30 minutes. The mixture was then adjusted to pH~5 using saturated NaHCO$_3$ (aq) The mixture was extracted with ether. The combined ether extracts were washed with water and brine, dried (Na$_2$SO$_4$), filtered, and concentrated in vacuo. The residue was purified by silica gel chromatography (0-50% EtOAc/hex over 30 minutes) to provide the indole boronic acid (0.20 g, 17%).

Step 3:

To the bromide (Table IIb, entry 14) (0.21 g, 0.46 mmol) in t-butanol (3 mL) a microwave reaction vial was added the boronic acid prepared in step 2 (0.20 g, 0.68 mmol) and 2M Scheme 33:

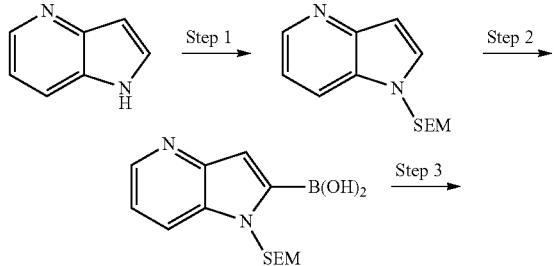

229
-continued

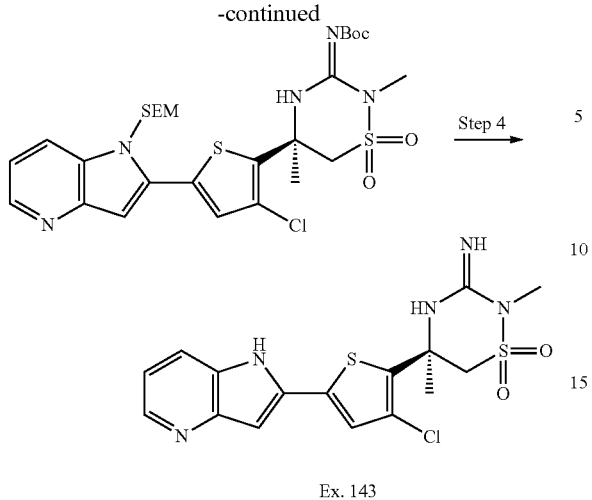

Ex. 143

Step 1:

The 4-azaindole was protected with the SEM group according to the procedure described in step 1 of Scheme 31.

Step 2:

The SEM protected indole prepared in step 1 was converted to the 2-boronic acid according to the procedure described in step 2 of Scheme 31.

Step 3:

To SEM-protected indole 2-boronic acid prepared in step 2 (0.40 g, 1.37 mmol) in a microwave reaction vial in t-butanol (3 mL) was added potassium carbonate (2M, 0.6 mL, 1.1 mmol) and the bromothiophene prepared in scheme 13 (0.36 g, 0.76 mmol). Nitrogen was bubbled through the reaction mixture for 10 minutes after which PdCl$_2$(dppf) (0.12 g, 0.15 mmol) was added. The reaction vessel was capped and warmed to 65° C. The reaction was stirred for 16 h and then cooled to room temperature. EtOAc was added and the mixture was washed with water and brine, dried (MgSO$_4$), filtered, and concentrated in vacuo. The residue was taken up into DCM (2 mL) and (Boc)$_2$O (166 mg) was added. The reaction was stirred at room temperature for 18 h. The reaction was concentrated in vacuo to provide a residue that was purified by silica gel chromatography (0-40% EtOAc/hex) to provide a mixture of desired product and bis-boc product (360 mg). The mixture was carried on directly to the next step Step 4:

The biaryl prepared in step 3 (0.28 g, 0.43 mmol) was heated in 4N HCl in ethanol (12 mL) to 65° C. for 12 h. The reaction was concentrated in vacuo to provide desired material and the indole N-hydroxymethyl intermediate. The mixture was taken up into acetone (2 mL) and ethanol (1 mL) and potassium carbonate was added (0.15 g, 1.1 mmol). The mixture was stirred at room temperature for 1 h and then added to saturated NH$_4$Cl$_{(aq)}$. The mixture was extracted with EtOAc. The combined organic layers were washed with water and brine, dried (MgSO$_4$), filtered, and concentrated in vacuo. The residue was purified by preparative silica gel TLC (10% MeOH/DCM) to provide Ex. 143 (0.10 g, 57%). LCMS data: (method D): t$_R$=1.67 min, m/e=410.0 (M±H). (Alternatively, the residue could be purified by reverse phase chromatography [C18 5% (2 column volumes (CV), 5-100% (10 CV), 100 (2 CV); 0.1% formic acid/water/0.1% formic acid/acetonitrile]).

230

TABLE XVI

Using the conditions described in Scheme 33, the following examples were prepared from the appropriate aryl bromides and aryl boronic acids.
Examples
(LCMS data: observed MH$^+$,
HPLC retention time and LCMS method)

144

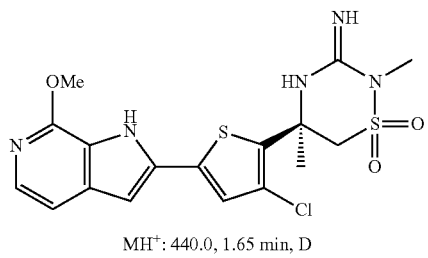 [SMILES: COc1nccc2cc(-c3cc(Cl)c([C@]4(C)CS(=O)(=O)N(C)C(=N)N4)s3)[nH]c12]

MH$^+$: 440.0, 1.65 min, D

145

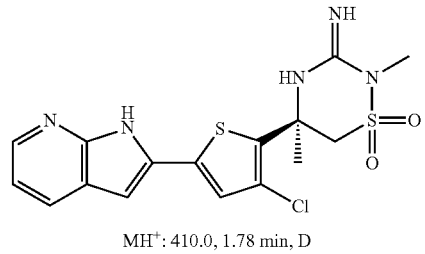 [SMILES: CN1C(=N)N[C@](C)(c2sc(-c3cc4cccnc4[nH]3)cc2Cl)CS1(=O)=O]

MH$^+$: 410.0, 1.78 min, D

146

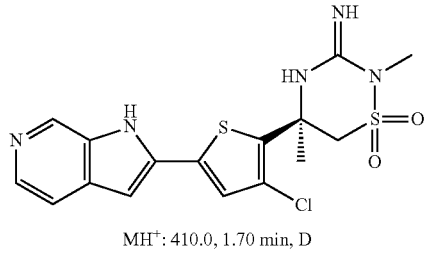 [SMILES: CN1C(=N)N[C@](C)(c2sc(-c3cc4ccncc4[nH]3)cc2Cl)CS1(=O)=O]

MH$^+$: 410.0, 1.70 min, D

147

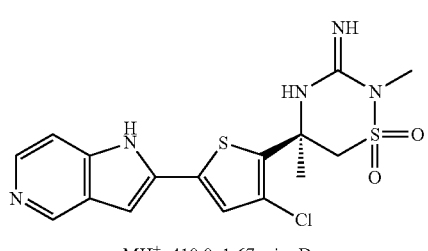

MH$^+$: 410.0, 1.67 min, D

Scheme 34:

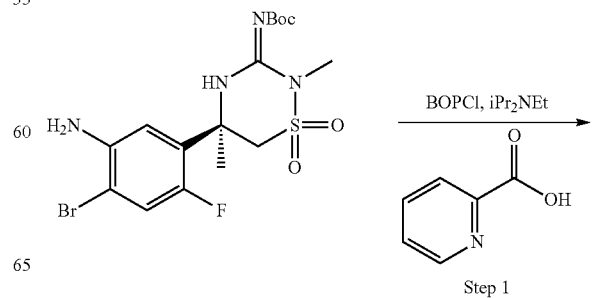

Step 1

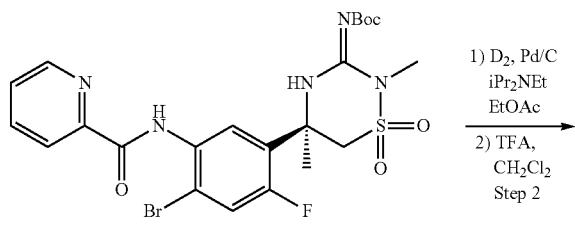

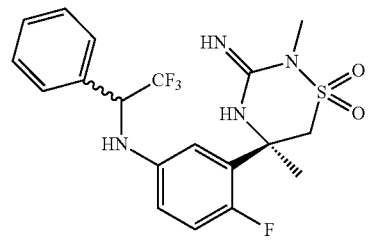

Example 149

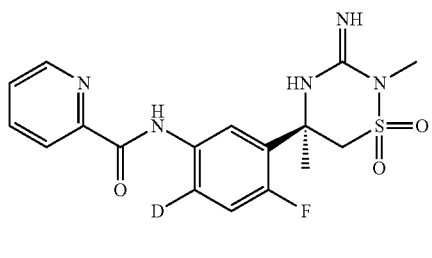

Ex. 148

Step 1:

To a slurry of the aniline from Scheme 10a (95 mg, 0.20 mmol), picolinic acid (30 mg, 0.25 mmol) and BOPCl (78 mg, 0.31 mmol) in CH$_2$Cl$_2$ (4 mL) at 0° C. was added iPr$_4$NEt (89 μL, 0.51 mmol). The resultant mixture was warmed to RT and stirred for 16 hours. The mixture was partitioned between CH$_2$Cl$_2$ and water. The aqueous layer was extracted with CH$_2$Cl$_2$ (3×). The combined organic layers were dried over Na$_2$SO$_4$, filtered and concentrated. The crude product was purified via preparative TLC (SiO$_2$: 1:1 hexanes:EtOAc) to afford the amide (47 mg, 40%) as a white solid.

Step 2:

Ex. 148 was prepared as its TFA salt from the above material using a procedure similar to that described in Scheme 23. LCMS data: (method D): t$_R$=1.75 min, m/e=393.0 (M+H).

Scheme 35:

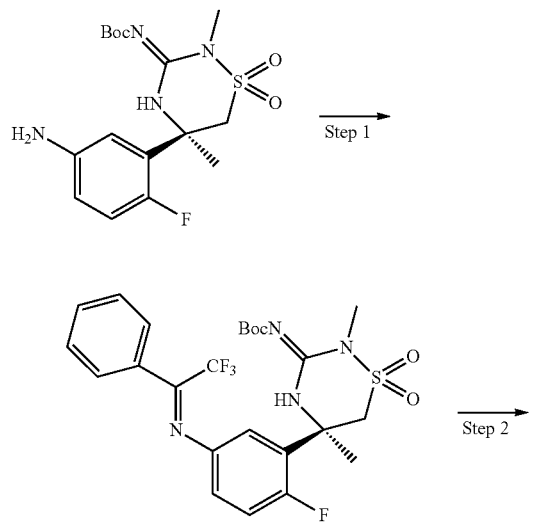

Step 1:

To a RT mixture of aniline (Scheme 10, 0.1 g, 0.26 mmol), 2 mL DCM, diisopropylethylamine (45 μl, 0.26 mmol), and trifluoroacetophenone (0.045 g, 0.26 mmol) was slowly added dropwise titanium tetrachloride (1.0 M in DCM, 0.26 mL, 0.26 mmol). The reaction was stirred for 2 hours. Saturated aqueous sodium bicarbonate was then poured into the reaction, forming a white precipitate, which was then filtered through celite. The celite was washed with DCM and the filtrate was extracted with DCM. The combined organic layers were dried (MgSO$_4$), filtered, and concentrated in vacuo. The residue was purified by silica gel chromatography (0-30% EtOAc/hexanes over 20 minutes) to provide the imine compound (0.051 g, 36%).

Step 2:

To the imine prepared in Step 1 (0.051 g, 0.09 mmol) stirring in 2 mL MeOH was added sodium borohydride (0.007 g, 0.18 mmol). The reaction was stirred at room temperature for 1 hour, then concentrated to dryness in vacuo. The reaction was purified by preparative RP HPLC (10-100% acetonitrile with 0.1% formic acid/water with 0.1% formic acid over 22 minutes) to provide the amine product. This material was treated with 2 mL 20% TFA/DCM for 1 hour, and then concentrated in vacuo to provide Example 149 (1:1 mixture of diastereomers) as a trifluoroacetate salt (39 mg, 75%). LCMS data: (method D): t$_R$=1.97 mitt, m/e=445.0 (M+H).

TABLE XVII

The following examples were made according to the methods described in Scheme 35:
Examples
(LCMS data: observed MH$^+$, HPLC retention time and LCMS method)

150

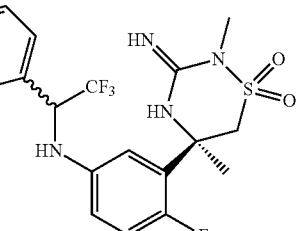

MH$^+$: 446.0, 1.87 min, D

TABLE XVII-continued

The following examples were made according to the methods described in Scheme 35:
Examples
(LCMS data: observed MH+, HPLC retention time and LCMS method)

151 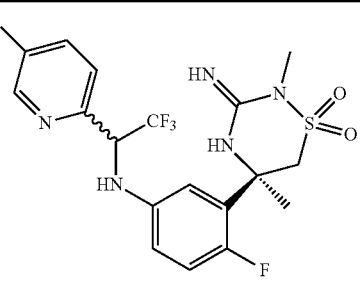

MH+: 464.0, 1.93 min, D

152 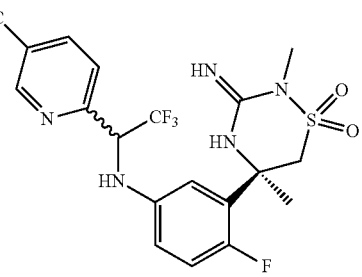

MH+: 514.0, 1.99 min, D

153 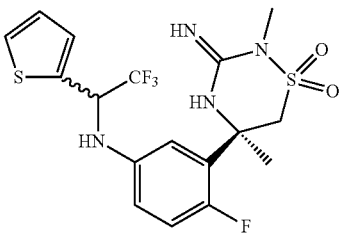

MH+: 451.0, 1.93 min, D

TABLE XVIII

The following Example was made as a mixture of diastereomers using the following sequence: (1) Scheme 35, Step 1, (2) Scheme 11b, Step 2:
Example
(LCMS data: observed MH+, HPLC retention time and LCMS method)

154 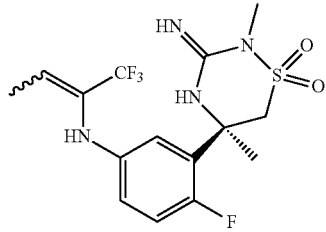

MH+: 395.0, 1.89 min, D

Scheme 36:

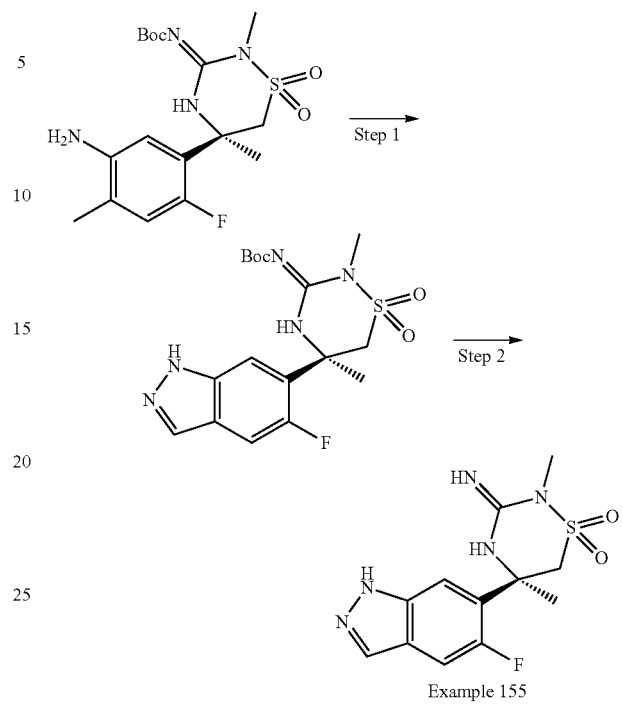

Example 155

Step 1:

To the aniline (Table IV, entry 5 0.2 g, 0.5 mmol) stirring at room temperature in glacial acetic acid (5 mL) was added dropwise a solution of sodium nitrite (0.035 g, 0.5 mmol) in water (0.25 mL). The reaction was stirred at room temperature 6 hrs, then concentrated to dryness in vacuo. The residue was purified by silica gel chromatography (0-100% EtOAc/hexanes over 30 minutes) to provide the indazole compound as a solid (0.060 g, 29%).

Step 2:

The material from step 1 (0.005 g, 0.012 mmol) was treated according to Scheme 11b, step 2 to afford Example 155 as the TFA salt (0.005 g, 97%). LCMS data: (method D): $t_R$=1.63 min, m/e=312.0 (M+H).

Scheme 37:

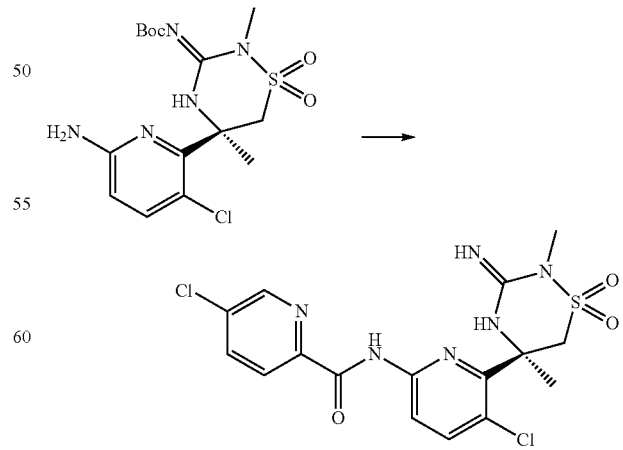

Example 156

To the aminopyridine compound (Table IIIb, 0.068 g, 0.17 mmol) stirring in 1.68 mL 4:1 DMF:diisopropylethylamine at room temperature was added 5-chloropicolinoyl chloride (Scheme 11p) and 1 crystal of DMAP. The reaction was heated to 50° C. and stirred for 48 hours. The reaction was cooled to room temperature and concentrated in vacuo. The residue was purified by silica gel chromatography (0-60% EtOAc/hexanes over 20 minutes, then 60-100% EtOAc/hexanes 20-30 minutes) to provide an amide product (0.014 g, 15%). This material was treated according to Scheme 11b, step 2 to provide Example 156 (0.014 g, 97%) as a trifluoroacetate salt. LCMS data: (method D): $t_R$=1.91 min, m/e=443.0 (M+H).

TABLE XIX

The following examples were made according to the methods described in Scheme 37 using acid chlorides from Table IVj:
Examples
(LCMS data: observed MH+, HPLC retention time and LCMS method)

157

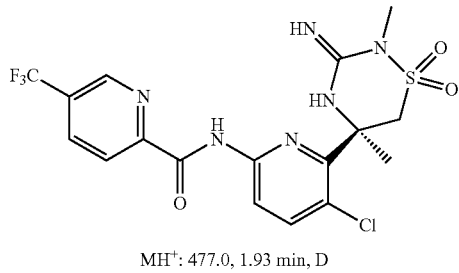 [SMILES: CN1C(=N)N[C@](C)(c2nc(NC(=O)c3ccc(C(F)(F)F)cn3)ccc2Cl)CS1(=O)=O]

MH+: 477.0, 1.93 min, D

158

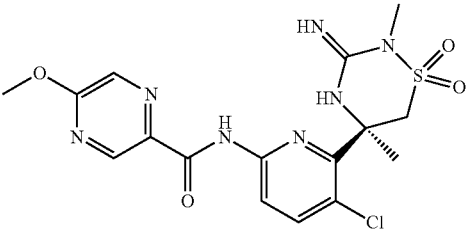

MH+: 440.0, 1.84 min, D

Scheme 38:

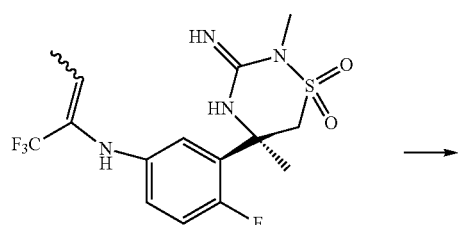

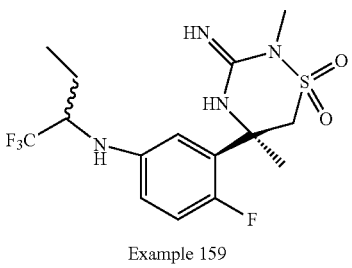

Example 159

To Example 154 (0.020 g, 0.04 mmol) stirring in 2 mL EtOH was added 10% palladium on carbon (0.010 g). This solution was subjected to a hydrogen atmosphere (balloon) and stirred 16 hours. The reaction was filtered through celite and washed with MeOH. The filtrate was concentrated to dryness in vacuo and purified by preparative RP HPLC (10-100% acetonitrile with 0.1% formic acid/water with 0.1% formic acid over 22 minutes) to provide Example 159 as a mixture of diastereomers as a formate salt (0.013 g, 65%). LCMS data: (method D): $t_R$=1.92 min, m/e=397.0 (M+H).

Scheme 39:

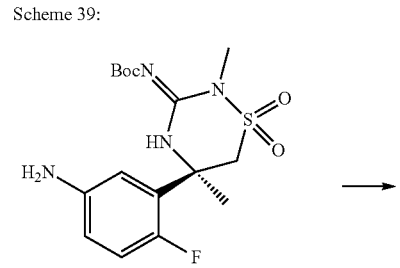

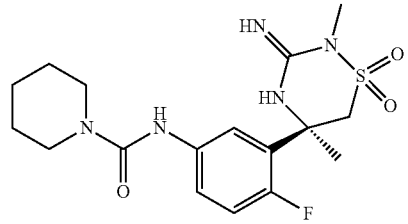

Example 160

Step 1:

To the aniline (Scheme 10, 0.1 g, 0.26 mmol) stirring in 3 mL DCM was added triethylamine (54 µL, 0.39 mmol) and 1-piperidinecarbonyl chloride (34 µL, 0.27 mmol), and the mixture was allowed to stir for 3 days at room temperature. The reaction was poured into water and extracted with DCM. The combined organic layers were dried (MgSO4), filtered, and concentrated in vacuo. The residue was purified by silica gel chromatography (0-80% EtOAc/hexanes over 20 minutes) to provide a urea product (0.093 g, 72%). This compound was then treated according to Scheme 11b, Step 2 to provide Example 160 (0.094 g, 98%) as a trifluoroacetate salt. LCMS data: (method D): $t_R$=1.75 min, m/e=398.2 (M+H).

TABLE XX

The following examples were made according to the methods described in Scheme 39 using the appropriate carbonl chloride:
Example
(LCMS data: observed MH+, HPLC retention time and LCMS method)

161
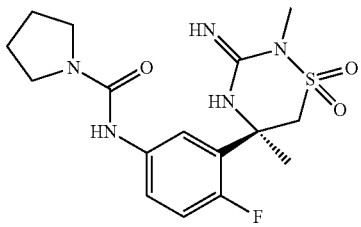
MH+: 384.2, 1.61 min, D

161a
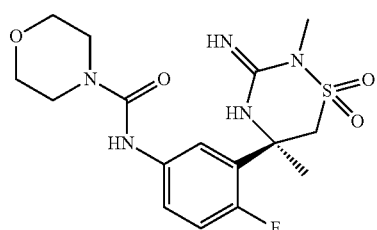
MH+: 400.0, 1.47 min, D

Scheme 40:

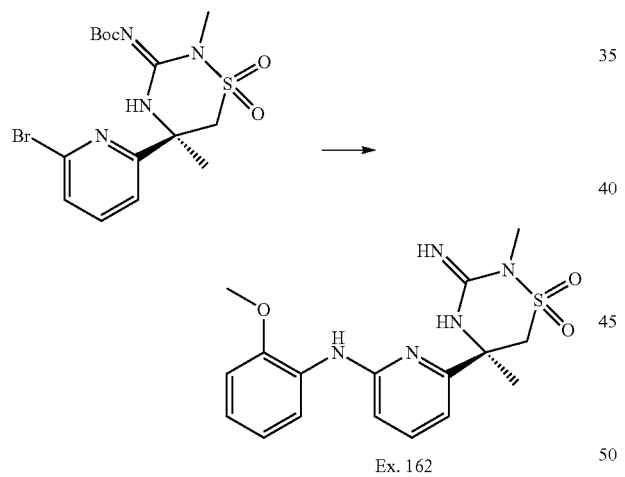

Ex. 162

The bromopyridine compound (Scheme 7a, step 6) 0.07 g, 0.16 mmol) along with O-anisidine (22 µL, 0.19 mmol), tris(dibenzylideneacetone)dipalladium (0.003 g, 0.003 mmol), racemic 2,2'-bis(diphenylphosphino)-1,1'-binaphthyl (0.004 g, 0.006 mmol), and sodium t-butoxide (0.022 g, 0.22 mmol) were stirred in a flame-dried, sealed microwave vial flushed with nitrogen in 2 mL anhydrous toluene at 80° C. for 3.5 hours. The reaction mixture was cooled to room temperature, poured into water, and extracted with DCM. The combined organic layers were dried (MgSO4), filtered, and concentrated in vacuo. The residue was purified by silica gel chromatography (0-60% EtOAc/hexanes over 20 minutes) to provide biarylamine product (0.007 g, 9%). This material was treated according to Scheme 11b, Step 2 to provide Example 162 as a trifluoroacetate salt (0.007 g, 97%). LCMS data: (method D): $t_R$=1.80 min, m/e=376.2 (M+H).

TABLE XXI

The following Examples were made according to the methods in Scheme 40: Examples
(LCMS data: observed MH+, HPLC retention time and LCMS method)

163
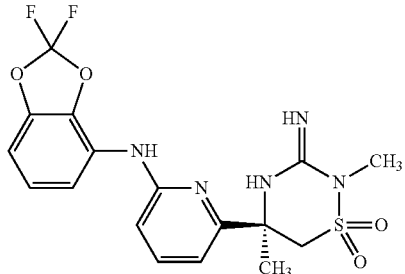
MH+: 426.0, 2.05 min, D

164
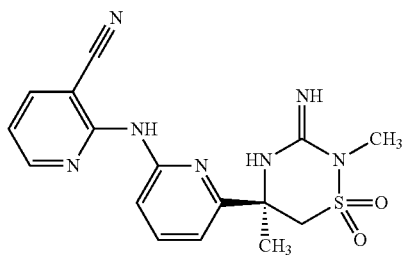
MH+: 372.0, 1.83 min, D

165
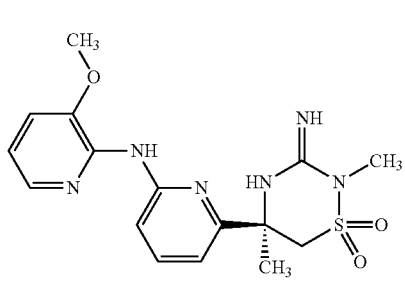
MH+: 377.0, 1.65 min, D

166
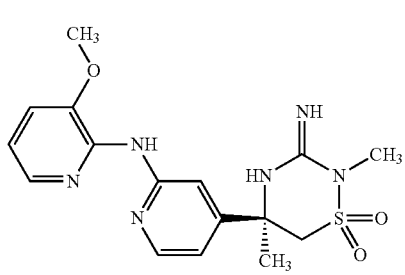
MH+: 377.0, 1.18 min, D

TABLE XXI-continued

The following Examples were made according to the methods in Scheme 40: Examples
(LCMS data: observed MH+, HPLC retention time and LCMS method)

167

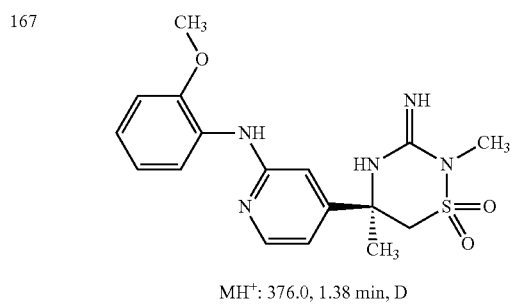

MH+: 376.0, 1.38 min, D

**

Scheme 41:

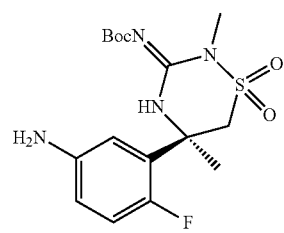

→

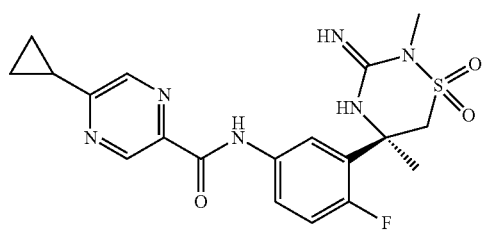

Example 168

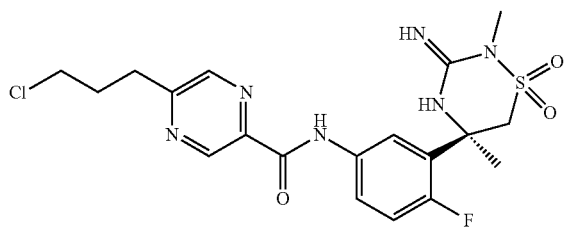

Example 169

The aniline shown (Scheme 10) was treated according to Scheme 11b using 5-cyclopropylpyrazine-2-carboxylic acid (Table IVg, entry 4) to afford, after separation, both Example 169 [LCMS data: (method D): $t_R$=1.80 min, m/e=433.0 (M+H)] and Example 168 [LCMS data: (method D): $t_R$=1.83 min, m/e=469.0 (M+H)] both as TFA salts.

Scheme 42:

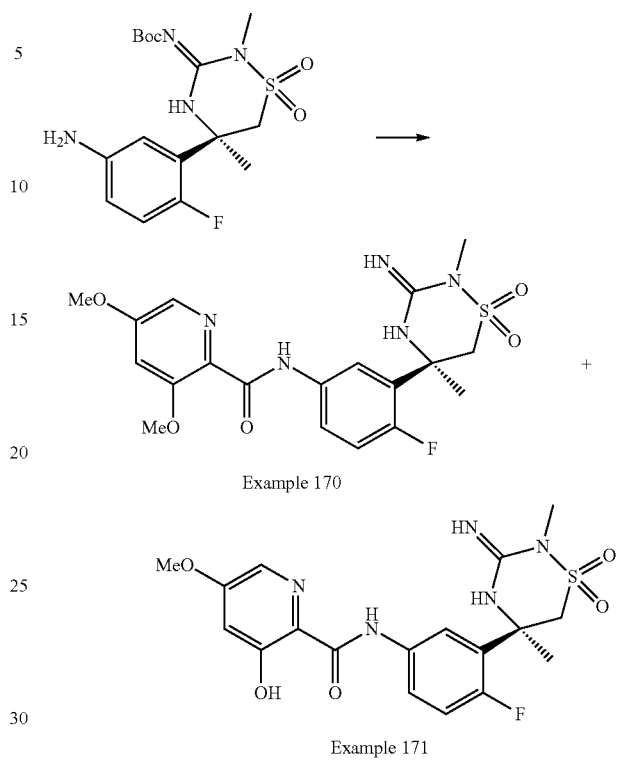

Example 170

Example 171

The aniline shown (Scheme 10) was treated according to Scheme 11b using 3,5-dimethoxypyridine-2-carboxylic acid (Scheme 11q) to afford, after separation, both Example 170 [LCMS data: (method D): $t_R$=1.73 min, m/e=452.0 (M+H)] and Example 171 [LCMS data: (method ID): $t_R$=1.85 min, m/e=438.0 (M+H)] both as TEA salts.

Scheme 43:

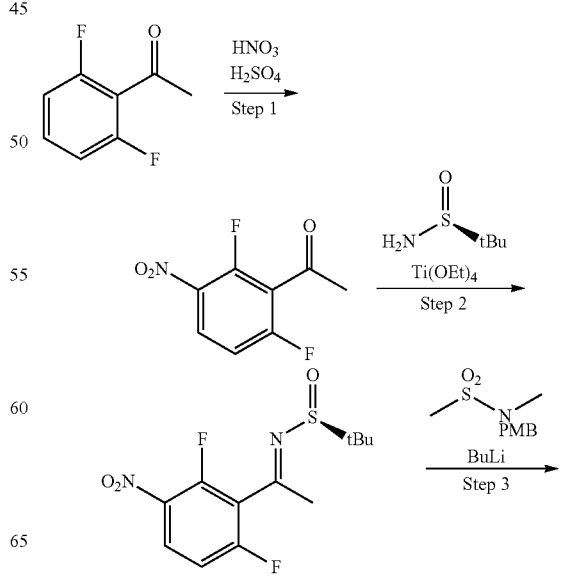

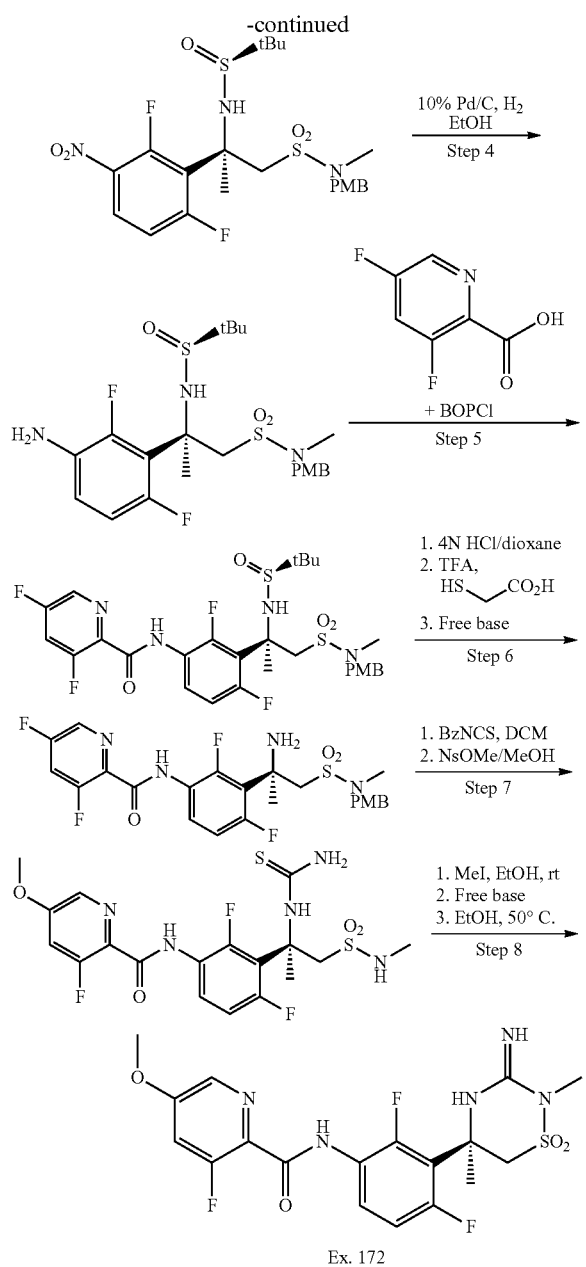

Step 3:

The ketimine from step 2 (17.1 g, 56.2 mmol) was treated according to Scheme 1a, Step 3 to give desired syn addition product (6 g, 20%) as well as a mixture of syn and anti diastereomers (6 g, 3:1, 20%).

Step 4:

To a solution of the syn addition product from Step 3 (2.71 g, 5.1 mmol) in 25 mL of ethanol was added 10% Pd/C (298 mg). The mixture was placed under $H_2$ balloon atmosphere overnight. After filtration through Celite, the filtrate was concentrated. The crude residue was purified by flash silica column (60%-100% EtOAc/hexanes) to give the aniline product (1.75 g, 68% yield).

Step 5:

A mixture of the aniline from Step 4 (453 mg, 0.9 mmol), 3,5-difluoropicolinic acid (215 mg, 1.4 mmol), and BOPCl (527 mg, 2.07 mmol) in 4 mL of pyridine was stirred overnight. After it was quenched with 1N HCl(aq), the mixture was extracted with ethyl acetate. The organic portions were combined, dried over $MgSO_4$ and concentrated. The crude residue was purified by flash silica column (40% EtOAc/hexane) to give an amide product (431 mg, 74% yield).

Step 6:

To a solution of the above material (431 mg, 0.67 mmol) in 3 mL of DCM and 1 mL of methanol was added 4N HCl in dioxane (1 mL, 4.0 mmol). After the mixture was stirred for 1 h, it was concentrated. This sample was treated with a mixture of TFA (4 mL) and thioglycolic acid (0.46 mL, 6.7 mmol). After the mixture was stirred for 4 h, it was concentrated. The crude residue was neutralized by carefully adding saturated sodium bicarbonate solution. The resulting mixture was extracted with ethyl acetate, the organic portions were combined, dried over magnesium sulfate, and concentrated to an amine product that was used in the subsequent step without further purification.

Step 7:

To the material from step 6 (assumed to be 0.67 mmol) in 5 mL of DCM was added benzoyl isothiocyanate (0.12 mL, 0.87 mmol). The mixture was stirred overnight at RT. After it was concentrated, the residue was dissolved in 5 mL of methanol, and sodium methoxide (25% in methanol, 0.37 mL) was added. The mixture was stirred for 2 h at RT. It was quenched with 2 drops of acetic acid. After the mixture was concentrated, the crude was diluted with saturated sodium carbonate, and extracted with DCM. The combined organic portions were dried over magnesium sulfate and concentrated to give an isothiourea product that was used in the subsequent step without purification.

Step 8:

To a solution of the material from step 7 (assumed to be 0.67 mmol) in 5 mL of ethanol was added methyl iodide (0.05 mL, 0.8 mmol). The mixture was stirred overnight at room temperature and then diluted with saturated sodium bicarbonate. After the mixture was extracted with ethyl acetate, the organic layers were combined, dried over magnesium sulfate, and concentrated. The crude residue was dissolved in 5 mL of ethanol, and the mixture was heated at 50° C. for 2 h. The mixture was then diluted with saturated sodium bicarbonate, and extracted with ethyl acetate. The organic portions were combined, dried over magnesium sulfate, and concentrated. The crude residue was purified by reverse phase HPLC (C18 radial compression, 10% to 100% MeCN/water with 0.1% TFA) to give Example 172 as a TFA salt (40.3 mg, 14% from the product of Step 5). LCMS (conditions A): $t_R$=2.43 min, m/e=458.3 (M+H).

Step 1:

To a −40° C. mixture of concentrated $H_2SO_4$ (100 mL) and fuming $HNO_3$ (100 mL) was added 1-(2,6-difluorophenyl)ethanone (20 g, 128 mmol) dropwise. The resulting mixture was stirred at −40° C. for 2 h then poured slowly onto ice. That mixture was diluted with DCM and the phases were separated. The aqueous layer was neutralized with sat. aq. $NaHCO_3$ and then extracted with DCM. All organic portions were combined, dried over $MgSO_4$, filtered, and concentrated to give 1-(2,6-difluoro-3-nitrophenyl)ethanone (26.3 g, 131 mmol, >theoretical) that was used without further purification.

Step 2:

The nitrophenyl ketone from the previous step was treated according to Scheme 1a, Step 1 [substituting (S)-2-methyl-2-propanesulfinamide for (R)-2-methyl-2-propanesulfinamide] to give a ketimine product (17.1 g, 44% based on 1-(2,6-difluorophenyl)ethanone from Step 1).

TABLE XXII

The following examples were made from 1-(2,6-difluorophenyl)ethanone using methods similar to those described in Scheme 43, substituting the appropriate acid in Step 5: Examples
(LCMS data: observed MH+, HPLC retention time and LCMS method)

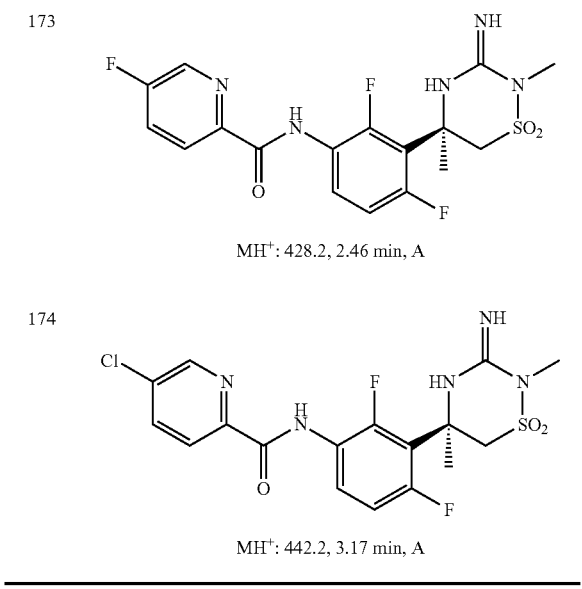

173
MH+: 428.2, 2.46 min, A

174
MH+: 442.2, 3.17 min, A

Scheme 44:

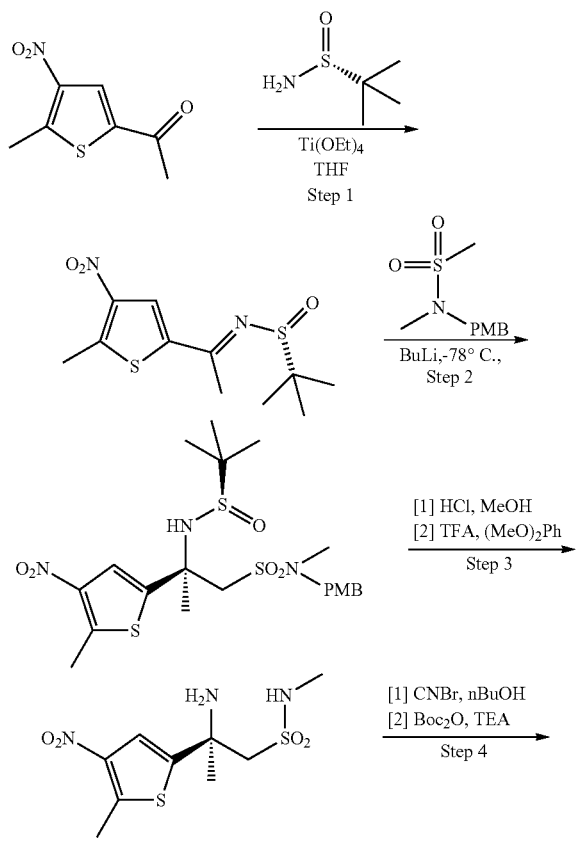

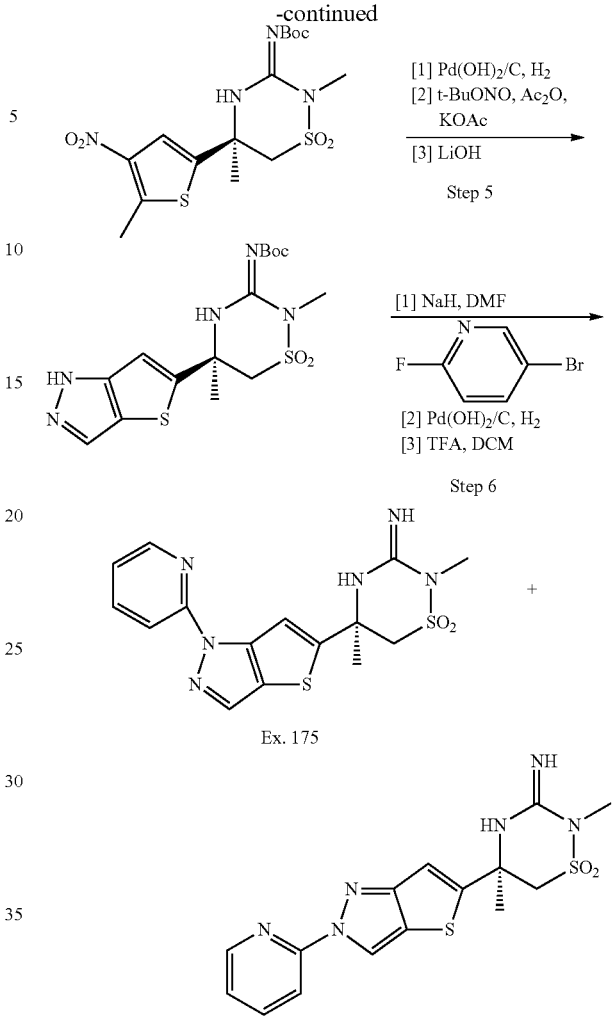

Ex. 175

Ex. 176

Steps 1-4:

1-(5-Methyl-4-nitrothiophen-2-yl)ethanone, obtained by nitration from 1-(5-methylthiophen-2-yl)ethanone according to the literature procedure (E. Campaigne, J. L. Diedrich, J. Am. Chem. Soc. 1951, 73, 5240-5243), was converted into the product of step 4 using similar procedures in the following sequence: (i) Scheme 1a, steps 1-4, (ii) Scheme 3b.

Step 5:

To a solution of the product of step 4 (570 mg, 1.37 mmol) in MeOH (25 mL) was added 10% Pd(OH)$_2$/C (250 mg), and the reaction was stirred in a Farr-shaker under an atmosphere of H$_2$ (50 psi) for 18 h. The reaction was filtered over a pad of celite, the filter residue rinsed with MeOH and the combined organic layers concentrated under reduced pressure to give a residue (423 mg, 80%). To a solution of this residue (423 mg, 1.08 mmol) in toluene (3 mL) was added KOAc (85 mg, 0.86 mmol), acetic anhydride (0.205 mL, 2.16 mmol) and tert-butylnitrite (0.145 mL, 1.2 mmol). The reaction was stirred at 90° C. for 4.5 h, then cooled to RT and diluted with EtOAc. After filtration through celite, the filtrate was concentrated under reduced pressure to give a residue that was subjected to silica gel chromatography (gradient elution 100:0 to 70:30 hexanes:EtOAc). The resulting mixture of acetylated and deacetylated materials (298 mg) was dissolved in THF (5 mL) and treated with aqueous 1 M LiOH (2 mL) for 30 min at RT. The reaction was diluted with EtOAc, the layers separated and the aqueous layer extracted with EtOAc (1×). The combined organic layers were washed with brine, dried over MgSO₄, and concentrated under vacuum to give the product of step 5 (282 mg, 65%).

Step 6:

Sodium hydride (60% in mineral oil, 20 mg, 0.5 mmol) was added to a solution of the product from step 5 (78 mg, 0.195 mmol) in DMF (2 mL) at RT. After 5 min, 2-fluoro-5-bromopyridine (54 mg, 0.306 mmol) was added and the reaction stirred for 19 h at RT, then quenched with water and EtOAc. The organic layer was washed with saturated aqueous NaHCO$_3$ $_{(aq.)}$, brine, and then dried over MgSO₄, and concentrated under vacuum. To a solution of this residue in MeOH was added 10% Pd(OH)₂/C (110 mg), and the reaction was stirred under a balloon-atmosphere of H₂ for 72 h. The catalyst was removed by filtration over celite, and the filtrate concentrated under reduced pressure to give a mixture of regioisomeric intermediates that were separated by silica gel chromatography (gradient elution with hexanes:EtOAc). Each regioisomer was deprotected according to the procedure described in Scheme 11b, Step 2, then subjected to reverse phase chromatography (C18: gradient elution, 90:10:0.1 to 0:100:0.1 water:MeCN:TFA) to provide Example 175 and Example 176 as their TFA salts. LCMS for Ex. 175 (conditions D): t$_R$=1.80 min, m/e=377.0 (M±H); LCMS for Ex. 176 (conditions D): t$_R$=1.78 min, m/e=377.0 (M+H).

TABLE XXIII

The following examples were prepared using a procedure similar to that described in Scheme 44 omitting the hydrogenation portion of step 6.

Example

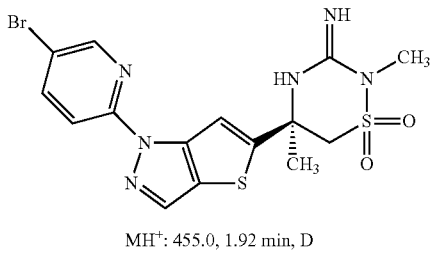 [SMILES: CN1C(=N)N[C@](C)(c2cc3c(cnn3-c3ccc(Br)cn3)s2)CS1(=O)=O]

177

MH⁺: 455.0, 1.92 min, D

Scheme 45:

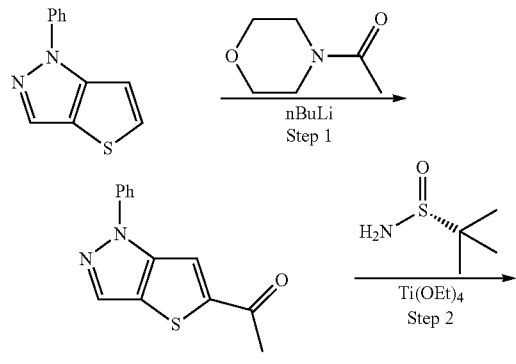

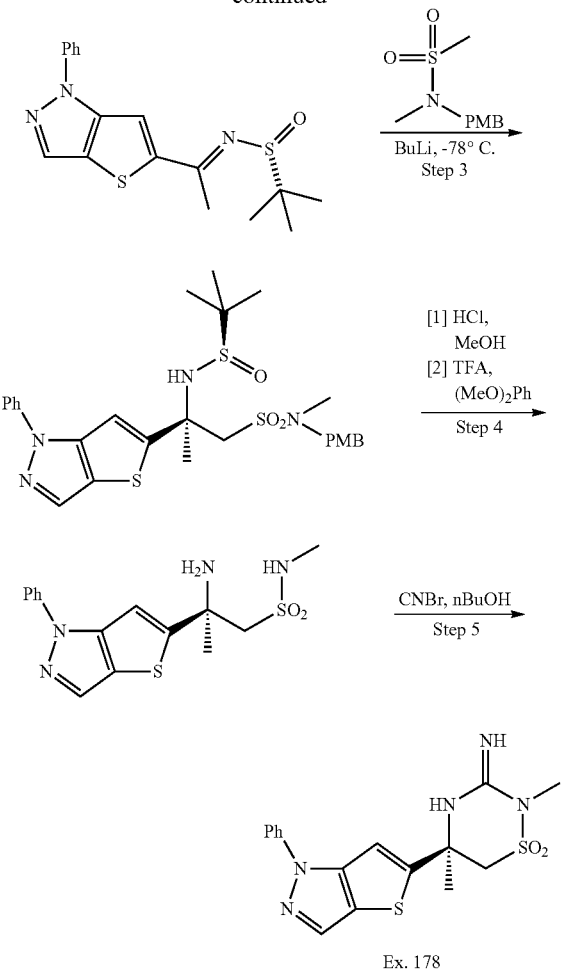

Ex. 178

Step 1:

To a −78° C. solution of 1-phenyl-1H-thieno[3,2-e]pyrazole (1.94 g, 9.68 mmol), obtained from 3-bromothiophene-2-carbaldehyde according to the literature procedure (Lehedev et al., *J. Org. Chem.* 2005, 70, 596-602), was added nBuLi (4.25 mL of a 2.5 M solution in hexanes, 10.65 mmol) over 5 min. After 30 min at −78° C., N-acetylmorpholine (2.3 mL, 20 mmol) was added and the reaction was stirred for 60 min at −78° C., then stirred for 6 h while slowly warming to RT. The reaction was quenched with saturated aqueous NH₄Cl and diluted with EtOAc. The organic layer was washed with sat. aqueous NaHCO₃ and brine, dried over MgSO₄ and concentrated under reduced pressure. The residue was subjected to silica gel chromatography (gradient elution 100:0 to 85:15 hexanes:EtOAc) to give 1-(1-phenyl-1H-thieno[3,2-c]pyrazol-5-yl)ethanone (682 mg, 2.81 mmol, 29%) along with recovered starting material (823 mg, 4.13 mmol, 43%).

Steps 2-5:

These steps were performed using similar procedures to the following sequence: (i) Scheme 1a, steps 1-4, (ii) Scheme 3b, omitting the coversion to the t-butyl carbamate. The final intermediate was subjected to reverse phase chromatography (C18: gradient elution, 90:10:0.1 to 0:100:0.1 water:MeCN:TFA) to provide Ex. 178 as its TFA salt. LCMS for Ex. 178 (conditions D): t$_R$=1.82 min, m/e=376.0 (M+H).

Scheme 46:

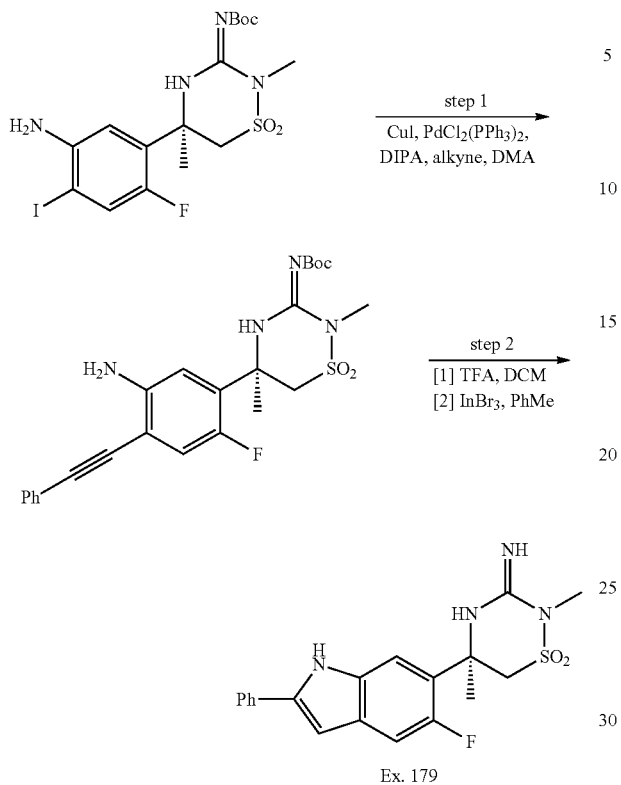

Ex. 179

Step 1:

CuI (7.6 mg, 0.04 mmol) was added to a solution of iodoaniline (200 mg, 0.39 mmol, Scheme 10a), diisopropylamine (0.169 mL, 1.2 mmol), PdCl$_2$(PPh$_3$)$_2$ (28 mg, 0.04 mmol) and phenyl acetylene (0.132 mL, 1.2 mmol) in dimethylacetamide (2 mL), and the reaction was stirred at 40° C. for 6 h. The reaction was diluted with sat. aqueous NaHCO$_3$ solution and EtOAc, then filtered reaction over celite. After rinsing the residue with EtOAc, the aqueous layer was extracted with EtOAc (3×). The combined organic layers were dried over Na$_2$SO$_4$, filtered, and concentrated to give a residue that was subsequently subjected to silica gel chromatography (10→20% EtOAc/hexanes) to provide the anilino acetylene intermediate (181 mg, 95%).

Step 2:

Trifluoroacetic acid (0.2 mL) was added to a solution of the product from step 1 (181 mg, 0.37 mmol) in DCM (1 mL) at RT. After 2 h, the reaction was concentrated under vacuum. To part of the residue (50 mg, 0.13 mmol) in toluene (1 mL) was added InBr$_3$ (46 mg, 0.13 mmol.), and the reaction was heated to 115° C. for 2 h. After removing volatiles under reduced pressure, the residue was suspended in MeOH, filtered through a PTFE-filter and the filtrate subjected to reverse phase chromatography (C18: gradient elution, 90:10:0.1 to 0:100:0.1 water:MeCN:TFA) to provide Ex. 179 as its TFA salt (11.7 mg, 30%). LCMS for Ex. 179 (conditions D): t$_R$=1.98 min, m/e=387.2 (M+H).

Scheme 47:

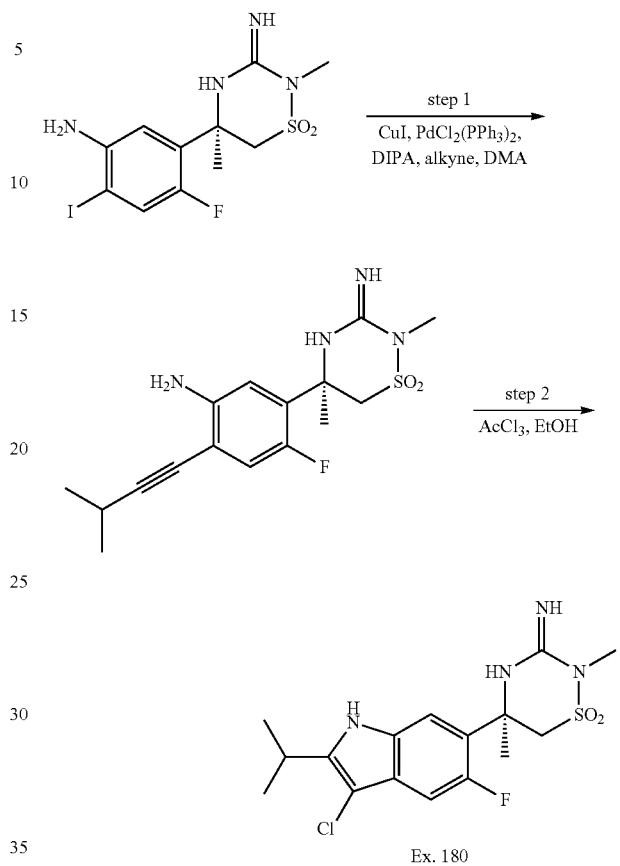

Ex. 180

Step 1:

The anilino acetylene intermediate was prepared in the same manner as in Scheme 46, Step 1 except that isoproylacetylene was used instead of phenylacetylene.

Step 2:

To the anilino acetylene intermediate from Step 1 (100 mg, 0.22 mmol) in EtOH (1 mL) was added AuCl$_3$ (133 mg, 0.44 mmol), and the reaction was heated to 70° C. for 3 h. After removing volatiles under reduced pressure, the residue was suspended in MeOH, filtered through a PTFE-filter and the filtrate subjected to reverse phase chromatography (C18: gradient elution, 90:10:0.1 to 0:100:0.1 water:MeCN:TFA) to provide Example 180 as its TFA salt (17.2 mg, 20%). LCMS for Example 180 (conditions D): t$_R$=2.04 min, m/e=387.0 (M+H).

Scheme 48:

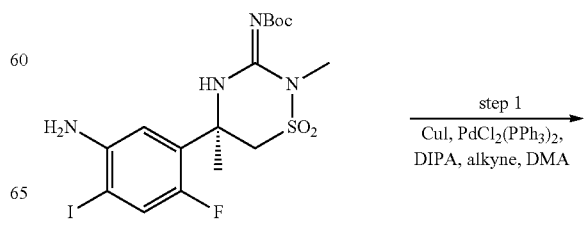

-continued

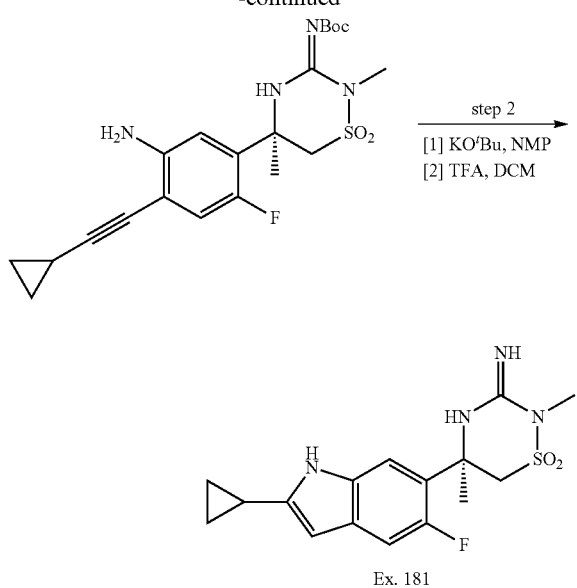

Ex. 181

Step 1:

The anilino acetylene intermediate was prepared in the same manner as in Scheme 46, Step 1 except that cyclo-proylacetylene was used instead of phenylacetylene.

Step 2:

To the anilino acetylene intermediate from Step 1 (54 mg, 0.11 mmol) in NMP (1 mL) was added potassium tert-butoxide (37 mg, 0.33 mmol), and the reaction was stirred for 18 h at RT. The mixture was then diluted with water and EtOAc, the organic layer was dried over $Na_2SO_4$, filtered, and concentrated to give a residue that was subsequently subjected to silica gel chromatography (10→25% EtOAc/hexanes) to provide the Boc-protected indole intermediate (35 mg, 70%). This intermediate was deprotected according to the procedure described in Scheme 11b, Step 2, then subjected to reverse phase chromatography ($C_{18}$: gradient elution, 90:10:0.1 to 0:100:0.1 water:MeCN:TFA) to provide Ex. 181 as its TFA salt. LCMS for Ex. 181 (conditions D): $t_R$=1.91 min, m/e=351.2 (M+H).

TABLE XXIV

The following examples were prepared using a procedure similar to that described in Schemes 46, 47 and 48.
Examples
(LCMS data: observed MH+, HPLC retention time and LCMS method)

182

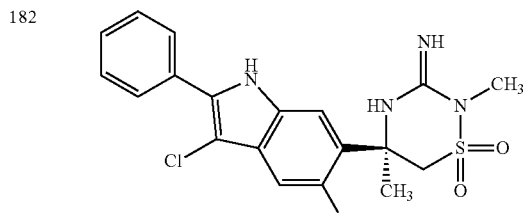

MH+: 421.2, 2.07 min, D

TABLE XXIV-continued

The following examples were prepared using a procedure similar to that described in Schemes 46, 47 and 48.
Examples
(LCMS data: observed MH+, HPLC retention time and LCMS method)

183

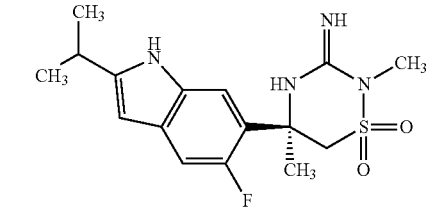

MH+: 353.2, 1.96 min, D

184

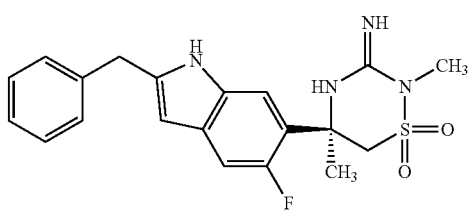

MH+: 401.2, 2.01 min, D

185

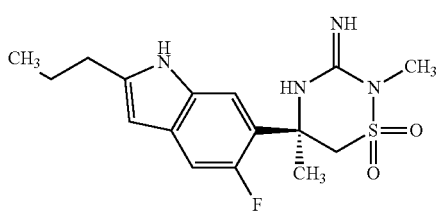

MH+: 353.0, 1.98 min, D

186

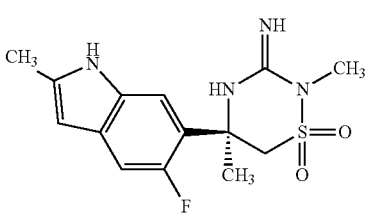

MH+: 325.0, 1.85 min, D

187

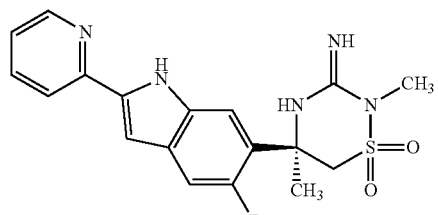

MH+: 388.0, 1.74 min, D

TABLE XXIV-continued

The following examples were prepared using a procedure similar to that described in Schemes 46, 47 and 48.

Examples
(LCMS data: observed MH+, HPLC retention time and LCMS method)

188

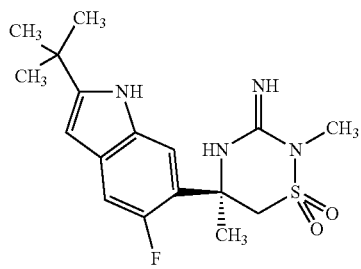

MH+: 367.0, 2.02 min, D

189

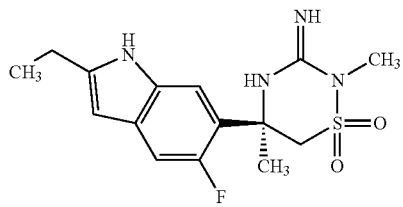

MH+: 339.0, 1.87 min, D

Scheme 49:

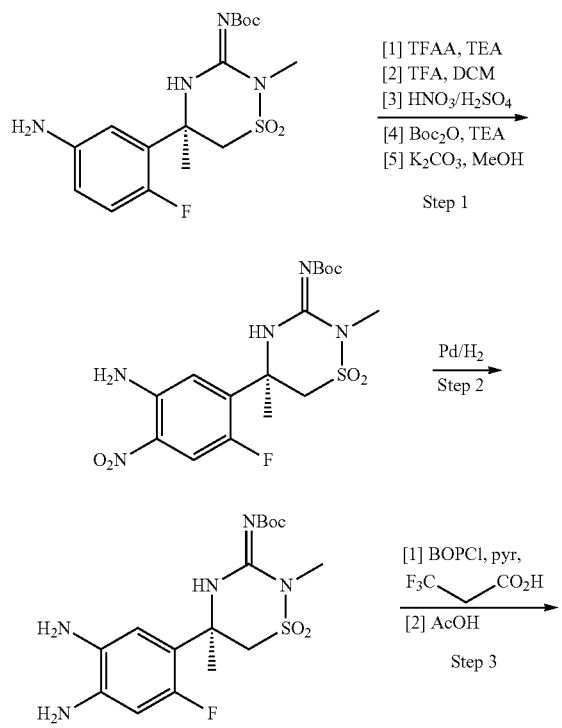

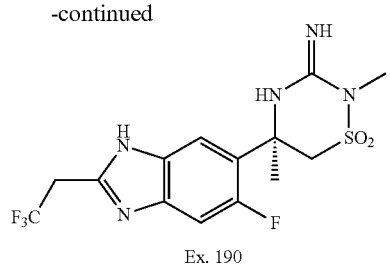

Ex. 190

Step 1:

Trifluoroacetic anhydride (2.34 mL, 16.85 mmol) was added dropwise to a solution of aniline (5.5 g, 14.24 mmol, Scheme 10) and triethylamine (2.39 mL, 17.1 mmol) in DCM (30 mL) at 0° C. After stirring at RT for 2 h, the reaction was quenched with saturated aqueous NaHCO$_3$ and diluted with EtOAc. The organic layer was dried over Na$_2$SO$_4$ and concentrated under reduced pressure to give a solid (6.0 g), which was dissolved in DCM (10 mL) and stirred with TFA (2 mL) for 1 h at RT. The reaction was concentrated under reduced pressure, and the residue dissolved in concentrated H$_2$SO$_4$ (9 mL). After cooling to 0° C., a mixture of fuming HNO$_3$/conc. H$_2$SO$_4$ (1.26 mL/3 mL) was slowly added via addition funnel. After 40 min, the reaction was carefully quenched with saturated aqueous NaHCO$_3$ and diluted with EtOAc. The aqueous layer was extracted with EtOAc (3×), and the combined organic layers were dried over Na$_2$SO$_4$, and concentrated under reduced pressure. The resulting residue was dissolved in DCM (100 mL), and triethylamine (7.93 mL, 56.56 mmol) and di-tert-butylcarbonate (3.09 g, 28.28 mmol) were added. After stirring for 18 h at RT, the reaction was quenched with saturated aqueous NH$_4$Cl and diluted with EtOAc. The organic layer was dried over Na$_2$SO$_4$, concentrated under reduced pressure, and the resulting residue was subjected to silica gel chromatography (gradient elution 80:20 to 75:25 hexanes:EtOAc) to give a mixture of acetylated and deacetylated material. To a solution of this mixture in MeOH (100 mL) at RT was added a solution of K$_2$CO$_3$ (5 g, 36 mmol) in water (20 mL), and the reaction stirred for 2b at RT. The reaction was quenched with 1 M HCl (aq) and diluted with EtOAc. The organic layer was dried over Na$_2$SO$_4$, and concentrated under reduced pressure to give product (3.3 g, 54%).

Step 2:

To a solution of the product from step 1 (600 mg, 1.39 mmol) in EtOAc/EtOH (10 mL/10 mL) was added 5% Pd/C (300 mg) and the resulting mixture agitated in a Parr Shaker for 4 h under a 45-psi atmosphere of H$_2$. The catalyst was filtered off over celite, the residue rinsed with EtOAc, and the organic layer was concentrated under reduced pressure. The resulting residue was subjected to silica gel chromatography (gradient elution 95:5 to 90:10 hexanes:EtOAc) to give product (377 mg, 68%).

Step 3:

To a solution of the product from step 2 (150 mg, 0.37 mmol) in pyridine (3 mL) was added 3,3,3-trifluoropropionic acid (0.032 mL, 0.37 mmol) and bis(2-oxo-3-oxazolidinyl)phosphinic chloride (188 mg, 0.74 mmol). After stirring for 18 h at RT, the volatiles were removed under vacuum, and the residue was subjected to silica gel chromatography (gradient elution 60:40 to 30:70 hexanes: EtOAc) to give a mixture of amides (102 mg, 54%). This mixture was dissolved in glacial AcOH (2 mL) and heated to 130° C. for 1 h. The volatiles were removed under reduced pressure, and the resulting residue purified by reverse phase chromatography (C18: gradient elution, 90:10:0.1 to 0:100:0.1 water:MeCN:TFA) to provide Ex. 190 as its TFA salt. LCMS for Ex. 190 (conditions D): $t_R$=1.29 min, m/e=394.2 (M±H).

TABLE XXV

The following examples were prepared using a procedure similar to that described in Scheme 49.
Examples
(LCMS data: observed MH⁺, HPLC retention time and LCMS method)

191

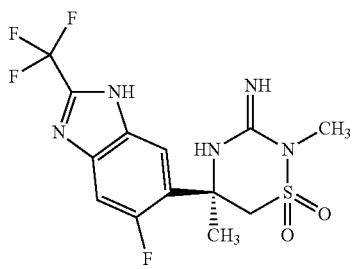

MH⁺: 380.2, 1.10 min, D

192

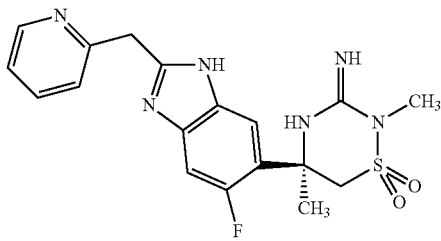

MH⁺: 403.2, 1.18 min, D

193

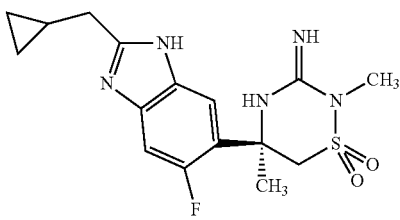

MH⁺: 366.2, 1.18 min, D

194

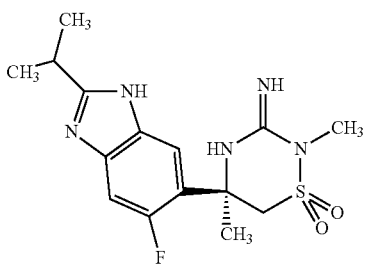

MH⁺: 354.0, 0.97 min, D

TABLE XXV-continued

The following examples were prepared using a procedure similar to that described in Scheme 49.
Examples
(LCMS data: observed MH⁺, HPLC retention time and LCMS method)

195

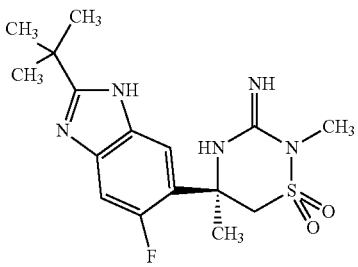

MH⁺: 368.0, 1.44 min, D

Scheme 50:

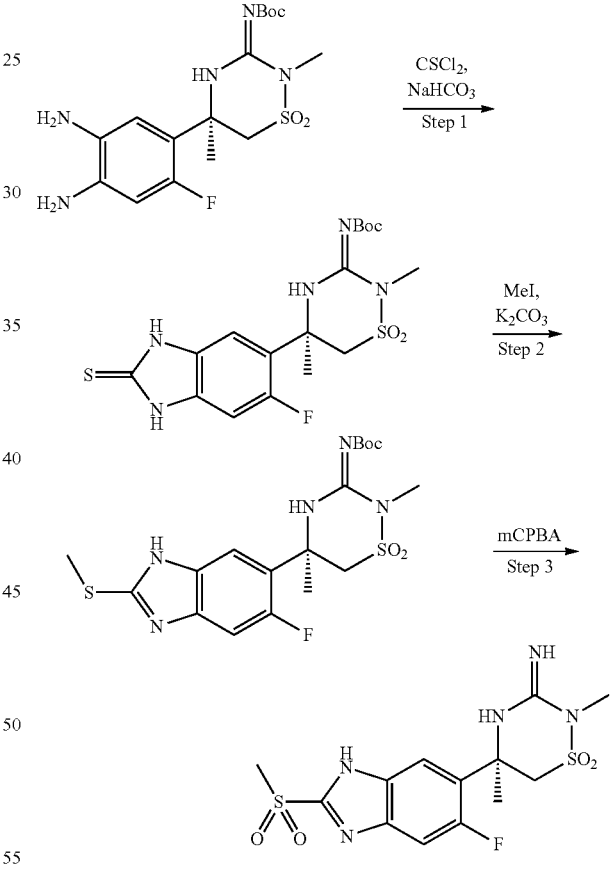

Ex. 196

Step 1:

Thiophosgene (0.320 mL, 4.21 mmol) was slowly added to a biphasic mixture of saturated aqueous NaHCO₃ and a solution of dianiline (1.566 g, 3.90 mmol, Scheme 49, Step 2) in DCM (15 mL). After 1 h at RT, the phases were separated and the aqueous layer extracted with DCM. The combined organic layers were washed with saturated aqueous NaHCO₃, brine, then dried over Na₂SO₄, filtered and concentrated under reduced pressure to give the thiourea (1.604 g, 93%).

Step 2:

Potassium carbonate (750 mg, 5.43 mmol) was added to a solution of the thiourea from Step 1 (1.604 g, 3.62 mmol) in DMF (18 mL) at RT. After 10 min, a solution of methyl iodide (0.23 mL, 3.68 mmol) in DMF (2 mL) was added over 10 min, and the reaction was stirred for 90 min. The reaction was quenched with saturated aqueous NaHCO$_3$ and diluted with EtOAc, and the organic layer was washed with brine, dried over MgSO$_4$ and concentrated under reduced pressure (1.725 g). The residue was subjected to silica gel chromatography (gradient elution 100:0 to 60:40 hexanes:EtOAc) to give the thiomethylurea (846 mg, 51%).

Step 3:

Meta-chloroperoxybenzoic acid (72%, 150 mg, 0.63 mmol) was added at RT to a solution of the thiomethylurea from step 2 (100 mg, 0.21 mmol) in DCM (5 mL). After 1 h, the mixture was diluted with EtOAc and washed with saturated aqueous NaHCO$_3$ (2×), brine, and dried over MgSO$_4$ and concentrated under reduced pressure to give a residue (150 mg) that was further subjected to reverse phase chromatography (C18: gradient elution, 90:10:0.1 to 0:100:0.1 water:MeCN:TFA) to provide Ex. 196 as its TFA salt. LCMS for Ex. 196 (conditions D): t$_R$=1.41 min, m/e=390.0 (M+H).

Scheme 51:

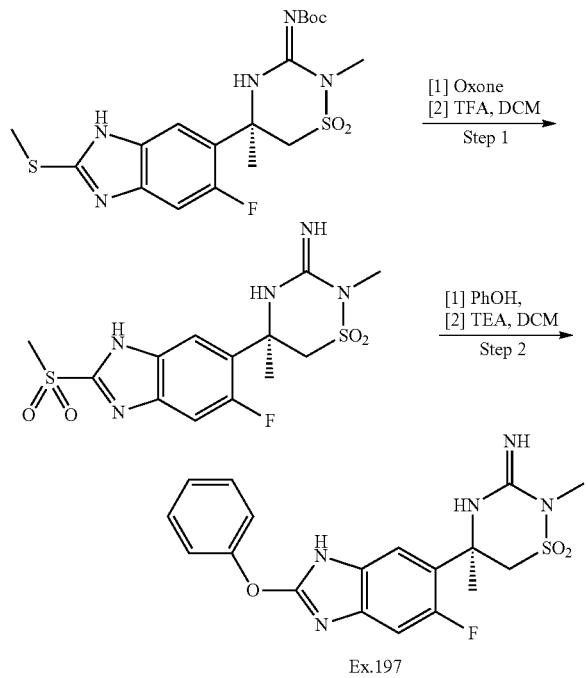

Step 1:

A solution of oxone (potassium peroxymonosulfate, 3.2 g, 5.20 mmol) in water (10 mL) was added at RT to a solution of the thiomethylurea from Scheme 50, step 2 (755 mg, 1.65 mmol) in MeOH (10 mL). After 1 h, the mixture was filtered over celite, the filter cake rinsed with EtOAc, and the filtrate diluted with EtOAc. The combined organic layers were washed with saturated aqueous NaHCO$_3$, dried over MgSO$_4$ and concentrated under reduced pressure to give the intermediate (681 mg) in 84% yield.

Step 2:

The product of Step 1 (93 mg, 0.19 mmol) was deprotected using a method similar to that described in Scheme 11b step 2. After deprotection, the resulting residue was concentrated under vacuum, and triethylamine (0.132 mL, 0.95 mmol) and phenol (90 mg, 0.95 mmol) were added. The mixture was heated at 120° C. for 22 h, then cooled to RT. The residue was subjected to reverse phase chromatography (C18: gradient elution, 90:10:0.1 to 0:100:0.1 water:MeCN:TFA) to provide Ex. 197 as its TFA salt. LCMS for Ex. 197 (conditions D): tr=1.78 min, m/e=404.2 (M+H).

TABLE XXVI

The following examples were prepared using a procedure similar to that described in Scheme 51, replacing phenol in Step 2 with thiophenol or aniline, respectively. Examples (LCMS data listed with each compound: observed MH$^+$, HPLC retention time and LCMS method)

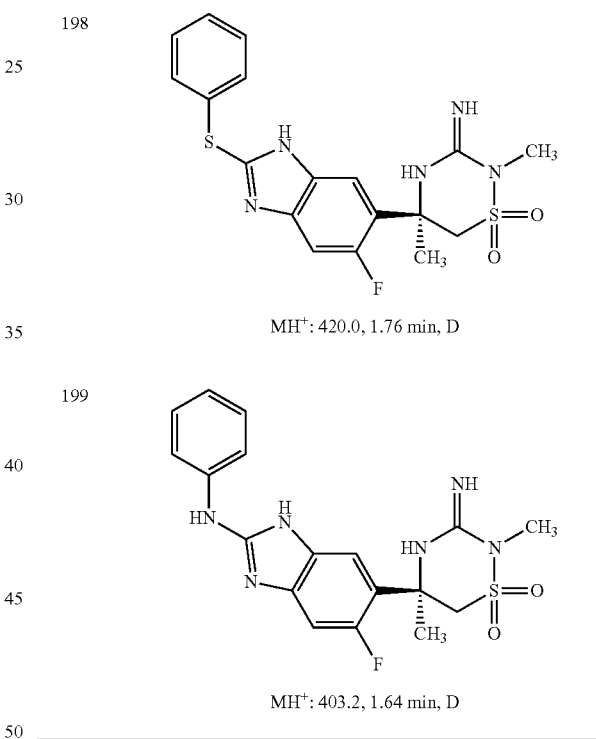

Scheme 52:

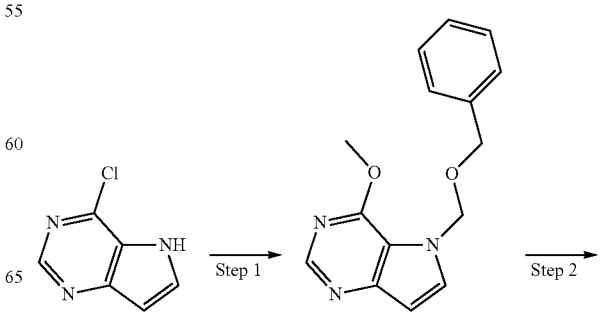

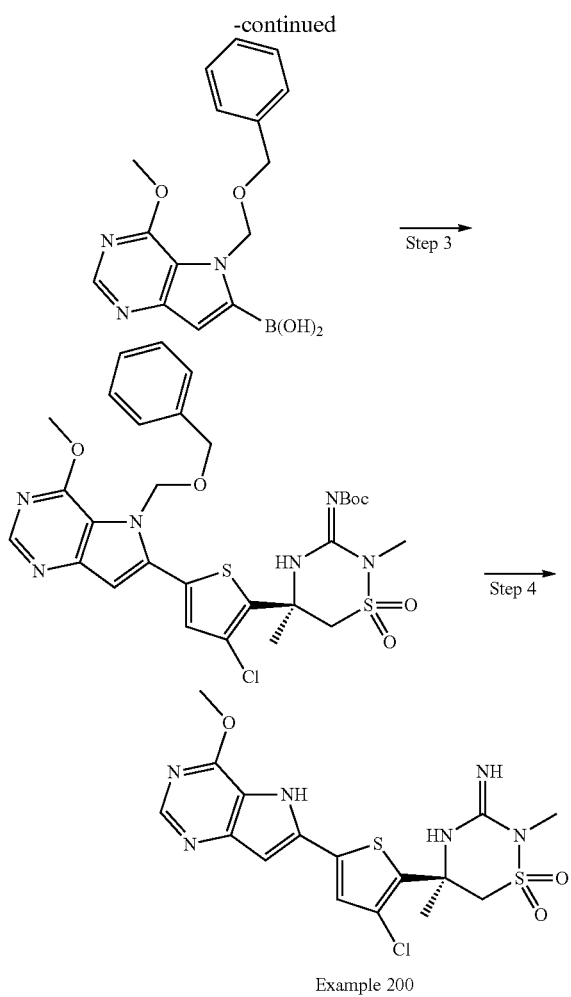

Example 200

Step 1:
To a suspension of 4-chloro-5H-pyrrolo[3,2-d]pyrimidine (1.53 g, 10.0 mmol) in 30 mL of THF was added NaH (560 mg, 14.0 mmol, 60% in mineral oil) by portion under $N_2$. After the mixture was cooled to 0° C., benzyl chloromethyl ether (1.71 mL, 13.0 mmol) was added. Then the mixture was stirred at RT for 1 h (monitored by TLC 40% EtOAc/Hex). 8 mL of anhydrous MeOH was added into the reaction mixture followed by NaH (400 mg, 10.0 mmol, 60% mineral oil) by portion. The resulting mixture was stirred at RT overnight. After being quenched with sat. $NH_4Cl$, the mixture was extracted with EtOAc (3×). The organic layer was washed with sat.NaHCOa (aq), brine, then dried ($MgSO_4$) and concentrated. Silica gel chromatography (elution with 0-30% EtOAc/Hex) afforded product 5-(benzyloxymethyl)-4-methoxy-5H-pyrrolo[3,2-d]pyrimidine (2.36 g).

Step 2 and 3:
5-(Benzyloxymethyl)-4-methoxy-5H-pyrrolo[3,2-d]pyrimidine was treated according to Scheme 31, Steps 2 and 3 to afford a biaryl product.

Step 4:
To a solution of the material from step 3 (26 mg, 0.039 mmol) in 8 mL of DCM was added a suspension of $AlCl_3$ (52 mg, 0.39 mmol) in 4 mL of DCM. After the mixture was stirred at RT for 1.5 h, 3 mL of water was added. The reaction mixture was basified with $NaHCO_3$ and extracted with DCM (3×). The organic layer was washed with brine and dried ($Na_2SO_4$), and concentrated. The crude residue was purified by preparative TLC (10% 2N $NH_3$MeOH in DCM) to provide Example 200 (10 mg). LCMS (conditions E): $t_R$=0.60 min, m/e=441.0 (M+H).

Scheme 53:

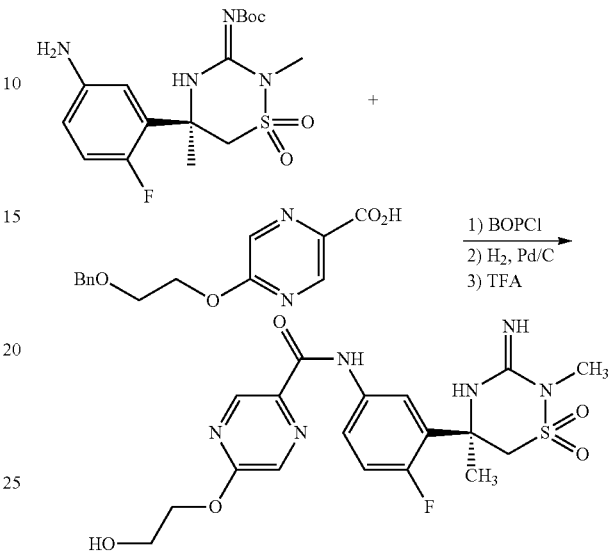

Ex. 201

Step 1:
The aniline from Scheme 10 and the acid (Entry 3, Table IVb) were coupled using a procedure similar to that described in Scheme 11b step 1.

Step 2:
To a pressure vessel containing a solution of the amide from step 1 (181 mg, 0.28 mmol) in EtOH (15 mL) was added 10% Pd/C (50% water-Degussa Type). The vessel was sealed, evacuated and backfilled with $N_2$ (3×). The vessel was then evacuated and backfilled with H2 (3×). The vessel was pressurized with $H_2$ to 50 psi and shaken at RT for 6 hours. The mixture was purged with $N_2$, filtered through Celite and concentrated. The crude product was purified via flash chromatography ($SiO_2$: gradient elution 100:0 to 1:1 hex.: EtOAc) to afford the hydroxy compound (24 mg, 15%).

Step 3:
Example 201 was prepared from the product of step 2 (24 mg) using a procedure similar to that described in Scheme 11b step 2. The crude product was purified via reverse phase flash chromatography ($C_{18}$; gradient elution 95:5:0.1 to 0:100:0.1 $H_2O$:MeCN:formic acid) to afford Example 201 (11 mg, 51%) as the formate salt.

LC/MS Conditions

Method A:
Column: Gemini C-18, 50×4.6 mm, 5 micron, obtained from Phenomenex.
Mobile phase:
A: 0.05% Trifluoroacetic acid in water
B: 0.05% Trifluoroacetic acid in acetonitrile
Gradient: 90:10 to 5:95 (A:B) over 5 min.
Flow rate: 1.0 mL/min
UV detection: 254 mu ESI-MS: Electro Spray Ionization Liquid chromatography-mass spectrometry (ESI-LC/MS) was performed on a PE SCIEX API-150EX, single quadrupole mass spectrometer.

Method B:
  Column: Waters SunFire C-18 4.6 mm×50 mm
  Mobile phase:
    A: 0.05% Trifluoroacetic acid in water
    B: 0.05% Trifluoroacetic acid in acetonitrile
  Gradient: 90:10 (A:B) for 1 min, 90:10 to 0:100 (A:B) over 4 min, 0:100 (A:B) for 2 min.
  Flow rate: 1.0 mL/min
  UV detection: 254 nm
  Mass spectrometer: Finnigan LCQ Duo electrospray.

Method C:
  Column: Agilent Zorbax SB-C18 (3.0×50 mm) 1.8 uM
  Mobile phase:
    A: 0.05% Trifluoroacetic acid in water
    B: 0.05% Trifluoroacetic acid in acetonitrile
  Gradient: 90:10 (A:B) for 0.3 min, 90:10 to 5:95 (A:B) over 5.1 min, 5:95 (A:B) for 1.2 min.
  Flow rate: 1.0 mL/min
  UV detection: 254 and 220 mu
  Mass spectrometer: Agilent 6140 quadrupole.

Method D:
  Column: Agilent Zorbax SB-C18 (3.0×50 μm) 1.8 uM
  Mobile phase:
    A: 0.05% Trifluoroacetic acid in water
    B: 0.05% Trifluoroacetic acid in acetonitrile
  Gradient: 90:10 (A:B) for 0.3 min, 90:10 to 5:95 (A:B) over 1.2 min, 5:95 (A:B) for 1.2 min.
  Flow rate: 1.0 mL/min
  UV detection: 254 and 220 nm
  Mass spectrometer: Agilent 6140 quadrupole.

Method E:
  Column: Agilent Zorbax SB-C18 (3.0×50 mm) 1.8 uM
  Mobile phase:
    A: 0.05% Trifluoroacetic acid in water
    B: 0.05% Trifluoroacetic acid in acetonitrile
  Gradient: 90:10 (A:B) for 0.1 min, 90:10 to 5:95 (A:B) over 1.0 min, 5:95 (A:B) for 0.36 min.
  Flow rate: 2.0 mL/min
  UV detection: 254 and 220 nm
  Mass spectrometer: Agilent 6140 quadrupole.

Method F:
  Column: Agilent Zorbax SB-C18 (3.0×50 mm) 1.8 uM
  Mobile phase:
    A: 0.05% Formic acid in water
    B: 0.05% Formic acid in acetonitrile
  Gradient: 90:10 to 5:95 (A:B) over 1.5 min, 5:95 (A:B) for 1.2 min.
  Flow rate: 1.0 mL/min
  UV detection: 254 and 220 nm
  Mass spectrometer: Agilent 6140 quadrupole.

Assays

The protocol that was used to determine the recited values is described as follows.

BACE1 HTRF FRET Assay

Reagents
  NatAcetate pH 5.0
  1% Brij-35
  Glycerol
  Dimethyl Sulfoxide (DMSO)
  Recombinant human soluble BACE1 catalytic domain (>95% pure)
  AFP Swedish mutant peptide substrate (QSY7-APP$^{swe}$-Eu): QSY7-EISEVNLDAEFC-Europium-amide A homogeneous time-resolved FRET assay was used to determine $IC_{50}$ values for inhibitors of the soluble human BACE1 catalytic domain. This assay monitored the increase of 620 nm fluorescence that resulted from BACE1 cleavage of an APPswedish APP$^{swe}$ mutant peptide FRET substrate (QSY7-EISEVNLDAEFC-Europium-amide). This substrate contained an N-terminal QSY7 moiety that served as a quencher of the C-terminal Europium fluorophore (620 nm Em). In the absence of enzyme activity, 620 nm fluorescence was low in the assay and increased linearly over 3 hours in the presence of uninhibited BACE1 enzyme. Inhibition of BACE1 cleavage of the QSY7-APP$^{swe}$-Eu substrate by inhibitors was manifested as a suppression of 620 nm fluorescence.

Varying concentrations of inhibitors at 3× the final desired concentration in a volume of 10 ul were preincubated with purified human BACE1 catalytic domain (3 nM in 10 μl) for 30 minutes at 30° C. in reaction buffer containing 20 mM Na-Acetate pH 5.0, 10% glycerol, 0.1% Brij-35 and 7.5% DSMO. Reactions were initiated by addition of 10 μl of 600 nM QSY7-APP$^{swe}$-Eu substrate (200 nM final) to give a final reaction volume of 30 μl in a 384 well Nunc HTRF plate. The reactions were incubated at 30° C. for 1.5 hours. The 620 nm fluorescence was then read on a Rubystar HTRF plate reader (BMG Labtechnologies) using a 50 μs delay followed by a 400 millisecond acquisition time window. Inhibitor 1050 values were derived from non-linear regression analysis of concentration response curves. $K_i$ values were then calculated from $IC_{50}$ values using the Cheng-Prusoff equation using a previously determined μM value of 8 μM for the QSY7-APP$^{swe}$-Eu substrate at BACE1.

All of the example compounds of the invention were tested (except for Examples 8, 9, 10, 14b, 14c, 14d, 14e, and 14f) in this BACE-1 assay and exhibited $K_i$ values of less than about 7.5 μM and greater than about 0.5 nM in this assay. All of the example compounds except for examples 19, 40×, 98, 101, and 189 exhibited $K_i$ values of less than about 5 μM in this assay. Some of the example compounds exhibited $K_i$ values of less than about 4 μM in this assay; others less than about 3 μM in this assay; others less than about 2 μM in this assay; others less than about 1 μM in this assay; others less than about 500 nM in this assay; others less than about 300 nM in this assay; others less than about 200 nM in this assay; others less than about 100 nM in this assay; others less than about 50 nM in this assay; others less than about 10 nM in this assay; others less than about 5 nM in this assay. The compound of Example 45 exhibited a Ki value of about 26 nM in this assay. The compound of Example 47 exhibited a Ki value of about 6.5 nM in this assay.

BACE-2 Assay

Inhibitor $IC_{50}$, at purified human autoBACE-2 were determined in a time-resolved endpoint proteolysis assay that measures hydrolysis of the QSY7-EISEV NLDAEFC-Eu-amide FRET peptide substrate (BACE-HTRF assay). BACE-mediated hydrolysis of this peptide results in an increase in relative fluorescence (RFU) at 620 nm after excitation with 320 nm light. Inhibitor compounds, prepared at 3× the desired final concentration in 1×BACE assay buffer (20 mM sodium acetate pH 5.0, 10% glycerol, 0.1% Brij-35) supplemented with 7.5% DMSO were preincubated with an equal volume of autoBACE-2 enzyme diluted in 1×BACE assay buffer (final enzyme concentration 1 nM) in black 384-well NUNC plates for 30 minutes at 30° C. The assay was initiated by addition of an equal volume of the QSY7-EISEVNLDAEFC-Eu-amide substrate (200 nM final concentration, $K_m$=8 μM for 4 μM for autoBACE-2)

prepared in 1×BACE assay buffer supplemented with 7.5% DMSO and incubated for 90 minutes at 30° C. DMSO was present at 5% final concentration in the assay. Following laser excitation of sample wells at 320 nm, the fluorescence signal at 620 nm was collected for 400 ms following a 50 us delay on a RUBYstar HTRF plate reader (BMG Labtechnologies). Raw RFU data was normalized to maximum (1.0 nM BACE/DMSO) and minimum (no enzyme/DMSO)RFU values. $IC_{50s}$ were determined by nonlinear regression analysis (sigmoidal dose response, variable slope) of percent inhibition data with minimum and maximum values set to 0 and 100 percent respectively. Similar $IC_{50s}$ were obtained when using raw RFU data. The $K_i$ values were calculated from the $IC_{50}$ using the Cheng-Prusoff equation.

All of the example compounds of the invention were tested in this BACE-2 assay except for the following examples: 2, 3, 4, 6, 7, 8, 9, 10, 11, 12, 13, 14, 14b, 14c, 14d, 14e, 14f, 15, 16, 17, 19, 40a, 40b, 40ea, 40h, 40o, 40p, 40q, 40u, 40w, 40x, 40y, 40aa, 40au, 40 cc, 40co, 40cp, 40cy, 40dj, 40gy, 40gz, 40ha, 40hb, 40hc, 40ih, 41, 43, 45, 49, 60, 61, 67, 68, 69, 70, 71, 73, 74, 75, 77, 85, 86, 88, 89, 90, 91, 96, 97, 98, 99, 100, 101, 102, 103, 105, 108, 109, 109, 115, 116, 117, 122, 123, 125, 130b, 137, 138, 143, 145, 161b, 176, 179, 182, 189, 192, 194, 195, 199. Of the example compounds of the invention that were tested in this BACE-2 assay, all exhibited $K_i$ values of less than about 900 nM and greater than about 0.04 nM in this assay. All of the example compounds that were tested in this assay, except for examples 40ex, 40do, 160, 161a, 164, and 197 exhibited $K_i$ values of less than about 500 nM in this assay. Some of the example compounds exhibited $K_i$ values of less than about 200 nM in this assay; others less than about 100 nM in this assay; others less than about 50 nM in this assay; others less than about 25 nM in this assay; others less than about 10 nM in this assay; others less than about 5 nM in this assay; others less than about 1 nM in this assay; others less than about 0.5 nM in this assay. The compound of Example 47 exhibited a Ki value of about 1 nM in this assay.

The novel iminothiadiazine dioxide compounds of the invention have surprisingly been found to exhibit properties which are expected to render them advantageous as BACE inhibitors and/or for the various methods of used herein.

Cortical $A\beta_{40}$

The iminothiadiazine dioxide compounds of the invention have been found, surprisingly and advantageously, to exhibit improved efficacy in lowering $A\beta_{40}$ production in the cerebral cortex than their iminopyrimidone analogs. The following procedures were used, Results are shown in the table below.

Rat Tissue Collection

Male CD rats (~100 g; Crl:CD(SD); Charles River Laboratories, Kingston, N.Y.) were group housed and acclimated to the vivarium for 5-7 days prior to use in a study. Compounds were formulated in 20% hydroxypropyl-β-cyclodextrin and administered orally with a dosing volume of 5 ml/kg for rats. Three h after drug administration, rats were euthanized with excess $CO_2$. The brain was removed from the skull and immediately frozen on dry ice. All tissues were stored at −70° C. until Aβ quantification.

Determination of $A\beta_{40}$ Levels in Rat Cortex by ELISA

The measurement of endogenous rat Aβ1-40 (Aβ40) in cortex relied on the 585 antibody (Ab585, BioSource), catalogue no. $NONO_{585}$), which specifically recognizes the N-terminal sequence of rodent Aβ40, and the monoclonal antibody, G2-10, which specifically recognizes the free C-terminus of Aβ40. Ab585 was labeled with biotin (b-Ab585) by first dialyzing the antibody sample extensively versus PBS (pH 7.8) to remove impurities, followed by dilution to between 1 and 2 mg/mL protein concentration. EZ-Link Sulfo-NHS-LC-Biotin (Pierce) was dissolved in PBS (pH 7.8) at a concentration of 1 mg/mL immediately prior to use. Ab585 was labeled with EZ-Link Sulfo-NHS-LC-biotin using a 10:1 biotin:antibody ratio by incubation at room temperature for 1 hour. The labeling reaction was quenched by addition of 1.0 M glycine to a final concentration of 0.1 M followed by 10 minute incubation at room temperature. Glycine was removed by extensive dialysis versus PBS.

The use of the Luminex based immunoassay for measurement of rat cortical Aβ40 required that the G2-10 antibody be labeled with Bio-Plex COOH Bead 25 (Bio-Rad laboratories catalogue no. 171506025). The antibody was coupled to the beads using the Bio-Plex Amine Coupling Kit (Bio-Rad) as per the manufacturer's recommendations.

Rat cortex Aβ40 levels were measured from guanidine HCl extracts of individual rat cortices using a Luminex-based immunodetection assay. Rat brains were thawed briefly at 37° C. and both mid- and hindbrain regions were removed. The remaining material, consisting primarily of cortex (~800 mg) was carried through the guanidine extraction procedure. Cortices were added to a 2 ml BioPur tube (Eppendorf) along with a 6.35 mm chrome-coated steel ball and 1.0 ml of sucrose homogenization buffer (20 nM HEPES [pH 7.5], 50 nM KCl, 50 mM sucrose, 2 mM EDTA, 2 mM EGTA supplemented with complete protease inhibitors [Roche, EDTA-free]). Samples were then homogenized by agitation for 1.5 min at 30 cylces/sec in a MM300 tissue mixer (Retsch®). The resulting cortical homogenate was extracted with guanidine-HCl by mixing 67 μl of homogenate with 133 μl of 5 M Guanidine HCl, 50 mM Tris HCl (pH 8.0). To maximize the efficiency of Aβ extraction, samples were vortexed and then sonicated for 2 minutes in an ice bath using an Ultrasonics XL cup horn sonicator at a power setting of 8 (Heat Systems, Inc.). Insoluble material was removed by ultracentrifugation using a using a TLA-55 rotor in a TL-100 benchtop centrifuge (Beckman) at 100,000×g for 30 minutes. The resulting supernatant was then either diluted 1:10 in 5 M guanidine HCl, 0.05 M Tris HCl (pH 8.0) for protein analysis (BCA protein assay, Pierce Biochemicals) or assayed neat for Aβ40 levels. The Luminex rodent Aβ40 assay was performed as follows. First, 96 well filter binding plates (Millipore, catalogue # MSBVN12) were wetted with 100 μl of 1×LAβ40 buffer (0.05 M HEPES [pH 7.5], 0.2% BSA, 0.2% Tween-20, 0.15 M NaCl) by vacuum filtration on a Millipore 96-well manifold. The plate bottom was sealed and 100 μl of 1×LAβ40 buffer was added to each well followed by addition of 50 μl each of G2-10:COOH beads (1000 beads/well) and 50 μl b-Ab585 at 0.5 μg/ml in 1×LAβ40 buffer. Guanidine HCl was added to synthetic rodent Aβ40 standards in order to control for the effect of guanidine in brain extracts on the assay performance. Ten microliters of coritical extract, rodent Aβ40 standards or cortical extract from amyloid precursor protein knockout mice (to define background immunoreactivity) was added to each well. Plates were covered and incubated overnight at 4° C. Following the incubation, wells were cleared by vacuum and washed twice with 100 μl of 1×Lβ40 buffer on a Millipore manifold. Phycoetythrin-conjugated streptavidin (PE-strepavidin, Bio-Rad) for detection of bound b-Ab585 was diluted 100-fold in 1×LAβ40 buffer and 50 μl was added to each well and incubated for 1 hour at room temperature with shaking. Unbound PE-streptavidin was removed by three 100 μl washes with cytokine assay buffer (BioRad). Washed beads were resuspended in 125 µl of cytokine assay buffer by shaking on a microplate shaker. Plates were read on a BioPlex suspension array system (BioRad) with target region beads set to 40 beads/region and the upper end of the DD gate set to 10,000. Raw fluorescence data was analyzed using nonlinear regression analysis and absolute Aβ40 levels were extrapolated from the standard curve using GraphPad Prism 4.0.2. Absolute amounts of $A\beta_{1\text{-}40}$ are expressed as picograms per micrograms protein. Percent change values for each compound were calculated by normalization of the average absolute cortical Aβ1-40 level in each compound treated cohort to the average absolute cortical Aβ1-40 levels in the vehicle cohort. Comparative results are shown in the table below. "NT" means not tested.

Change in Cortical $A\beta_{40}$ in Rats 3 h After a 10 mg/kg Oral Dose of Compound

| | Iminothiadiazine Dioxide | | | | Iminopyrimidinone | |
|---|---|---|---|---|---|---|
| Ex. # | Structure | BACE-1 Ki (nm) BACE-2 Ki (nm) | Change in rat cortex $A\beta_{40}$ | Structure | | Change in rat cortex $A\beta_{40}$ |
| 34 | | 0.949 0.22 | −51% | | | −19% |
| 26 | | 1.261 2.46 | −33% | | | 0% |
| 25 | | 1.753 0.37 | −49% | | | −11% |
| 36 | | 10 4.85 | −25% | | | NT |
| 40di | | 1.05 2.15 | −38% | | | +5% |

-continued

Change in Cortical Aβ$_{40}$ in Rats 3 h After a 10 mg/kg Oral Dose of Compound

| | Iminothiadiazine Dioxide | | | Iminopyrimidinone | |
|---|---|---|---|---|---|
| Ex. # | Structure | BACE-1 Ki (nm) / BACE-2 Ki (nm) | Change in rat cortex Aβ$_{40}$ | Structure | Change in rat cortex Aβ$_{40}$ |
| 35 | | 3.0 / 0.45 | NT | | NT |
| 173 | | 4.88 / 0.47 | −27% | | −3% |
| 45 | | 25.6 / NT | NT | | −5% |
| 46 | | 46 / 8.23 | NT | | NT |
| 52 | | 2.387 / 0.37 | −53% | | −54% |

-continued

Change in Cortical Aβ₄₀ in Rats 3 h After a 10 mg/kg Oral Dose of Compound

| | Iminothiadiazine Dioxide | | | Iminopyrimidinone | |
|---|---|---|---|---|---|
| Ex. # | Structure | BACE-1 Ki (nm) BACE-2 Ki (nm) | Change in rat cortex Aβ₄₀ | Structure | Change in rat cortex Aβ₄₀ |
| 40ai |  | 1.64 1.99 | −51% | 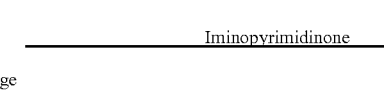 | |

Caco-2 Bi-Directional Permeability

It has been found that compounds of the invention exhibit unexpectedly reduced susceptibility to efflux by P-glycoprotein. (P-gp) versus compounds having an iminopyrimidinone moiety that are otherwise structurally identical. P-gp is found, among other locations, at the blood-brain barrier, and reduced susceptibility to efflux by this protein is a desirable characteristic of centrally acting compounds (A. Schinkel *Advanced Drug Delivery Reviews* 1999, 36, 179-194). The following procedures were used. Results are shown in the table below.

Caco-2 Bi-directional Permeability

The bi-directional permeability with efflux potential of selected compounds of the invention vs. otherwise structurally identical iminopyrimidinones (collectively referred to as test compounds, shown in the table below) were assessed using Caco-2 cell line. The Caco-2 cells were maintained in DMEM (Dulbecco's Modified Eagle Medium) containing 10% fetal bovine serum, 1% non-essential amino acids, 2 mM L-glutamine, and 1% penicillin-streptomycin in an incubator at ~37° C. in an atmosphere of 5% $CO_2$ and about 90% relative humidity. The cell culture medium was changed three times weekly. Caco-2 cell monolayers were grown on polyethylene terephthalate filters using 24-well BD Falcon™ Cell Culture Insert Plates (0.33 cm² insert area, 1 μm pore size; BD BioSciences, Bedford, Mass.). The culture medium of the plate was changed every other day until used for the transport experiment (21-28 days post seeding).

The transport buffer (TM) was Hank's balanced salt solution (HBSS) with 10 mM HEPES and 25 mM glucose (pH 7.4) for dosing and TM with 4% bovine serum albumin for receiver (pH 7.4). The bi-directional permeability of the test compounds were tested at concentrations of 1, 10 and 100 μM was measured in triplicate with 2-hr incubation. The cell monolayer integrity was monitored with pre- and post-experimental trans-epithelial electrical resistance and post-experimental Lucifer Yellow (LY) permeability with 1 hr incubation. Test article samples were analyzed using LC-MS/MS and the concentration of LY was measured using a Perkin Elmer HTS 7000 Plus Bio Assay Reader (Waltham, Mass.) with an excitation and emission wavelength of 485 nm and 538 nm, respectively.

The apparent permeability, recovery and efflux ratio values were calculated using the following equations:

$$P_{app}(\text{nm/s}) = \frac{dM/dt}{S*C_0} = \frac{dC_R/dt*V_R}{S*C_0}*10^7$$

$$\text{Efflux Ratio} = \frac{P_{app\_BLtoAP}}{P_{app\_APtoBL}}$$

$$\text{Total Recovery (\%)} = \frac{C_{D,final}}{C_0} \times 100 + \frac{\text{Receiver Accumulated Amount}}{C_0*V_D} \times 100$$

where,
$dC_R/dt$: The slope of the accumulative concentration in the receiver compartment versus time incubation (μM-s⁻¹)
$C_{Ohr}$: Donor concentration (μM) immediately after dosing
$C_{D,final}$ Donor concentration (μM) at the end of incubation
S: Membrane surface area (cm²)
$V_D$: Volume of donor compartment (mL)
$V_R$: Volume of receiver compartment (mL)
$P_{app\_BLtoAP}$: Permeability from basolateral (BL) to apical (AP) transport
$P_{app\_APtoBL}$: Permeability from AP to BL transport Evaluation of P-gp Efflux Inhibition Using Caco-2 Bi-Directional Permeability Assay A preliminary study to assess the compounds in the table below as potential P-gp substrates were performed using the Caco-2 bi-directional transport assay. Digoxin was used as a probe P-gp substrate. The $^1$H-digoxin dosing solution was prepared by diluting a digoxin DMSO stock with TM and/or the inhibitor solutions and titrating with $^3$H-digoxin (final digoxin concentration was 5 μM with 0.5 μCi/mL radioactivity). Two concentrations of test compounds (5 and 50 μM) were prepared by diluting a DMSO stock solution with TM (pH 7.4). The Caco-2 bi-directional permeability of $^3$H-digoxin with or without test compound as inhibitor was measured as described in the Caco-2 bi-directional permeability section. The total radioactivity for each sample was counted using a Packard 2250CA Tri-Carb Liquid Scintillation Analyzer.

The percentage of digoxin efflux inhibition was calculated using the following equation:

$$\%\_Inhibition = \left(1 - \frac{P_{app\_BLtoAP}^{inhibitor} - P_{app\_APtoBL}^{inhibitor}}{P_{app\_BLtoAP} - P_{app\_APtoBL}}\right) * 100$$

where, $P_{app\_BLtoAP}$: Digoxin permeability from BL to AP transport $P_{app\_APtoBL}$: Digoxin permeability from AP to BL transport $P_{app\_BLtoAP}^{inhibitor}$: Digoxin permeability with inhibitor from BL to AP transport:

Digoxin permeability with inhibitor from AP to BL transport

| | Iminothiadiazine Dioxide | | | Iminopyrimidinone | | |
|---|---|---|---|---|---|---|
| Ex. # | Structure | Caco-2 AP→BL (nm/s) | Caco-2 Efflux ratio | Cmpd. # | Caco-2 AP→BL (nm/s) | Caco-2 Efflux ratio |
| 34 | | 118 | 3.1 | | 0 | NA |
| 26 | | 89 | 2.9 | | 17 | 11.3 |
| 25 | | 128 | 2.4 | | 22 | 10.6 |
| 36 | | 54 | 3.3 | | 11 | 12.9 |
| 40di | | 136 | 2.0 | | 65 | 3.2 |

-continued

Permeability (AP→BL) and efflux ratio in Caco-2 cells
(AP = apical, BL = basolateral)

| | | Iminothiadiazine Dioxide | | | Iminopyrimidinone | | |
|---|---|---|---|---|---|---|---|
| Ex. # | Structure | Caco-2 AP→BL (nm/s) | Caco-2 Efflux ratio | Cmpd. # | | Caco-2 AP→BL (nm/s) | Caco-2 Efflux ratio |
| 35 | | 151 | 2.1 | | | 0 | NA |
| 173 | | 126 | 2.2 | | | 25 | 6.1 |
| 45 | | 226 | 1.4 | | | 174 | 2.6 |
| 46 | | 189 | 1.9 | | | 136 | 2.6 |
| 52 | | 278 | 1.6 | | | 153 | 2.4 |

-continued

Permeability (AP→BL) and efflux ratio in Caco-2 cells
(AP = apical, BL = basolateral)

| | Iminothiadiazine Dioxide | | | Iminopyrimidinone | | |
|---|---|---|---|---|---|---|
| Ex. # | Structure | Caco-2 AP→BL (nm/s) | Caco-2 Efflux ratio | Cmpd. # | Caco-2 AP→BL (nm/s) | Caco-2 Efflux ratio |
| 40ai | | 133 | 1.8 | NA | | |

Solution Stability

The iminothiadiazine dioxide compounds of the invention have been found, surprisingly and advantageously, to exhibit improved solution stability (e.g., by resistance to hydrolysis) compared with structurally similar iminopyrimidinones. The following comparative procedures were used. Results are reported as Examples A and B below.

A 1.05 mg/mL stock solution (5 mL) of Ex. 45 in MeOH was prepared. From the stock solution was taken out 1.25 mL and diluted to 25 mL with the addition of 23.75 mL of 10 mM phosphate buffer (pH 7.4)/MeOH (70/30 v/v). This new solution was split into three. One solution was incubated at 4° C., another incubated at 25° C. and the third incubated at 40° C. Each solution was analyzed by LC/MS after day 1, day 2 and day 6 and compared to a standard calibration curve for Ex. 45.

Example A

Stability Studies Comparing Example 45 With Compound Z

In the following study, the solution stability of the compound of Example 45 was measured and compared to that of Compound Z. The compound of Example 45 is an iminothiadiazine dioxide compound of the invention. Compound Z is the corresponding iminopyrimidinone compound. The structures of the compound of Example 45 and of Compound Z are shown below. Studies were performed in aqueous pH 7.4 buffer containing methanol at 4° C., 25° C. and 40° C. At 4° C., the compound of Example 45 showed 0.93% degradation after 6 days while Compound Z showed 18.3% degradation after 1 day. At 25° C., the compound of Example 45 showed 7.4% degradation after 6 days while Compound Z showed 53.87% degradation. At 40° C., the compound of Example 45 showed 30.71% degradation after 6 days while Compound Z showed 79.93% degradation after 1 day.

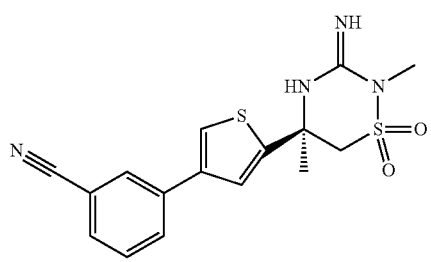

Example 45

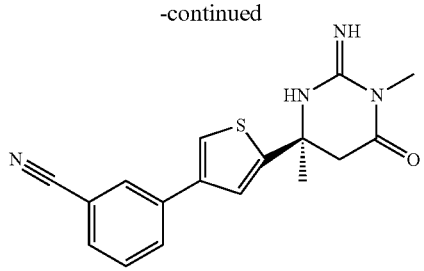

Compound Z
(US20060111370)

| Solution Stability for Ex. 45 in pH 7.4 | | | | |
|---|---|---|---|---|
| Condition 4° C. Batch Number 7 | | | | |
| Time, days | Initial | 1 | 2 | 6 |
| Assay (Area %) | 99.82 | 99.69 | 99.04 | 98.89 |
| Condition | | 25° C. | | |
| Assay (Area %) | 99.82 | 98.45 | 96.07 | 92.43 |
| Condition | | 40° C. | | |
| Assay (Area %) | 99.82 | 96.32 | 89.70 | 69.11 — | a: Results by area normalization
ND = Not Detected.
(—) stands for >20% degradation

| Solution Stability for Compound Z in pH 7.4 | | | | |
|---|---|---|---|---|
| Condition 4° C. Batch Number 7 | | | | |
| Time, days | Initial | 1 | 2 | 6 |
| Assay (Area %) | 88.15 | 69.84 | — | — — |
| Condition | | 25° C. | | |
| Assay (Area %) | 88.15 | 34.28 | — | — — |
| Condition | | 40° C. | | |
| Assay (Area %) | 88.15 | 8.22 | — | — — | a: Approximate RRT for related compounds. Results by area normalization
ND = Not Detected.
(—) stands for >20% degradation Stock solutions of the tested compounds were prepared by dissolving about 3 mg of each compound in 3 mL of acetonitrile. Standards for test compounds were prepared by diluting 1 mL of the stock solution with an additional 4 mL of acetonitrile. These standards were stored at 4° C. Samples were prepared by diluting 1 mL of the stock solution with 4 mL of 50 mM pH 7.4 phosphate buffer. These samples were stored at 25° C. in the absence of light. Standards and samples were analyzed by LC/MS initially and at day 1, day 4, and day 6.

|  | HPLC conditions |
| --- | --- |
| Mobile phase A: | 10 mM pH 5 ammonium acetate buffer: methanol (90:10) |
| Mobile phase B: | 10 mM pH 5 ammonium acetate buffer: methanol (10:90) |
| Column: | Zorbax SB-Phenyl 4.6 × 50 mm, 1.8 μm |
| Column temperature: | 40° C. |
| Flow: | 0.8 mL/min. |

|  | Time (min.) | % B |
| --- | --- | --- |
| Gradient: | 0 | 40 |
|  | 9 | 100 |
|  | 11 | 100 |
| Detectors: | UV at 220 nm and 236 nm | |

MS, ES ionization, positive mode, for identification only at final time point.

The terms reported in the tables below have the following meanings:

Area % is the integration of peak from HPLC as reported by Waters Empower II software.

RRT is the relative retention time of new product compared to the standard of the test compound.

Formula for RRT is:

$$\frac{\text{Retention time of new product}}{\text{Retention time of standard}}$$

M+1 is the mass observed including protonation (±1 mass unit).

ND stands for no peak detected by the UV detector.

* stands for no ion detected by the mass spectrometer.

Example B

Stability Studies Comparing Example 47 with Compound Y

In the following study, the solution stability of the compound of Example 47 was measured and compared to that of Compound Y. The compound of Example 47 is an iminothiadiazine dioxide compound of the invention. Compound Y is the corresponding iminopyrimidinone compound. The structures of the compound of Example 47 and of Compound Y are shown below. Studies were performed in pH 7.4 buffer at 25° C. Under these conditions, the compound of Example 47 showed 0% hydrolysis product after 6 days while Compound Z showed 12.45% hydrolysis product.

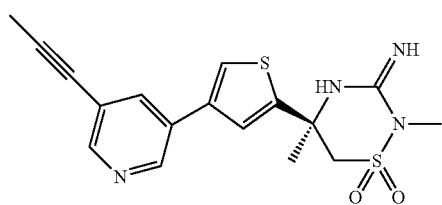

Example 47

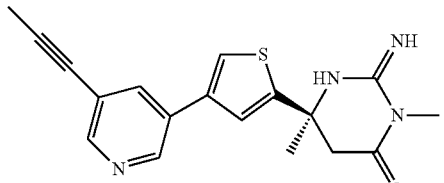

Compound Y
(US 20070287692)

Example 20

Free Base MW=374.09

|  | Peak Description | RRT | M + 1 | Area %, Initial | Area %, Day 1 | Area %, Day 4 | Area %, Day 6 |
| --- | --- | --- | --- | --- | --- | --- | --- |
| Standard | Example 47 | 1.00 | 375.10 | 98.53 | 98.55 | 98.52 | 98.52 |
|  | Unknown | 1.49 | * | 1.47 | 1.45 | 1.48 | 1.48 |
| Sample at pH 7.4 | Example 47 | 1.00 | 375.10 | 98.55 | 98.56 | 98.53 | 98.53 |
|  | Unknown | 1.49 | * | 1.45 | 1.44 | 1.47 | 1.47 |

Compound Y: Free Base MW=338.12

|  | Peak Description | RRT | M + 1 | Area %, Initial | Area %, Day 1 | Area %, Day 4 | Area %, Day 6 |
| --- | --- | --- | --- | --- | --- | --- | --- |
| Standard | Compound Y | 1.00 | 339.15 | 100.0 | 100.0 | 100.0 | 100.0 |
| Sample at pH 7.4 | Compound Y | 1.00 | 339.10 | 99.36 | 96.89 | 93.02 | 87.55 |
|  | Hydrolysis product | 0.76 | 357.10 | 0.64 | 3.11 | 6.98 | 12.45 |

While the present invention has been described in view of the specific embodiments set forth above, many alternatives, modifications and other variations thereof will be apparent to those of ordinary skill in the art. All such alternatives, modifications and variations are intended to fall within the spirit and scope of the present invention.

We claim:

1. A method of treating Alzheimer's disease in a human in need thereof comprising administering to the human a therapeutically effective amount of a compound, or a tautomer thereof, or a pharmaceutically acceptable salt of said compound or said tautomer, said compound selected from the group consisting of:

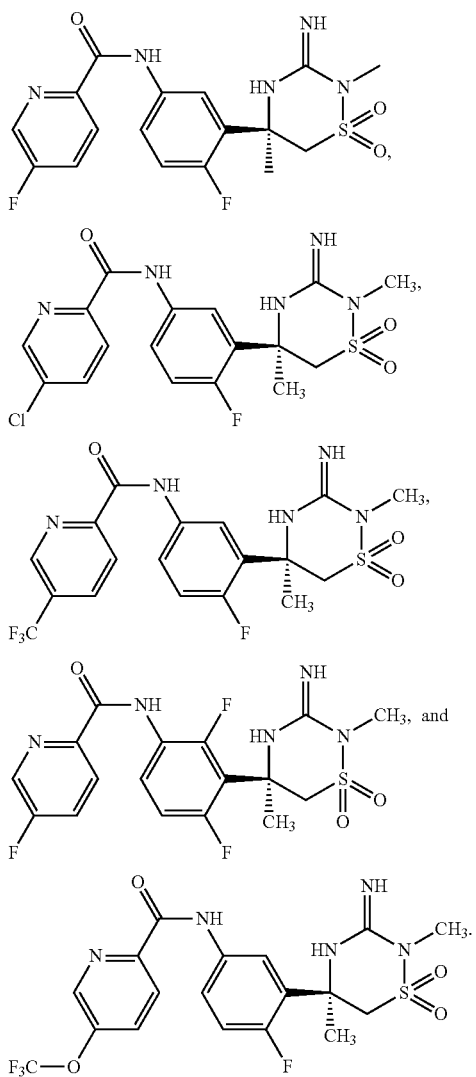

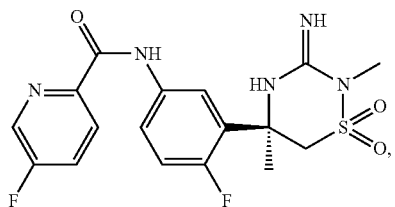 [SMILES: CN1C(=N)N[C@](C)(c2cc(NC(=O)c3ccc(F)cn3)ccc2F)CS1(=O)=O]

2. A method of treating Alzheimer's disease in a human in need thereof comprising administering to the human a therapeutically effective amount of a compound having a structure:

or a tautomer thereof, or a pharmaceutically acceptable salt of said compound or said tautomer.

3. A method of treating Alzheimer's disease in a human in need thereof comprising administering to the human a therapeutically effective amount of a compound having a structure:

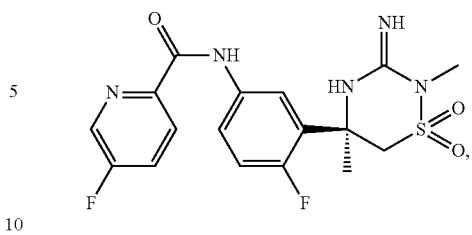

or a tautomer thereof.

4. The method of claim 2, wherein said compound is a pharmaceutically acceptable salt of a compound having a structure:

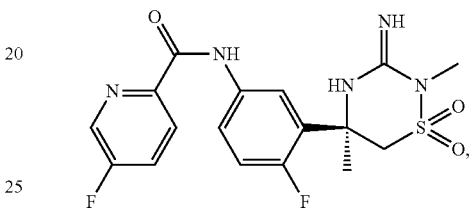

or a pharmaceutically acceptable salt of a tautomer thereof, wherein said pharmaceutically acceptable salt is selected from the group consisting of acetate, ascorbate, benzoate, benzenesulfonate, bisulfate, borate, butyrate, citrate, camphorate, camphorsulfonate, fumarate, hydrochloride, hydrobromide, hydroiodide, lactate, maleate, methanesulfonate, naphthalenesulfonate, nitrate, oxalate, phosphate, propionate, salicylate, succinate, sulfate, tartarate, thiocyanate, and toluenesulfonate.

5. The method of claim 2, wherein said pharmaceutically acceptable salt is a hydrochloride salt.

6. The method of claim 2, wherein said pharmaceutically acceptable salt is a toluenesulfonate salt.

7. A method of treating mild cognitive impairment in a human in need thereof comprising administering to the human a therapeutically effective amount of a compound, or a tautomer thereof, or a pharmaceutically acceptable salt of said compound or said tautomer, said compound selected from the group consisting of:

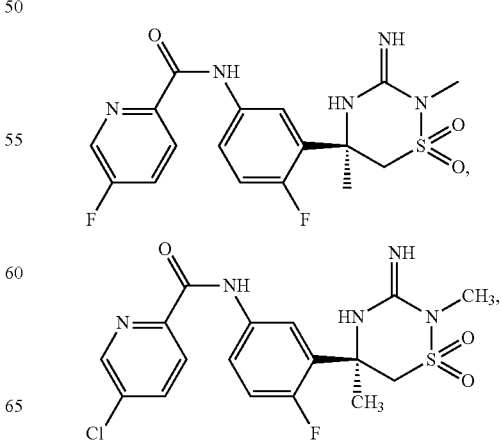

-continued

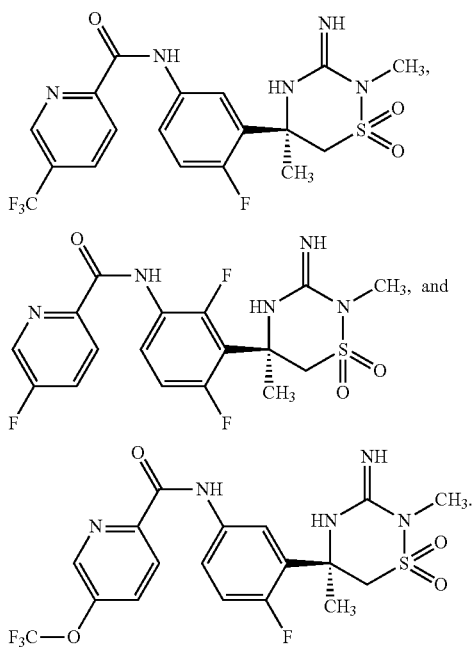

8. A method of treating mild cognitive impairment in a human in need thereof comprising administering to the human a therapeutically effective amount of a compound having a structure:

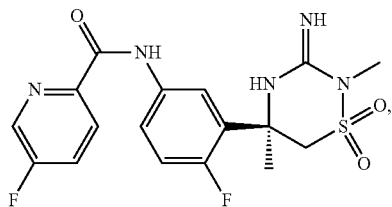 [SMILES: CN1C(=N)N[C@](C)(c2cc(NC(=O)c3ccc(F)cn3)ccc2F)CS1(=O)=O]

or a tautomer thereof, or a pharmaceutically acceptable salt of said compound or said tautomer.

9. A method of treating mild cognitive impairment in a human in need thereof comprising administering to the human a therapeutically effective amount of a compound having a structure:

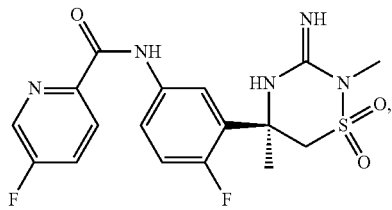 [SMILES: CN1C(=N)N[C@](C)(c2cc(NC(=O)c3ccc(F)cn3)ccc2F)CS1(=O)=O]

or a tautomer thereof.

10. The method of claim 8, wherein said compound is a pharmaceutically acceptable salt of a compound having a structure:

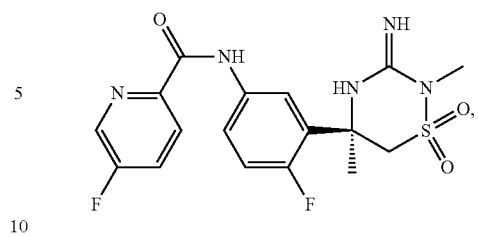

or a pharmaceutically acceptable salt of a tautomer thereof, wherein said pharmaceutically acceptable salt is selected from the group consisting of acetate, ascorbate, benzoate, benzenesulfonate, bisulfate, borate, butyrate, citrate, camphorate, camphorsulfonate, fumarate, hydrochloride, hydrobromide, hydroiodide, lactate, maleate, methanesulfonate, naphthalenesulfonate, nitrate, oxalate, phosphate, propionate, salicylate, succinate, sulfate, tartarate, thiocyanate, and toluenesulfonate.

11. The method of claim 8, wherein said pharmaceutically acceptable salt is a hydrochloride salt.

12. The method of claim 8, wherein said pharmaceutically acceptable salt is a toluenesulfonate salt.

13. A method of lowering the production of $A\beta_{40}$ in the cerebral cortex of a human in need thereof comprising administering to the human a therapeutically effective amount of a compound, or a tautomer thereof, or a pharmaceutically acceptable salt of said compound or said tautomer, said compound selected from the group consisting of:

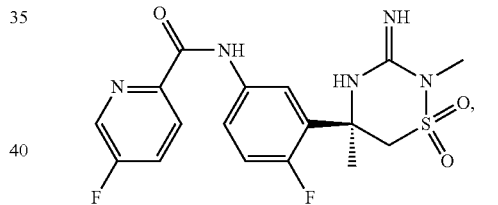

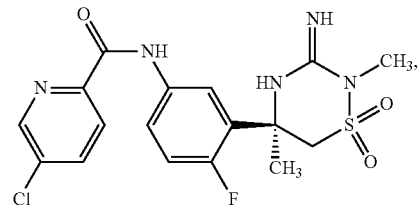

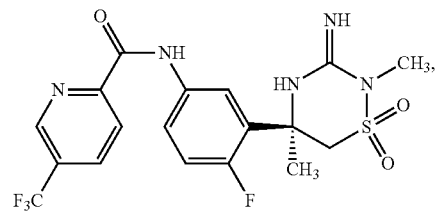

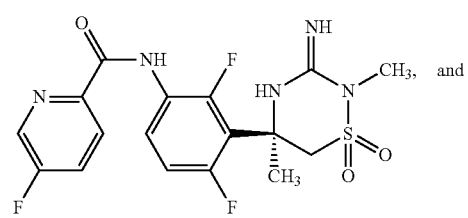

14. A method of lowering the production of Aβ₄₀ in the cerebral cortex of a human in need thereof comprising administering to the human a therapeutically effective amount of a compound, having a structure:

or a tautomer thereof, or a pharmaceutically acceptable salt of said compound or said tautomer.

15. A method of lowering the production of Aβ₄₀ in the cerebral cortex of a human in need thereof comprising administering to the human a therapeutically effective amount of a compound having a structure:

or a tautomer thereof.

16. The method of claim 14, wherein said compound is a pharmaceutically acceptable salt of a compound having a structure:

or a pharmaceutically acceptable salt of a tautomer thereof, wherein said pharmaceutically acceptable salt is selected from the group consisting of acetate, ascorbate, benzoate, benzenesulfonate, bisulfate, borate, butyrate, citrate, camphorate, camphorsulfonate, fumarate, hydrochloride, hydrobromide, hydroiodide, lactate, maleate, methanesulfonate, naphthalenesulfonate, nitrate, oxalate, phosphate, propionate, salicylate, succinate, sulfate, tartarate, thiocyanate, and toluenesulfonate.

17. The method of claim 14, wherein said pharmaceutically acceptable salt is a hydrochloride salt.

18. The method of claim 14, wherein said pharmaceutically acceptable salt is a toluenesulfonate salt.

19. A method of inhibiting the formation of AP peptides in a human in need thereof, which method comprises administering to the human a therapeutically effective amount of a compound, or a tautomer thereof, or a pharmaceutically acceptable salt of said compound or said tautomer, wherein said compound is selected from the group consisting of:

20. A method of inhibiting the formation of AP peptides in a human in need thereof comprising administering to the human a therapeutically effective amount of a compound having a structure:

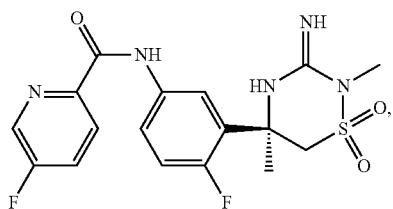 [SMILES: CN1C(=N)N[C@](C)(c2cc(NC(=O)c3ccc(F)cn3)ccc2F)CS1(=O)=O]

or a tautomer thereof, or a pharmaceutically acceptable salt of said compound or said tautomer.

21. A method of inhibiting the formation of Aβ peptides in a human in need thereof, which method comprises administering to the human a therapeutically effective amount of a compound having a structure:

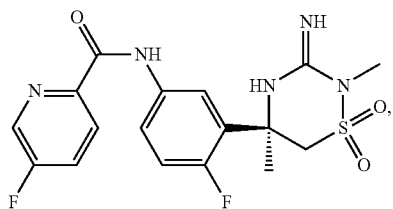 [SMILES: CN1C(=N)N[C@](C)(c2cc(NC(=O)c3ccc(F)cn3)ccc2F)CS1(=O)=O]

or a tautomer thereof.

22. The method of claim 20, wherein said compound is a pharmaceutically acceptable salt of a compound having a structure:

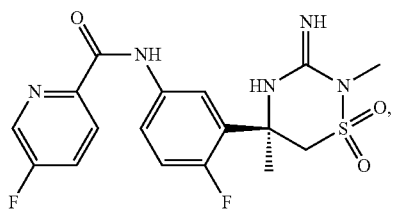 [SMILES: CN1C(=N)N[C@](C)(c2cc(NC(=O)c3ccc(F)cn3)ccc2F)CS1(=O)=O]

or a pharmaceutically acceptable salt of a tautomer thereof, wherein said pharmaceutically acceptable salt is selected from the group consisting of acetate, ascorbate, benzoate, benzenesulfonate, bisulfate, borate, butyrate, citrate, camphorate, camphorsulfonate, fumarate, hydrochloride, hydrobromide, hydroiodide, lactate, maleate, methanesulfonate, naphthalenesulfonate, nitrate, oxalate, phosphate, propionate, salicylate, succinate, sulfate, tartarate, thiocyanate, and toluenesulfonate.

23. The method of claim 22, wherein said pharmaceutically acceptable salt is a hydrochloride salt.

24. The method of claim 22, wherein said pharmaceutically acceptable salt is a toluenesulfonate salt.

25. The method of claim 1, wherein said compound has a structure:

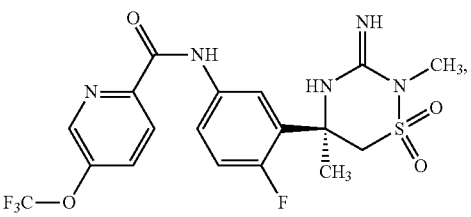 [SMILES: CN1C(=N)N[C@](C)(c2cc(NC(=O)c3ccc(OC(F)(F)F)cn3)ccc2F)CS1(=O)=O]

or a tautomer thereof, or a pharmaceutically acceptable salt of said compound or said tautomer.

26. The method of claim 7, wherein said compound has a structure:

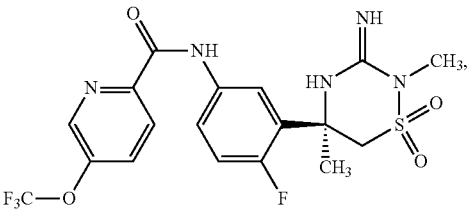 [SMILES: CN1C(=N)N[C@](C)(c2cc(NC(=O)c3ccc(OC(F)(F)F)cn3)ccc2F)CS1(=O)=O]

or a tautomer thereof, or a pharmaceutically acceptable salt of said compound or said tautomer.

27. The method of claim 13, wherein said compound has a structure:

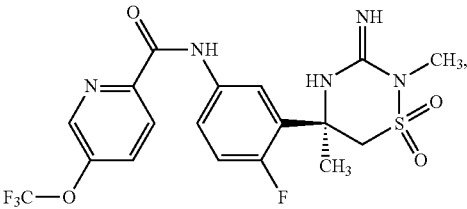 [SMILES: CN1C(=N)N[C@](C)(c2cc(NC(=O)c3ccc(OC(F)(F)F)cn3)ccc2F)CS1(=O)=O]

or a tautomer thereof, or a pharmaceutically acceptable salt of said compound or said tautomer.

28. The method of claim 19, wherein said compound has a structure:

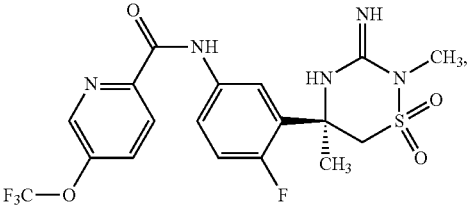 [SMILES: CN1C(=N)N[C@](C)(c2cc(NC(=O)c3ccc(OC(F)(F)F)cn3)ccc2F)CS1(=O)=O]

or a tautomer thereof, or a pharmaceutically acceptable salt of said compound or said tautomer.

* * * * *